Figure 3:
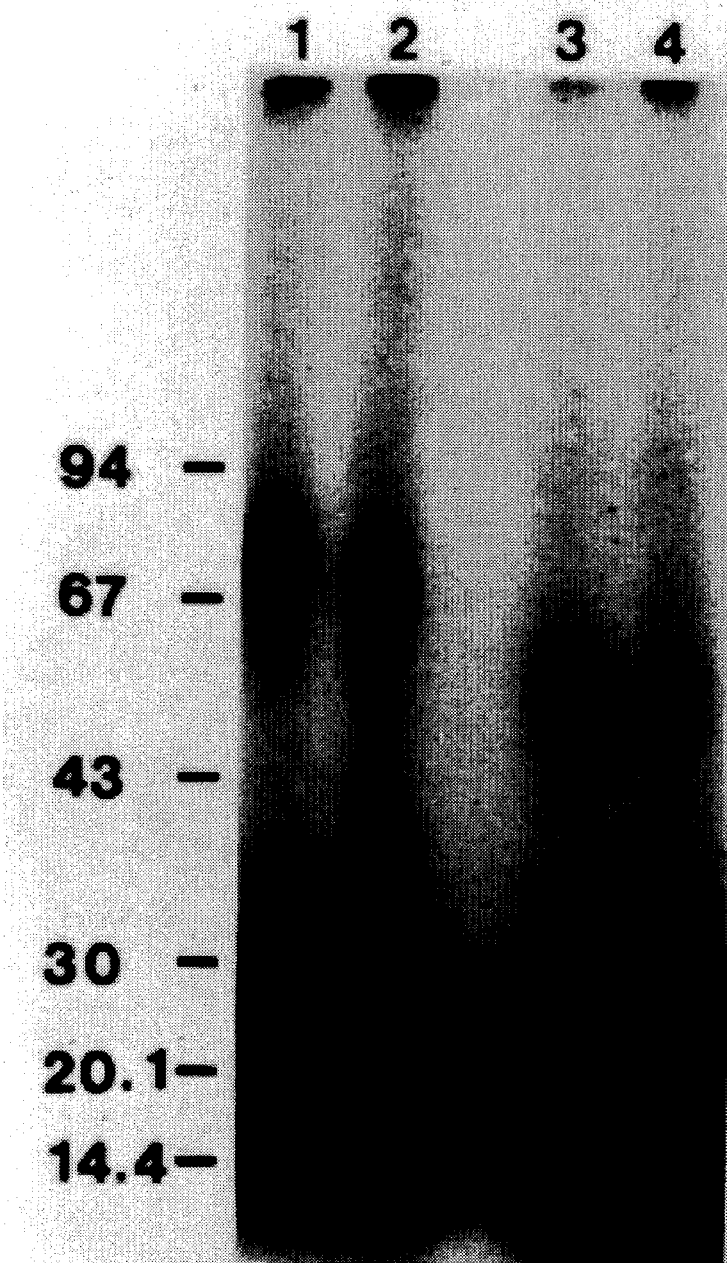

United States Patent [19]

Danø et al.

[11] Patent Number: 5,519,120
[45] Date of Patent: May 21, 1996

[54] UROKINASE-TYPE PLASMINOGEN ACTIVATOR RECEPTOR ANTIBODIES

[75] Inventors: Keld Danø, Charlottenlund; Ebbe Rønne, Copenhagen; Niels Behrendt, Bagsvaerd; Vincent Ellis, Copenhagen; Gunilla Høyer-Hansen, Gentofte; Charles Pyke, Søborg; Nils Bruenner, Virum, all of Denmark

[73] Assignee: Cancerforskningsfondet af 1989, Copenhagen, Denmark

[21] Appl. No.: 85,122

[22] Filed: Jun. 17, 1993

Related U.S. Application Data

[63] Continuation-in-part of Ser. No. 824,189, Dec. 6, 1991, abandoned, which is a continuation-in-part of Ser. No. 374,854, Jul. 3, 1989, abandoned, which is a continuation-in-part of Ser. No. 334,613, Apr. 7, 1989, abandoned.

[51] Int. Cl.$^6$ .................... C07K 16/40; C07K 16/18; C07K 16/00; C12N 5/12
[52] U.S. Cl. .................... 530/388.22; 530/388.1; 530/388.8; 530/388.26; 530/391.1; 530/391.3; 435/240.27
[58] Field of Search .................... 530/391.1, 391.3, 530/388.22, 388.26, 388.1, 388.8; 435/240.27

[56] References Cited

U.S. PATENT DOCUMENTS 4,791,068 12/1988 Loskutoff et al. .................... 436/518

FOREIGN PATENT DOCUMENTS 0278696 8/1987 European Pat. Off. .

OTHER PUBLICATIONS

Sevier, E. D. et al, Clin Chem, 27(11):1797–1806, 1981.
Behrendt, N. et al., "The Human Receptor for Urokinase Plasminogen Activator," *The Journal of Biological Chemistry*, 265(11):6453–6460 (Apr. 15, 1990).
Blasi, F., "A Surface Receptor for Urokinase Plasminogen Activator: a Link Between the Cytoskeleton and the Extracellular Matrix," *Protoplasma* 145:95–98 (1988).
Blasi, F. et al., "The Urokinase Receptor and Regulation of Cell Surface Plasminogen Activation," *Cell Differentiation and Development*, 32:247–254 (1990).
Fibbi, G. et al., "The 17500 Molecular Weight Region of the A Chain of Urokinase is Required for Interaction with a Specific Receptor in A431 Cells," *Biological Abstracts* 82(2):AB–355 (Abstract No. 12855).
Hearing, V. et al., "Modulation of Metastatic Potential by Cell Surface Urokinase of Murine Melanoma Cells," *Biological Abstracts*, 85(10):AB–645 (Abstract No. 102514).
Kirchheimer, J. et al., "Functional Inhibition of Endogenously Produced Urokinase Decreases Cell Proliferation in a Human Melanoma Cell Line," *Proc. Natl. Acad. Sci. USA*, 86:5424–5428 (Jul. 1989).
Lin, W.–Ch., et al., "Bacterial lacZ Gene as a Highly Sensitive Marker to Detect Micrometastasis Formation During Tumor Progression," *Cancer Research*, 50:2808–2817 (May 1, 1990).

Nolli, M. L., et al., "A Monoclonal Antibody that Recognizes the Receptor Binding Region of Human Urokinase Plasminogen Activator," *Thrombosis and Haemostasis*, 56(2):214–218 (1986).
Ossowski, L. "In Vivo Invasion of Modified Chorioallantoic Membrane by Tumor Cells: the Role of Cell Surface-bound Urokinase" The Journal of Cell Biology, 107(6):2437–2445 (Dec. 1988).
Roldan, A. L., et al., "Cloning and Expression of the Receptor for Human Urokinase Plasminogen Activator, a Central Molecule in Cell Surface Plasmin Dependent Proteolysis," *The EMBO Journal*, 9(2):467–474 (1990).
Ronne, E. et al., "Cell–induced Potentiation of the Plasminogen Activation System is Abolished by a Monoclonal Antibody the Recognizes the NH2–Terminal Domain of the Urokinase Receptor," *FEBS Letters*, 288(1,2):233–236 (Aug. 1991).
Appella, E., et al., "The Receptor–binding Sequence of Urokinase," *J. Biol Chem.*, 262(10):4437–4440 (1987).
Bajpai, A., et al., "Cryptic Urokinase Binding Sites on Human Foreskin Fibroblasts," *Biochem. Biophys. Res. Commun.* 133(2):475–482 (1985).
Blasi, F., "Surface Receptors for Urokinase Plasminogen Activator," *Fibrinolysis*, 2:73–84 (1988).
Blasi, F., et al., "The Receptor for Urokinase–Plasminogen Activator," *J. Cell. Biochem.*, 32:179–186 (1986).
Blasi, F., et al., "Urokinase–Type Plasminogen Activator: Proenzyme, Receptor, and Inhibitors," *J. Cell. Biol.*, 104:801–804 (1987).

(List continued on next page.)

*Primary Examiner*—Lila Feisee
*Assistant Examiner*—Susan A. Loring
*Attorney, Agent, or Firm*—Iver P. Cooper

[57] ABSTRACT

A monoclonal or polyclonal antibody directed against urokinase plasminogen activator receptor (u-PAR), or a subsequence, analogue or glycosylation variant thereof. Antibodies are disclosed which react with free u-PAR or with complexes between u-PA and u-PAR and which are capable of 1) catching u-PAR in ELISA, or 2) detecting u-PAR, e.g. in blotting, or 3) in radioimmunoprecipitation assay precipitate purified u-PAR in intact or fragment form, or 4) is useful for immunohistochemical detection of u-PAR, e.g. in immunostaining of cancer cells, such as in tissue sections at the invasive front, or 5) inhibits the binding of pro-u-PA and active u-PA and thereby inhibits cell surface plasminogen activation. Methods are disclosed 1) for detecting or quantifying u-PAR, 2) for targeting a diagnostic to a cell containing a u-PAR on the surface, 3) for preventing or counteracting proteolytic activity in a mammal. Methods for for selecting a substance suitable for inhibiting u-PA/u-PAR interaction, for preventing or counteracting localized proteolytical activity in a mammal, for inhibiting the invasion and/or metastasis comprise the use of the antibodies and of nude mice inoculated with human cancer cells which are known to invade and/or metastasize in mice and having a distinct color, f.x. obtained by means of an enzyme and a chromogenic substrate for the enzyme, the color being different from the cells of the mouse.

13 Claims, 35 Drawing Sheets

OTHER PUBLICATIONS

Boyd, D., et al., "Determination of the Levels of Urokinase and Its Receptor in Human Colon Carcinoma Cell Lines," *Cancer Research*, 48:3112–3116 (Jun. 1, 1988).

Boyd, D., et al., "Modulation of the urokinase receptor in human colon cell lines by N,N–dimethylformamide," *Biochimica et Biophysica Acta*, 947:96–100 (1988).

Burtin, P., et al., "Receptor for Plasmin on Human Carcinoma Cells," *J. Nat'l. Cancer Inst.*, 80(10):762–765 (Jul. 20, 1988).

Cubeilis, M. V., et al., "Binding of Single–chain Prourokinase to the Urokinase Receptor of Human U937 Cells," *J. Biol. Chem.* 261(34):15819–15822 (Dec. 1986).

Danø, K., et al., "Plasminogen Activators, Tissue Degradation, and Cancer," *Advances in Cancer Research*, 41:140–264, (1985).

Danø, K., et al., "Plasminogen Activators and Neoplasia," *Tissue–Type Plasminogen Activator (t–PA): Physiological and Clinical Aspects*, Kluft, ed., CRC Press, Boca Raton, pp. 19–46 (1988).

Ellis, V., et al. "Role of human U937 monocytes in controlling single–chain urokinase–initiated plasminogen activation," *Fibrinolysis*, 2:112–114 (1988).

Ellis, V., et al., "Plasminogen Activation Initiated by a Single–Chain Urokinase–ytpe Plasminogen Activator," *J. Biol. Chem.*, 264:2185–2188, (1988).

Estreicher, A., et al., "Characterization of the Cellular Binding Site for the Urokinase–Type Plasminogen Activator," *J. Biol. Chem.*, 264(2):1180–1189, (Jan. 1989).

Hearing, V. J., et al., "Modulation of Metastatic Potential by Cell Surface Urokinase of Murine Melanoma Cells," *Cancer Research*, 48:1270–1278, (Mar., 1988).

Hebert, C. A., et al., "Linkage of Extracellular Plasminogen Activator to the Fibroblast Cystoskeleton: Colocalization of Cell Surface Urokinase with Vinculin," *J. Cell Biol.*, 106:1241–1247, (Apr., 1987).

Mignatti, P., et al., "Tumor Invasion through the Human Amniotic Membrane: Requirement for a Proteinase Cascade," *Cell*, 47:487–498 (Nov. 1986).

Miles, L. A., et al., "Receptor Mediated Binding of the Fibrinolytic Components, Plasminogen and Urokinase, to Peripheral Blood Cells," *Thrombosis and Haemostasis*, 58(3):936–942 (1987).

Needham, G. K., et al., "Binding of urokinase to specific sites on human breast cancer membranes," *Br. J. Cancer*, 55:13–16 (1987).

Nelles, L., et al., "Characterization of Recombinant Human Single Chain Urokinase–type Plasminogen Activator Mutants Produced by Site–specific Mutagenesis of Lysine 158," *J. Biol. Chem.*, 262(12):5682–89, (1987).

Nielsen, L. S., et al., "A 55,000–60,000 $M_r$ Receptor Protein for Urokinase–type Plasminogen Activator," *J. Biol. Chem.*, 263(5):2358–2363, (Feb. 1988).

Ossowski, L., "Plasminogen Activator Dependent Pathways in the Dissemination of Human Tumor Cells in the Chick Embryo," *Cell*, 52:321–328 (Feb. 1988).

Ossowski, L., et al., "Antibodies to Plasminogen Activator Inhibit Human Tumor Metastasis," *Cell*, 35:611–619 (Dec. 1983).

Pannell, R., et al., "Activation of Plasminogen by Single–Chain Urokinase or by Two–Chain Urokinase—A Demonstration That Single–Chain Urokinase Has A Low . . . ," *Blood*, 69(1):22–26 (Jan. 1987).

Petersen, L. C., et al., "One–Chain Urokinase–type Plasminogen Activator from Human Sarcoma Cells Is a Proenzyme with Little or No Intrinsic Activity," *J. Biol. Chem.*, 263(23):11189–11195, (Aug. 1988).

Picone, R., et al., "Regulation of Urokinase Receptors in Monocyte–like U937 Cells by Phorbol Ester PMA," *J. Cell. Biol.*, 1989.

Plow, E. F., et al., "The Plasminogen System and Cell Surfaces: Evidence for Plasminogen and Urokinase Receptors on the Same Cell Type," *J. Cell. Biol.*, 103(6):2411–2420 (Dec. 1986).

Pöllänen, J., et al., "Ultrastructural Localization of Plasma Membrane–associated Urokinase–type Plasminogen Activator at Focal Contacts," *J. Cell. Biol.*, 106:87–95, (Jan. 1988).

Pöllänen, J., et al., "Distinct Localizations of Urokinase–type Plasminogen Activator and Its Type 1 Inhibitor under Cultured Human Fibroblasts and Sarcoma Cells," *J. Cell. Biol.*, 104:1085–1096, (Apr., 1987).

Reich, R., et al., "Effects of Inhibitors of Plasminogen Activator, Serine Proteinases, and Collagenase IV on the Invasion of Basement Membranes by Metastatic Cells," *Cancer Research*, 48:3307–3312, (Jun. 1988).

Saksela, O., "Plasminogen activation and regulation of pericellular proteolysis," *Biochimica et Biophysica Acta*, 823:35–65, (1985).

Skriver, L., et al., "Immunocytochemical Localization of Urokinase–type Plasminogen Activator in Lewis Lung Carcinoma," *J. Cell Biol.*, 99:752–757, (Aug. 1984).

Stoppelli, M. P., et al., "Differentiation–enhanced binding of the amino–terminal fragment of human urokinase plasminogen activator to a specific receptor on U937 monocytes," *Proc. Natl. Acad. Sci. USA*, 82:4939–43, 1985.

Stoppelli, M. P., et al., "Autocrine Saturation of Pro–Urokinase Receptors on Human A431 Cells," *Cell*, 45:675–684, (Jun. 1986).

Vassalli, J., et al., "A Cellular Binding Site for the $M_r$ 55,000 Form of the Human Plasminogen Activator, Urokinase," *J. Cell. Biol.*, 100:86–92, (Jan. 1985).

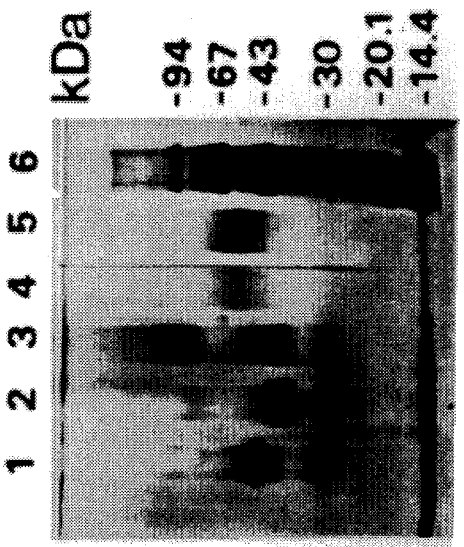
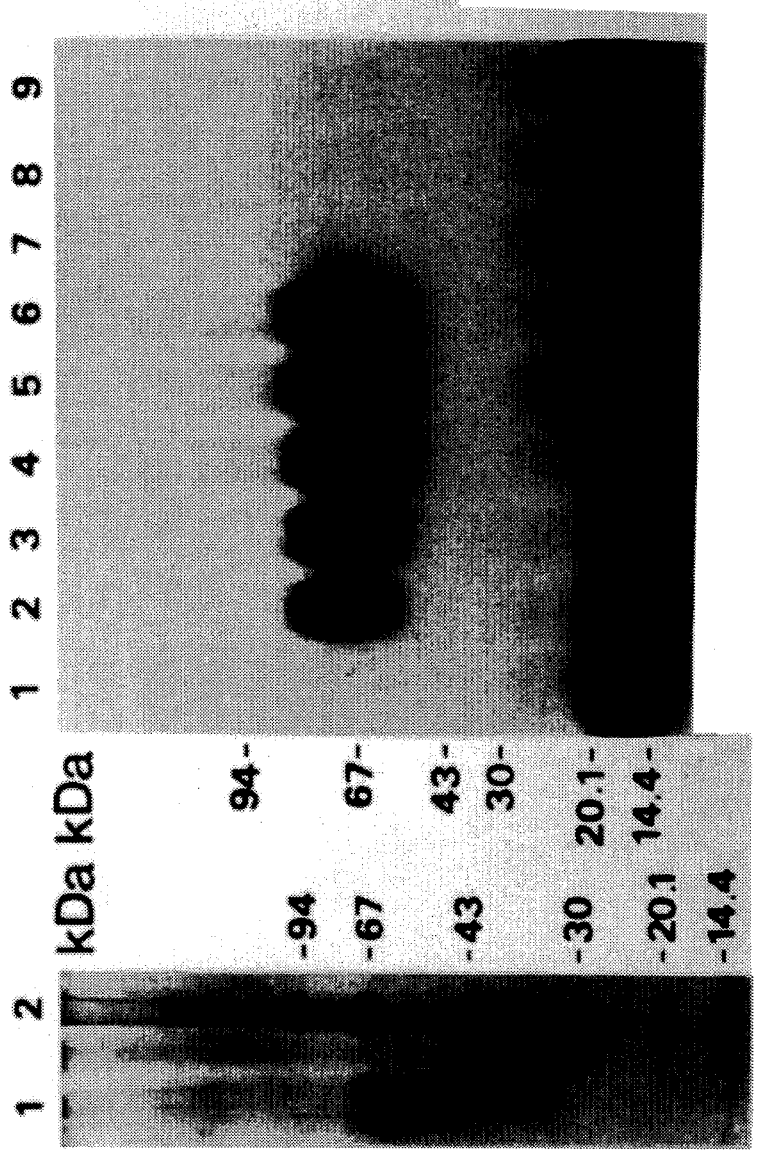
FIG. 1A  FIG. 1B  FIG. 1C

FIG. 2

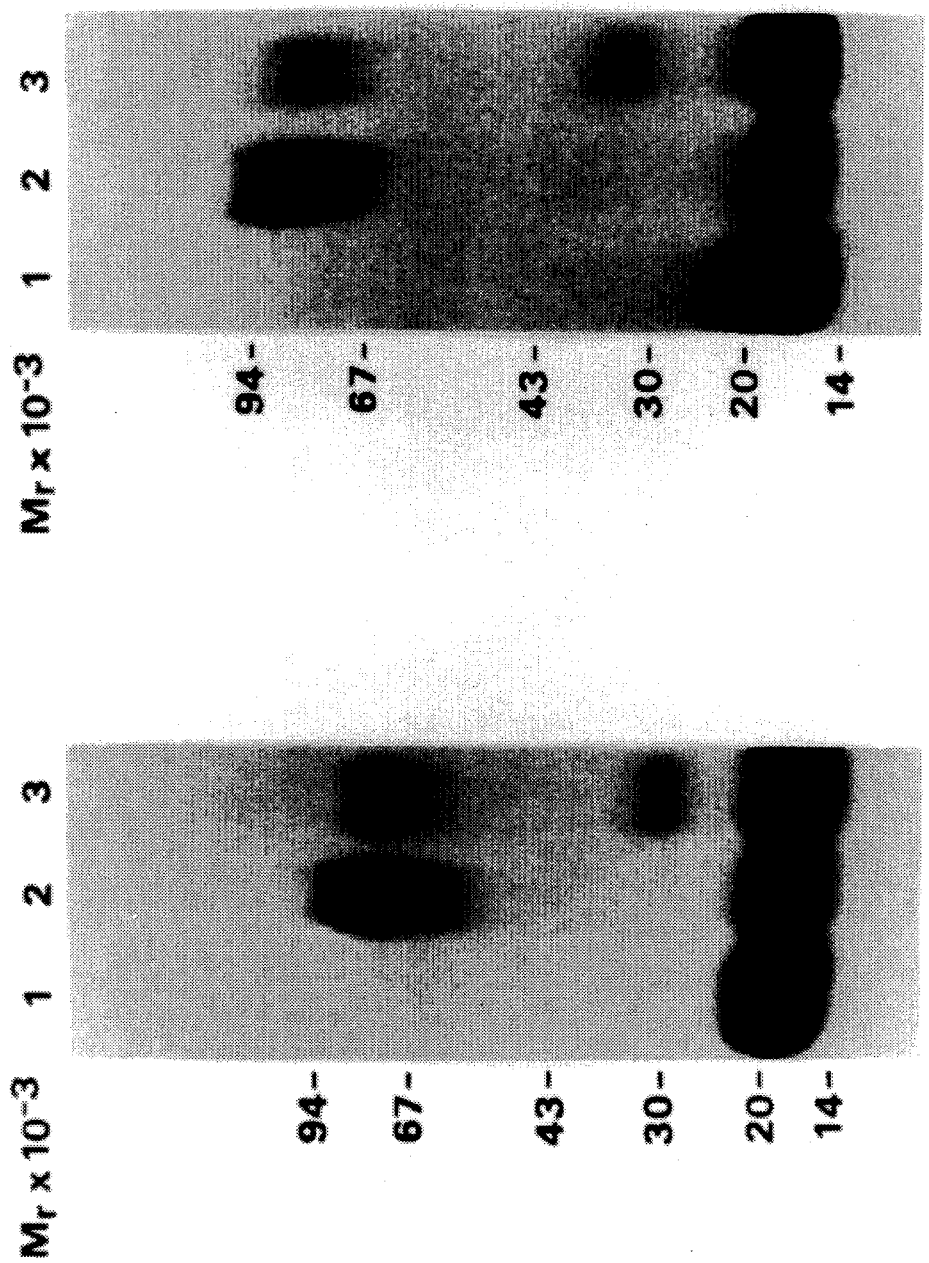

Fig. 8

```
u-PAR 1   LRCMQCKTN    GDCRVE         ECALGQDLCRTTIVRLWEEGEELELVEKSCTHS
u-PAR 2   LECISCGSSD   MSCERG         RHQSLQCRSPEEQCLDVVTHWIQEGEEGRPKDDRIHLRG
u-PAR 3   RQCYSCKGNS   THGCSSE        ETFLIDCRGPMNQCLVATGTH      EPKNQSYMVRG
co        xxCxxCxxxg   gxxCxxx        ggggxxxxxxCxxxxxxxxggggxxxxxxxxxx Ly-6a     LECYQCYGVPFETSCPSI          TCPYPDGVCVTQEAAV           IVDSQTRKVKNNL
Ly-6c     LQCYECYGVPIETSCPAV          TCRASDGFCIAQNIEL           IEDSQRRKLKTRQ
Sgp-2     IKCFVCNSYH QQDCGDWFDNATHSVHQCEPSQDRCKIVQQI             KLDEEWQVRYIRQ
CO        xxCxxCxxxxxxxxxxCxxxgxxxxCxxxxxxxxxggggggggxCxxxxxC    xxDxxxxxxxxxx ↓
u-PAR 1   EKTNRTLSYRT  GLKITSLTEVV    CGLDLCNQGNSGRAVTYSRSRY
u-PAR 2   CGYLPGCPGSN  GFHNNDTFHFLKC  CNTTKCNEGPILELENLPQNG
u-PAR 3   CATASMCQHAHL GDAFSMNHIDVSC  CTKSGCNH PDLDVQYRS - (anchor)
co        xxxxxxxxxxx  ggxxxxxxxxxx   CxxxxxCNxgxxxxxxxxx Ly-6a     CLPICPPNIESM EILGTKVNVKTSC  CQEDLCN  - anchor ?
Ly-6c     CLSFCPAGVPI  KDPNIRERTSC    CSEDLCN  - anchor ?
Sgp-2     CAEGGEIGAYDGRVCKDRIGTSGVKMTYCHCQTEGCN - anchor
CO        CxxxxxxxxxxxgggxxxxxxxxxxxxxxxxxxTxCgCxxxxCN
```

Fig. 13

| PROTEIN | | C-TERMINAL SEQUENCE |
|---|---|---|
| PARP: | - - - - - EPG | AATLKSVALPFAIAAAALVAAF |
| VSG: | - - - - - CKD | SSILVTKKFALTVVSAAFVALLF |
| PLAP: | - - - - - TTD | AAHPGRSVVPALLPLLAGTLLLLETATAP |
| CEA: | - - - - - VSA | SGTSPGLSAGATVGIMIGVLVGVALI |
| THY-1: | - - - - - VKC | GGISLLVQNTSWLLLLLSLSFLQATDFISL |
| u-PAR: | - - YRSGA | APQPGPAHLSLTITLLMTARLWGGTLLWT |

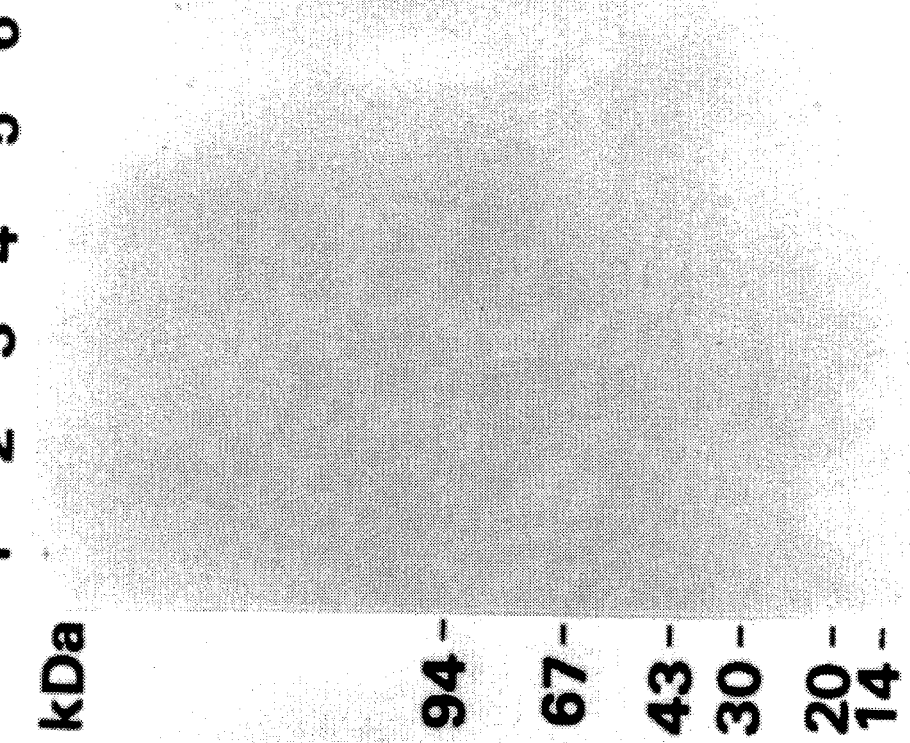
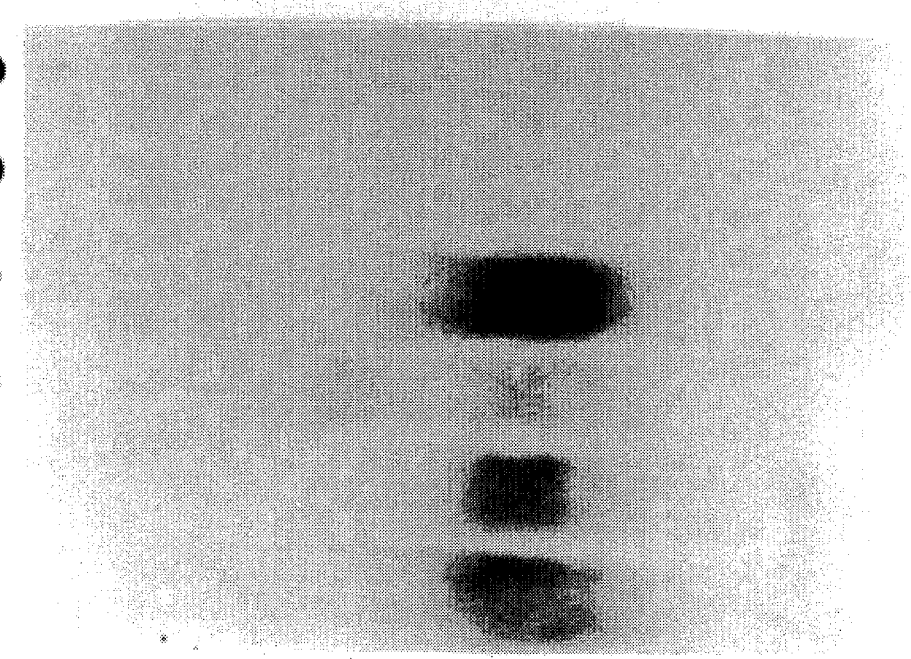
Fig. 18B
Fig. 18A

UROKINASE-TYPE PLASMINOGEN ACTIVATOR RECEPTOR ANTIBODIES

This application is a continuation-in-part of Ser. No. 07/824,189, filed Dec. 6, 1991, now abandoned, which is a continuation of PCT/DK90/00090, filed Apr. 9, 1990, now abandoned; which is a continuation-in-part of Ser. No. 07/374,854, filed Jul. 3, 1989, now abandoned; which is a continuation-in-part of Ser. No. 07/334,613, filed Apr. 7, 1989, now abandoned. It is also a continuation-in-part of PCT/DK91/00319, filed Oct. 18, 1991, and of PCT/DK90/00270, filed Oct. 18, 1990, both now abandoned.

A related application Ser. No. 08/319,052, a continuation of Ser. No. 07/824,189, was filed Oct. 6, 1994 and is now pending.

FIELD OF THE INVENTION

The present invention relates to important further developments of certain aspects of the invention disclosed in International Patent Application No. PCT/DK90/00090, and U.S. patent application Ser. Nos. 334,613 and 374,854, the developments of the present invention relating, in particular, to special types of antibodies, especially monoclonal antibodies, and the use of these special types of antibodies, in particular for detecting and quantitating u-PAR, for therapeutic use, and for drug screening.

GENERAL BACKGROUND

According to the literature, urokinase-type plasminogen activator (u-PA) has been found in all mammalian species so far investigated. Several findings relate u-PA to tissue degradation and/or cell migration, presumably through a breakdown of the extracellular matrix, caused by plasmin together with other proteolytic enzymes. This relation has been most extensively studied in postlactational involution of the mammary and prostate gland and the early phase of trophoblast invasion after implantation of the fertilized egg in the uterus. The hypothesis of a role of u-PA in tissue degradation and cell migration is further supported by the more exact localization made possible by the immunocytochemical findings of u-PA in epithelial cells of involuting mammary glands, in areas with tissue degradation in psoriasis, in association with the release of spermatocytes during spermatogenesis, and in keratinocytes of the epithelial outgrowth during wound healing (see Danø et al., 1988, 1990, Grondal-Hansen et al., 1988, Andreasen et al, 1990).

It is also conceivable that u-PA plays a role in the degradative phase of inflammation, and there have also been reports that u-PA interferes with the lymphocyte-mediated cytotoxicity against a variety of cells, and a direct role of u-PA in the cytotoxic effect of natural killer cells has been proposed. A role of u-PA has been proposed in angiogenesis and in endothelial cell migration, a process important in tumor growth.

u-PA is produced by many cultured cell types of neoplastic origin. It has been found that explants of tumor tissue released more u-PA than the corresponding normal tissue. u-PA has been identified in extracts from human lung, colon, endometrial, breast, prostate and renal carcinomas, human melanomas, murine mammary tumors, the murine Lewis lung tumor, and in ascites from human peritoneal carcinomatosis. An immunohistochemical study of invasively growing and metastasing Lewis lung carcinomas in mice consistently showed the presence of u-PA, but also a pronounced heterogenecity in the content of u-PA in different parts of the individual tumors. A high u-PA content was found in areas with invasive growth and degradation of surrounding normal tissue, while other areas were devoid of detectable u-PA. The u-PA was located in the cytoplasm of the tumor cells and extracellularly surrounding the tumor cells.

Degradation of the surrounding normal tissue is a central feature of invasiveness of malignant tumors. The constant finding of u-PA in malignant tumors and the findings indicating that u-PA plays a role in tissue degradation in normal physiological events have led to the assumption that u-PA plays a similar role in cancer development. The hypothesis of u-PA playing a role in tissue destruction involves the assumption that plasmin, together with other proteolytic enzymes, degrades the extracellular matrix. It is noteworthy in this context that most components of the extracellular matrix can be degraded by plasmin. These include laminin, fibronectin, proteoglycans, and possibly some types of collagen, but not all. In addition, as originally reported by Vaes and collaborators, plasmin can activate latent collagenases which in turn can degrade the other types of collagen (see Danø et al., 1988, 1990).

The majority of the cancer patients in the treatment failure group succumb to the direct effects of the metastases or to complications associated with the treatment of metastases. Therefore, much research has been focused on identifying specific biochemical factors which can be the basis for diagnostic or therapeutic strategies. The extracellular matrix is composed of glycoproteins such as fibronectin and laminin, collagen and proteoglycans. Extracellular matrix becomes focally permeable to cell movement only during tissue healing and remodelling, inflammation, and neoplasia. Liotta (1986) has proposed a three-step hypothesis: The first step is tumor cell attachment via cell surface receptors. The anchored tumor cell next secretes hydrolytic enzymes (or induces host cells to secrete enzymes) which can degrade the matrix locally (including degradation of the attachment components). Matrix lysis most probably takes place in a highly localized region close to the tumor cell surface. The third step is tumor cell locomotion into the region of the matrix modified by proteolysis. Thus, invasion of the matrix is not merely due to passive growth pressure but requires active biochemical mechanisms.

Many research groups have proposed that invasive tumor cells secrete matrix-degrading proteinases. A cascade of proteases including serine proteases and thiol proteases all contribute to facilitating tumor invasion. One of the crucial cascades is the plasminogen activation system. Regulation of the proteolysis can take place at many levels including tumor cell-host cell interactions and protease inhibitors produced by the host or by the tumor cells themselves. Expression of matrix-degrading enzymes is not tumor cell specific. The actively invading tumor cells may merely respond to different regulatory signals compared to their non-invasive counterparts (Liotta, 1986).

The assumption that the plasminogen activation system, through a breakdown of extracellular matrix proteins, plays a role in invasiveness and destruction of normal tissue during growth of malignant tumors is supported by a variety of findings. These include a close correlation between transformation of cells with oncogenic viruses and synthesis of u-PA, the finding that u-PA is involved in tissue destruction in many non-malignant conditions, and the immunohistochemical localization of u-PA in invading areas of tumors (see Danø et al., 1985, Saksela, 1985, for reviews).

Further support for this hypothesis has come from studies with anti-catalytic antibodies to u-PA in model systems for invasion and metastasis. Such antibodies were found to decrease metastasis to the lung from a human u-PA producing tumor, HEp-3, transplanted onto the chorioallantoic membrane of chicken embryos (Ossowski and Reich, 1983, Ossowski 1988), penetration of amniotic membranes by B16 melanoma cells (Mignatti et al., 1986), basement membrane invasion by several human and murine cell lines of neoplastic origin (Reich et al., 1988), and formation of lung metastasis after intravenous injection of B16 melanoma cells in mice (Hearing et al., 1988). In some of these studies (Mignatti et al., 1986, Reich et al., 1988), a plasmin-catalyzed activation of procollagenases (see Tryggvason et al., 1987) appeared to be a crucial part of the effect of plasminogen activation.

A requirement for the regulation of a proteolytic cascade system in extracellular processes is the precise localization of its initiation and progression. For example, in the complement and coagulation systems, cellular receptors for various components are known and serve to localize reactions that either promote or terminate the reaction sequence (Müller-Eberhard, 1988, Mann et al., 1988). In the plasminogen activation system, the role of fibrin in the localization of plasminogen activation catalyzed by the tissue-type plasminogen activator (t-PA) is well known (Thorsen et al., 1972, Hoylaerts et al., 1982).

Immunocytochemical studies have suggested that in the invasive areas of tumors, u-PA is located at the membrane of the tumor cells (Skriver et al., 1984), and recent findings indicate that at cell surfaces, u-PA is generally bound to a specific receptor and that this localization may be crucial for the regulation of u-PA catalyzed plasminogen activation in time and space (see Blasi et al., 1987, Danø et al, 1990). Preliminary reports suggest that also t-PA may bind to cell surface receptors and retain its enzymatic activity (Beebe, 1987, Barnathan et al., 1988, Hajjar and Nachmann, 1988, Kuiper et al., 1988). This phenomenon, however, awaits further clarification concerning the nature of the binding sites.

Surface Receptor for u-PA

The cellular receptor for u-PA (u-PAR) was originally identified in blood monocytes and in the monocyte-like U937 cell line (Vassalli et al., 1985), and its presence has been demonstrated on a variety of cultured cells, including several types of malignant cells (Stoppelli et al., 1985, Vassalli et al., 1985, Plow et al., 1986, Boyd et al., 1988a, Nielsen et al., 1988), human fibroblasts (Bajpai and Baker, 1985), and also in human breast carcinoma tissue (Needham et al., 1987). The receptor binds active 54 kD u-PA, its one-polypeptide chain proenzyme, pro-u-PA (see below), as well as 54 kD u-PA inhibited by the active site reagent DFP, but shows no binding of the low molecular weight (33 kD) form of active u-PA (Vassalli et al., 1985; Cubellis et al., 1986). Thus, binding to the receptor does not require the catalytic site of u-PA, and in agreement with these findings, the binding determinant of u-PA has been identified in the amino-terminal part of the enzyme, in a region which in the primary structure is remote from the catalytic site. The receptor binding domain is located in the 15 kD amino-terminal fragment (ATF, residues 1–135) of the u-PA molecule, more precisely within the cysteine-rich region termed the growth factor region as this region shows homologies to the part of epidermal growth factor (EGF) which is responsible for binding to the EGF receptor. The amino acid residues which appear to be critical for binding are located within the sequence 12-32 (Appella et al., 1987). Synthetic peptides have been constructed that inhibit the binding of very low (100 nM) concentrations. The lack of cross-reactivity between the murine and the human peptides indicates that the binding between u-PA and u-PAR is strongly species specific.

Binding of u-PA to u-PAR is specific in the sense that as yet no other protein has been found to compete for binding to the receptor, though several proteins structurally related to u-PA, including t-PA and plasminogen, have been tested (Stoppelli et al., 1985, Vassalli et al., 1985, Nielsen et al., 1988). Fragments of u-PA containing only the receptor binding domain, e.g. ATF, ensure specificity of the binding to the receptor, since other molecules that might bind u-PA (protease nexin and the specific plasminogen activator inhibitors PAI-1 and PAI-2) recognize the catalytically active region (Stoppelli et al., 1985; Nielsen et al., 1988). PAI-1 is able to form a covalent complex with u-PA but not with pro-u-PA (Andreasen et al., 1986).

The number of receptors reported varies strongly among the cell types studied, from a few thousand molecules per cell on normal monocytes (Miles and Plow, 1987) up to $3 \times 10^5$ on some colon carcinoma cell lines (Boyd et al., 1988a), and some variation apparently also occurs in the binding affinity, which is in the 0.1–10 nM range (for a review, see Blasi 1988, Danø et al, 1990). Further, on certain cell lines the number of receptors can be regulated by the addition of various agents such as phorbol myristate acetate (PMA) in U937 cells (Stoppelli et al., 1985, Nielsen et al., 1988), epidermal growth factor in A431 cells (Blasi et al., 1986) and HeLa cells (Estreicher et al., 1989) and dimethylformamide in colon carcinoma cells (Boyd et al., 1988b). In the first-mentioned case, a large decrease in affinity for the ligand occurs concomitantly with an increase in the number of receptors (Nielsen et al., 1988, Picone et al., 1989).

The human u-PA receptor was recently purified and characterized (Behrendt et al. 1990) and its full length cDNA has been cloned (Roldan et al, 1990). u-PAR is a 55–60 kD glycoprotein, the molecular weight of which is unchanged after cleavage of disulfide bonds, suggesting that it consists of a single polypeptide chain. Several variants with different electrophoretic mobility identified appear to be glycosylation variants. The full length human u-PAR cDNA (SEQ ID NO:12) was 1363 bp long and the nucleotide sequence is shown below together with the deduced amino acid sequence (SEQ ID NO:13) of the 313 residues long u-PAR molecule. The signal peptide is underlined and the first 30 amino acids, the sequence of which was determined on the purified protein are overlined. A putative transmembrane domain is doubly underlined. The star symbols indicate the potential N-linked glycosylation sites.

```
             AGAGAA GACGTGCAGG GACCCCGCGC ACAGGAGCTGC CCTCGCGAC      46

ATG  GGT  CAC  CCG  CCG  CTG  CTG  CCG  CTG  CTG  CTG  CTG  CTG  CAC  ACC  TGC    94
    Met  Gly  His  Pro  Pro  Leu  Leu  Pro  Leu  Leu  Leu  Leu  Leu  His  Thr  Cys
        -20                                              -10
```

-continued

| | | | | | | | | | | | | | | | | |
|---|---|---|---|---|---|---|---|---|---|---|---|---|---|---|---|---|
| GTC | CCA | GCC | TCT | TGG | GGC | CTG | CGG | TGC | ATG | CAG | TGT | AAG | ACC | AAC | GGG | 142 |
| Val | Pro | Ala | Ser | Trp | Gly | Leu | Arg | Cys | Met | Gln | Cys | Lys | Thr | Asn | Gly | |
| | | | | | 1 | | | | | | | | | | 10 | |
| GAT | TGC | CGT | GTG | GAA | GAG | TGC | GCC | CTG | GGA | CAG | GAC | CTC | TGC | AGG | ACC | 190 |
| Asp | Cys | Arg | Val | Glu | Glu | Cys | Ala | Leu | Gly | Gln | Asp | Leu | Cys | Arg | Thr | |
| | | | | | | | | | 20 | | | | | | | |
| ACG | ATC | GTG | CGC | TTG | TGG | GAA | GAA | GGA | GAA | GAG | CTG | GAG | CTG | GTG | GAG | 238 |
| Thr | Ile | Val | Arg | Leu | Trp | Glu | Glu | Gly | Glu | Glu | Leu | Glu | Leu | Val | Glu | |
| | | | 30 | | | | | | | | | | 40 | | | |
| AAA | AGC | TGT | ACC | CAC | TCA | GAG | AAG | ACC | AAC | AGG | ACC | CTG | AGC | TAT | CGG | 286 |
| Lys | Ser | Cys | Thr | His | Ser | Glu | Lys | Thr | Asn | Arg | Thr | Leu | Ser | Tyr | Arg | |
| | | | | | | | 50 | | * | | | | | | | |
| ACT | GGC | TTG | AAG | ATC | AGC | AGS | CTT | ACC | GAG | GTT | GTG | TGT | GGG | TTA | GAC | 334 |
| Thr | Gly | Leu | Lys | Ile | Thr | Ser | Leu | Thr | Glu | Val | Val | Cys | Gly | Leu | Asp | |
| | | 60 | | | | | | | | | | 70 | | | | |
| TTG | TGC | AAC | CAG | GGC | AAC | TCT | GGC | CGG | GCT | GTC | ACC | TAT | TCC | CGA | AGC | 382 |
| Leu | Cys | Asn | Gln | Gly | Asn | Ser | Gly | Arg | Ala | Val | Thr | Tyr | Ser | Arg | Ser | |
| | | | | 80 | | | | | | | | | | | 90 | |
| CGT | TAC | CTC | GAA | TGC | ATT | TCC | TGT | GGC | TCA | TCA | GAC | ATG | AGC | TGT | GAG | 430 |
| Arg | Tyr | Leu | Glu | Cys | Ile | Ser | Cys | Gly | Ser | Ser | Asp | Met | Ser | Cys | Glu | |
| | | | | | | | | | 100 | | | | | | | |
| AGG | GGC | CGG | CAC | CAG | AGC | CTG | CAG | TGC | CGC | AGC | CCT | GAA | GAA | CAG | TGC | 478 |
| Arg | Gly | Arg | His | Gln | Ser | Leu | Gln | Cys | Arg | Ser | Pro | Glu | Glu | Gln | Cys | |
| | | | 110 | | | | | | | | | | 120 | | | |
| CTG | GAT | GTG | GTG | ACC | CAC | TGC | ATC | CAG | GAA | GGT | GAA | GAA | GGG | CGT | CCA | 526 |
| Leu | Asp | Val | Val | Thr | His | Trp | Ile | Gln | Glu | Gly | Glu | Glu | Gly | Arg | Pro | |
| | | | | | | | | 130 | | | | | | | | |
| AAG | GAT | GAC | CGC | CAC | CTC | CGT | GGC | TGT | GGC | TAC | CTT | CCC | GGC | TGC | CCG | 574 |
| Lys | Asp | Asp | Arg | His | Leu | Arg | Gly | Cys | Gly | Tyr | Leu | Pro | Gly | Cys | Pro | |
| | | 140 | | | | | | | | | | 150 | | | | |
| GGC | TCC | AAT | GGT | TTC | CAC | AAC | AAC | GAC | ACC | TTC | CAC | TTC | CTG | AAA | TGC | 622 |
| Gly | Ser | Asn | Gly | Phe | His | Asn | Asn | Asp | Thr | Phe | His | Phe | Leu | Lys | Cys | |
| | | | | | | 160 | * | | | | | | | | 170 | |
| TGC | AAC | ACC | ACC | AAA | TGC | AAC | GAG | GGC | CCA | ATC | CTG | GAG | CTT | GAA | AAT | 670 |
| Cys | Asn | Thr | Thr | Lys | Cys | Asn | Glu | Gly | Pro | Ile | Leu | Glu | Leu | Glu | Asn | |
| | * | | | | | | | | 180 | | | | | | | |
| CTG | CCG | CAG | AAT | GGC | CGC | CGC | TGT | TAC | AGC | TGC | AAG | GGG | AAC | AGC | ACC | 718 |
| Leu | Pro | Gln | Asn | Gly | Arg | Arg | Cys | Tyr | Ser | Cys | Lys | Gly | Asn | Ser | Thr | |
| | | | 190 | | | | | | | | | | | * | | |
| CAT | GGA | TGC | TCC | TCT | GAA | GAG | ACT | TTC | CTC | ATT | GAC | TGC | CGA | GGC | CCC | 766 |
| His | Gly | Cys | Ser | Ser | Glu | Glu | Thr | Phe | Leu | Ile | Asp | Cys | Arg | Gly | Pro | |
| | | | | | | | | | 210 | | | | | | | |
| ATG | AAT | CAA | TGT | CTG | GTA | GCC | ACC | GGC | ACT | CAC | GAA | CCG | AAA | AAC | CAA | 814 |
| Met | Asn | Gln | Cys | Leu | Val | Ala | Thr | Gly | Thr | His | Glu | Pro | Lys | Asn | Gln | |
| | * | | | | | | | | | | | 230 | | | | |
| AGC | TAT | ATG | GTA | AGA | GGC | TGT | GCA | ACC | GCC | TCA | ATG | TGC | CAA | CAT | GCC | 862 |
| Ser | Tyr | Met | Val | Arg | Gly | Cys | Ala | Thr | Ala | Ser | Met | Cys | Gln | His | Ala | |
| | | | | 240 | | | | | | | | | | | 250 | |

```
CAC CTG GGT GAC GCC TTC AGC AGC AAC CAC ATT GAT GTC TCC TGC TGT    910
His Leu Gly Asp Ala Phe Ser Met Asn His Ile Asp Val Ser Cys Cys
                                        260

ACT AAA AGT GGC TGT AAC CAC CCA GAC CTG GAT GTC CAG TAC CGC AGT    958
Thr Lys SeR Gly Cys Asn His Pro Asp Leu Asp Val Gln Tyr Arg Ser
            270                                 280

GGG GCT GCT CCT CAG CCT GGC CCT GCC CAT CTC AGC CTC ACC ATC ACC    1006
Gly Ala Ala Pro Gln Pro Gly Pro Ala His Leu Ser Leu Thr Ile Thr

290

CTG CTA ATG ACT GCC AGA CTG TGG GGA GGC ACT CTC CTC TGG ACC TAA    1054
Leu Leu Met Thr Ala Arg Leu Trp Gly Gly Thr Leu Leu Trp Thr End
    300                                     310

ACCTGAAATC CCCCTCTCTG CCCTGGCTGG ATCCGGGGGA CCCCTTTGCC              1104

CTTCCCTCGG CTCCCAGCCC TACAGACTTG CTGTGTGACC TCAGGCCAGT              1154

GTGCCGACCT CTCTGGGCCT CAGTTTTCCC AGCTATGAAA ACAGCTATCT              1204

CACAAAGTTG TGTGAAGCAG AAGAGAAAAG CTGGAGGAAG GCCGTGGGCA              1254

ATGGGAGAGC TCTTGTTATT ATTAATATTG TTGCCGCTGT TGTGTTGTTG              1304

TTATTAATTA ATATTCATAT TATTTATTTT ATACTTACAT AAAGATTTTG              1350

TACCAGTGGA AAAAAAAAAA AAAAAAAAAA AAAAAAAAAA AAAAAA                  1400
```

Preparation of polyclonal antibodies to u-PAR were described in the International Patent Application No. PCT/DK90/00090 while special monoclonal antibodies to the receptor are described herein.

Proenzyme to u-PA (pro-u-PA)

Several studies have indicated that u-PA is released from many types of cultured cells as a single-chain proenzyme with little or no plasminogen activating capacity (Nielsen et al., 1982, Skriver et al., 1982, Eaton et al., 1984, Kasai et al., 1985, Pannell and Gurewich 1987). By limited proteolysis with catalytic amounts of plasmin, this proenzyme can be converted to its active two-chain counterpart. The proenzyme nature of single-chain u-PA is also reflected in the finding that it has essentially no amidolytic activity with synthetic substrates (Wun et al., 1982, Eaton et al., 1984, Lijnen et al., 1986, Stump et al., 1986a, 1986b, Nelles et al., 1987, Pannell and Gurewich 1987), and that it has little or no reactivity with macromolecular inhibitors (Eaton et al., 1984, Vassalli et al., 1985, Andreasen et al., 1986, Stephens et al., 1987) and synthetic inhibitors (Nielsen et al., 1982, Skriver et al., 1982, Wun et al., 1982, Gurewich et al., 1984, Kasai et al., 1985).

This picture of single-chain u-PA as an essentially inactive proenzyme is in contrast to the interpretation reached by some other investigators (Collen et al., 1986, Lijnen et al., 1986, Stump et al., 1986a, 1986b). They concluded that single-chain u-PA from several sources had considerable plasminogen activating capability, and that recombinant single-chain u-PA had an activity that was even higher than that of two-chain u-PA. For these studies, a coupled plasminogen activation assay was used in which the activity of generated plasmin was measured with a chromogenic substrate. Such assays for pro-u-PA are self-activating and are strongly influenced by small amounts of contaminating or generated two-chain u-PA or plasmin. As discussed in detail elsewhere (Petersen et al., 1988), it is therefore possible that the high activity of one-chain u-PA found in these studies was apparent and not due to intrinsic activity of single-chain u-PA. Consistent with this interpretation is a report on a variant of recombinant single-chain u-PA which by site-directed mutagenesis was made partly resistant to plasmin cleavage. This variant of single-chain u-PA had an activity that in coupled assays was 200-fold lower than that of two-chain u-PA (Nelles et al., 1987).

Recent kinetic studies, which included measures to prevent self-activation in the assays for pro-u-PA, have confirmed the low intrinsic activity of pro-u-PA (Ellis et al., 1987, Petersen et al., 1988, Urano et al., 1988). In one study with a highly purified preparation of pro-u-PA from HT-1080 fibrosarcoma cells, it was shown that the pro-u-PA had a capacity for plasminogen activation that was lower than that of a 250-fold lower concentration of two-chain u-PA. It was not possible to decide whether this low activity was intrinsic or due to contamination (Petersen et al., 1988).

In the intact organism, pro-u-PA is the predominant form of u-PA in intracellular stores, and it also constitutes a sizable fraction of the u-PA in extracellular fluids (Skriver et al., 1984, Kielberg et al., 1985). Extracellular activation of pro-u-PA may therefore be a crucial step in the physiological regulation of the u-PA pathway of plasminogen activation. The plasmin-catalyzed activation of pro-u-PA provides a positive feedback mechanism that accelerates and amplifies the effect of activation of a small amount of pro-u-PA. The initiation of the u-PA pathway of plasminogen activation under physiological conditions, however, involves triggering factors that activate pro-u-PA as described herein. Mutants of human single-chain pro-u-PA in which lysine 158 is changed to another amino acid (e.g. Glu or Gly) are not, or are only to a small extent, converted to active two-chain u-PA (Nelles et al., 1987).

u-PA at Focal Contact Sites

At the surface of HT-1080 fibrosarcoma cells and human fibroblasts, u-PA has been found to be unevenly distributed, distinctly located at cell-cell contact sites and at focal contacts that are the sites of closest apposition between the cells and the substratum (Pöllänen et al., 1987, 1988, Hébert and Baker 1988). u-PA was not detected in the two other types of cell-substratum contact, i.e. close contacts and fibronexuses, making it an intrinsic component at focal contact sites (Pöllänen et al., 1988). u-PA at the focal contact sites is receptor-bound (Hébert and Baker, 1988). The focal contact sites are located at the termini of actin-containing microfilament bundles, the so-called stress fibers or actin cables (Burridge, 1986). These sites contain several structural components (actin, talin) and regulatory factors (the tyrosine kinase protooncogene products $P60^{src}$, $P120^{gag-abl}$, $P90^{gag-yes}$, $P80^{gag-yes}$) that are all located on the cytoplasmic side (see Burridge, 1986).

Plasminogen Binding Sites on Cell Surfaces

Plasminogen, as well as plasmin, binds to many types of cultured cells, including thrombocytes, endothelial cells and several cell types of neoplastic origin (Miles and Plow, 1985, Hajjar et al., 1986, Plow et al., 1986, Miles and Plow 1987, Burtin and Fondaneche, 1988). The binding is saturable with a rather low affinity for plasminogen ($K_D$ 1 µM). At least in some cell types, binding of plasmin appears to utilize the same site as plasminogen, but the binding parameters for plasmin indicate that more than one type of binding site for plasminogen and plasmin may exist. Thus, on some cell types, plasmin and plasminogen bind with almost equal affinity (Plow et al., 1986), while on others plasmin apparently binds with a higher affinity ($K_D$ 50 nM) than plasminogen (Burtin and Fondaneche, 1988). The binding is inhibited by low amounts of lysine and lysine analogues and appears to involve the kringle structure of the heavy chains of plasminogen and plasmin (Miles et al., 1988).

The binding capacity varies between cell types and in many cell types is quite high ($10^5$–$10^7$ binding sites per cell). The chemical nature of the binding sites are not known. A membrane protein, GPIIb/IIIa, seems to be involved in the binding of plasminogen to thrombocytes (Miles et al., 1986) and, particularly on thrombin-stimulated thrombocytes, also fibrin may be involved in plasminogen binding (Miles et al., 1986). In its purified form, the thrombocyte protein thrombospondin forms complexes ($K_D$ 35 nM) with plasminogen (Silverstein et al., 1984). Also immobilized laminin (Salonen et al., 1984) and fibronectin (Salonen et al., 1985) bind plasminogen ($K_D$ 3 nM and 90 nM, respectively).

Surface Plasminogen Activation

Some cell types bind both u-PA and plasminogen (Plow et al., 1986, Miles and Plow, 1987, Burtin and Fondaneche, 1988, Ellis et al., 1988). Receptor-bound pro-u-PA can be activated by plasmin (Cubellis et al., 1986) and, at least in part, receptor-bound two-chain u-PA retains its ability to activate plasminogen (Vassalli et al., 1985). Addition of u-PA and plasminogen to cells holding binding sites for both molecules leads to the occurrence of cell-bound plasmin (Plow et al., 1986, Burtin and Fondaneche, 1988). These studies did not allow a rigorous discrimination between an activation process occurring in solution or between surface-bound reactants.

An interaction between binding sites for u-PA and plasminogen is suggested by the finding that u-PA binding in two cell lines led to an increased binding capacity for plasminogen. Binding of plasminogen in these studies had no effect on the binding capacity for u-PA (Plow et al., 1986). An enhancement of u-PA binding caused by plasminogen was also found by Burtin and Fondaneche (1988) in a cell line of neoplastic origin, even though the plasminogen binding sites demonstrated in the two studies were apparently not identical (see above).

Recently, Ossowski (1988) published findings that the invasive ability of human tumor cells (into modified chick embryo chorioallantoic membranes in an in vivo assay) which have surface u-PA receptors, but which do not produce u-PA, could be augmented by saturating their receptors with exogenous u-PA. This finding, however, is only suggestive (as stated by the author) and it does not demonstrate that binding to the receptor per se is necessary.

Ellis et al. (1989) have published evidence indicating that the reactions leading to plasminogen activation can take place when pro-u-PA and plasminogen are added to U937 cells, and that they occur more efficiently when both plasminogen and pro-u-PA are bound to the surface. This experiment was performed in the absence of serum, i.e. under conditions where the plasminogen activation with the preparations used by Ellis et al. will also take place in solution (cf. Ellis et al., 1987), and these studies do not exclude the possibility that one or more of the processes involved (e.g. the plasminogen activation catalyzed by two-chain u-PA) actually occurred when the u-PA was not receptor-bound. Stephens et al (1989) have demonstrated that plasmin formation on the surface of HT 1080 fibrosarcoma cells cultured in the presence of serum only occurs when u-PA that is produced by the cells is bound to u-PAR on the surface. Particularly interesting is the finding that exogeneously added DFP-inactivated u-PA can displace the endogenous receptor bound u-PA and thereby inhibit the plaminogen activation, a prerequisite for any therapeutic use of this approach.

SUMMARY OF THE INVENTION

The present invention relates to monoclonal and polyclonal antibodies to the u-PA receptor. Under conditions similar to those present extracellularly in the intact organism (i.e. in the presence of serum containing inhibitors of plasmin and of plasminogen activators), plasminogen activation initiated by endogenous pro-u-PA occurs virtually only when the pro-u-PA is receptor-bound. On the basis of this, new and potentially extremely valuable therapeutic and diagnostic methods and products are provided by these antibodies.

Binding of pro-u-PA to its receptor localizes pro-u-PA and u-PA not only to the cell surface, but focalizes them to distinct parts of the surface that at least in some cell types are the cell-cell and cell-substrate contact. The location of pro-u-PA and u-PA at the focal contact sites suggests that u-PA catalyzed plasminogen activation is involved in the breakdown of the contacts, e.g. during cell movement. A selective activation of pro-u-PA at these sites provides a means of obtaining a directional pericellular proteolysis. pro-u-PA activation might be intracellularly initiated and mediated by a transmembrane signal through the u-PA receptor.

Human tumor cells are very commonly found to secrete plasminogen activator of the urokinase type (u-PA). By this means they are able to recruit the proteolytic potential available in the high concentration of plasminogen in plasma and other body fluids. The invasive properties of tumor cells may be at least partly dependent on their proteolytic capability mediated through the broad spectrum of activity of plasmin and including its indirect actions in activating other latent proteases, such as collagenases. The expression of protease activity by tumor cells facilitates their penetration of basement membranes, capillary walls and interstitial connective tissues, allowing spread to other sites and establishment of metastases.

A stepwise pathway of pericellular proteolysis geared to cell migration can be envisaged: binding of u-PA and plasminogen to the cell surface will lead to extracellular proteolysis and to the local severing of cell-cell and cell-substrate connections. This region of the cell is therefore free to move and this will transpose u-PA to a region in which PAI-1 is present. PAI-1 will inactivate u-PA and in the absence of local proteolytic activity, the cell will form new connections with the matrix, a process required for further migration.

Further characterization of the interaction of u-PA and u-PAR required the purification of the u-PAR. The number of u-PAR produced by the monocyte-like cell U937 can be increased several fold by phorbol esters like PMA. This fact was used to produce sufficient quantities of the receptor for purification. In Example 1, a complete purification of the u-PA receptor is described, involving temperature-induced phase separation of a detergent extract from cells, and affinity chromatography with immobilized DFP-inactivated u-PA. This resulted in a preparation that shows one band at approximately 55–60 kD after SDS-PAGE and silver staining, with a load of approximately 1 μg of the receptor.

The purified protein could be chemically cross-linked with u-PA. Its amino acid composition and N-terminal sequence were determined (30 residues, some of which with some uncertainty). It was found to be heavily N-glycosylated, deglycosylation resulting in a protein with an apparent molecular weight of about 30–35 kD. The apparent molecular weight of u-PAR from different cell lines and from PMA-stimulated and non-stimulated U937 cells varied somewhat. This heterogeneity disappeared after deglycosylation and was thus due to differences in glycosylation of u-PAR from the various sources.

The presence of several variants of the same receptor appears to be rather common in mammalian cells. The modulation of the u-PAR molecules demonstrated in Example 1 may represent an important feature in the regulation of extracellular proteolysis and thus in the degradation of the extracellular matrix and basement membrane components, processes that are at the core of cell migration and invasiveness. In cases where different cell types have different kinds of receptors where the protein part of u-PAR is glycosylated in different ways, it is possible to distinguish between the cell types for which a prevention of the localized proteolytic activity is needed, which is of a particular value when cancer cells produce a u-Par which is glycosylated in a way sufficiently different from the glycosylating of the u-PAR of normal cells to permit distinguishing by means of e.g. u-PAR antibodies.

In Example 2, isolation of a ligand binding domain of u-PAR is identified and characterized. This provides potentially therapeutically valuable information on peptides that may inhibit the ligand binding.

The deduced amino acid sequence indicated that u-PAR is produced as a 313 residues long protein with a 282 residues long hydrophilic N terminal part (probably extracellular) followed by 21 rather hydrophobic amino acids (probably a trans-membrane domain). The potential extracellular part is organised in 3 repeats with striking homologies, particularly with respect to the pattern of cysteines. This may indicate the presence of distinct domains that may bind different ligands.

Studies on the purified u-PAR allowed to recognize that the u-PAR is at least in some cases terminally processed and anchored to the cell surface via a glycolipid anchor, and that the surface location can be regulated by the phospholipase PI-PLC, but not by the phospholipases $A_2$ and D (Example 3). Furthermore, it was found that also harvest fluid from cells that were not treated contain some free u-PAR, indicating release from the cells that may be mediated by an endogenous phospholipase. This may be a physiological mechanism and it is possible that measurement of free receptor, e.g. in serum, may be a diagnostically valuable indicator of some pathological processes.

In Example 4 is described the production of polyclonal mouse and rabbit antibodies against u-PAR as well as 4 monoclonal mouse antibodies against the receptor.

The polyclonal antibodies precipted $^{125}$I-labelled purified u-PAR in a dose-dependent manner, with a significant precipitation being obtained by the antiserum in a dilution of 1:7500. In a reverse-phase radioimmunoassay, the antiserum was found to immunocapture radiolabelled u-PAR, and in an ELISA immobilized u-PAR in an amount of 1 ng was detected with the immune serum diluted 1:8000. By Western blotting, the antibodies detected both purified u-PAR and u-PAR in the crude detergent phase of extracts of PMA-treated U937 cells. In the latter case, no reaction with proteins with electrophoretic mobility different from u-PAR was detected, indicating a high degree of specificity of the antibodies. The polyclonal antibodies to u-PAR can be used to specifically prevent ligand binding. It is furthermore shown that the polyclonal u-PAR antibodies inhibit u-PA-catalyzed cell surface plasminogen activation.

The monoclonal antibodies were selected by several procedures, including a screening ELISA with immobilized purified u-PAR, Western blotting experiments with phospholipase-solubilized u-PAR, inhibition of binding of $^{125}$I-ATF (aminoterminal fragment of u-PA) to intact cells, and ability to stain cells in tissue sections positive for u-PAR mRNA. Out of 24 stably ELISA positive hybridoma cultures, 4 were selected for cloning. One cloned hybridoma culture was selected deriving from each of the four original cultures and was used for further studies.

Purified monoclonal antibodies from these four hybridomas were characterized by their ability to immunoprecipitate intact purified u-PAR and u-PAR degraded by chymotrypsin to yield a Mr 16 kD u-PA binding domain and an Mr 35–45 kD non-u-PA-binding fragment. Also the ability to stain u-PAR and glycosylation variants thereof in cell extracts was assessed in Western blotting experiments.

These studies led to the conclusion that the four antibodies recognize four different epitopes in u-PAR. One (designated 3R) is directed against an epitope in the u-PA binding domain of u-PAR, while the other three (designated 1R, 2R, 4R) are directed against the non-binding part of u-PAR.

It was demonstrated that the antibodies could be used to quantitate u-PAR in double antibody sandwich type ELISA, exemplified in an ELISA in which one of the monoclonal antibodies (4R) was used as catching antibody, and another monoclonal antibody (2R) in a biotinylated form was used as detecting antibody. In another example, the polyclonal rabbit antibodies against u-PAR were used as catching antibodies, and a biotinylated monoclonal antibody (2R) as detecting antibody.

Furthermore, it was demonstrated that the antibodies could be used in a drug screening scheme for identifying substances inhibiting u-PA/u-PAR interaction, cell surface plasmin generation and invasion and metastasis of human cancer cells inoculated into a substrain of nude mice.

The antibodies of the invention, together with commercially available reagents, provide means for selective quantitation of 1) u-PAR independently of whether it is complexed with u-PA or not 2) complexes of u-PAR and u-PA 3) u-PAR which is not complexed with u-PA (free u-PAR)

4) glycosylation variants of u-PAR.

A procedure is described for preparation of monoclonal antibodies specific for the u-PA binding domain in u-PAR and the non-u-PA binding part of u-PAR, respectively; such antibodies are useful in quantitation of u-PAR in its different states.

In Example 7, it is demonstrated that one of the monoclonal antibodies (3R) strongly inhibits cell surface plasminogen activation, while this activation is not or only slightly affected by the three other antibodies. The monoclonal antibody 3R also efficiently inhibits binding of radiolabelled DFP-treated u-PA on the surface of U937 cells, while no inhibition was seen with 2R and 4R and only a slight inhibition with 1R. Furthermore, it was found that the antibodies 3R and 4R by flow cytometry using FITC-labelled antibodies to mouse IgG effectively binds to human monocytes. The binding of the 4R antibody is not affected by pre-treatment of the monocytes with u-PA, while the binding of the 3R antibody is completely inhibited by pre-treatment with u-PA.

In Example 8, it is demonstrated that two of the monoclonal antibodies (2R and 4R) in immunohistochemical studies specifically stain the same subpopulation of the cells, this subpopulation being characterized by containing mRNA for u-PAR as demonstrated by in situ hybridization.

Based upon the previous findings, it was concluded that inhibition of receptor binding of u-PA is a means of inhibiting some of its physiological functions in relationship to therapeutic prevention of localized proteolytic activity, e.g. invasion and metastasis of cancer cells, inflammatory bowel disease, premalignant colonic adenomas, septic arthritis, osteoarthritis, rheumatoid arthritis (for which a direct involvement of excess u-PA production has been demonstrated), osteoporosis, cholesteatoma, and a number of skin and corneal diseases for which an excess plasminogen activation has been shown to be the pathogenetic cause, such as corneal ulcers, keratitis, epidermolysis bullosa, psoriasis, and pemphigus. Since u-PA receptors are present in several blood cells (neutrophilic granulocytes and monocytes) and endothelial cells, their regulation might also significantly affect intravascular fibrinolytic activity in physiological, pathological and pharmacological conditions. The above-mentioned diseases would be the first obvious targets for a therapy based on administration of substances that block or decrease cell surface plasminogen activation. Because of a role of u-PA in implantation of the fertilized egg, a contraceptive effect is expected of measures that inhibit receptor binding. The therapy and prophylaxis will involve systemic or topical treatment with agents that block or reduce receptor bound plasminogen activator activity, such as will be explained below.

A method for preventing or counteracting localized proteolytic activity in a mammal, in particular a human, comprises inhibiting the activation of plasminogen to plasmin by preventing the binding pro-u-PA to a u-PA receptor (u-PAR) in the mammal and thereby preventing u-PA from converting plasminogen into plasmin.

In the present specification and claims, the term "localized proteolytic activity" is intended to designate a proteolytic activity which is located at one or several distinct regions in a human body, or at distinct cells, as opposed to an overall proteolytic activity exerting itself substantially anywhere in the body. The localized proteolytic activity can be inhibited generally in a mammal, in particular a human, or locally. The term "preventing or counteracting" is intended to designate a situation where the binding of u-PA to u-PAR is completely inhibited, or a situation where the binding is sufficiently inhibited so as to inhibit the undesired effect of the plasminogen activator.

The usage of the term "a u-PAR" indicates that even though the polypeptide part of u-PAR in a species might be the same for all u-PARs, there is a plurality of u-PARs as for example the carbohydrate part or the mechanism of surface attachment of the u-PAR can be different. It may even be so that some cells, e.g. cancer cells, have substantially different u-PARs which might have important therapeutic significance as it might be possible, e.g. by the use of monoclonal antibodies specific for receptor variants on cancer cells, to block the binding of u-PA to u-PARs residing on a cancer cell without affecting the binding of u-PA to u-PARs on non-pathological cells or of specifically killing cancer cells that express u-PAR, e.g. by administration of toxic substances bound to monoclonal antibodies specific for receptor variant of the cancer cells.

The enzyme urokinase-type plasminogen activator (u-PA) has only one well-defined macromolecular substrate, namely plasminogen. By cleavage at $Arg^{560}$, plasminogen is activated to the broad spectrum protease plasmin. By the term "preventing u-PA from converting plasminogen into plasmin" is therefore meant that this activation by u-PA is substantially inhibited or a situation where the activation is sufficiently inhibited so as to inhibit or reduce the undesired effect of the plasmin.

The prevention of the binding of a receptor binding form of u-PA to a u-PAR is, e.g. suitably performed by blocking the u-PAR by administration, to the mammal, of a monoclonal antibody binding to the u-PAR, such as the 3R antibody of the present invention, so as to occupy a site of the receptor to which a receptor binding form of u-PA is normally bound, the monoclonal antibody being administered in an amount effective to reduce the binding of the receptor binding form of u-PA to the receptor. The term "binding to a u-PAR so as to occupy a site of the receptor to which a receptor binding form of u-PA is normally bound" is intended to mean that the antibody binds to the u-PAR so that a receptor binding form of u-PA can not be bound to the u-PAR.

As mentioned above, a very interesting method of preventing the binding of a receptor binding form of u-PA to a u-PAR and thereby preventing the cell surface plasminogen activation is the use of antibodies against u-PAR. The antibody may be a monoclonal antibody that is reactive with non-carbohydrate moieties of the u-PAR, or it may be a monoclonal antibody that is reactive with carbohydrate moieties of the u-PAR, the latter permitting a valuable distinction between target cells where cells expressing distinct variants of u-PAR are the cells involved in the undesired proteolysis. The antibodies may be administered in various ways as described below.

It is likely that some disorders are related to a reduced amount or an impaired function of u-PAR. These may include some cases of impaired wound healing and also some cases of thromboembolic disorders. A role of u-PA (and therefore probably also of u-PAR) in thrombolysis under some conditions is suggested by the finding by inventors of the present invention of u-PA being present in endothelial cells during acute inflammation and in cancer. Under normal conditions, the endothelial cells contain t-PA, but no u-PA. It is furthermore interesting that the disease paroxysmal nocturnal hemoglobinuria is associated with an impaired ability to form glycerolphosphoinositol anchors and impaired anchoring of u-PAR. This disease is often associated with thromboembolic disorders (See: Selvaraj et al., 1988, and references therein).

The finding that the extracellular part of u-PAR consists of three repeats with considerable mutual homologies (Example 2) renders it probable that it can bind different ligands, that is, that it can bind other ligands apart from the proven binding of u-PA. It would be justified to assume that some of these may involve yet unknown plasminogen receptors or plasminogen binding sites because of the strong enhancing effect obtained by concomitant binding of pro-u-PA and plasminogen to the cell surface. The focalisation of u-PAR to cell-cell and cel-substratum binding sites, and the polarisation of u-PAR to the leading edge of some migrating cells also indicate an interaction between u-PAR and molecules other than u-PA. Such other potential alternative ligands for u-PAR may be proteins located at cell-cell and focal cell-substratum contact sites such as various integrins. Antibodies to u-PAR that inhibit binding of such ligands may be valuable in inhibition of cell surface plasminogen activation, and prevention of binding of u-PAR to such alternative ligands may be functionally important and therapeutically valuable in a broad spectrum of diseases.

u-PAR exists in various forms, such as the glycosylation variants described in Example 1, the variants with different sensitivity to the lipase PI-PLC suggested by the findings described in Example 3. In some diseases that involve increased u-PAR function, some of these forms may be preferentially changed. Monoclonal antibodies selectively directed against some distinct forms may therefore be particularly therapeutically valuable in such diseases.

The administration of the various antibodies to a mammal, preferably a human being, may be performed by any administration method which is suitable for administering antibodies.

Topical administration may be performed by formulating the antibody or derivative thereof in a salve, an ointment, a lotion, a creme, etc.

Pharmaceutical compositions of the invention may for example include human monoclonal antibodies or derivatives thereof.

Another strategy of treating the conditions and diseases mentioned above is to target a cell that contains a u-PAR on the surface by a medicament, comprising administering the medicament bound to an antibody against u-PAR such as a polyclonal or a monoclonal antibody, e.g. an antibody particularly directed to a variant of u-PAR present in a cancer cell type.

The medicament may typically be an anti-cancer agent such an alkylating agent, e.g. melphalan, chlorambucil, busulfan, cisplatin, thiotepa, an antimetabolite such as methotrexate, fluracil, azathioprin, an antimitoticum, typically vincristine, vinblastine, or an antibiotic such as doxorubicin, daunorubicin or bleomycin. The medicament may also comprise bacterial or other toxins.

Particularly interesting antibodies are antibodies that distinguish between various forms of u-PAR. A detailed description of diagnostic kits, materials and methods based on antibodies is given further below.

One aspect of the invention relates to a method of producing pure u-PAR, the method comprising subjecting a u-PAR-containing material to affinity chromatography with immobilized monoclonal antibodies according to the invention to u-PAR and eluting the u-PAR, e.g. under acidic conditions.

The term "analogue" is used in the present context to indicate a protein or polypeptide of a similar amino acid composition or sequence as the characteristic amino acid sequence derived from the u-PAR, allowing for minor variations which do not have an adverse effect on the immunogenicity of the analogue. The analogous polypeptide or protein may be derived from mammals or may be partially or completely of synthetic origin.

The monoclonal antibodies of the invention may also be used for the obtainment of a u-PAR containing fraction with high yield and purity. The procedure may be performed by immobilizing the specific monoclonal antibodies to a matrix., contacting said matrix with the preparation containing the released u-PAR compounds, washing, and finally treating the antigen-antibody complex fixed to the matrix so as to release the u-PAR compounds in a purified form. A preferred way is to isolate the u-PAR compounds by means of column affinity chromatography involving antibodies fixed to the column matrix.

In the present context, the term "antibody" refers to a substance which is produced by a vertebrate or more precisely a cell of vertebrate origin belonging to the immune system as a response to exposure to the polypeptides of the invention.

The variant domain of an antibody is composed of variable and constant sequences. The variant part of the domain is called the idiotype of the antibody. This part of the antibody is responsible for the interaction with the antigen, the antigen binding.

The idiotypic structure is antigenic and can thus give rise to specific antibodies directed against the idiotypic structure. This has been done in mice. The antibodies raised against the idiotype, the anti-idiotypic antibodies, may mimic the structure of the original antigen and therefore may function as the original antigen to raise antibodies reactive with the original antigen. This approach may be advantageous as it circumvents the problem associated with the characterization and synthesis of the important immunogenic parts of the protein in question. This is most important in the case of conformational epitopes, which might otherwise be difficult to identify. It has been shown for a number of organisms that protective immunity can be induced in this way (e.g. *Trypanosoma druzei, Trypanosoma brucei,* Hepatitis B virus, and *Plasmodium knowlesii*).

The antibodies of the present invention may be produced by a method which comprises administering in an immunogenic form at least a natural or synthetic part of the polypeptide of the invention to obtain cells producing antibodies reactive with said polypeptide and isolating the antibody containing material from the organism or the cells. The methods of producing antibodies of the invention will be explained further below.

The antibody is preferably a monospecific antibody. The monospecific antibody may be prepared by injecting a suitable animal with a substantially pure preparation of the polypeptide of the invention followed by one or more booster injections at suitable intervals (e.g. one or two weeks to a month) up to four or five months before the first bleeding. The established immunization schedule is continued, and the animals are bled about one week after each booster immunization, and antibody is isolated from the serum in a suitable manner (cf. e.g. Harboe and Ingild, *Scand. J. Immun.* 2 (Suppl. 1), 1973, pp. 161–164.)

For purposes not requiring a high assay specificity, the antibody may be a polyclonal antibody. Polyclonal antibodies may be obtained, e.g. as described in Harboe and Ingild, see above. More specifically, when polyclonal antibodies are to be obtained, the u-PAR compound preparation is, preferably after addition of a suitable adjuvant, such as Freund's incomplete or complete adjuvant, injected into an animal. When the immunogens are human u-PAR compounds, the animals may be rabbits. The animals are bled regularly, for instance at weekly intervals, and the blood obtained is separated into an antibody containing serum fraction, and optionally said fraction is subjected to further conventional procedures for antibody purification, and/or procedures involving use of purified u-PAR compounds.

In another preferred embodiment, monoclonal antibodies are obtained. The monoclonal antibody may be raised against or directed substantially against an essential component of u-PAR compounds, i.e. an epitope. The monoclonal antibody may be produced by conventional techniques (e.g. as described by Köhler and Milstein, Nature 256, 1975, p. 495) e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells of a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium.

The immunized animal used for the preparation of antibodies of the invention is preferably selected from the group consisting of rabbit, monkey, sheep, goat, mouse, rat, pig, horse and guinea pigs. The cells producing the antibodies of the invention may be spleen cells or lymph cells, e.g. peripheric lymphocytes.

When hybridoma cells are used in the production of antibodies of the invention, these may be grown in vitro or in a body cavity of an animal. The antibody-producing cell is injected into an animal such as a mouse resulting in the formation of an ascites tumor which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

An example of a suitable manner in which the monoclonal antibody may be produced is as a result of fusing spleen cells from immunized mice (such as Balb/c mice) with myeloma cells using conventional techniques (e.g. as described by R. Dalchau, J. Kirkley, J. W. Fabre, "Monoclonal antibody to a human leukocyte-specific membrane glycoprotein probably homologous to the leukocyte-common (L-C) antigen of the rat", *Eur. J. Immunol.* 10, 1980, pp. 737–744). The fusions obtained are screened by conventional techniques such as binding assays employing u-PAR compounds isolated by the above-described methods.

In a further aspect, the invention relates to a diagnostic agent comprising an antibody according to the invention capable of detecting and/or quantitating u-PAR or a derivative thereof in a sample.

In accordance with the above discussion, antibodies according to the invention are valuable in diagnosis of cancer and other disorders involving tissue invasion and tissue remodelling, considering the involvement of u-PAR in these processes. The finding that u-PAR mRNA and protein is consistently found in cells located in the invasive front in a variety of different forms of cancer including colon adenocarcinomas, ductal mammary carcinomas and squamous skin carcinomas strongly supports this notion. A further support of this notion is the finding that u-PA mRNA and/or protein in all these cases are produced either by the u-PAR-containing cells or by cells located adjacent to the u-PAR-containing cells. In this connection, it is also interesting that serum from breast cancer patients has an increased concentration of u-PA compared with normal individuals (Grøndahl-Hansen et al., 1988) and that the u-PA content in breast cancer tissue has been shown to be a valuable prognostic marker in this disease such as has been published in the priority year of the present application (Jänicke et. al., 1989, 1990). The fact that the presence of u-PAR is a prerequisite to u-PA function makes it likely that u-PAE content in cancer tissue is an even better diagnostic and prognostic marker. A new aspect of the potential diagnostic and prognostic use of u-PAR determinations is the release of u-PAR from cultured cells (described in Example 3) that occurs even in the absence of exogeneously added phospholipase. This finding raises the possibility that u-PAR is also released into body fluids under some physiological and pathophysiological conditions and particularly in cancer. Determination of concentrations of u-PAR or degradation products thereof in body fluids, such as serum, urine, and ascites fluid may therefore prove to be diagnostically and/or prognostically valuable.

For most assay uses it preferred that the antibody is provided with a label for the detection of bound antibody or, alternatively (such as in a double antibody assay), a combination of labelled and unlabelled antibody may be employed. The substance used as label may be selected from any substance which is in itself detectable or which may be reacted with another substance to produce a detectable product. Thus, the label may be selected from radioactive isotopes, enzymes, chromophores, fluorescent or chemiluminescent substances, and complexing agents.

Examples of enzymes useful as labels are β-galactosidase, urease, glucose oxidase, carbonic anhydrase, peroxidases (e.g. horseradish peroxidase), phosphatases (e.g. alkaline or acid phosphatase), glucose-6-phosphate dehydrogenase and ribonuclease.

Enzymes are not in themselves detectable, but must be combined with a substrate to catalyze a reaction the end product of which is detectable. Thus, a substrate may be added to the reaction mixture resulting in a coloured, fluorescent or chemiluminescent product or in a colour change or in a change in the intensity of the colour, fluorescence or chemiluminescence. Examples of substrates which are useful in the present method as substrates for the enzymes mentioned above are $H_2O_2$, p-nitrophenylphosphate, lactose, urea, β-D-glucose, $CO_2$, RNA, starch, or malate. The substrate may be combined with, e.g. a chromophore which is either a donor or acceptor.

Fluorescent substances which may be used as labels for the detection of the components as used according to the of invention may be 4-methylumbelliferyl-phosphate, 4-methylumbelliferyl-D-galactopyranoside, and 3-(p-hydroxyphenyl) propionic acid. These substances may be detected by means of a fluorescence spectrophotometer. Chemiluminescent substances which may be peroxidase/eosin/EDTA, isoluminol/EDTA/$H_2O_2$ and a substrate therefor.

Chromophores may be o-phenylenediamine or similar compounds. These substances may be detected by means of a spectrophotometer. Radioactive isotopes may be any detectable and in a laboratory acceptable isotope, e.g. $^{125}I$, $^{131}I$, $^3H$, $^{35}P$, $^{35}S$ or $^{14}C$. The radioactivity may be measured in a γ-counter or a scintillation counter or by radioautography followed by densitometry.

Complexing agents may be Protein A, Protein G (which form a complex with immunoglobulins), biotin (which forms a complex with avidin and streptavidin), and lectin (which forms a complex with carbohydrate determinants, e.g. receptors). In this case, the complex is not in itself directly detectable, necessitating labelling of the substance with which the complexing agent forms a complex. The marking may be performed with any of the labelling substances described above.

In an embodiment of the invention an antibody of the invention may be coupled to a bridging compound coupled to a solid support. The bridging compound, which is designed to link the solid support and the antibody may be hydrazide, Protein A, glutaraldehyde, carbodiimide, or lysine.

The solid support employed is e.g. a polymer or it may be a matrix coated with a polymer. The matrix may be of any suitable solid material, e.g. glass, paper or plastic. The polymer may be a plastic, cellulose such as specially treated paper. nitrocellulose paper or cyanogenbromide-activated paper. Examples of suitable plastics are latex, a polystyrene, polyvinylchloride, polyurethane, polyacrylamide, polyvinylacetate and any suitable copolymer thereof. Examples of silicone polymers include siloxane.

The solid support may be in the form of a tray, a plate such as a mitrotiter plate, e.g. a thin layer or, preferably, strip, film, threads, solid particles such as beads, including Protein A-coated bacteria, or paper.

The antibody of the invention may be used in an assay for the identification and/or quantification of at least a form and/or a part of said polypeptide present in a sample. The identification and/or quantification performed by the use according to the present invention may be any identification and/or quantification involving u-PAR compounds or a form of u-PAR compounds. Thus, both a qualitative and a quantitative determination of u-PAR compounds may be obtained according to the use of the present invention. The identification and/or quantification may be performed for both a scientific, a clinical and an industrial purpose. As will be further described below, it is especially important in clinical routine to identify or quantify u-PAR compounds.

The sample may be a specimen obtained from a living organism such as a human or an animal. The specimen may be blood, e.g. an erythrocyte enriched fraction, or a tissue sample e.g. comprising liver cells. In a very interesting embodiment of the present invention, the specimen is urine.

In one preferred embodiment of the invention it is preferred that the antibody used in the method of the invention is a monoclonal antibody as this generally provides a higher precision and accuracy of the assay, at the same time possibly requiring less time to perform. Furthermore, a mixture of two or more different monoclonal antibodies may be employed as this may increase the detection limit and sensitivity of the test. The monoclonal antibody may be obtained by the method described below. Antibodies possessing high avidity may be selected for catching techniques.

The antibody used in the present method is preferably in substantially pure form (purified according to suitable techniques or by the methods of the invention, see below) in order to improve the precision and/or accuracy of the assays of the invention.

One aspect of the invention relates to a monoclonal antibody which reacts with u-PAR and thereby inhibits the binding of pro-u-PA and active u-PA, and cell surface plasminogen activation, such as explained herein.

A monoclonal antibody having these properties is useful in a number of diagnostic and therapeutic utilities as explained in the following.

A hybridoma clone producing a monoclonal antibody, termed 3R, which antibody reacts with u-PAR and thereby inhibits the binding of pro-u-PA and active u-PA as well as cell surface plasminogen activation, has been deposited under the provisional accession number 90101009 in the European Collection of Animal Cell Cultures under the terms and conditions of the Budapest Treaty.

While this clone and the monoclonal antibody produced thereby constitute embodiments of this aspect of the present invention, this aspect evidently extends to functional equivalents to the monoclonal antibody, that is, any monoclonal antibody which reacts with u-PAR and thereby inhibits the binding of pro-u-PA and active u-PA and cell surface plasminogen activation. Thus, the monoclonal antibody according to this aspect of the invention can also be characterized as a monoclonal antibody which is a functional equivalent of the monoclonal antibody 3R produced by the clone 90101009 in that, like the antibody 3R, it reacts with u-PAR and thereby inhibits the binding between u-PAR and pro-u-PA or active u-PA, and cell surface activation of plasminogen to plasmin.

As explained above, the u-PA binding domain of u-PAR is located to the domain comprising the N-terminal 87 residues of u-PAR. Thus, another definition of the monoclonal antibody according to this aspect of the invention is a monoclonal antibody which reacts with a polypeptide of the sequence shown as u-PAR 1 in FIG. 8 herein or any subsequence or analogue thereof which is capable of binding to u-PAR so as to inhibit the binding between u-PAR and u-PA.

The reaction of the monoclonal antibody according to this aspect of the invention with u-PAR with the resulting inhibition of the binding of pro-u-PA and active u-PA to u-PAR and of cell surface plasminogen activation may be a reaction with the u-PA binding domain in u-PAR, or it may, as a special possibility, be a binding to another part of u-PAR than the u-PA binding domain, but, through an allosteric effect, causing a change in the binding domain. When the reaction of the monoclonal antibody with u-PAR is a reaction with the u-PA binding domain of u-PAR (such as has been found to be the case for the monoclonal antibody 3R), the reaction may be a binding directly involving the binding site of u-PAR (which is contemplated to comprise an amino acid sequence of about 30 or less (or more), such as 15–30 or perhaps even less (but perhaps 30–50 or even more) or a binding which does not involve the binding site proper, but which binding nevertheless inhibits u-PA binding, such as antibody binding having an allosteric effect so as to inhibit u-PA binding. In any of the above-mentioned cases, the monoclonal antibody binding to the u-PA binding domain of u-PAR so as to inhibit the binding of pro-u-PA or u-PA to u-PAR and cell surface plasminogen activation has, for therapeutical purposes, the same overall functionality and utility and constitutes one and the same embodiment of this aspect of the present invention.

The monoclonal antibody according to this aspect of the invention may be prepared by immunising an immunisable animal with u-PAR or a subsection or immunogenic variant thereof, e.g. the u-PA binding domain of u-PAR, fusing cells from the immunized animal with a myeloma cell line, and screening for clones producing an antibody which is capable of reacting with u-PAR with resulting inhibition of the binding of pro-u-PA and active u-PA to u-PAR and cell surface plasminogen activation.

As will appear from the explanation given below and in the examples, particular selection schemes at an early stage of the production of monoclonal antibodies were used to produce a hybridoma clone producing an antibody having the above-mentioned reaction with u-PAR with its resulting inhibition effect and at the same time being useful in immunoassays such as ELISA.

Once it has been found that such a monoclonal antibody can be established, it will possible for a person skilled in the art to produce other monoclonal antibodies that may differ from the particular species disclosed herein with respect to their "micro"-specific mode of action, protein-chemical composition, etc., but which show the same essential functionality, that is, capability of binding to the u-PA binding domain of u-PAR and thereby inhibiting the binding of pro-u-PA or active u-PA to u-PAR and cell surface plasminogen activation.

In accordance with the above explanation, a subclass of this aspect of monoclonal antibodies are monoclonal antibodies which react with the u-PAR binding domain of u-PAR and thereby inhibit the binding of pro-u-PA and active u-PA and cell surface plasminogen activation.

Methods for assessing that an antibody complies with the above definition comprise measuring the inhibition of surface plasminogen activation caused by reaction between the antibody and u-PAR or measuring the inhibition of binding of u-PA or pro-u-PA to u-PAR caused by reaction between the antibody and u-PAR.

A special, narrow embodiment of this aspect of the invention is a monoclonal antibody which in competition experiments is capable of competing with the monoclonal antibody 3R produced by the hybridoma cell line deposited under the provisional accession number 90101009 in the European Collection of Animal Cell Cultures under the terms and conditions of the Budapest Treaty.

In the present context, the term "antibody" is intended to designate not only complete antibody molecules, but also binding fragments thereof such as the Fab fragment. The antibodies of the examples are produced by murine hybridomas, but antibodies used for therapeutic purposes would suitably be produced by human hybridomas. The establishment and use of human hybridomas is well-known in the art, cf., e.g., Glassy, M. C., Handley, H. H., Hagiwara, H. and Royston, I., A human lymphoblastoid B-cell line useful for generating antibody secreting human/human hybridomas, Proc. Natl. Acad. Sci. USA, 80:6327– 6331, 1983, and Irie, F. F., Sze, L. L, and Saxton, R. E., Human antibody to OFA-1, a tumor antigen, produced in vitro by Epstein-Barr virus-transformed human B lymphoid cell lines, Proc. Natl. Acad. Sci. USA, 79:5666–5670, 1982.

One of the most important utilities of the antibodies of the invention is for diagnostic purposes, in particular in assays to detect of quantify the presence of u-PAR in a sample. In the following, such assays, in particular ELISAS (enzyme-linked immunosorbent assays), and monoclonal antibodies according to the invention are discussed in greater detail.

Also certain specific polyclonal antibodies are discussed. A procedure for producing such specific polyclonal antibodies is described in Example 4, the antibodies being developed by immunisation with the 16 kD u-PA-binding fragment of u-PAR obtained by degradation of intact u-PAR wich chymotrypsin. Another interesting specific polyclonal antibody can be obtained by immunisation with the 35–45 kD non-u-PA-binding fragment of u-PAR.

One aspect according to the invention of such use is a method for detecting or quantifying u-PAR in a sample, the detection of quantitation being substantially independent of whether the u-PAR has bound u-PA or not, comprising using, as a catching or detecting antibody or both, an antibody capable of binding to u-PAR irrespective of whether u-Par has bound to u-PA or not.

Each antibody used in this method may be a monoclonal antibody according to the invention which reacts with u-PAR, but not with its u-PA binding domain, or a monoclonal antibody according to the invention which reacts both with free u-PAR and with complexes between u-PA and u-PAR.

Also useful in this method are polyclonal antibodies which react with u-PAR, but not with its u-PA binding domain, and polyclonal antibodies which react both with free u-PAR and with complexes between u-PA and u-PAR.

One useful embodiment of this method is a method wherein one monoclonal antibody which reacts with u-PAR, but not with its u-PA binding domain, or one monoclonal antibody which reacts both with free u-PAR and with complexes between u-PA and u-PAR, is used as catching antibody, and another monoclonal antibody which reacts with u-PAR, but not with its u-PA binding domain, or another monoclonal antibody which reacts both with free u-PAR and with complexes between u-PA and u-PAR, such other monoclonal antibody being directed against a different epitope, is used as detecting antibody.

Another embodiment of such method is a method in which polyclonal antibodies which react with u-PAR, but not with its u-PA binding domain, or polyclonal antibodies which react both with free u-PAR and with complexes between u-PA and u-PAR, are used as catching antibodies, and a monoclonal antibody which reacts with u-PAR, but not with its u-PA binding domain, or a monoclonal antibody which reacts both with free u-PAR and with complexes between u-PA and u-PAR, is used as detecting antibody.

Another embodiment is a method which a monoclonal antibody which reacts with u-PAR, but not with its u-PA binding domain, or a monoclonal antibody which reacts both with free u-PAR and with complexes between u-PA and u-PAR, is used as catching antibody, and polyclonal antibodies which react with u-PAR, but not with its u-PA binding domain, or polyclonal antibodies which react both with free u-PAR and with complexes between u-PA and u-PAR are used as detecting antibodies.

A further embodiment is a method according in which polyclonal antibodies which react with u-PAR, but not with its u-PA binding domain, or polyclonal antibodies which react both with free u-PAR and with complexes between u-PA and u-PAR, are used as catching antibodies, and polyclonal antibodies which react with u-PAR, but not with its u-PA binding domain, or polyclonal antibodies which react both with free u-PAR and with complexes between u-PA and u-PAR, are used as detecting antibodies.

Another method according to the invention is a method for detecting or quantifying complexes of u-PAR and u-PA in a sample, comprising using, as catching or detecting antibody, an antibody capable of binding to u-PAR which has bound u-PA or pro-u-PA, together with an antibody which detects bound u-PA or pro-u-PA as detecting or catching antibody, respectively.

An embodiment hereof is a method in which a monoclonal antibody which reacts with u-PAR, but not with its u-PA binding domain, or a monoclonal antibody which reacts both with free u-PAR and with complexes between u-PA and u-PAR, is used as catching antibody or detecting antibody.

Another embodiment hereof is a method in which polyclonal antibodies which react with u-PAR, but not with its u-PA binding domain, og polyclonal antibodies which react both with free u-PAR and with complexes between u-PA and u-PAR, are used as catching antibodies or detecting antibodies.

Another important method according to the invention is a method for detecting or quantitating u-PAR which has not bound u-PA, in a sample, comprising using, as catching or detecting antibody, an antibody capable of binding free u-PAR, but not complexes between u-PA and u-PAR.

The antibody used in this method may be a monoclonal antibody which reacts with the u-PA binding domain of u-PAR, or a monoclonal antibody which reacts with free u-PAR, but not with complexes between u-PA and u-PAR, or polyclonal antibodies which react with the u-PA binding domain of u-PAR, but not with complexes between u-PA and u-PAR, or polyclonal antibodies which react with free u-PAR, but not with complexes between u-PA and u-PAR.

One embodiment of this method is a method wherein a monoclonal antibody which reacts with the u-PA binding domain of u-PAR or a monoclonal antibody which reacts with free u-PAR, but not with complexes between u-PA and u-PAR, is used as catching antibody, and another monoclonal antibody which reacts with the u-PA binding domain of u-PAR or another monoclonal antibody which reacts with free u-PAR, but not with complexes between u-PA and u-PAR, such other antibody being directed against a different epitope, is used as detecting antibody.

According to another embodiment of this method, polyclonal antibodies which react with the u-PA binding domain of u-PAR, but not with complexes between u-PA and u-PAR, or polyclonal antibodies which react with free u-PAR, but not with complexes between u-PA and u-PAR, are used as catching antibodies, and a monoclonal antibody which reacts with the u-PA binding domain of u-PAR or a monoclonal antibody which reacts with free u-PAR, but not with complexes between u-PA and u-PAR, is used as detecting antibody.

According to a further embodiment of this method, a monoclonal antibody which reacts with the u-PA binding domain of u-PAR or a monoclonal antibody which reacts with free u-PAR, but not with complexes between u-PA and u-PAR, is used as a catching antibody, and polyclonal antibodies which react with the u-PA binding domain of u-PAR, but not with complexes between u-PA and u-PAR, or polyclonal antibodies which react with free u-PAR, but not with complexes between u-PA and u-PAR is used as a detecting antibody.

According to a still further embodiment of this method, polyclonal antibodies which react with the u-PA binding domain of u-PAR, but not with complexes between u-PA and u-PAR, or polyclonal antibodies which react with free u-PAR, but not with complexes between u-PA and u-PAR, are used as catching antibodies, and polyclonal antibodies which react with u-PAR, but not with its u-PA binding domain, or polyclonal antibodies which react both with free u-PAR and with complexes between u-PA and u-PAR, are used as detecting antibodies.

Another method according to the present invention is a method for detecting or quantifying u-Par which has not bound u-PA, in a sample, comprising using, as catching or detecting antibody, an antibody capable of binding free u-PAR, but not inhibiting u-PA binding, and using, as detecting or catching reagent, u-PA or a u-PAR binding variant thereof.

Another method according to the invention is a method for immunohistochemical detection of u-PAR in tissue sections, using, as the detecting antibody, any monoclonal antibody which reacts with u-PAR, or any polyclonal antibody which reacts with u-PAR, including a monoclonal antibody which reacts with the u-PA binding domain of u-PAR, or a monoclonal antibody which reacts with free u-PAR, but not with complexes between u-PA and u-PAR, or a monoclonal antibody which reacts with u-PAR, but not with its u-PA binding domain, or a monoclonal antibody which reacts both with free u-PAR and with complexes between u-PA and u-PAR, or polyclonal antibodies which react with the u-PA binding domain of u-PAR, but not with complexes between u-PA and u-PAR, or polyclonal antibodies which react with u-PAR, but not with its u-PA binding domain, or polyclonal antibodies which react with free u-PAR, but not with complexes between u-PA and u-PAR, or polyclonal antibodies which react both with free u-PAR and with complexes between u-PA and u-PAR.

In particular, the antibody is one of the monoclonal antibodies defined above.

One embodiment of this method, this embodiment which detecting u-PAR independent of whether it has bound u-PA or not, comprising using a monoclonal antibody which reacts with u-PAR, but not with its u-PA binding domain, or a monoclonal antibody which reacts both with free u-PAR and with complexes between u-PA and u-PAR, or polyclonal antibodies which react with u-PAR, but not with its u-PA binding domain, or polyclonal antibodies which react both with free u-PAR and with complexes between u-PA and u-PAR.

Another embodiment of this method, which embodiment detects free u-PAR, comprises using, as detecting antibody, an antibody capable of detecting free u-PAR, but not complexes between u-PA and u-PAR.

In this embodiment, the detecting antibody may be a monoclonal antibody which reacts with the u-PA binding domain of u-PAR or a monoclonal antibody which reacts with free u-PAR, but not with complexes between u-PA and u-PAR, or polyclonal antibodies which react with the u-PA binding domain of u-PAR, but not with complexes between u-PA and u-PAR, or polyclonal antibodies which react with free u-PAR, but not with complexes between u-PA and u-PAR.

One example of a monoclonal antibody according to the invention which detects u-PAR independently of whether it has bound u-PA or not is the monoclonal antibody designated 4R and produced by the hybridoma cell line deposited under the provisional accession number 90101010. 1R and 2R are other monoclonal antibodies of the invention which are contemplated to be useful in this regard.

An example of a monoclonal antibody according to the invention which reacts with free u-PAR, but not with complexes of u-PA and u-PAR, is the antibody 3R, which is discussed in detail above.

Analogously to what is discussed above with respect to the antibody 3R, each functional type of monoclonal antibody discussed herein is not limited to the specific products of the specific clones deposited, but is rather to be understood as the class of monoclonal antibodies showing the same functionality with respect to its utility as described in the present specification, including the examples and claims.

One aspect of the invention relates to a method for the detection or quantitation of a glycosylations variant of u-PAR in a sample, comprising using, as detecting antibody, a monoclonal antibody which solely or preferentially binds to the variant.

The glycosylation variant of u-PAR is typically a variant characteristic to a particular type of cancer cell.

In all of the above-mentioned cases, the sample may typically be serum, plasma or urine from a cancer patient or a suspected cancer patient, but it may, of course, also be another sample relevant in the particular case, such as, e.g. a faeces sample.

The sample may also be an extract from a cancer tissue or a suspected cancer tissue.

In all of the above-mentioned cases, the sample may also be sample is serum, plasma or urine from a patient suffering from or suspected to suffer from a non-malignant disease involving tissue destruction, such as rheumatiod arthritis, collitis ulcerosa, or psoriasis.

As mentioned in greater detail above, the detecting antibody is provided with a detectable label, and examples of these labels are given herein.

The monoclonal antibodies according to the invention may also be used in a method for targeting a diagnostic to a cell that contains a u-PAR on the surface, the method comprising administering, to a mammal, in particular a human, in particular a mammal suffering from cancer or suspected to suffer from cancer, the diagnostic bound to a monoclonal antibody of the invention against u-PAR. The diagnostic may be a radioactive substance, such as technetium.

The antibody according to the invention used for this purpose may be any of the monoclonal antibodies of the invention as mentioned above, that is, including a monoclonal antibody which solely or preferentially binds to a particular glycosylation variant of u-PAR.

Summarizing the above and with particular reference to the properties of the monoclonal antibodies as described in the legend to the figures and in the examples, the monoclonal antibodies according to the invention can be characterized by one or several of a number of characteristic properties, that is, as monoclonal antibodies against u-PAR which 1) when immobilized as a catching antibody in a sandwich ELISA is capable of catching u-PAR, or 2) when used as a biotin-labelled detecting antibody in a sandwich ELISA is capable of detecting u-PAR, or 3) when used in an ELISA, is capable of binding to immobilized u-PAR, or 4) when immobilized as a catching antibody in an ELISA is capable of binding u-PAR in such a way that u-PAR retains its u-PA binding capacity, or 5) in a radioimmunoprecipitation assay precipitates purified u-PAR in an intact form, or 6) in a radioimmunoprecipitation assay precipitates a u-PA binding $M_r$ 16,000 fragment of u-PAR obtained by chymotrypsin digestion, or 7) in a radioimmunoprecipitation assay precipitates a $M_r$ 30,000–50,000 fragment of u-PAR which is obtained by chymotrypsin digestion and which does not bind u-PA, or 8) reacts with u-PAR in Western blotting where detergent phase of a u-PAR-containing extract has been subjected to separation on SDS-PAGE under non-reducing conditions on 6–16% gradient gels, or 9) in Western blotting does not react with a u-PAR glycosylation variant in the 50–65 kD range produced by U937 cells, and does not react with a u-PAR glycosylation variant around 40–45 kD produced by U937a cells, 10) in Western blotting, reacts with a u-PAR glycosylation variant in the 50–65 kD range produced by U937 cells, and reacts with a u-PAR glycosylation variant around 40–45 kD produced by U937a cells, 11) in Western blotting, reacts weakly with a u-PAR glycosylation variant in the 50–65 kD range produced by U937 cells, and reacts strongly with a u-PAR glycosylation variant around 40–45 kD produced by U937a cells, 12) in sections of formalin-fixed and paraffin-embedded colon cancer tissue blocks immunostains cancer cells at the invasive front, the localization of the immunostained cells being virtually identical to the distribution of u-PAR mRNA as detected by in situ hybridization, or 13) inhibits the binding of pro-u-PA and active u-PA, and cell surface plasminogen activation, or 14) reacts with the u-PA binding domain of u-PAR and thereby inhibits the binding of pro-u-PA and active u-PA, and cell surface plasminogen activation, or 15) A monoclonal antibody which reacts with a polypeptide having the sequence shown as u-PAR 1 in FIG. 8 or any subsequence or analogue thereof which is capable of binding to u-PAR so as to inhibit the binding between u-PAR and u-PA, or 16) is capable of binding to u-PAR in tissue sections, including paraffine-embedded tissue sections, and thereby being useful for immunohistochemical detection of u-PAR, or 17) is capable of selectively binding to a particular glycosylation variant of u-PAR, or 18) reacts with the non-u-PA binding part of the u-PAR molecule comprising its C-terminal part and starting with amino acid residue 88 in the intact u-PAR molecule, or 19) when using flow cytometry with fluorescein isothiocyanate-labelled antibodies against mouse IgG binds to human monocytes, the binding not being affected by pre-incubation with exogeneously added u-PA, or 20) when using flow cytometry with fluorescein isothiocyanate-labelled antibodies against mouse IgG binds to human monocytes, the binding being completely inhibited by pre-incubation with exogeneously added u-PA.

It is evident from the present description that these properties, singly or in combinations, make the monoclonal antibodies of the invention extremely useful, both for the detection, the quantitation, the characterization, and the functional analysis of u-PAR and of u-PA/u-PAR interaction and thus also for diagnostic, prognostic and therapeutic uses in cancer and other diseases involving a u-PA/u-PAR interaction.

One important use of the monoclonal antibodies according to the invention is for establishing tools for screening substances for their potential inhibition of u-PA/u-PAR interaction and, thus, for their potential anti-invasive and anti-metastatic effect in cancer as well as in other diseases where u-PA/u-PAR interaction is involved. One such use is a screening assay in which the possible inhibition of u-PA/u-PAR interaction by the substance is determined by adding the substance to a system comprising immobilized u-PAR and solubilized u-PA, u-PA bound to u-Par being detected by being labelled or by means of a labelled anti-u-PA antibody, or adding the substance to a system comprising immobilized u-PA and solubilized u-PAR, u-PAR bound to u-PA being detected by being labelled or by means of a labelled anti-u-PAR antibody.

As an example of such an assay may be mentioned a very practical screening ELISA using immobilized monoclonal antibodies against u-PAR for catching u-PAR and subsequently measuring u-PA binding to u-PAR and the possible interference of candidate substances thereon, receptor-bound u-PA being detected by a labelled anti-u-PA antibody, the labelling being, e.g., biotin.

When a substance has been found positive in the above simple and fast screening, it can suitably be further tested in a much more laborious assay in which the possible inhibition of u-PA/u-PAR interaction by the substance is determined by adding the substance to a system comprising u-PAR and radiolabelled u-PA or a derivative thereof, cross-linking any u-Par bound to u-PA and detecting any cross-linked product by SDS PAGE and autoradiography. A positive result in this assay confirms that the substance does indeed inhibit the u-PA/u-PAR binding.

Normally, the next step will be to subject a substance which has been found, in the above assay, to positively inhibit u-PA/u-PAR binding, to an assay in which the possible inhibition of binding of u-PA to u-PAR on the surface of cultured cells is determined by adding the substance to a system comprising radiolabelled u-PA or a derivative thereof and cells carrying u-PAR and detecting any u-PA or derivative binding to u-PAR by gamma counting of the cells. A positive result in this assay shows that the inhibition of u-PA/u-PAR binding found in the previous assays is not an artefact related to the use of solubilized u-PAR, but is indeed also obtained when u-PAR is bound to cell surface, such as it will be in a clinical situation.

The aim of inhibiting the u-PA/u-PAR interaction is to inhibit u-PA enzymatic activity in biological settings. This can be directly tested in an assay in which the possible inhibition of cell surface plasminogen activation by receptor-bound exogeneous pro-u-PA is determined by adding the substance to cells carrying u-PAR and subsequently adding pro-u-PA, followed by measurement of plasmin generation on the cell surface. This situation with exogeneously added u-PA is similar to the situation in some types of cancer, such as, e.g., colon adenocarcinoma, in which cancer cells produce and contain u-PAR while u-PA is produced by adjacent non-malignant cells in the tumour stroma.

In some types of cancer, however, such as, e.g., squamous skin carcinoma, the cancer cells themselves produce both u-PAR and u-PA. In this situation, the inhibition of u-PA/u-PAR interaction will be more difficult than when the two components are produced by different cells. In order to test whether a given substance will be capable of inhibiting u-PA/u-PAR interaction under these circumstances, an assay is used in which the possible inhibition of cell surface plasminogen activation by receptor-bound endogeneous pro-u-PA is determined by incubating cells carrying u-PAR and producing pro-u-PA with the substance, followed by measurement of plasmin generation on the cell surface.

An inherent problem in studying the effect of substances inhibiting u-PA/u-PAR interaction on invasion and metastasis in animal studies is a species-specificity in u-PA/u-PAR interaction. Therefore, substances inhibiting u-PA/u-PAR interaction in the human system will not necessarily inhibit u-PA/u-PAR interaction in experimental animals such as the mouse. This problem is further aggravated When monoclonal antibodies are to be used as the substances inhibiting u-PA/u-PAR interaction, because mouse monoclonal antibodies against the human u-PAR do not react with mouse u-PAR. Therefore, a system has been developed according to the invention in which invasion and metastasis of human cancer cells inoculated in the nude mouse can be readily measured. Human cancer cells inoculated in conventional nude mice do not regularly invade and metastasize. According to the invention, a substrain of the nude mouse designated nu/nu META/Bom has been identified in which several cancer cell lines invade and metastasize in substantially all cases. Furthermore, according to the invention, the human cancer cells inoculated into the mouse have, prior to their inoculation, been transduced with the lacZ gene which encodes the enzyme β-D-galactosidase. This enzyme will give rise to a blue staining when subjected to the substrate X-gal. Thus, this system makes it possible to obtain a distinct colour difference between the human cancer cells and the mouse's own cells, thereby very considerably facilitating detection and quantitation of invading cells and metastases. In the experiments described in Example 9, cancer cells invading and metastasizing in this mouse model were found to produce both u-PA and u-PAR. Furthermore, it was found that their invasion and metastasis could be almost completely inhibited by administration of a monoclonal antibody against u-PA, inhibiting cell surface plasmin generation. Together with the above finding that inhibition of receptor binding of pro-u-PA also inhibits plasmin generation, this may indicate that substances efficiently inhibiting u-PA/u-PAR interaction on cells which produce both u-PA and u-PAR will also inhibit invasion and metastasis in the nude mouse model.

In addition to a model where the mouse is inoculated with human cancer cells producing both u-PA and u-PAR, a number of other models are also interesting, such as a model in which two types of cancer cells, one producing u-PA, the other producing u-PAR, are inoculated and therefore simulate the clinical situation occurring in some types of cancer where the two components are produced in two distinct cell types. In a third interesting version, human cancer cells producing u-PAR are inoculated together with human tumour-infiltrating fibroblasts producing u-PA.

u-PA/u-PAR interaction-inhibiting substances found to inhibit invasion and metastasis in these nude mouse models are likely to be anti-invasive anti-metastatic in human cancer types in which u-PA/u-PAR interaction is believed to be crucial to the invasion and metastasis, such as colon adenocarcinoma, ductal mammary carcinoma and squamous skin carcinoma. Such compounds should therefore, after appropriate toxicological studies in animals, be further studied in phase 1 and phase 2 clinical trials, as they are strong candidates to be efficient anti-invasive and anti-metastatic drugs.

Thus, one aspect of the invention relates to a substance for preventing or counteracting localized proteolytical activity in a mammal, in particular a human, by inhibiting the activation of plasminogen to plasmin by preventing the binding of a receptor-binding form of u-PA to a u-PAR in the mammal, when selected by the method described above.

In another aspect, the invention relates to a substance for preventing or counteracting localized proteolytic activity in a mammal, in particular a human, when the substance complies with the various criteria as tested in one or several of the assays described above, in particular when the substance complies with the criteria shown in the assays 1)–4) as claimed in claim 75, as the substance is then likely to be active in clinical situations in which u-PA and u-PAR are produced by different cell types.

When the substance even additionally complies with the criteria according to 5) of claim 76, it is likely also to be active in clinical situations in which u-PA and u-PAR are produced by the same cells.

If the substance is also positive in the mouse model, it is strongly indicated that it will inhibit invasion and metastasis of human cancer cells in the human body.

One chemical compound which has been found, using the methods of the invention, to prevent u-PA/u-Par binding, is suramin. While suramin itself is likely to be too toxic to be acceptable as generally used cancer drug, the finding indicates that less toxic analogues or derivatives of suramin, still capable of inhibiting u-PA/u-PAR interaction, are suitable cancer drugs.

LEGENDS TO FIGURES

FIG. 1. SDS-PAGE of affinity-purified u-PAR and chemical cross-linking to specific ligands.

1A) The Triton X-114 fraction containing membrane proteins from PMA-treated U937a cells was subjected to affinity chromatography using immobilized DFP-treated u-PA. The neutralized column eluate was dialyzed against 0.1% acetic acid and concentrated by lyophilization. A portion, representing $2\times10^8$ cells before purification, was run on 6–16% gradient SDS-PAGE under reducing conditions (lane 1). The gel was silver-stained. The molecular weights of marker proteins (lane 2) are indicated.

1B) Affinity column eluate was diluted to yield an approximate concentration of u-PAR of 1 nM during the assay. The samples were preincubated alone (lane 2) or in the presence of the following unlabelled reagents at a concentration of 100 nM: bovine serum albumin (lane 3), t-PA (lane 4), plasminogen (lane 5), murine epidermal growth factor (lane 6), ATF (lane 7), active 54 kD u-PA (lane 8), DFP-inactivated 54 kD u-PA (lane 9). After preincubation for 15 min at room temperature, $^{125}$I-labelled ATF (approximately 1 nM) was added, followed by incubation for 1 hour at 4° C. After incubation, chemical cross-linking was performed with DSS, after which the samples were analyzed by SDS-PAGE on a 6–16% gradient gel under non-reducing conditions and autoradiography. Lane 1 shows the cross-linked control with $^{125}$I-ATF and no addition of u-PAR or competitors. Electrophoretic mobilities of molecular weight standard proteins are inducated (kD).

1C) Neutralized affinity column eluate was concentrated as in (A) to yield a u-PAR concentration of approximately 15 µg/ml, and subjected to cross-linking with DSS in the presence of 50 µg/ml DFP-treated u-PA (lane 3) or alone (lane 4). Controls included: purified u-PAR alone, without chemical cross-linking (lane 5); DFP-treated u-PA alone, without chemical cross-linking (lane 1); DFP-treated u-PA, cross-linked alone (lane 2). The samples were run on Phast-SDS-PAGE under non-reducing conditions. Each lane contained 10 ng of u-PAR and/or 33 ng of DFP-u-PA. The gel was silver-stained. Note that the chemical cross-linking led to a minor increase in the migration rate of DFP-treated u-PA alone, probably due to internal cross-binding, but not of u-PAR alone. Electrophoretic mobilities of molecular weight standard proteins (lane 6) are indicated (kD).

Figure 2:
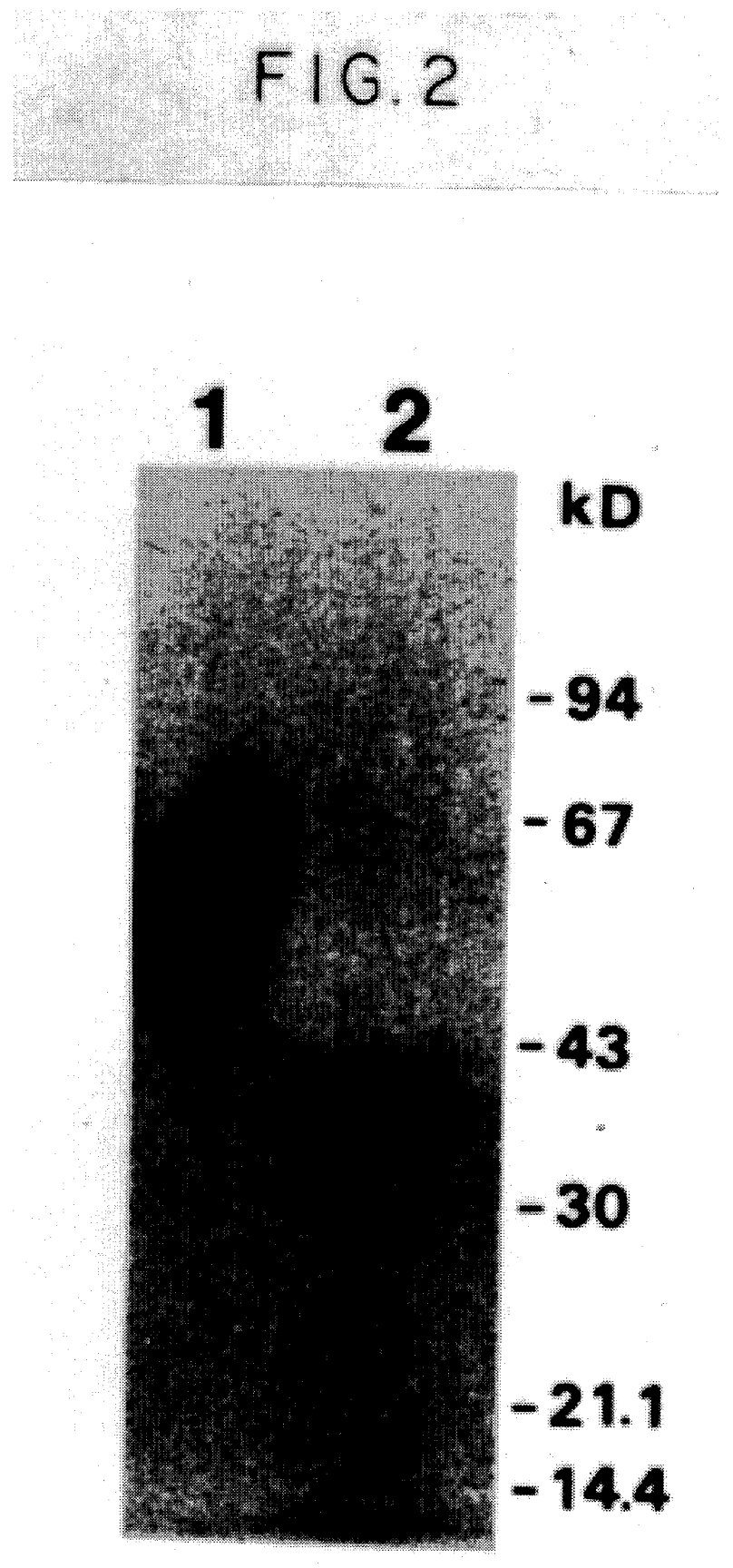

FIG. 2. Enzymatic deglycosylation of purified u-PAR. Affinity purified $^{125}$I-labelled u-PAR was pretreated for deglycosylation by denaturation under mildly reducing conditions (see "Experimental Procedures") and treated with peptide:N-glycosidase F (lane 2) or analyzed directly (lane 1). Analysis was performed by SDS-PAGE under reducing conditions on a 6–16% gradient gel, followed by autoradiography on a Kodak XAR film. Electrophoretic mobilities of standard proteins are indicated (kD).

FIG. 3. Deglycosylation of cross-linked $^{125}$I-ATF: u-PAR complexes from PMA-treated and nontreated U937a cells. PMA-treated (lanes 1 and 3) and nontreated (lanes 2 and 4) cells were acid-treated and lysed with 0.5% CHAPS. The lysates were incubated with $^{125}$I-ATF, cross-linked with disuccinimidyl suberate, denatured under mildly reducing conditions, and then further incubated in the presence (lanes 3 and 4) or absence (lanes 1 and 2) of peptide:N-glycosidase F, and analyzed by SDS-polyacrylamide (6–16%) gel electrophoresis under reducing conditions, followed by autoradiography. Electrophoretic mobilities of standard proteins are indicated (kD).

FIGS. 4A–4B. Detection of a ligand-binding u-PAR fragment by chemical cross-linking.

Purified u-PAR (30 µg/ml) was treated with chymotrypsin (40 ng/ml) for 7 h at 37° C. (lane 3), or analyzed directly, without degradation (lane 2). The control (lane 1) included buffer, incubated with chymotrypsin under the same conditions. Analysis was performed by incubation of the 67-fold diluted samples with $^{125}$I-labelled ATF (1 nM) and cross-linking with DSS, followed by SDS-PAGE on a 6–16% T gradient gel under reducing (4A) or non-reducing (4B) conditions and autoradiography of the gels. The electrophoretic mobilities of molecular mass marker proteins are indicated.

FIG. 5. Electrophoretic analysis of u-PAR fragments.

5(A) Non-degraded, purified u-PAR (0.4 µg; lane 3), purified u-PAR (0.4 µg) treated with chymotrypsin as described in the legend to FIG. 4 (lane 4), or buffer treated with chymotrypsin under the same conditions (lane 2) were analyzed by Tricine SDS-PAGE (10% T, 3% C) under reducing conditions. The gel was silver-stained. The molecular masses of marker proteins (lanes 1 and 5) are indicated.

5(B) Purified u-PAR was degraded with chymotrypsin as described in the legend to FIG. 4. Samples of the degradation mixture were subjected to chemical cross-linking with DSS in the absence of ligand (lane 2) or in the presence of ATF (lane 3). Lane 4 shows the ATF preparation alone, after chemical cross-linking. Cross-linking was performed in a volume of 12 µl, and each sample contained 0.27 µg u-PAR material and/or 0.50 µg ATF. The DSS-treated samples, and a 0.27 μg sample of the u-PAR degradation mixture which had not been subjected to cross-linking (lane 1), were analyzed by Tricine SDS-PAGE (10% T, 3% C) under reducing conditions, followed by silver staining. The electrophoretic mobilities of molecular mass marker proteins are indicated.

Figure 6:
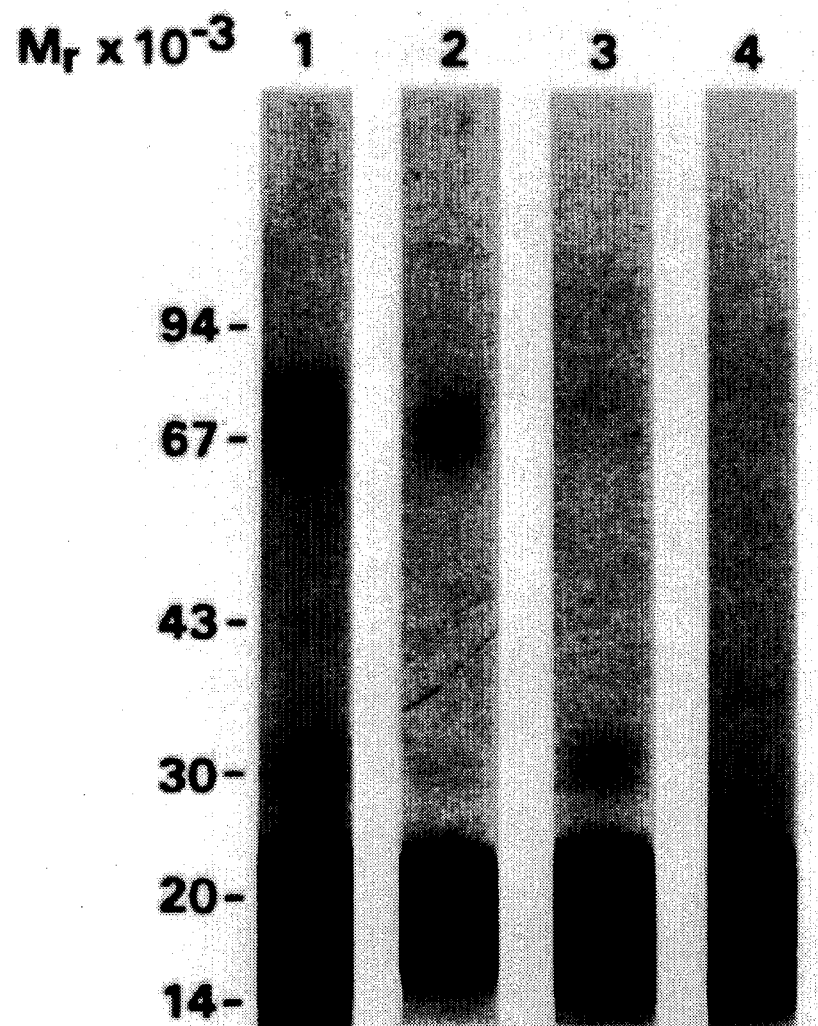

FIG. 6. Detergent phase separation of u-PAR and its ligand-binding fragment.

Purified u-PAR was degraded with chymotrypsin, as described in the legend to FIG. 4. The sample was diluted 100-fold and subjected to temperature-induced phase separation in the presence of 1% Triton X-114. The resulting water phase (lane 3), the detergent phase (lane 2), a sample of the degradation mixture which had not been subjected to phase separation (lane 1) and a blind sample (i.e. chymotrypsin-treated buffer, not subjected to phase separation) (lane 4) were incubated with $^{125}$I-ATF (1 nM) and subjected to chemical cross-linking with DSS. All samples were made up to the same final dilution factor (138-fold) during the assay by addition of a CHAPS-containing buffer. The cross-linked samples were analyzed by SDS-PAGE under reducing conditions followed by autoradiography of the gel. The electrophoretic mobilities of molecular mass marker proteins are indicated.

Figure 7A:
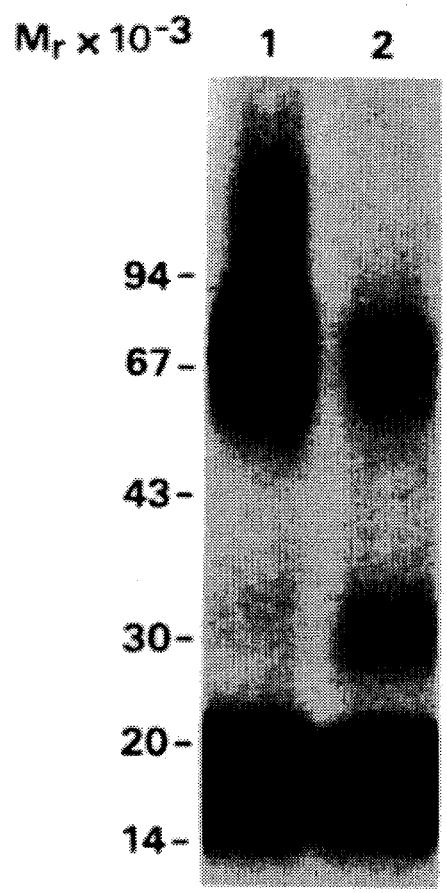
Figure 7B:
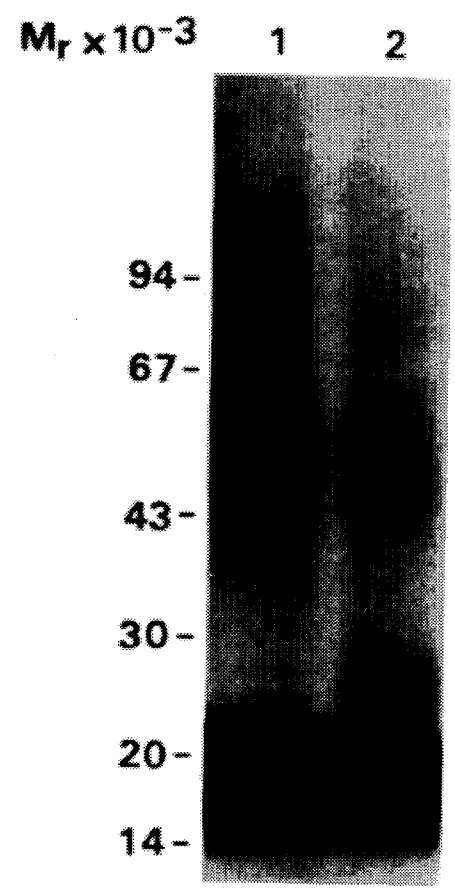

FIGS. 7A–7B. Deglycosylation of the ligand-binding fragment.

Samples of intact, purified u-PAR (lanes A1 and B1) or chymotrypsin-treated u-PAR (lanes A2 and B2) were prepared as described in the legend to FIG. 4, except that the chymotrypsin concentration was 200 ng/ml. The samples were diluted 67-fold, incubated with $^{125}$I-labelled ATF (1 nM) and subjected to chemical cross-linking with DSS. The cross-linked samples were pretreated for deglycosylation under mildly denaturing conditions (see Experimental Procedures) and incubated for 18 h at 37° C. in the absence 7(A) or presence 7(B) of Peptide:N-glycosidase F. The products were analyzed by SDS-PAGE under reducing conditions on a 6–16% T gradient gel, followed by autoradiography. The electrophoretic mobilities of molecular mass marker proteins are indicated.

FIG. 8. Internal amino acid sequence repeats of u-PAR and homology of these repeats with the extracellular domains of T-cell-activating proteins/Ly-6 antigens and squid protein Sgp-2.

Cysteine residues are underlined. Abbreviations are: u-PAR 1 (SEQ ID NO:3), 2 (SEQ ID NO:4); and 3 (SEQ ID NO:5), the first, second and third repeats of u-PAR (residues 1–92, 93–191 and 192–282, respectively, of the amino acid sequence deduced from cDNA sequencing (18)); co, consensus sequence for the three repeats of u-PAR; Ly-6, Ly-6a, Ly-6c, Ly-6 antigens/T-cell activating proteins (residues 1–79 and 1–76, respectively) (28–31); Sgp-2, squid glycoprotein Sgp-2(residues 1–92) (32); CO, consensus sequence for Ly-6a, Ly6c and Sgp-2. "Anchor" denotes the attachment sites for glycophospholipid tails. Question mark indicates that the attachment site was proposed by alignment with the Sgp-2sequence (32). For u-PAR, the attachment site was tentatively assigned to either Ser 282 (i.e. the last residue shown) or to one of the residues Gly 283 or Ala 284 (Ploug et al., submitted).

In the consensus sequences shown, residues conserved in all sequences were defined as consensus residues, variable positions were marked with x and positions containing gaps in any of the member sequences were marked with g. The arrow indicates the bond cleaved during limited chymotryptic digestion. Note the similarity of the consensus sequence for u-PAR repeats with that for Ly-6 and Sgp-2sequences (pattern of cysteines, location of gap regions).

Figure 9A:
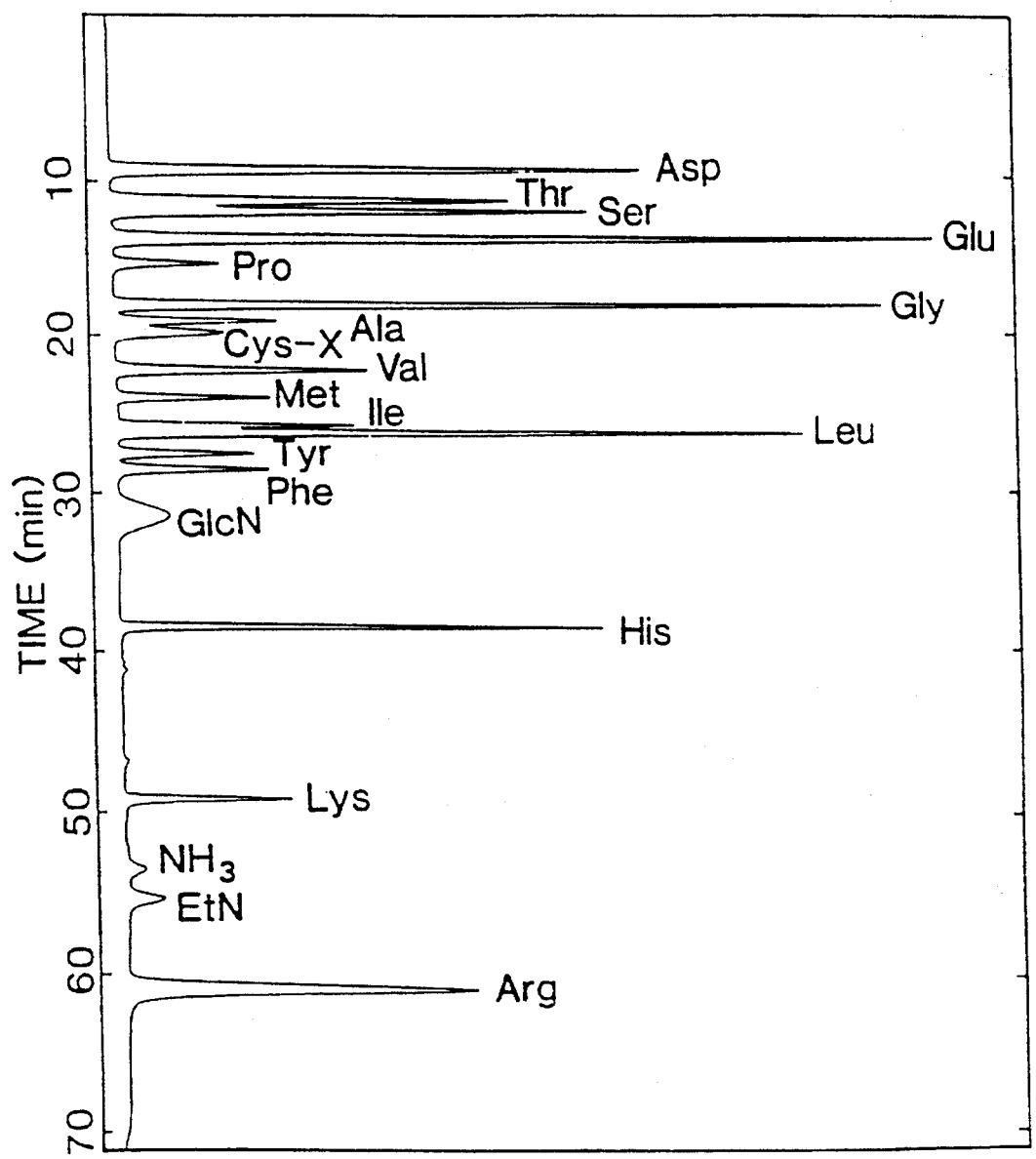
Figure 9B:
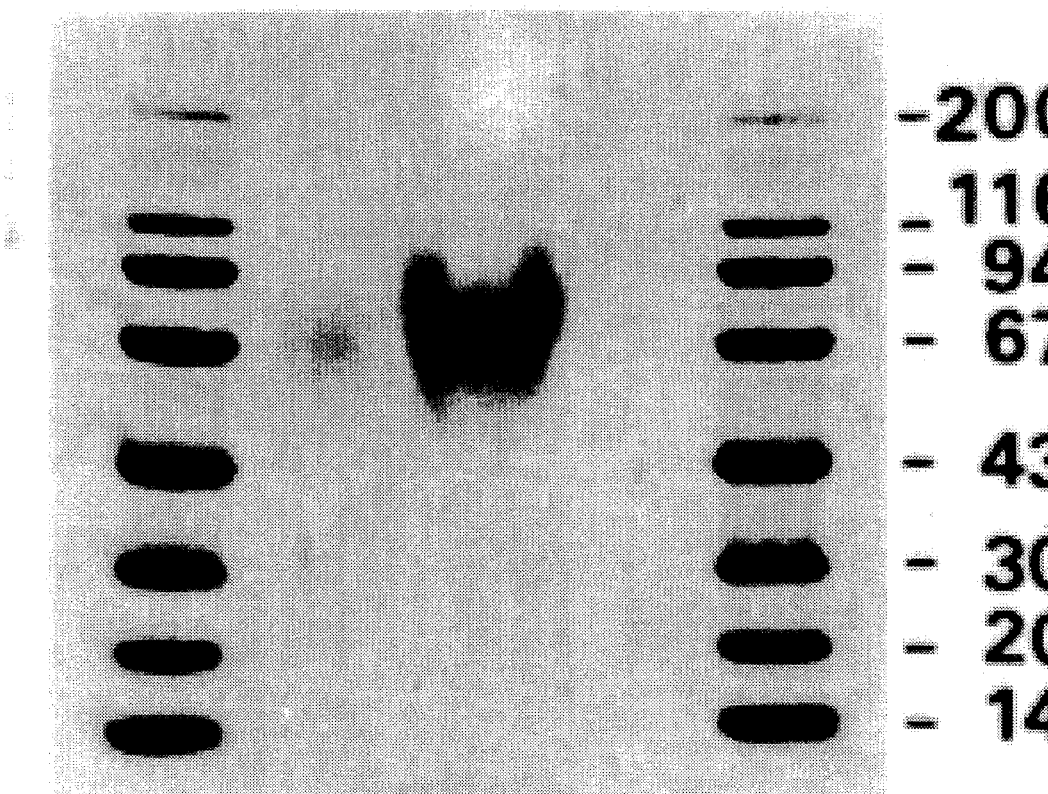

FIG. 9A shows an elution profile from cation-exchange chromatography of amino acids released from u-PAR after acid hydrolysis. The protein was initially purified from PMA-stimulated U937 cells (6×10$^9$ cells) by Triton X-114 detergent-phase separation and affinity chromatography (DFP-u-PA Sepharose). To improve purity and eliminate interference on amino acid analysis from low molecular weight compounds, this receptor preparation was dialysed thoroughly against 0.1% acetic acid, lyophilized and then subjected to Tricine-SDS-PAGE followed by electrotransfer onto a 0,45 μm PVDF-membrane (8 cm×8 cm). FIG. 9B shows the immobilized u-PAR after staining with Coomassie Brilliant Blue R-250. A slight decrease in mobility of u-PAR was observed in this experiment, due to a large excess of the zwitterionic detergent CHAPS in the lyophilized preparation. The stained area of the PVDF-membrane representing u-PAR was excised and hydrolysed in vacuo for 20 hours at 110° in the presence of 3,3'-dithiodipropionic acid (DTDPA). Cys-X is the product formed between cysteine and DTDPA during hydrolysis, GlcN is glucosamine and EtN is ethanolamine.

Figure 10:
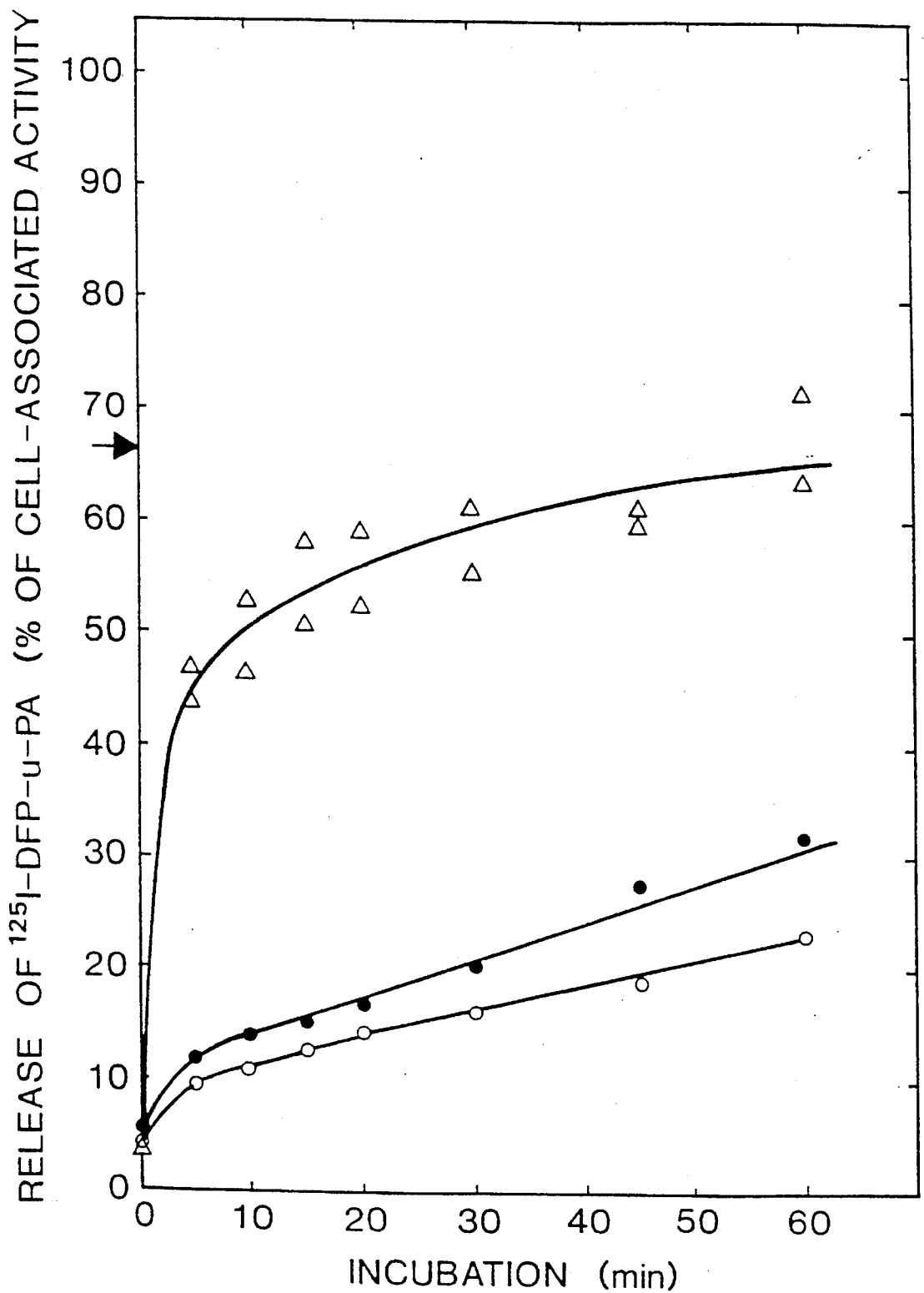
Figure 11:
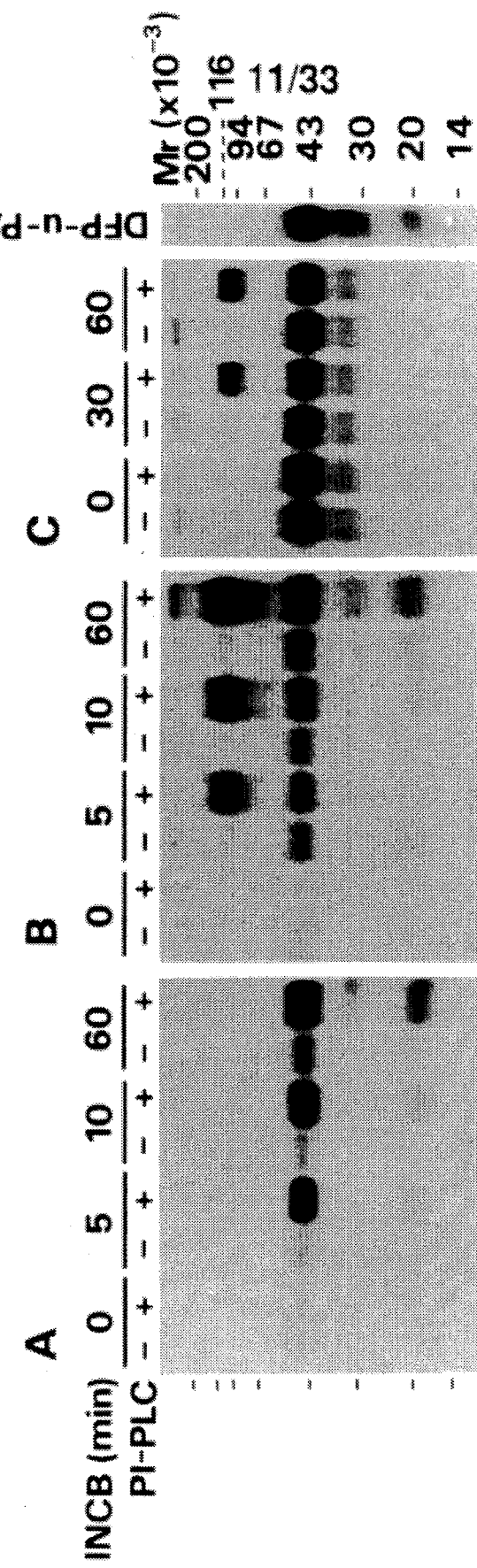

FIG. 10 shows the release of $^{125}$I-labelled DFP-treated u-PA from adherent, PMA-stimulated U937 cells by phosphatidylinositol-specific phospholipase C from *Bacillus cereus* (PI-PLC). Initially, endogenously produced u-PA was eluted from the PMA-stimulated U937 cells (2× 10$^7$ cells/dish) by acid treatment. Binding of exogenously added $^{125}$I-labelled DFP-treated u-PA (1 nM and 4.5×10$^6$ cpm) was performed at 4° C. for 2 hours in 5 ml serum free RPMI 1640 medium including 25 mM HEPES, pH 7.4. After washing the cells 3 times with this buffer, one dish was extracted with 5% SDS, defining 100% cell-associated radioactivity, whereas another was acid treated once more to determine the acid extractable activity (this level is indicated by an arrow at the ordinate). Two dishes received 0.6 μg PI-PLC/ml each (Δ), one received 8 μg/ml phospholipase A$_2$ (o), while the last dish constituted the buffer control (•). Two aliquots (100 μl) of medium were withdrawn from each dish during incubation on a shaking table at 37° C. and the released radioactivity was determined in the supernatant after centrifugation (20,000×g for 5 min). The samples were later analysed by SDS-PAGE as shown in FIG. 11.

FIGS. 11A–11C show complex formation and molecular analysis by SDS-PAGE of $^{125}$I-labelled DFP-treated u-PA and u-PAR released to the medium by PI-PLC. Aliquots of supernatants from the experiment described in FIG. 10 were analysed by SDS-PAGE (10% T, 2.5% C) under nonreducing conditions either directly 11(A) or subsequent to cross-linking with 1 mM disuccinimidyl suberate (DSS), performed immediately after sampling 11(B). In a separate experiment 11(C), 2 dishes of PMA-stimulated U937 cells were cultured and acid treated as described in the legend to FIG. 10. After neutralization, one dish was incubated at 37° C. in 5 ml of serum-free medium (RPMI 1640 including 25 mM HEPES, pH 7.4) with 0.6 μg PI-PLC, whereas the other was incubated in 5 ml of medium only. Aliquots were withdrawn at 0 min, 30 min and 60 min after the addition of lipase and centrifuged immediately (20,000×g for 5 min). Supernatants were preincubated for 1 hour at 4° C. with $^{125}$I-labelled DFP-inactivated u-PA (1 nM) and then cross-linked with 1 mM DSS. The rightmost lane (DFP-u-PA) represents the $^{125}$I-labelled ligand cross-linked in the absence of u-PAR. Samples were analysed by SDS-PAGE as above.

Figure 12:
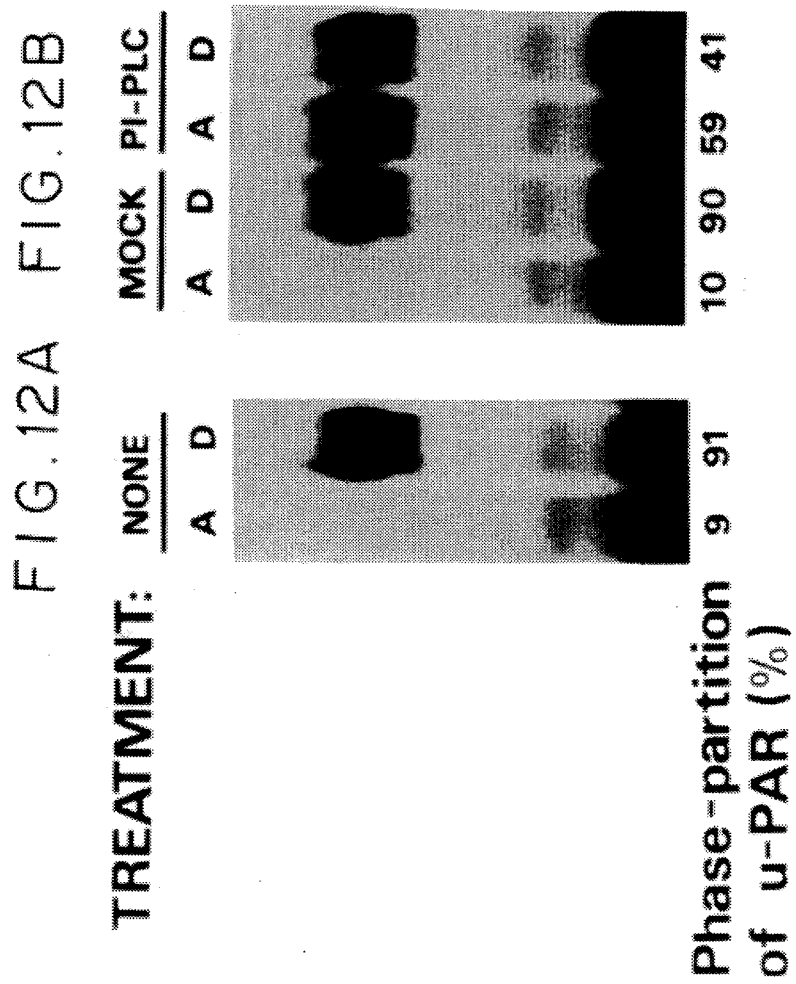

FIGS. 12A–12C show the change in hydrophobic properties of purified u-PAR upon treatment with PI-PLC.

u-PAR, purified from PMA-stimulated U937 cells, were either untreated (NONE) or incubated for 30 min at 37° C. in 50 mM triethylamine/HCl (pH 7.5), 5 mM EDTA and 0.1% Triton X-100 without any phospholipases (MOCK) or in the presence of 20 µl/ml PI-PLC (PI-PLC). One sample was incubated with 200 µg/ml phospholipase D purified from cabbage in 50 mM acetate (pH 6.0), 10 mM $CaCl_2$ (PLD), and another with 100 µg/ml phospholipase $A_2$ purified from bee venom in 50 mM HEPES (pH 8,0), 10 mM $CaCl_2$ ($PLA_2$).

These u-PAR preparations were then subjected to temperature-induced detergent-phase separation in 1% Triton X-114. This phase separation was repeated once for the resulting aqueous and detergent phases by addition of extra Triton X-114 and 0.1M Tris (pH 8.1), respectively. Finally, cross-linking analysis with 1 nM $^{125}$I-labelled ATF was performed on parallel aliquots of aqueous (A) and detergent (D) phases, followed by SDS-PAGE (10% T and 2.5% C) under non-reducing conditions. Areas corresponding to $^{125}$I-ATF/u-PAR complexes (Mr 70,000) were excised from the polyacrylamide gel and the radioactivity was determined (shown as % of total radioactivity in A+D at the bottom of each lane).

FIG. 13 shows a comparison of COOH-terminal amino acid sequences from proteins, in which the processing sites during GPI-membrane anchoring are known, to that predicted for u-PAR (SEQ ID NO:11) (based on amino acid analysis, Table 5). The amino acids involved in attachment to the glycolipid are highlighted. VSG (SEQ ID NO:7) and PARP (SEQ ID NO:6) refers to variant surface glycoprotein (and procyclic acidic repetitive protein from *Trypanosoma brucei*. CEA (SEQ ID NO:9) is carcinoembryonic antigen; PLAP (SEQ ID NO:8) is placental alkaline phosphatase and Thy-1 (SEQ ID NO:10) refers to the surface glycoprotein isolated from rat thymocytes.

Figure 14:
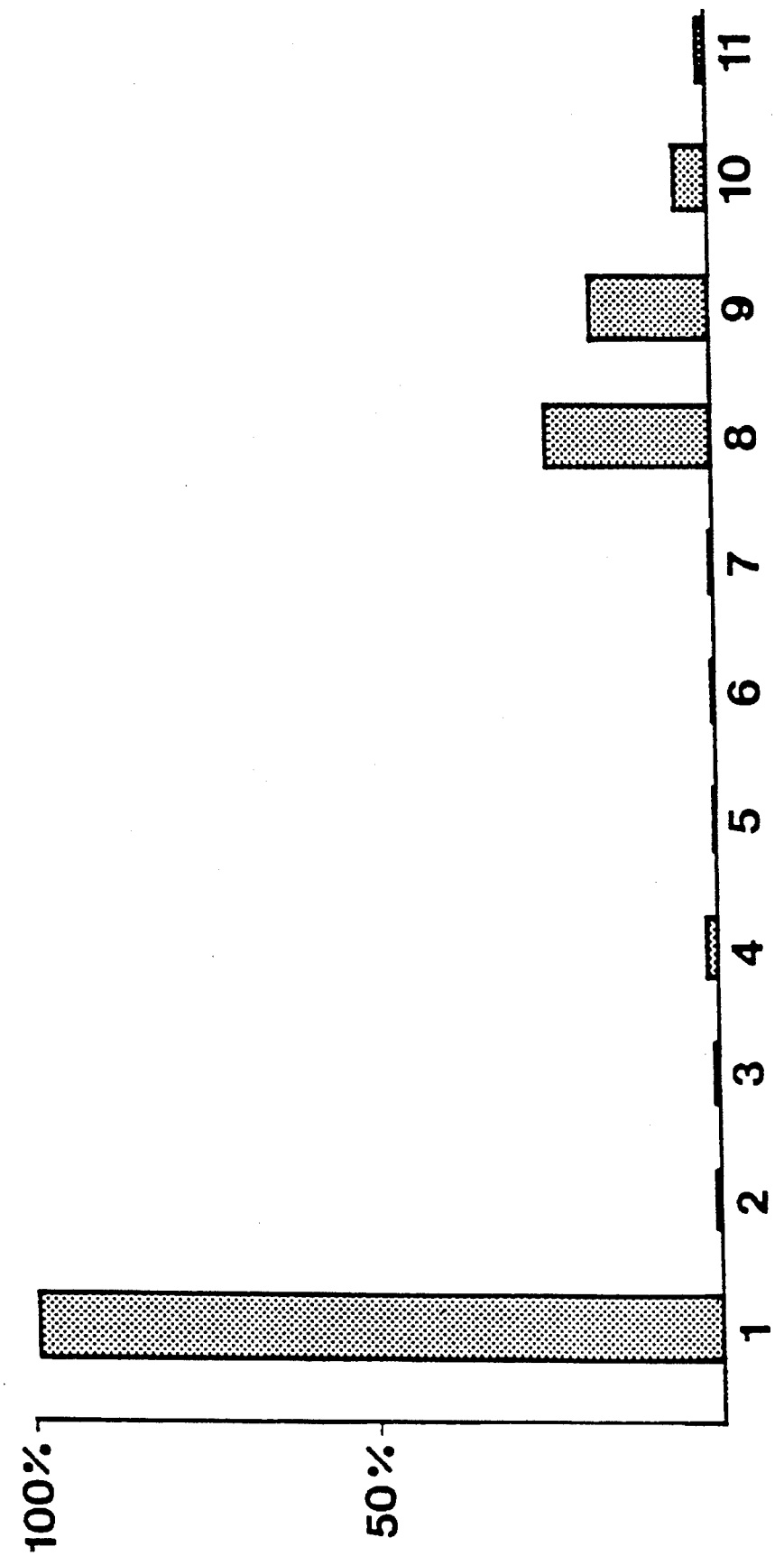

FIG. 14. Radioimmunoprecipitation of $^{125}$I-labelled purified u-PAR. Ordinate: % $^{125}$I-u-PAR precipitated. Abscissa: dilution of immune/non-immune sera 1:75, 1:750, 1:7500 and 1:75000.

Bars 1–11 represent: 1) Total amount of $^{125}$I-u-PAR added to each sample, 44000 cpm; 2) control of binding of radioactivity to the test tubes; 3) control of binding of $^{125}$I-u-PAR to Protein A Sepharose; 4–7) binding of $^{125}$I-u-PAR to non-immune serum; 8–11) binding of $^{125}$I-u-PAR to immune serum.

Figure 15:
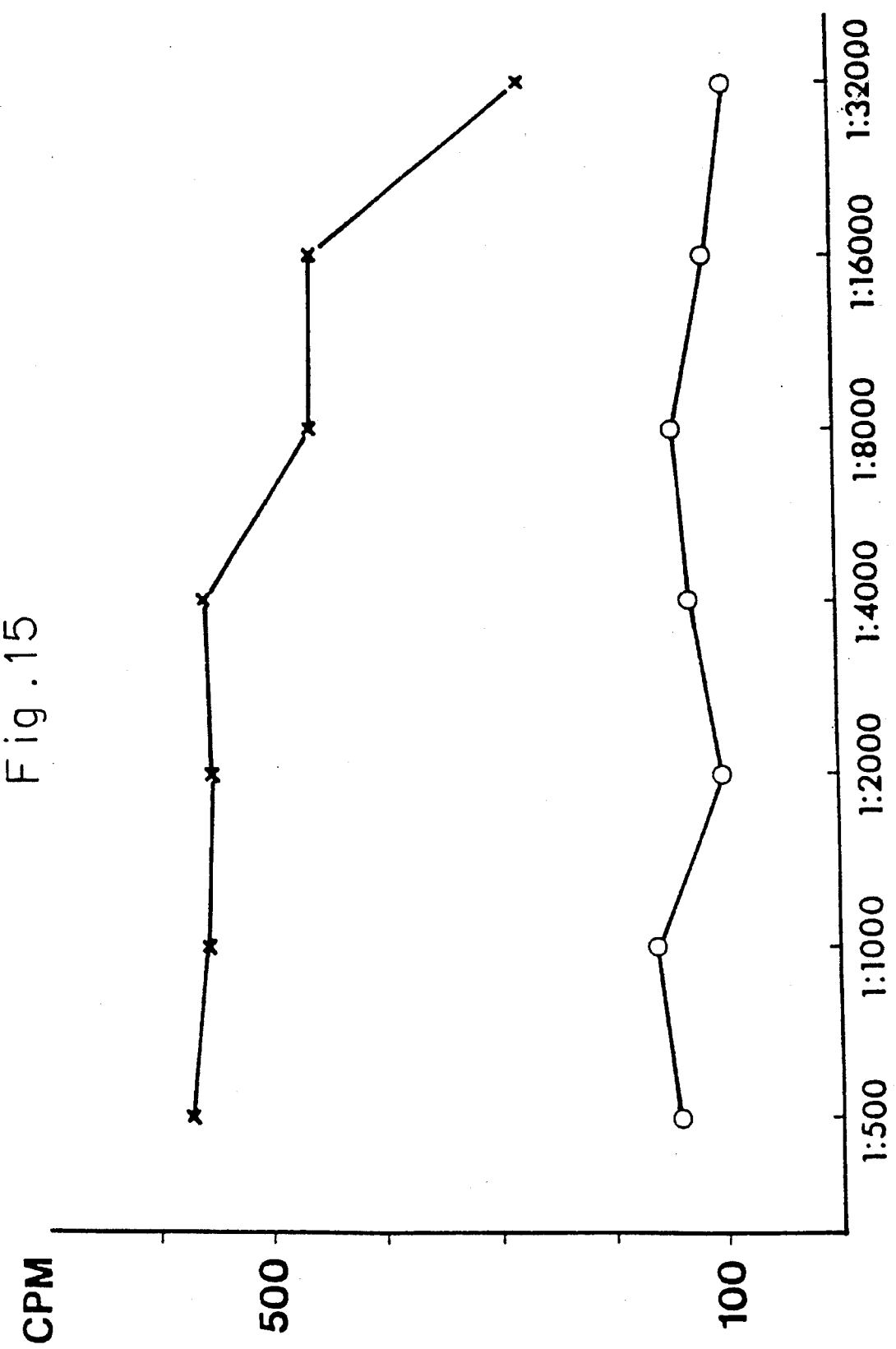

FIG. 15. Reverse solid phase radioimmunoassay, as described under Methods. Catching of $^{125}$I-u-PAR by immune/non-immune sera. Ordinate: cpm bound. Abscissa: a 2-fold serial dilution of antibodies, 1:500–1:32000. x-x immune; o-o non-immune. Total amount of $^{125}$I-u-PAR added to each sample: 33000 cpm.

Figure 16:
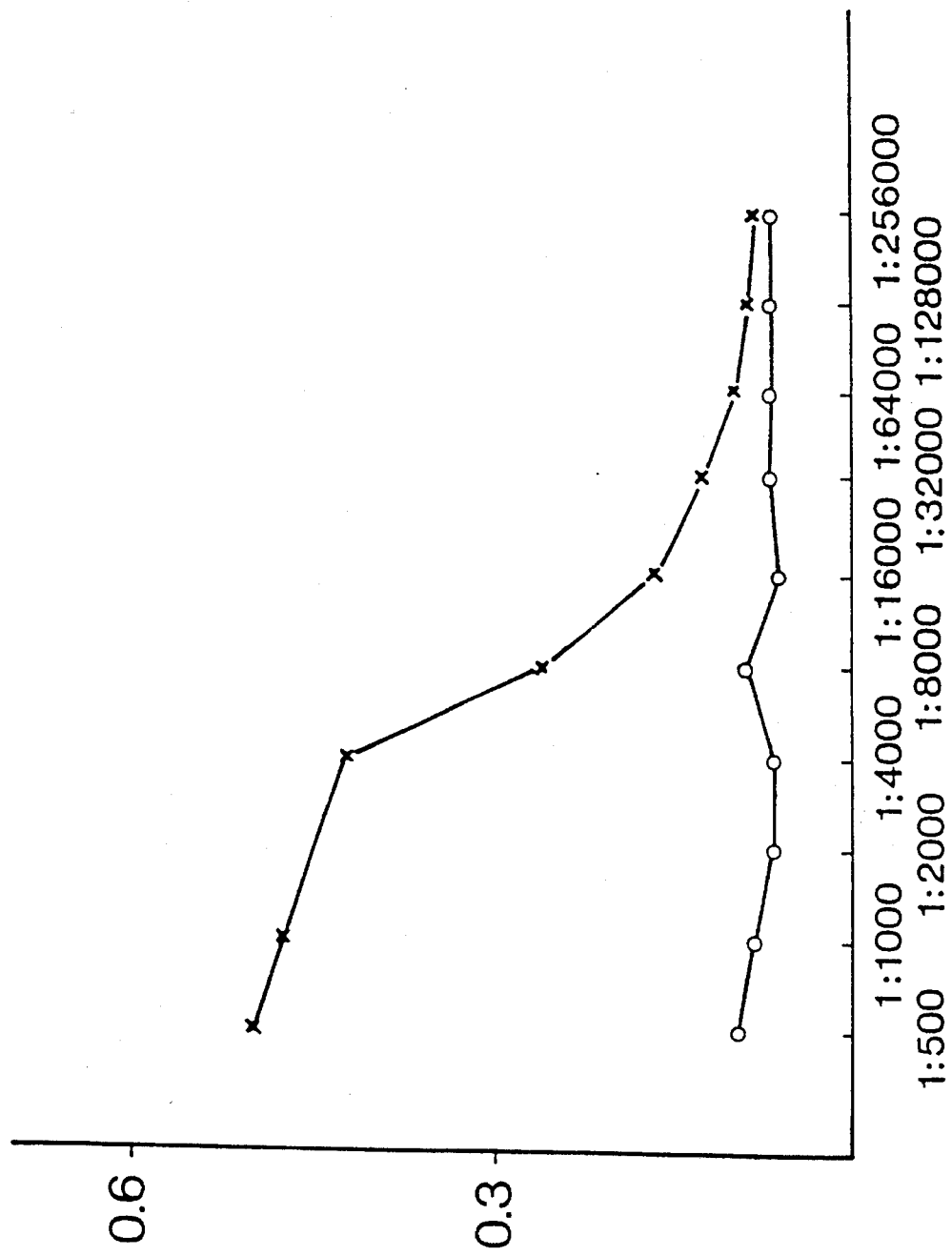

FIG. 16. ELISA. Purified u-PAR was coated in a concentration of 1 ng/well. Immune/non-immune sera (primary antibody) were added in a 2-fold serial dilution, ranging from 1:500 to 1:256000. Peroxidase-conjugated secondary antibody diluted 1:500 was used. The substrate was OPD. Colour development from the enzyme substrate reaction was read at 490 nm. The reaction was stopped after 10 minutes. y-axis: OD 490 nm. x-axis: Dilution of immune/non-immune sera. x-x immune; o-o non-immune.

FIG. 17. Inhibition of cellular ATF binding by antibodies raised against purified u-PAR. $5 \times 10^5$ U937a cells were preincubated with mouse antiserum raised against purified u-PAR (•-•) or with a control mouse antiserum raised against porcine mucins (o-o) for 1 hour at 4° C., followed by addition of 2.2 nM $^{125}$I-ATF and incubation for another hour at the same temperature. The cells were then washed 3 times after which the cell-bound radioactivity was measured in a gamma counter. The abscissa represents a two-fold dilution series of the antisera, the final dilutions ranging from 1:153, 600 to 1:300. The ordinate axis expresses the cell-associated radioactivity as a percentage of the value obtained with no antiserum present. Substitution of the antiserum with 700 nM unlabelled u-PA led to a 90% inhibition of binding.

Figure 17A:
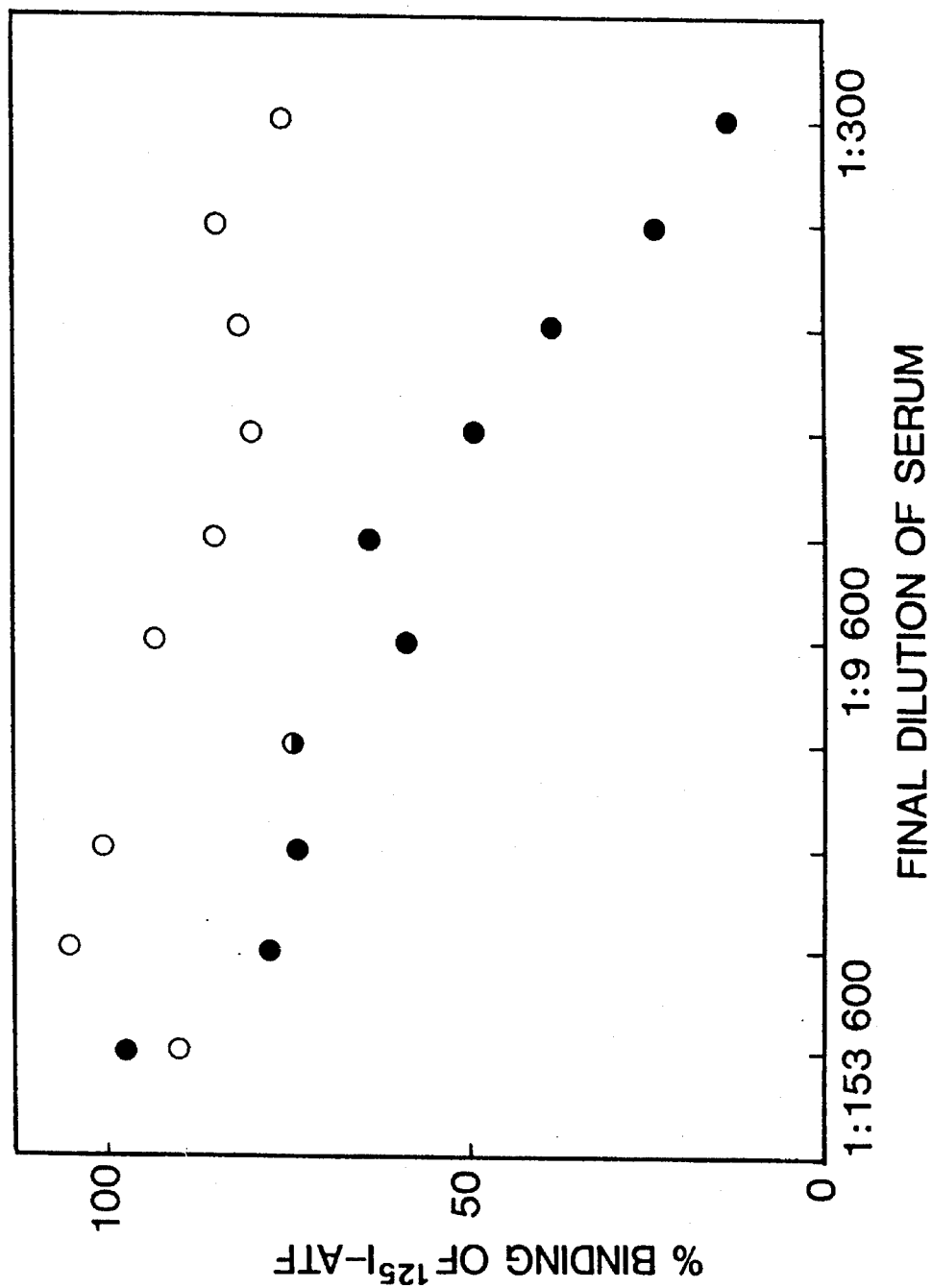
Figure 17B:
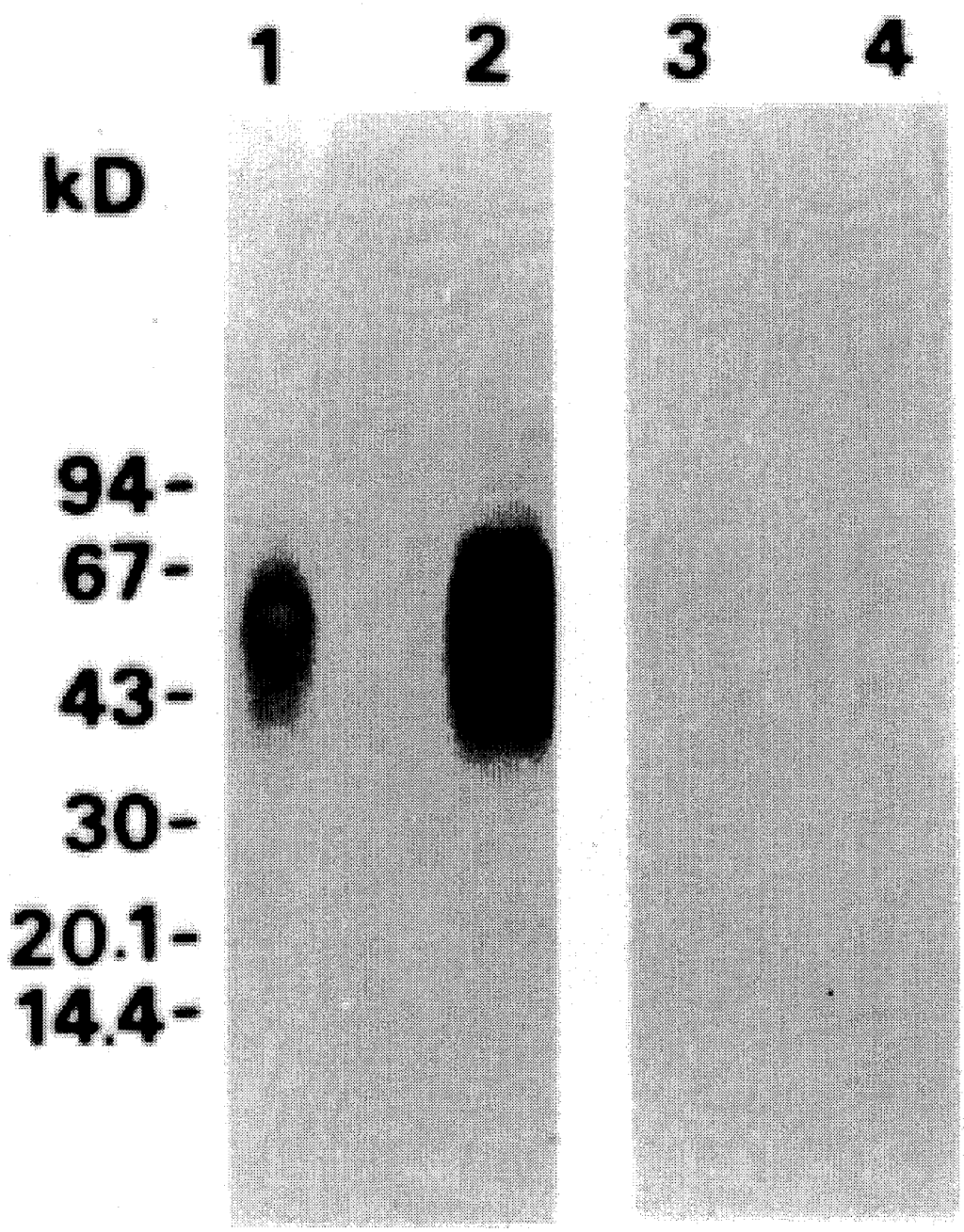

FIG. 17B is a Western blot showing the reactivity of the antisera used. 500 ng of purified u-PAR (lanes 2 and 4) or the Triton X-114 detergent phase obtained from $2.5 \times 10^6$ PMA-stimulated U937 cells (lanes 1 and 3) were analyzed by SDS-PAGE under reducing conditions on a 6–16% gradient gel, and Western blotting using as the primary antisera mouse anti-u-PAR serum diluted 1:250 (lanes 1 and 2) or the above control serum at the same dilution (lanes 3 and 4).

FIGS. 18A–18B show a Western blot, demonstrating the reactivity of polyclonal rabbit antibody against u-PAR. 75 µl samples of Triton X-114 detergent phase from lysates of PMA-stimulated U937 cells were analyzed alone (lane 1), after mixing with DFP-treated u-PA (Example 1; final concentration 10 µg/ml) (lane 4), or after mixing with the same amount of DFP-treated u-PA, followed by chemical cross-linking (lane 3). As a control, the same amount of DFP-treated u-PA was analyzed alone, after the performance of cross-linking (lane 5), or directly (lane 6). The sample in lane 2 contained 75 µl of the cell lysate detergent phase, which was subjected to chemical cross-linking without the addition of DFP-treated u-PA. The samples were run on 6–16% gradient SDS-PAGE under non-reducing conditions, followed by electroblotting onto nitrocellulose. The sheets were incubated with purified and absorbed IgG from rabbit anti-u-PAR serum 18(A), or with purified and absorbed IgG from pre-immune serum from the same rabbit 18(B). The IgG concentration during the incubation was 12 µg/ml in both cases. The sheets were developed with alkaline phosphatase-coupled antibody against rabbit IgG, followed by detection of alkaline phosphatase activity.

FIG. 19 Immunoprecipitation of $^{125}$I-labelled u-PAR(I) and u-PAR(D) by 4 monoclonal antibodies.

Purified u-PAR (30 µg/ml) was treated with chymotrypsin (40 ng/ml) for 7 h at 37° C. Both non-degraded intact u-PAR and degraded u-PAR were radiolabelled with $^{125}$I-iodine. An amount of $^{125}$I-u-PAR(I) and $^{125}$I-u-PAR(D) corresponding to $3.5 \times 10^5$ cpm/ml was subjected to immunoprecipitation as described under materials and methods. All antibody solutions were of the same concentration (20 µg/ml).

19A. Immunoprecipitation of $^{125}$I-u-PAR(I) Lane 1–10 represent the following samples: Starting material, Prot. A seph. solution 50 µl (control), affinity purified rabbit anti u-PAR serum, affinity purified rabbit preimmune serum, 2R, 3R, 1R, 4R, pool of the monoclonal antibodies, anti TNP monoclonal antibody (neg control).

19B. Immunoprecipitation of $^{125}$I-u-PAR(D). Lane 1–10 represent the same antibodies as above.

FIG. 20 Western blot showing the reactivity of 4 monoclonal antibodies raised against u-PAR.

Triton X-114 detergent phase obtained from $3 \times 10^7$ PMA-stimulated U937 and U937a cells, respectively, was applied in one big slot and analyzed by SDS-PAGE under non-reducing conditions on a 6–16% gradient gel. The separated proteins were transferred to nitrocellulose and subjected to Western blotting using the 4 monoclonal antibodies and control sera (mouse anti-u-PAR serum and mouse non-immune serum).

20A. Samples from U937 cells. Strips of nitrocellulose sheets were reacted with a 1:1 dilution of spent media from the hybridomas secreting the monoclonal antibodies 1R, 2R, 3R, 4R (lanes 1–4), mouse anti-u-PAR serum diluted 1:500 (lane 5) and mouse non-immune serum diluted 1:500 (lane 6). Molecular weight markers are indicated.

20B. Samples from U937a cells. Strips of nitrocellulose sheets were incubated as above.

Figure 21:
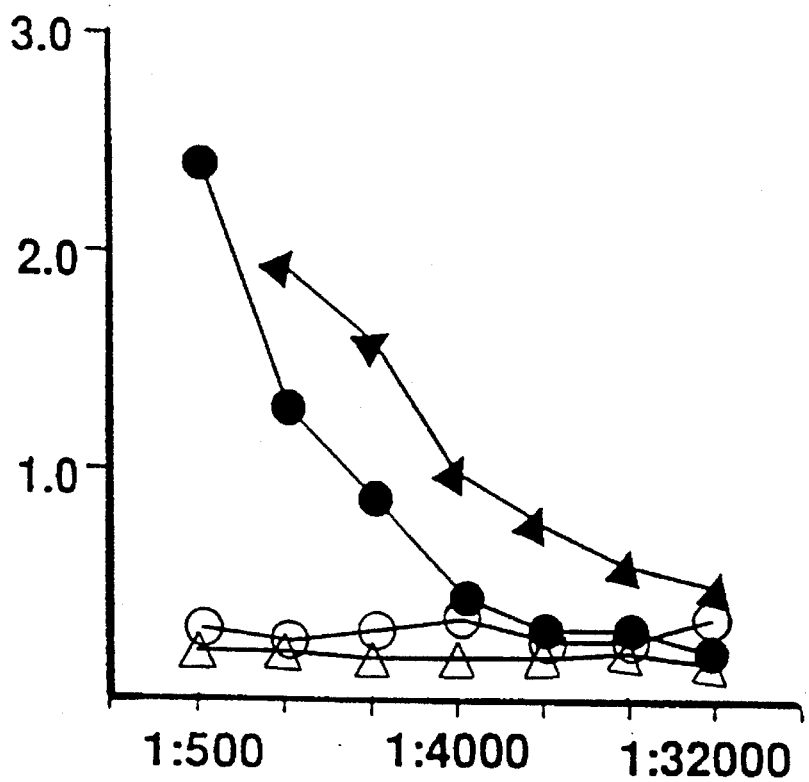

FIG. 21 Two antibody sandwich ELISA showing the quantification of purified u-PAR. The ELISA was performed as described in Example 6. As catching antibodies were used: the monoclonal antibody 4R, monoclonal antibody to trinitrophenol (TNP), affinity purified polyclonal rabbit antibodies to u-PAR prepared as described in Example 4 and pre-immune serum prepared as described in Example 4 at a concentration of 20 µg/ml. Purified u-Par was added in a two-fold serial dilution, ranging from 1:500 to 1:32000. Detection antibody was biotinylated monoclonal antibody 2R in a concentration of 500 ng/ml and the peroxidase-conjugated avidin was diluted 1:5000. The colour developed by the enzyme substrate reaction after 7 minutes and was measured at both 490 nm and 540 nm.

X-axis: 2-fold serial dilution of purified u-PAR.

Y-axis: OD 490 nm/540 nm.

21A: 4R (filled-in circles) and monoclonal antibody to TNP (open circles).

21B: Polyclonal rabbit anti-u-PAR antibodies (filled-in triangles) and rabbit pre-immune serum (open triangles).

Note: At 1:500 dilution of u-PAR, the OD value was too high to be measured.

Figure 22:
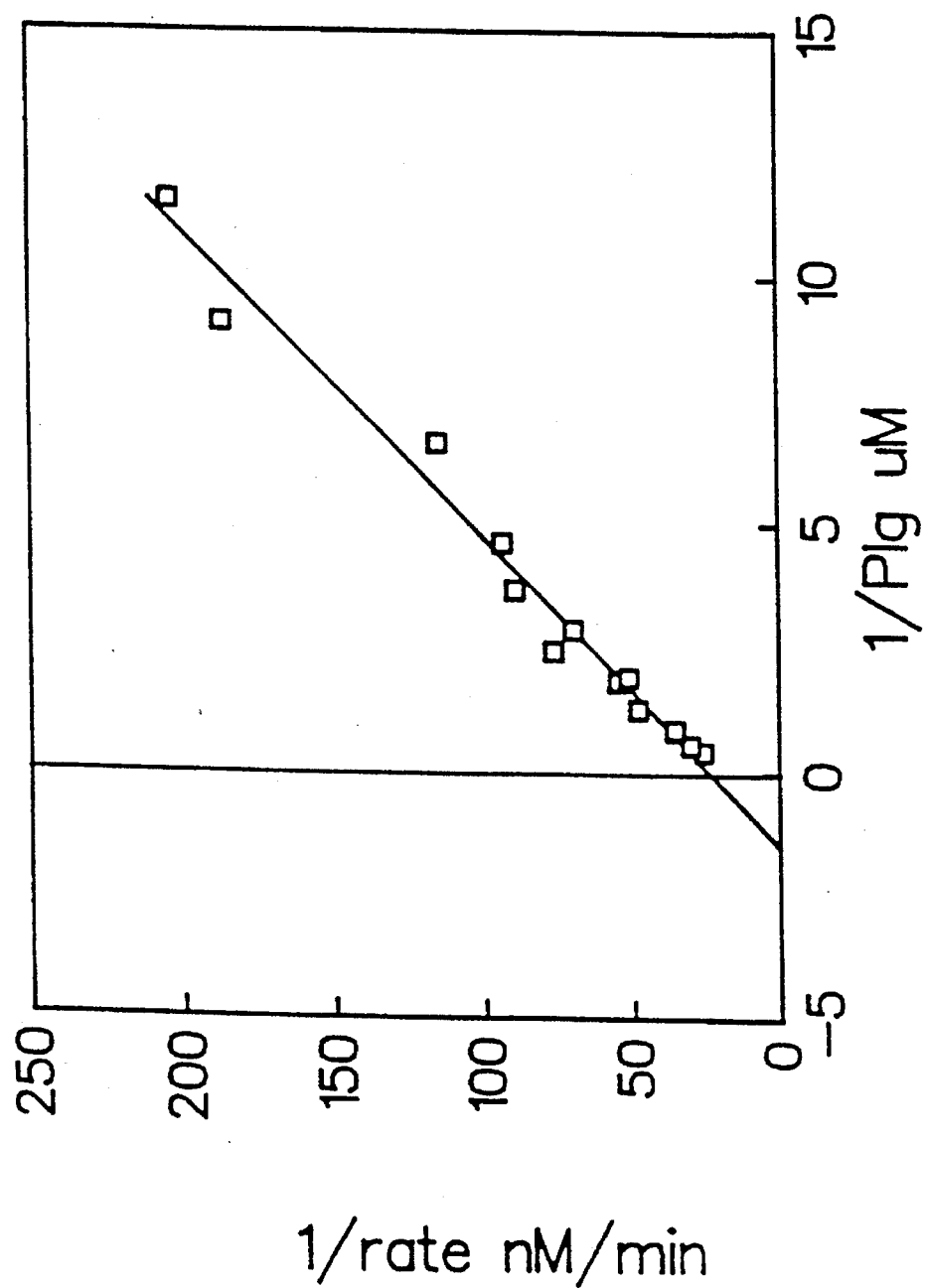

FIG. 22 shows the kinetics of plasminogen activation by u-PA bound to u-PAR on U937 cells. U937 cells pre-incubated with u-PA, which was demonstrated to be specifically bound to u-Par by competition with DFP-u-PA and anti-u-PAR antibodies, were incubated with Glu-plasminogen (0.09–2.26 µM). Rates of plasmin generation were plotted against plasminogen concentrations in a double-reciprocal manner. $K_m$ was determined as 0.67 µM and $V_{max}$ as 0.043 nM min$^{-1}$ which, at an experimentally determined cell-bound u-PA concentration of 7.7 pM, is equivalent to a $k_{cat}$ of 5.6 min$^{-1}$.

Figure 23:
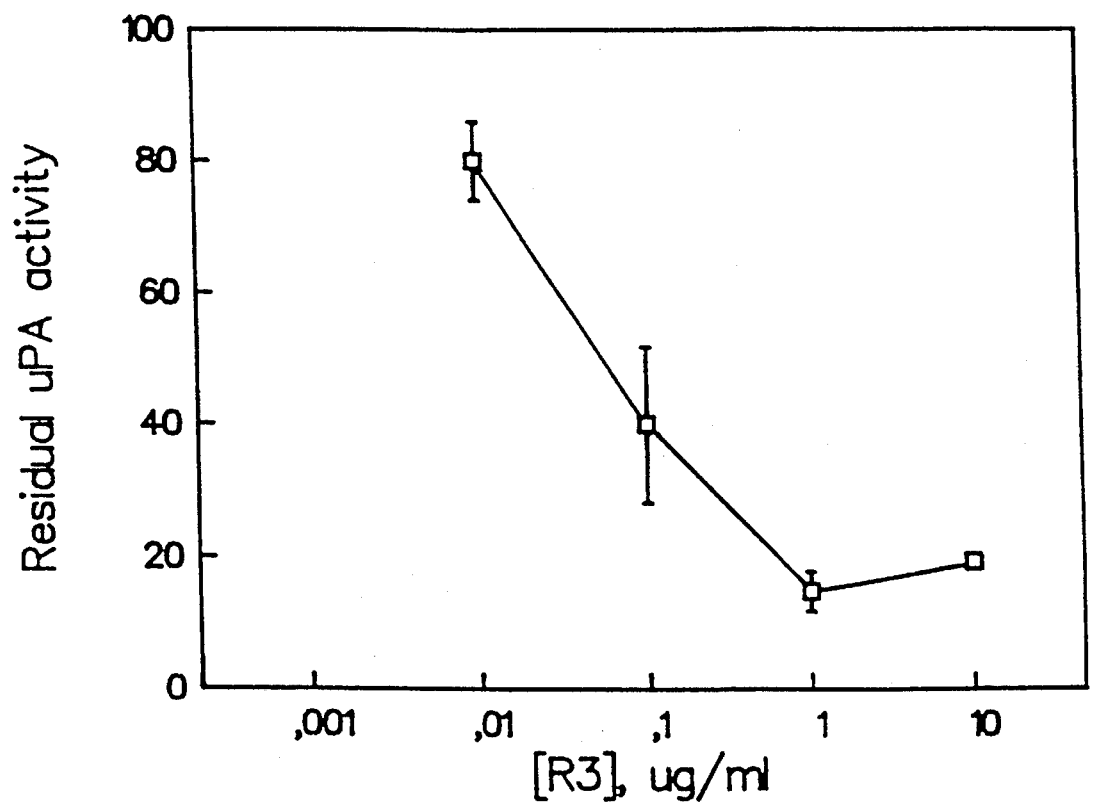

FIG. 23 Residual u-PA catalysed cell-surface plasminogen activation, subsequent to incubation of acid-washed U937 cells with varying concentrations of the monoclonal antibody 3R followed by the binding of u-PA to the cells. Residual u-PA activity (i.e. rate of plasmin generation) is expressed in percentage relative to cells not incubated with antibody. The data shown are the mean ±1 standard deviation for 3 independent experiments.

FIG. 24. Acid washed U937a cells were pre-incubated for 30 minutes in the presence or absence of 2 µg/ml of each of the monoclonal antibodies 1R (FIG. 24A), 2R (FIG. 24B), 3R (FIG. 24C), and 4R (FIG. 24D), prior to incubation with pro-u-PA, plasminogen 2 and the fluorogenic plasmin substrate H-D-Val-Leu-Lys-7-amido-4-methylcoumarin. (Δ) Plasmin generation in the absence of cells, (□) in the presence of U937a cells pre-incubated with antibodies, (∇) in the presence of U937a cells without antibodies.

FIG. 25 shows hybridization to paraffin sections of human colon adenocarcinoma using antisense RNA generated from the cDNA subclone pHUR06. Disrupted tumor glands at invasive foci (25a and 25b) show hybridization to cells at the leading edge of strands of tumor cells (arrows in 25b; 25b is a magnification of squared area in 25a). In tumor glands consisting of coherent cells, hybridization signal is located above cells at the abluminal surface of the malignant epithelium (25c; arrows), or above cells located in stromal tissue surrounding the gland (25d; arrow). In areas of neovascularization cells of seemingly mesenchymal origin show hybridization (25e). Magnifications: 216×(25a), 540× (25b–25d), 870×(25e).

Figure 26A:
Figure 26B:
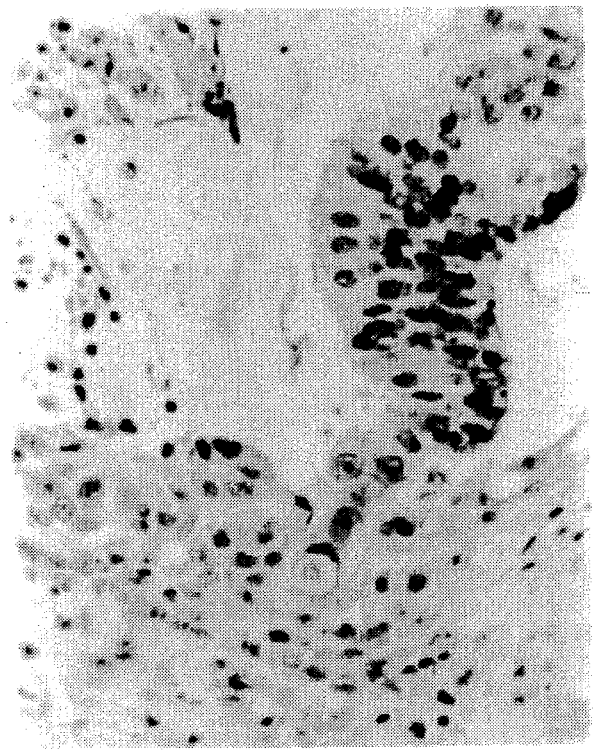

FIG. 26 Immunostaining of one of case of colon adenocarcinoma with monoclonal anti-uPAR antibody clone R2 (26A). Numerous tumor cells (straight arrows) located at the tumoral-stromal interface (at stippled line) are strongly positive for u-PAR. Note also a few positive histiocytes in the section (curved arrow). No staining is seen with a negative control (anti-TNP) antibody (26B).

Figure 27:
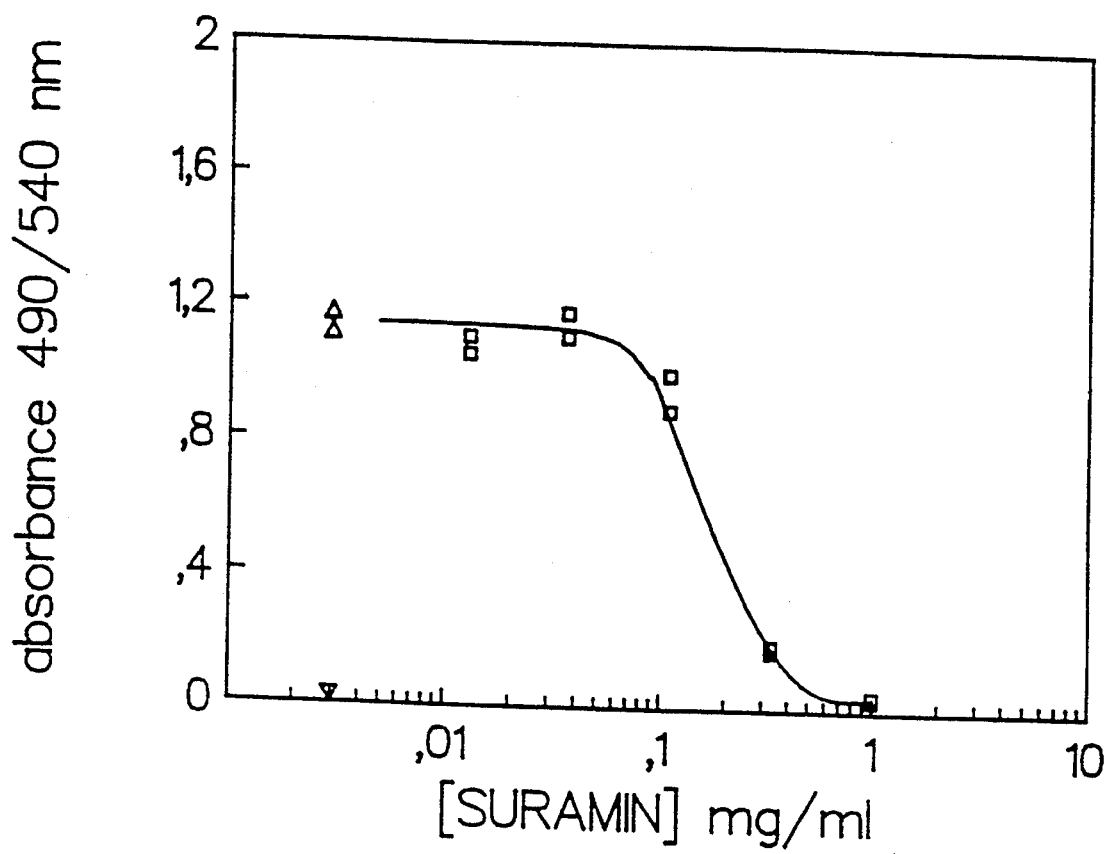

FIG. 27 The effect of the compound suramin on the inhibition of the binding between u-PA and u-PAR was examined in the substance screening ELISA constructed as a two antibody sandwich ELISA and performed as explained in Example 9. R4 was used as catching antibody at a concentration of 20 µg/ml. Purified u-PAR was added at a concentration of 20 ng/ml. Purified u-PAR was added at a concentration of 20 ng/ml. DFP-u-PA was added in a final concentration of 5 ng/ml either with the blocking buffer or in a mixture with suramin in a 3-fold serial dilution. Detection antibody was biotinylated anti-u-PA antibody clone 5 in a concentration of 2 µg/ml and the peroxidase-conjugated avidin was diluted 1:5000. The colour developed by enzyme-substrate reaction after 3 minutes and was measured at both 490 nm and 540 nm. As a control served the omission of the reactants in the various steps of the assay.

X-axis: 3-fold serial dilution of suramin

Y-axis: absorbency at 490 nm/540 nm.

DFP-u-PA alone (Δ), DFP-u-PA and suramin (□) blocking buffer (∇).

Figure 28:
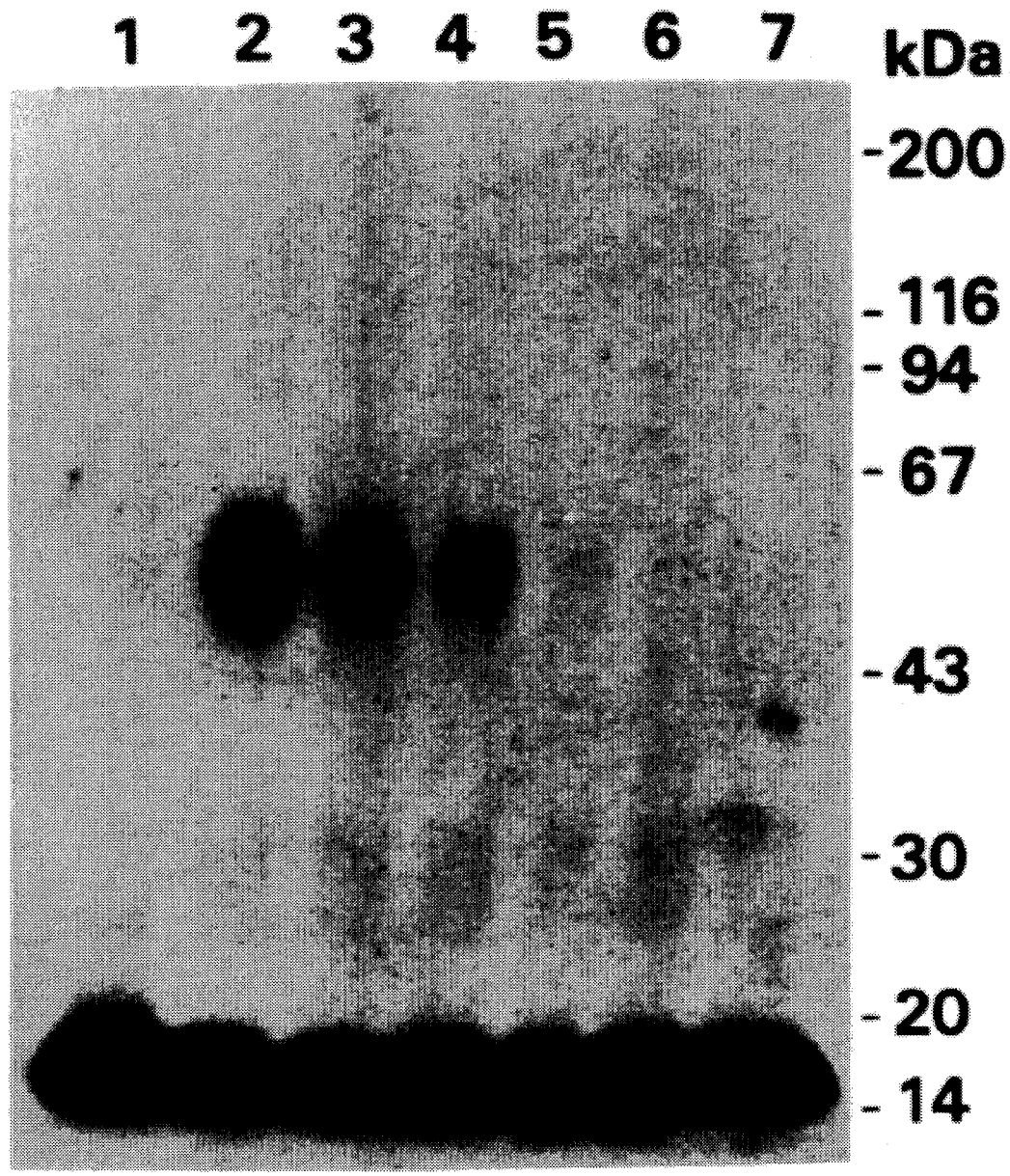

FIG. 28 Shows the inhibition of the cross-linking between $^{125}$I-labeled ATF and u-Par by the compound suramin determined by measuring the chemical cross-linking of $^{125}$I-labeled ATF to u-PAR in a HEp-2 cell lysate in the presence or absence of suramin. The following suramin concentrations (mg/ml) were used: 0 (lane 2), 0.1 (lane 3), 0.25 (lane 4), 1.0 (lane 5), 2.5 (lane 6), 10.0 (lane 7). Lane 1 shows the negative control with the addition of buffer instead of cell lysate and without the addition of suramin. The numbers to the right indicate molecular masses of marker proteins. Suramin was found to inhibit the binding reaction between u-PAR and the ligand $^{125}$I-labeled ATF in dose-dependent manner as appears from the figure. No binding activity was detected in the presences of a concentration of 1 mg/ml suramin and more than 50% inhibition of the binding activity was obtained in the presence af a concentration of 0.1 mg/ml suramin. The binding activity was defined as the formation of radiolabeled covalent conjugate.

Figure 29:
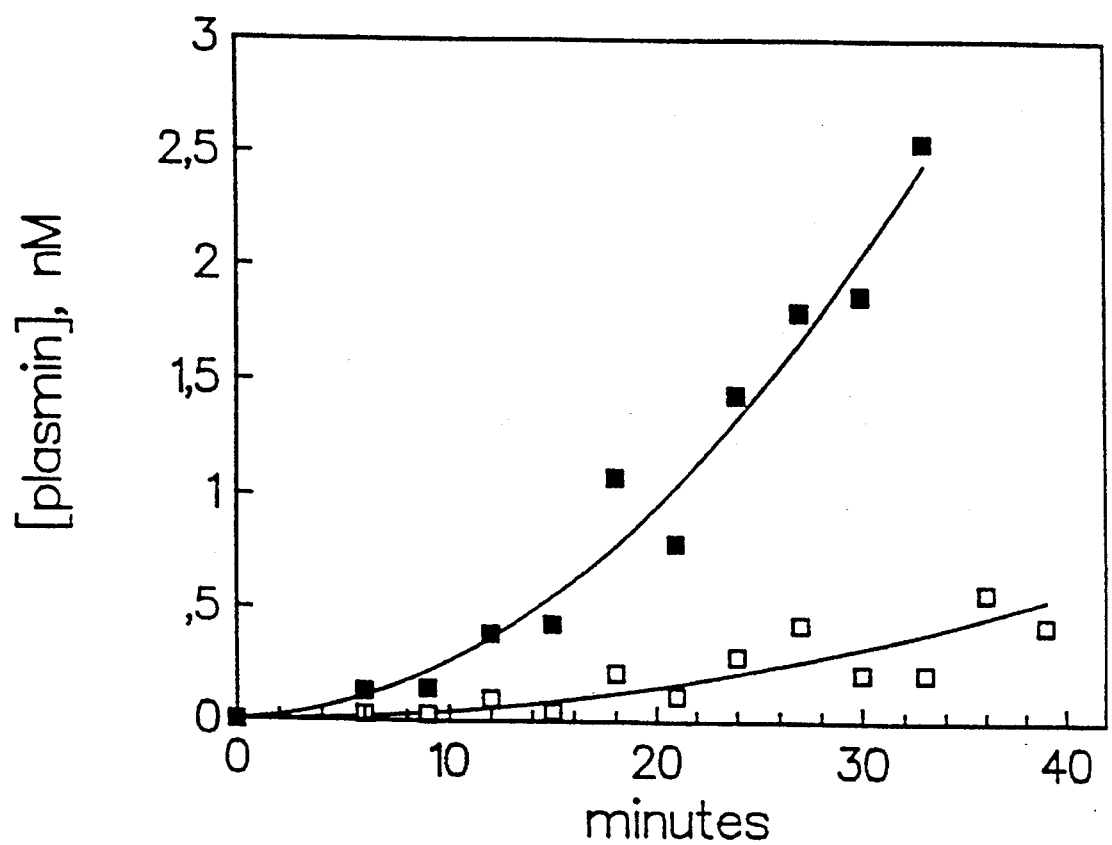
Figure 30A:
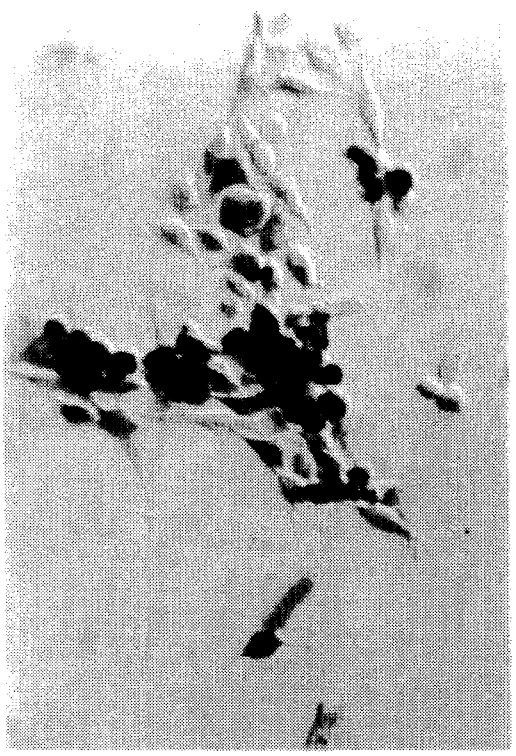
Figure 30B:
Figure 30C:
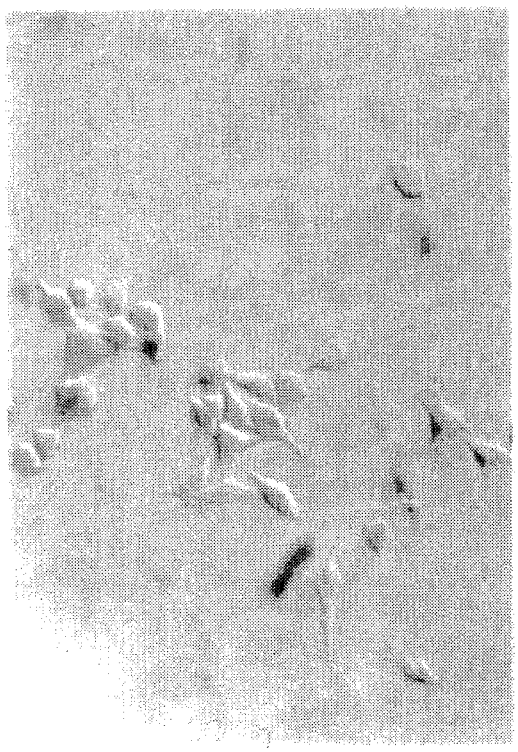
Figure 30D:

FIG. 29 Shows the effect of culturing MDA-MB-231 cells in the presence of monoclonal antibody 3R on the binding of endogenously produced pro-uPA to PAR, as determined by the ability of the bound pro-uPA to mediate plasminogen activation by the mechanism described in Ellis et al., 1989. Antibody 3R reduced the rate of plasmin generation to 20% of that of the control cells cultured in the absence of the antibody, demonstrating that 3R was effective in blocking the binding of endogenously secreted pro-uPA to PAR and thereby also its functional activity.

FIG. 30. X-gal staining of tumor cells grown in vitro and in vivo. Cells and tumors were fixed and processed for X-gal staining (see Example 9). A: MDA-MB-435 BAG cells; B: MDA-MB-435 BAG cells at passage 20; C: Subcutaneous MDA-MB-231 xenograft; D: Subcutaneous MDA-MB-231 BAG xenograft passage 2 in nude mice.

Figure 31A:
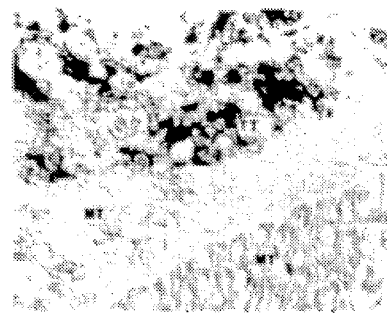
Figure 31B:
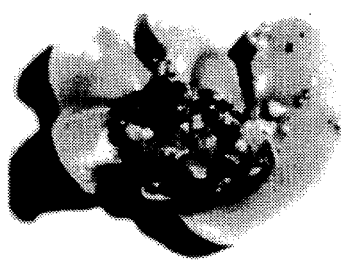
Figure 31C:
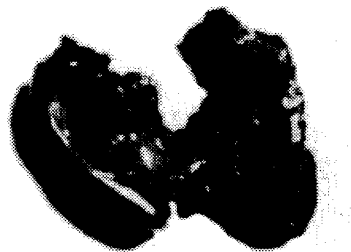
Figure 31D:
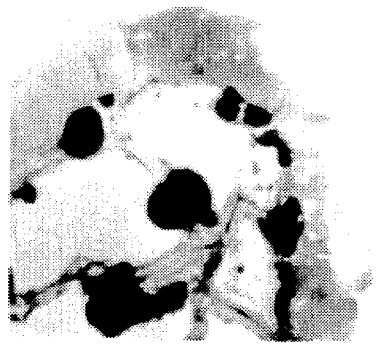
Figure 31E:
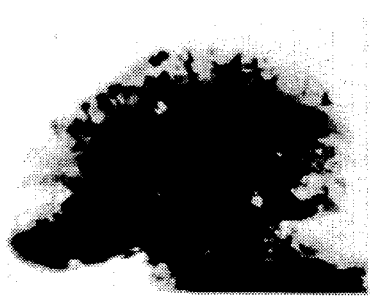
Figure 31F:
Figure 31G:
Figure 31H:
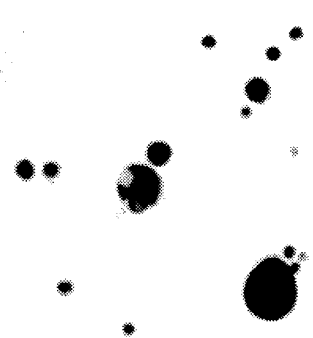

FIG. 31A: Cryosection of a primary MDA-MB-435 BAG tumor. Tumor tissue was processed for cryo-sectioning and stained with X-gal (see Example 9). Only the tumor cells stained positive with X-gal. TT: tumor tissue; MT: mouse tissue.

31B–D: Macroscopic appearance of secondary MDA-MB-435 BAG tumors. Whole organ staining with X-gal. 31B: liver; 31C: spleen and pancreas; 31D: intestine.

3E–G: Metastatic spread of MDA-MB-435 BAG tumor cells to mouse lung. 31E: Macroscopic appearance of lung metastases; 31F: Single lung metastasis (arrow); 31G: Histological section of the lung metastasis (arrow) seen in 31F. H. E. staining, 40 X.

31H: X-gal staining of ascites from a mouse inoculated sc with MDA-MB- 435 BAG tumor cells.

EXAMPLE 1

Purification and Characterization of u-PAR

Materials and Methods

SDS-PAGE.

When not stated otherwise, SDS-PAGE was performed according to Laemmli, U.K., "Cleavage of structural proteins during the assembly of the head of bacteriophage T4", Nature 227: 680–682, 1970, using 6–16% gradient slab gels. Pretreatment of samples under nonreducing conditions was performed without boiling. When reducing conditions were used, the samples were boiled for 5 minutes in the presence of 20 mM DTT.

Phast-gel SDS-PAGE was performed on a Phast gel apparatus (Pharmacia), using ready-made 10–15% gradient gels. Electrophoresis was performed according to the recommendations of the manufacturer. Silver staining was performed according to Heukeshoven and Dernick, 1988.

Tricine-SDS-PAGE of samples to be electroblotted for amino acid analysis or NH$_2$-terminal amino-acid sequencing was performed in a Mini Protean II apparatus (BioRad) according to Schägger and von Jagow, 1987, on a 0.75 mm homogeneous 7.7% T, 3% C gel. The gel was pre-electrophoresed for 3 hours at 15 mA in the gel buffer with 12 mM 3-mercaptopropanoic acid added as a scavenger. The freeze-dried sample was dissolved directly in 50 μl of the sample buffer with 40 mM dithioerythritol as the reducing agent, and boiled for 2 minutes. The gel buffer used for pre-electrophoresis was replaced with electrophoresis buffer, after which electrophoresis was performed for 4 hours at 60 V.

Electroblotting of samples for amino acid analysis or NH$_2$-terminal amino acid sequencing.

After electrophoresis, the Tricine-SDS-polyacrylamide gel was electroblotted onto a polyvinylidene difluoride (PVDF) membrane (Millipore), using a semi-dry electroblotting apparatus (JKA Instruments, Denmark). Electroblotting took place at pH 11.0 in 10 mM CAPS (3-(cyclohexylamino)-1-propanesulfonic acid), including 0.4 mM dithioerythritol and 10% methanol, and was performed at 0.8 mA/cm$^2$ for 2 hours. The protein was localized by staining with Coomassie R250 for 2 minutes and brief destaining, followed by wash in water (Matsudaira, 1987).

Alkylation of electroblotted protein and amino acid sequencing.

The Coomassie-stained protein band was cut out from the PVDF-membrane and treated with 25 mM iodoacetamide in 50 mM sodium borate, pH 8.0, for 1 hour in the dark at room temperature. After the reaction, it was washed extensively with water and dried under argon. The protein on the dried filter was sequenced on an Applied Biosystems protein sequencer, model 477A. The on-line HPLC identification system for the PTH amino acid derivatives included the derivative of carboxymethylcysteine (produced by deamidation of the amidomethyl derivative during conversion). The correct identification of this derivative was assured by a test-sequencing of chicken lysozyme (with cysteine at residue no. 6) after parallel preparative electrophoresis, electroblotting and alkylation.

Determination of amino acid composition and amino sugars.

For hydrolysis of electroblotted u-PAR, areas of PVDF membranes containing Coomassie-stained and in situ alkylated protein were treated with 6M HCl containing 0.05% phenol for 20 h in vacuo at 110° C. Amino acid analysis was performed on a Waters amino acid analyzer equipped with a post-column o-phthaldialdehyde identification system, as described (Barkholt and Jensen, 1989).

Cell culture for analytical studies.

The following human cell lines were obtained from the indicated sources: the histiocytic lymphoma cell line U937 (E. K. O. Kruithof, University Hospital Center, Lausanne, Switzerland), a variant of this cell line, designated U937a (A. Fattorossi, Research Lab of Aeronautica Militare, Rome, Italy), the promyeloid leukemic cell line HL-60 (American Type Culture Collection (ATCC)), the bladder carcinoma cell line 5637 (ATCC), the larynx epidermoid carcinoma cell line HEp-2 (ATCC), the epidermoid carcinoma cell line A-431 (E. Helseth, University of Trondheim, Norway), the cervix carcinoma cell line HeLa (ATCC), the colon carcinoma cell line HCT 116 (ATCC), the conjunctiva cell line Chang (ATCC), the choriocarcinoma cell line JEG-3 (A. Vaheri, University of Helsinki, Finland), the amnion cell line AV3 (ATCC), and the fibrosarcoma cell line HT-1080 (A. Vaheri). The U937 and U937a and HL-60 cells were grown in suspension, while all the other cell lines were grown as monolayers. The HT-1080 and A-431 cells were grown in Dulbecco's modified Eagle's medium with 10% heat-inactivated fetal calf serum. All other cell lines were propagated in RPMI 1640 medium with 5% heat-inactivated fetal calf serum and 2 mM L-glutamine. All media were supplemented with 200 units/ml penicillin, 25μg/ml streptomycin. All cells were cultured at 37° C. in a humid atmosphere with 5% CO$_2$. Adherent cells were harvested with a rubber scraper. PMA induction of U937 cells was performed at a density of 0.5–1×10$^6$ cells/ml with 150 nM PMA. A 4-day treatment was used whereby the cells adhere to the plastic surface. The PMA-induced adherent U937 cells were harvested with a rubber scraper.

Large-scale production of U937 cells.

The U937 cells were grown in 1-liter spinner flasks to reach a density of 1.0–1.5×10$^6$ cells/ml in RPMI 1640 medium supplemented with 2 mM L-glutamine, 5% fetal calf serum (heat inactivated), 200 units/ml penicillin, 25 μg/ml streptomycin (or without antibiotics). Each flask contained 500 ml cell culture.

Phorbol 12-myristate 13-acetate (PMA) induction and harvest of U937 cells.

The 500 ml cell suspension of one spinner flask was added to 1 liter of fresh medium without serum. 150 μl of PMA stock solution in dimethylsulfoxide (1 mg PMA/ml) was added, to reach a final concentration of 150 nM PMA. The culture was transferred to a 10-layer cell factory (Nunc, Denmark) and grown for 3.5 days in the factory. Upon addition of the PMA solution, the cells stop dividing and attach to the surface.

The 1.5 liter supernatant, still containing a large number of less adherent cells, was harvested. The more strongly adherent cells were harvested by washing the factory with 500 ml of PBS (without Ca$^{++}$ and Mg$^{++}$) containing 0.1%

EDTA, and vigorous shaking. The two cell suspensions were pooled to yield a total 2-liter harvest. The cells were collected by centrifugation.

Cell lysis and detergent phase separation.

PMA-stimulated U937 cells were washed and acid-treated as described by Nielsen et al., 1988. 20 ml lysis buffer (0.1M Tris/HCl, pH 8.1, 1% Triton X114, 10 mM EDTA, 10 µg/ml Aprotinin) and 0.2 ml of 100 mM phenylmethylsulfonylfluoride in dimethylsulfoxide were added to $10^9$ acid-treated cells at 0° C. The suspension was mixed thoroughly, left on ice for 5 minutes, mixed again and left at 0° C. for another 5 minutes, after which it was clarified by centrifugation at 4° C., 16,000×g for 10 minutes.

The clarified lysate was subjected to temperature-induced phase separation (Bordier, 1981) by incubation at 37° C. for 10 minutes, after which the detergent phase was collected by centrifugation for 10 minutes at 20° C., 1,800×g. The upper phase was discarded. The lower phase (approximately 2 ml) was washed by addition of 18 ml of 0.1M Tris/HCl, pH 8.1, at 0° C., followed by complete mixing to restore a clear, one-phase solution, and repeated phase separation by warming and centrifugation, as above.

After removal of the new upper phase, the lower phase was made up to 20 ml by addition of 0.1M Tris/HCl, pH 8.1. In order to avoid renewed phase separation during subsequent handling and purification, 500 µl 10% w/v 3-((3-cholamidopropyl)dimethylammonio)-1-propanesulfonate (CHAPS) was added to yield a clear, single-phase detergent fraction. Minor amounts of non-dissolved material were removed from this solution by centrifugation for 15 minutes at 4° C., 3,300×g.

Lysates and detergent phases from other cell types (as indicated) were prepared in the same manner, except that smaller amounts of cell material were used. The amounts of all reagents were reduced proportionally. In one experiment, 0.5% CHAPS was used as the lysis detergent instead of 1% Triton X114. In that experiment, no phase separation was performed.

Preparation of affinity matrix.

$2.5 \times 10^6$ IU (approximately 25 mg) of u-PA (Serono) was dissolved in 25 ml of 0.1M Tris/HCl, pH 8.1, 0.1% Tween 80. The enzyme was inactivated by addition of 250 µl of a fresh 500 mM stock solution of diisopropylfluorophosphate (DFP) in isopropanol and incubation for 4 hours at 37° C., with a further addition of the same amount of DFP after the first 2 hours.

The reaction was stopped by extensive dialysis at 0° C. against 0.25M NaHCO$_3$, 0.5M NaCl, 0.1% Triton X-100, pH 8.5.

In a total volume of 50 ml, the dialyzed material was coupled to 12.5 ml of CNBr-activated Sepharose (Pharmacia) that had been freshly equilibrated with 0.25M NaHCO$_3$, 0.5M NACl, pH 8.5 (coupling buffer). The reaction proceeded overnight at 4° C. and was stopped by equilibration of the matrix with 1M ethanolamine/HCl, pH 8.0 and incubation for 24 hours at 4° C. The matrix (DFP-u-PA-Sepharose) was washed with the coupling buffer and pre-eluted with the appropriate elution buffer (see below) before use.

Affinity purification.

The clarified detergent fraction obtained from $6 \times 10^9$ U937 cells was diluted with 1 vol washing buffer-1 (10 mM sodium phosphate, 140 mM sodium chloride, 0.1% CHAPS, pH 7.4) and chromatographed on a column containing 8 ml of DFP-u-PA-Sepharose, equilibrated with the same buffer. After application of the sample, the column was washed with washing buffer-1, followed by washing buffer-2 (10 mM sodium phosphate, 1M sodium chloride, 0.1% CHAPS, pH 7.4). The column was eluted from below with elution buffer (0.1M acetic acid, 0.5M sodium chloride, 0.1% CHAPS, pH 2.5). Elution fractions were immediately titrated to pH 7.5 by addition of the appropriate volume of 0.1M sodium phosphate, 1.0M sodium carbonate, pH 9.0. u-PAR-containing fractions were identified by chemical cross-linking to the $^{125}$I-labelled amino terminal (ATF) fragment of urokinase, followed by SDS-PAGE and autoradiography. Purified u-PAR samples for amino acid analysis or NH$_2$-terminal amino acid sequencing were dialyzed against 0.1% acetic acid and lyophilized.

Protein labelling with $^{125}$I.

$^{125}$I-labelling of ATF was performed as described previously (Nielsen et al., 1988), except that 0.1% Triton X100 was replaced by 0.01% Tween 80. Purified u-PAR, concentrated by freeze-drying after dialysis against 0.1% acetic acid, was iodinated in the same manner, except that 1.5 µg of protein was treated with 250 µCi $^{125}$I in a volume of 25 µl.

Chemical cross-linking assay.

Cross-linking of u-PAR in complex mixtures or purified fractions to $^{125}$I-labelled ATF was performed as described for solubilized receptor (Nielsen et al., 1988), except that 2 mM disuccinimidylsuberate (DSS) was used for cross-linking. Cross-linking of purified u-PAR to DFP-treated u-PA for analysis by SDS-PAGE and silver-staining was performed in the same manner, except that non-labelled DFP-treated u-PA was used as the ligand.

Enzymatic deglycosylation.

For the deglycosylation studies on u-PAR in cell lysates and detergent fractions, the receptor was selectively labelled before the degradation by chemical cross-linking to $^{125}$I-labelled ATF.

Lyophilized, purified u-PAR was radioiodinated directly.

For complete removal of N-bound carbohydrate, the samples were denatured under mildly reducing conditions by the addition of SDS and dithiothreitol to final concentrations of 0.5% and 1.6 mM, respectively, and boiling for 3 minutes. Aliquots of the denatured samples (10 µl) were adjusted to include 200 mM sodium phosphate, pH 8.6, 1.5% Triton X-100, 10 mM 1,10 phenanthroline (added from a methanol stock solution) and either 1 unit of peptide:N-glycosidase F (N-glycanase, Genzyme), or no enzyme, in a total volume 30 µl. Deglycosylation was performed at 37° C. for 20 hours. During studies on non-fractionated cell lysates obtained after lysis with CHAPS, 100 mM β-mercaptoethanol was used for reduction instead of dithiothreitol, and 10 mM EDTA was included during deglycosylation instead of 1,10 phenanthroline.

For desialylation, 70 µl lysate samples labelled by cross-linking to $^{125}$I-ATF, were made up to 200 µl with 0.05M sodium acetate, pH 5.0. 90 µl aliquots of the mixture received either 14 µl of 33 ng/µl neuraminidase (Boehringer-Mannheim) or no enzyme. Desialylation was performed overnight at 37° C.

Results

Purification.

PMA-stimulated U937 cells were acid-treated to remove any surface-bound u-PA and lysed in a Triton X114 containing buffer. The detergent extract was subjected to temperature-induced phase separation, and the isolated detergent phase was used as the raw material for affinity chromatography. The acid eluates were neutralized and analyzed, either directly or after concentration by dialysis against 0.1% acetic acid and lyophilization. The electrophoretic appearance of the purified material is shown in FIGS. 1A–1C.

After SDS-PAGE and silver staining (FIG. 1A), the eluted protein migrated as one broad band, covering the range from approximately 55 to 60 kDa. Outside this range, no protein material was detected. A single band with the same apparent molecular mass was also found when SDS-PAGE was performed under nonreducing conditions (FIG. 1C, lane 5).

Analysis for binding activity toward the ATF of urokinase was performed by chemical cross-linking to $^{125}$I-labelled ATF followed by SDS-PAGE and autoradiography. ATF-binding activity co-eluted with silver-stainable protein. The conjugate formed between ATF and the purified protein migrated as a 70–75 kDa component during electrophoresis (FIG. 1B, lane 2). As demonstrated previously for partially purified u-PAR (Nielsen et al., 1988), the formed conjugate was indistinguishable from the cross-linked product formed with ATF on intact, PMA-stimulated U937 cells (not shown), as well as in non-purified detergent extracts from the same cells. Binding and cross-linking to $^{125}$I-labelled ATF was specific and saturable. Thus, it could be competed for by an excess of unlabelled ATF, active u-PA or DFP-treated u-PA, while no competition was obtained with unrelated proteins such as, for example, bovine serum albumin, or with related proteins, such as t-PA, plasminogen or epidermal growth factor (FIG. 1B).

To study the functional integrity and the purity of the purified protein, a cross-linking experiment was performed with non-labelled components (FIG. 1C). In this experiment, DFP-treated u-PA was chosen as the u-PAR-specific ligand instead of ATF, since, because of the higher molecular weight, this ligand would lead to a conjugate clearly separable from the purified protein itself by SDS-PAGE. It is seen that all protein material present in the purified preparation was able to bind to the nonlabelled ligand (compare lanes 4 and 3), thus confirming the identity to u-PAR (Nielsen et al., 1988) and the purity of the purified protein. The binding capability was indeed a property of the only protein detectable in the preparation by silver staining.

Quantification by amino acid analysis indicated a purification yield of 6–9 μg of polypeptide (corresponding to about 10–15 μg of u-PAR glycoprotein; see below) from $6 \times 10^9$ cells.

Amino acid composition and NH$_2$-terminal amino acid sequences.

The amino acid composition of the purified protein after preparative electrophoresis, electroblotting and alkylation with iodoacetamide is shown in Table 1. This composition includes a strikingly high content of cysteine residues. Further, it is noted that rather few lysine residues are present. The analysis system employed allows the quantification of glucosamine and galactosamine in addition to the amino acids. Glucosamine was detected in an amount corresponding to approximately 30 moles of N-acetylglucosamine per mole of protein, correcting for loss during hydrolysis. In contrast, no galactosamine was identified.

The high number of glucosamine residues detectable after acid hydrolysis, as well as the large decrease in apparent molecular mass following treatment with peptide:N-glycosidase F (see below), indicate that large side chains of N-linked carbohydrate are present in the protein. The failure to detect any galactosamine indicates that this type of O-linked carbohydrate is absent in u-PAR. However, the presence of other O-linked oligosaccharides that escape detection by amino acid analysis cannot be excluded.

Two amino acid sequencing experiments were performed. In the first sequencing experiment, direct NH$_2$-terminal sequencing of affinity-purified u-PAR was performed after dialysis and lyophilization. A partial sequence (Table 2A) was obtained, and it was demonstrated that only one sequence was present in the purified material.

In the second sequencing experiment, dialyzed and lyophilized, purified u-PAR was subjected to Tricine-SDS-PAGE, electroblotted onto a PVDF-membrane, Coomassie-stained, alkylated, and excised as described above, and then subjected to NH$_2$-terminal sequencing. This sequence is shown in Table 2B.

As seen in Table 2, all amino acid residues identified proved identical when comparing the two sequences. Furthermore, positions 3, 6 and 12, which were identified only in the second experiment, all proved to be cysteines. Thus, the lack of any identification at these positions in the first experiment was to be ascribed to the lack of alkylation. It was clear that the only detectable NH$_2$-terminal sequence in the preparation was associated with the electrophoretic mobility of u-PAR. Consequently, no additional sequences were hidden in the form of, for example, low molecular weight peptide components associated with the major polypeptide chain.

A search in the Georgetown University protein database did not reveal any identity, nor even pronounced homology, of the u-PAR NH$_2$-terminal amino acid sequence to any known protein.

The amino terminus, like the amino acid composition of the entire protein, is rich in cysteine residues.

Data for probe construction (Example 2) were derived from the sequencing shown in Table 2A. For this construction, position 6 of the amino acid sequence was tentatively assigned Asn; see footnote a of Table 2A.

Glycosylation.

Purified $^{125}$I-labelled u-PA receptor was treated with Peptide:N-glycosidase F. This enzyme is capable of removing all kinds of N-bound carbohydrate, the cleavage site being between the asparagine side chain and the innermost N-acetyl glucosamine residue (Tarentino et al., 1985). FIG. 2 shows the electrophoretic appearance of the deglycosylated protein. The electrophoretic band observed after autoradiography of the $^{125}$I-labelled protein was always slightly broader than that seen after direct protein staining. However, the reaction turned the heterogeneous 55–60 kDa receptor (lane 1) into a deglycosylated protein of only 35 kDa that migrated as a much sharper band (lane 2), thus further confirming that the initially heterogeneous material all represented variants of the same protein.

Glycosylation heterogeneity and variation among cell lines.

In another series of experiments, unpurified detergent fractions from cell lysates, or non-fractionated lysates, containing the receptor were subjected to treatment with the same enzyme as used above. In these experiments, a selective labelling of u-PAR was performed before the deglycosylation reaction by chemical cross-linking to $^{125}$I-labelled amino terminal fragment (ATF) of urokinase (Nielsen et al., 1988).

It is seen (FIG. 3) that the cell lysates from which the receptor was purified gave rise to a 70–75 kDa u-PAR-ATF conjugate (lane 1) that could be deglycosylated to yield an approximately 50 kDa product (lane 3). ATF is known not to contain N-bound carbohydrate. Thus, as the change in apparent molecular weight was the same as that seen for the purified protein above, this experiment provided independent evidence that the heavy glycosylation found is indeed a property of the only significant ATF binding component in the detergent lysates of these cells.

When cross-linking was performed on nonstimulated U937 cell extracts (FIG. 3, lane 2), the conjugate formed reproducibly migrated with a slightly higher electrophoretic mobility than that found after PMA stimulation, the apparent molecular mass being 70 kDa. After deglycosylation, however, the conjugates from the PMA-treated and the non-treated cells became indistinguishable (compare lanes 3 and 4). The receptor purified from PMA-stimulated U937 cells, therefore, is a glycosylation variant of that present in non-stimulated cells.

When detergent lysates obtained from other cell lines were analyzed by chemical cross-linking to ATF, variations in the electrophoretic migration of the radiolabelled product were observed in certain cases. In these analyses, for comparison, individual adjustment of dilution factors was necessary in order to correct for the large variation in u-PAR content among various cell types (Nielsen et al., 1988). In separate experiments, however, it was assured that the dilution had no effect on the migration of the individual conjugates.

Including the patterns described above, a total of 4 distinguishable electrophoretic patterns were found. As reported previously (Nielsen et al., 1988), the majority of cell lines yielded a single conjugate band of 70 kDa, as was the case for e.g. U937 cells not treated with PMA (FIG. 3, lane 2). Thus, this pattern was found for e.g. A-431 epidermoid carcinoma cells, HeLa cervix carcinoma cells, 5637 bladder carcinoma cells, HCT 116 colon carcinoma cells, AV3 amnion cells, JEG-3 choriocarcinoma cells, and Chang conjunctiva cells.

The fibrosarcoma cell line HT-1080 contained a third u-PAR variant, giving rise to a single conjugate band of a slightly lower molecular weight (approximately 65 kDa; not shown).

The fourth pattern was found during studies on a strain of U937 cells different from the strain used as raw material for purification. When not treated with PMA, this strain (here designated U937a) showed the same conjugate band as did the above U937 cells. However, the response to PMA treatment was reproducibly different. Thus, PMA-treated U937a cells gave rise to two conjugate bands. The uppermost band seemed identical to that found in PMA-treated U937. The lower band appeared sharp and migrated as a 55 kDa component (not shown). The latter band was found only after cross-linking in solubilized material. When cross-linking was performed on intact cells (Nielsen et al., 1988), only the uppermost band was present (not shown), suggesting that the lower band could represent an intracellular precursor or degradation product of the receptor.

However, when samples representing the 4 patterns above were subjected to enzymatic deglycosylation after the cross-linking to $^{125}$I-ATF, the molecular weight variation was abolished. The resulting conjugate band was sharp, and migrated as a 50 kDa component, irrespective of the identity of the parent cell line (not shown).

Thus, N-bound glycosylation was responsible, not only for molecular u-Par heterogeneity within the PMA-stimulated U937 line and occurrence of two bands in the PMA-stimulated U937a line, but also for the electrophoretic difference between u-PARs from non-stimulated and PMA-stimulated U937 cells and for the variation among different cell lines (i.e. HT-1080 fibrosarcoma cells compared to the other cell lines tested).

Removal of sialic acids.

The above cross-linking labelling system for u-PAR in unpurified detergent fractions was employed for the study of enzymatic desialylation (not shown). Neuraminidase treatment of cross-linked detergent fractions from PMA-stimulated U937 cells led to an approximately 5 kDa reduction in the apparent molecular weight of the ATF-u-PAR conjugate. Thus, the glycosylation includes several sialic acid residues. The change in molecular weight, though undoubtedly present, appeared somewhat smaller when U937 cells without PMA-stimulation were used in the desialylation experiment. However, a preliminary comparison suggested that sialylation could not account for the whole difference between the u-PARs in non-stimulated and PMA-stimulated cells.

TABLE 1

Amino acid composition of affinity purified u-PAR, determined after Tricine-SDS-PAGE, electroblotting onto a PVDF membrane, and alkylation

| | |
|---|---|
| Asp/Asn | 33.2 |
| Thr[a] | 21.4 |
| Ser[b] | 26.3 |
| Glu/Gln[c] | 43.2 |
| Pro | 11.4 |
| Gly | 28.2 |
| Ala | 8.4 |
| Cys (as Cys(Cm)) | 28.4 |
| Val | 11.9 |
| Met[d] | 7.7 |
| Ile | 6.7 |
| Leu | 26.5 |
| Tyr | 8.0 |
| Phe | 5.7 |
| His | 12.8 |
| Lys | 11.1 |
| Arg | 20.0 |
| Glucosamine[e] | 30.8 |

[a]Corrected for a 5% loss during hydrolysis.
[b]Corrected for a 10% loss during hydrolysis.
[c]Slight overestimation possible, due to formation of pyro-glutamic acid in amino acid standard mixture.
[d]Corrected for a 30% loss normally observed during electrophoresis and blotting (35).
[e]Corrected for a 50% loss during hydrolysis.

Hydrolysis of 70 pmol of protein was performed for 20 hours directly on the PVDF membrane. The number of residues is calculated assuming a total of 310 residues. Correction for losses during electrophoresis and blotting (Met) and during hydrolysis (Thr, Ser, glucosamine) has been performed according to correction factors found for standard proteins analyzed under the same conditions.

TABLE 2

N-terminal amino acid sequence of u-PAR (SEQ ID NO: 1). Parentheses indicate an identification classified as tentative. Question mark indicates no identification. Where footnotes are present, they indicate the best guess.

A. Direct sequencing of affinity purified u-PAR after dialysis against 0.1M acetic acid and lyophilization. The initial yield was 70 pmol PTH-Leu at step 1. Note that direct sequencing does not allow the identification of cysteine residues.

| Res. no. | 1 | 2 | 3 | 4 | 5 | 6 |
|---|---|---|---|---|---|---|
| Amino acid residue | Leu | ? | ? | Met | Gln | ?[a] |
| Res. no. | 7 | 8 | 9 | 10 | 11 | 12 |
| Amino acid residue | Lys | Thr | Asn | Gly | Asp | ? |
| Res. no. | 13 | 14 | 15 | 16 | | |
| Amino acid residue | Arg | Val | (Glu) | Glu | | |

B. Sequence obtained after Tricine-SDS-PAGE (SEQ ID NO: 2), electroblotting and alkylation. The PVDF membrane contained 35 pmol u-PAR, as estimated from a parallel amino acid analysis experiment (Table 1). The initial yield was 19.5 pmol PTH-Leu at step 1. The repetitive yield, based on Leu 1, Leu 19 and Leu 23, was 96%. Cys indicates the

TABLE 2-continued

N-terminal amino acid sequence of u-PAR (SEQ ID NO: 1).
Parentheses indicate an identification classified as tentative.
Question mark indicates no identification. Where footnotes are
present, they indicate the best guess.

identification of the PTH derivative of carboxymethyl cysteine
in the alkylated protein.

| Res. no. | 1 | 2 | 3 | 4 | 5 | 6 |
|---|---|---|---|---|---|---|
| Amino acid residue | Leu | ? | Cys | Met | Gln | Cys |
| Res. no. | 7 | 8 | 9 | 10 | 11 | 12 |
| Amino acid residue | Lys | Thr | Asn | Gly | Asp | Cys |
| Res. no. | 13 | 14 | 15 | 16 | 17 | 18 |
| Amino acid residue | (Arg) | Val | Glu | Glu | (His) | Ala |
| Res. no. | 19 | 20 | 21 | 22 | 23 | 24 |
| Amino acid residue | Leu | Gly | Gln | ?[b] | Leu | ?[c] |
| Res. no. | 25 | 26 | 27 | 28 | 29 | 30 |
| Amino acid residue | (Arg) | Thr | (Thr) | Ile | Val | ?[d] |

[a]Asn?
[b]Asp?
[c]Arg/Cys?
[d]Arg/Thr?

EXAMPLE 2

Isolation and Identification of the Ligand and Binding Domain of u-PAR

Experimental Procedures

Purified u-PAR was obtained from phorbol-12-myristate-13-acetate treated U937 cells as described above. All the protein detectable in the purified preparation by SDS-PAGE and silver-staining was able to bind to non-labelled DFP-treated u-PA or ATF in a chemical cross-linking assay as described above.

Enzymatic digestion

Chymotrypsin (67 u/mg) and tosylphenylchloromethylketone-treated trypsin (255 u/mg) were from Worthington Biochemical Corporation, Freehold, N.J. Endoproteinases Glu-C and Lys-C (sequencing grade) and bromelain were from Boehringer Mannheim, FRG. Search for degradation conditions was carried out by overnight incubation of purified u-PAR (3 µg/ml, used directly in the form of neutralized affinity column eluate obtained as described above) with the protease indicated, added in the form of a dilution series (final concentrations ranging from 8 ng/ml to 1 µg/ml, or to 0.2 µg/ml in the case of Lys-C). For systematic studies on degradation with chymotrypsin, purified u-PAR was concentrated by dialysis and lyophilization as described above and redissolved at 30 µg/ml final concentration in 0.05M Tris/HCl, 0.05% CHAPS, pH 8.1, followed by addition of chymotrypsin (40 ng/ml, or as indicated). After incubation for 7 h at 37° C., the degradation was stopped by addition of 1 mM phenylmethylsulfonylfluoride (Merck, FRG), added in the form of a fresh 20 mM stock solution in dimethylsulfoxide.

Chemical cross-linking assay for ligand-binding activity of u-PAR and u-PAR fragments ATF (amino acid residues nos. 1–135 of human urokinase) was a kind gift from Dr. G. Cassani, Le Petit, Italy. Chemical cross-linking of intact or degraded u-PAR to $^{125}$I-labelled ATF, using N,N'-disuccinimidylsuberate (DSS), was performed as described above. Visualization of the formed cross-linked conjugates was performed by SDS-PAGE according to Laemmli (supra) on slab gels, followed by autoradiography.

In some experiments, non-labelled ATF was used as the ligand. These experiments were performed in the same manner, except that the protein concentrations were those indicated and that electrophoretic analysis was performed by Tricine-SDS-PAGE and silver-staining (see Example 4 below).

Triton X-114 phase separation for hydrophobicity analysis of ATF-binding components Intact or chymotrypsin-treated u-PAR was diluted in 0.1M Tris/HCl, 1% Triton X-114, pH 8.1, at 0° C. and incubated for 5 min at 37° C. The resulting detergent and water phases, respectively, were separated by centrifugation. Each phase was made up to the starting volume by addition of 0.1M Tris/HCl, pH 8.1, after which CHAPS (0.25% final concentration) was added in order to avoid renewed phase separation. The presence of ATF-binding components in each phase was analyzed by chemical cross-linking to $^{125}$I-ATF (see above).

Deglycosylation analysis

For enzymatic deglycosylation, samples cross-linked to $^{125}$I-labelled ATF were 1.5-fold diluted and denatured by boiling for 3 min in the presence of 0.5% SDS and 1.7 mM dithiothreitol. The denatured samples were further 6-fold diluted by addition of a deglycosylation buffer, to include final concentrations of 0.12M sodium phosphate, 0.9% Triton X-100, 5 mM 1,10 phenanthroline and 33 U/ml Peptide:N-glycosidase F (N-glycanase; Genzyme, Boston, Mass.), respectively, pH 8.6. 1,10 phenanthroline was added in the form of a 250 mM stock solution in methanol. Deglycosylation was performed by overnight incubation of the samples at 37° C.

Electrophoretic techniques for fragment analyses and isolation of components for amino acid sequencing Samples of degraded u-PAR for amino acid sequence analysis were concentrated by lyophilization before electrophoresis. Samples for gels to be silver-stained were analyzed directly.

Tricine-SDS-PAGE according to Schägger and von Jagow (*Anal. Biochem.* 166, 1987, 368–379) was performed as described above, except that 10% T, 3% C gels were used. Silver-staining was carried out using the reagent system of Heukeshoven and Dernick (*Electrophoresis* 9, 1988).

Electroblotting of samples onto polyvinylidene difluoride (PVDF) membranes for amino acid sequencing was performed as described by Ploug et al. (*Anal. Biochem.* 181, 1989, 33–39), except that the concentrations of methanol and dithioerythritol in the transfer buffer were 15% and 0.5 mM, respectively, and that blotting was performed for 90 min at a current density of 0.4 mA/cm$^2$. No alkylation was performed.

Amino acid sequencing

NH$_2$-terminal amino acid sequencing was performed directly on excised pieces of PVDF membranes, containing electroblotted protein bands (above). An Applied Biosystems protein sequencer, model 477A, was used.

Alignment and homology analyses

The search for internal repeats in u-PAR, the construction of multiple alignment and consensus sequences for the internal repeats were performed according to the method described by L. Patthy (*J. Mol. Biol.* 198, 1987, 567–577). The National Biomedical Research Foundation/Protein Identification Resource database was searched for homologous sequences using a procedure suitable for detection of distant homologies (L. Patthy, supra; L. Patthy, *J. Mol. Biol.*

202, 1988, 689–696; L. Patthy, *Cell* 61, 1990, 13–14). In this procedure, similarity to a consensus sequence characteristic of a protein family is used to decide whether a test protein has the features typical of that protein family.

Results

Liberation of a ligand-binding fragment by proteolytic digestion of u-PAR

In order to study the structural features of u-PAR important for the ligand-binding capability, samples of the purified receptor were treated with dilution series of various proteases under non-denaturing conditions and subsequently analyzed for binding activity towards $^{125}$I-labelled ATF, using the chemical cross-linking assay (L. S. Nielsen et al., *J. Biol. Chem.* 263, 1988, 2358–2363).

Of the five proteases tested, trypsin and chymotrypsin were capable of eliminating the ligand-binding activity of the receptor, whereas Lys-C, Glu-C and bromelain had no effect. However, while treatment with trypsin, in the whole concentration range tested, led to the complete disappearance of all cross-linking activity, low concentrations of chymotrypsin generated a distinct, ligand-binding fragment of u-PAR, as evidenced by the formation of a conjugate with ATF of approximately $M_r$ 32,000 (FIGS. 4A and 4B, lane 3). This component was absent in those samples where the intact receptor was tested (lane 2), showing only the $M_r$ 70–80,000 conjugate described above. The intensity of the latter conjugate was strongly reduced in the chymotrypsin-treated samples, reflecting a rather efficient cleavage of the active receptor (see also below; this band disappeared completely when higher chymotrypsin concentrations were used). No other ATF-binding products were detected.

The electrophoretic patterns were identical, whether SDS-PAGE was performed with reduced or non-reduced samples (compare FIG. 4A and 4B); in particular, the conjugates formed between ATF and the chymotrypsin cleavage product of u-Par migrated with the same apparent $M_r$.

Figure 5B:
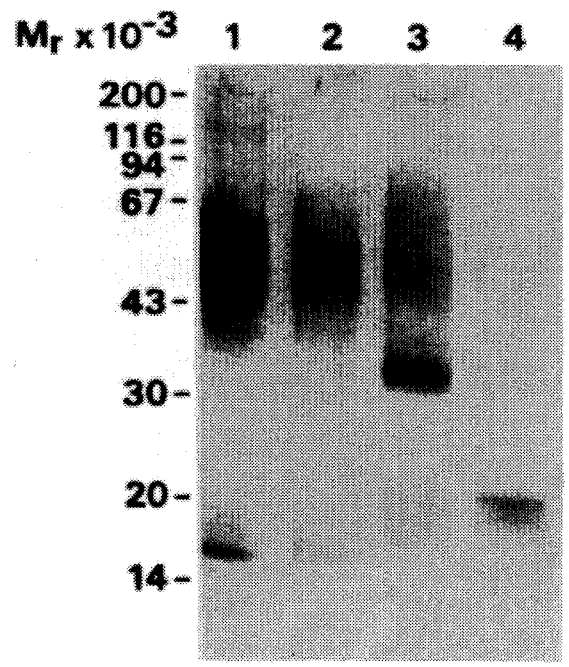
Figure 5A:
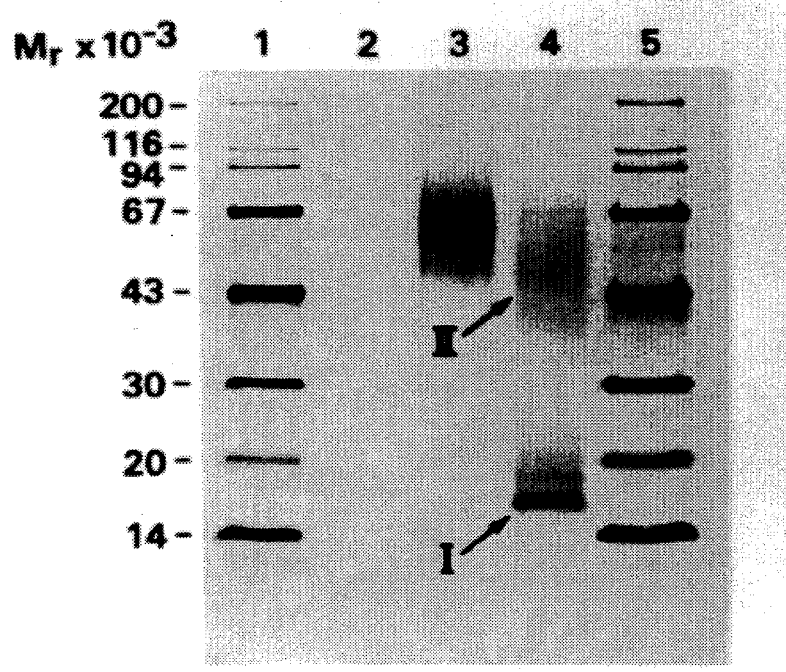

Direct analysis of the chymotrypsin-treated samples by SDS-PAGE and silver staining revealed a very simple cleavage pattern (FIG. 5A). The intact u-PAR, purified from the present source, migrated as a heterogeneous component covering the $M_r$ 50–65,000 region (lane 3), this heterogeneity being due to variations in N-linked carbohydrate (see above). The chymotrypsin treatment led to the appearance of one major fragment of $M_r$ 16,000, which migrated as a sharp band, and a heterogeneous component in the $M_r$ 35–50,000 range, which appeared to represent the rest of the molecule (i.e., the starting material degraded by the removal of an approximately $M_r$ 16,000 fragment) (lane 4). In addition, a small amount of intact u-PAR was observed in this sample, consistent with the residual ligand-binding activity observed above.

This pattern suggested that the ligand-binding u-PAR degradation product was identical to the $M_r$ 16,000 fragment, since this molecular weight is in agreement with the formation of an $M_r$ 32,000 conjugate with ATF (apparent $M_r$ 18,000). Alternatively, however, the cross-linking activity could be due to a trace fragment undetected by silver staining. To test this possibility, a cross-linking experiment was performed with non-labelled components, followed by SDS-PAGE and silver staining of the formed conjugates (FIG. 5B).

It is seen that the electrophoretic appearance of the chymotrypsin-treated sample (lane 1) was unaffected by the performance of the cross-linking procedure when no ligand was added (lane 2). On the other hand, when cross-linking was performed in the presence of ATF (lane 3), a unique $M_r$ 32,000 product was formed, while the $M_r$ 16,000 band almost disappeared. Some staining was observed in the $M_r$ 18–20,000 region in this sample, but this was due to the surplus of added ATF, which migrated with this electrophoretic mobility in the electrophoretic system used (lane 4).

Thus, the $M_r$ 32,000 conjugate was clearly detectable by silver staining, and since its formation was accompanied by consumption of the $M_r$ 16,000 fragment, this cleavage product was directly responsible for the ligand-binding activity.

Degradation of u-PAR using higher concentrations of chymotrypsin (0.2–1 µg/ml) led to the appearance of an additional silver-stainable fragment which migrated as an $M_r$ 13,000 component in SDS-PAGE under reducing conditions (not shown). The use of a chymotrypsin dilution series indicated that this product arose from further degradation of the ligand-binding fragment; its formation was accompanied by the disappearance of the $M_r$ 16,000 component, while the larger fragment was not degraded. When parallel analyses were performed using the $^{125}$I-ATF cross-linking assay, no conjugate that included the $M_r$ 13,000 fragment could be detected. The gradual disappearance of the $M_r$ 16,000 fragment on the silver-stained gel was accompanied by the disappearance of the $M_r$ 32,000 radiolabelled conjugate in the cross-linking assay, while no new radiolabelled band appeared, thus indicating that the ligand-binding ability was lost. The cross-linked product of $M_r$ 70–80,000 also gradually disappeared and was completely absent after treatment of u-PAR with 1 µg of chymotrypsin/ml. This experiment therefore also confirmed that the $M_r$ 70–80,000 cross-linked ATF-conjugate (FIGS. 4A and 4B) was formed exclusively by the residual, intact u-PAR present after treatment with the lower amounts of chymotrypsin and not by the $M_r$ 35–50,000 cleavage product which was unchanged on the silver-stained gel also at the highest chymotrypsin concentrations.

Identification of the ligand-binding fragment

Approximately 20 µg of purified u-PAR was treated with chymotrypsin (40 ng/ml) under the same conditions as used above for the generation of the $M_r$ 16,000 fragment. The sample was concentrated by lyophilization and subjected to Tricine-SDS-PAGE, using the same system as employed in FIGS. 5A and 5B. The gel was electroblotted onto a PVDF membrane, and after Coomassie-staining, the following stained areas were ex- from the membrane (see arrows in the parallel electrophoretic pattern shown in FIG. 5A): I) the $M_r$ 16,000 cleavage product; II) the stained area corresponding to the $M_r$ 35–45,000 region, i.e. the region containing the larger cleavage product, excluding the residual undegraded u-PAR.

The excised polypeptides were subjected to $NH_2$-terminal amino acid sequencing to yield the sequences shown in Table 3. Only one sequence was found in each case. The $M_r$ 16,000 fragment had the same $NH_2$-terminus as that of the intact u-PAR shown above, while the larger cleavage product had $NH_2$-terminus at residue no. 88 of the intact protein, as identified by comparison with the complete amino acid sequence of u-PAR, deduced from cDNA sequencing (Roldan et al., 1990).

Hydrophilicity and Dissociation After Cleavage

Temperature-induced Triton X-114 phase separation (C. Bordier, *J. Biol. Chem.* 256, 1981, 1604–1607) has been shown to direct the intact u-PAR to the detergent phase (Behrendt et al., *J. Biol. Chem.* 265, 1990, 6453–6460), this hydrophobicity being due to the presence of a COOH-terminal glycosyl-phosphatidyl-inositol glycolipid membrane anchor (Example 3). In order to analyze whether the ligand-binding u-PAR fragment remained attached to the rest of the molecule by non-covalent forces or whether it was dissociable under non-denaturing conditions, chymotrypsin-treated, purified u-PAR was subjected to detergent phase separation, and the resulting phases were analyzed in the $^{125}$I-ATF cross-linking assay (FIG. 6). The radiolabelled conjugate of $M_r$ 70–80,000 (i.e. the adduct of $^{125}$I-ATF and the residual, intact u-PAR after digestion) was formed almost exclusively in the detergent phase, while the $M_r$ 32,000 conjugate (reflecting the activity of the ligand-binding u-PAR fragment) was observed only in the water phase (compare lanes 2 and 3). The former observation provided an internal control of the phase separation, and furthermore it assured that the COOH-terminal, hydrophobic character had not been lost as caused by e.g. contaminating phospholipases or undetected proteolytic attack. The exclusive occurrence of the $NH_2$-terminal, ligand-binding fragment in the water phase therefore indicated that this fragment had dissociated from the COOH-terminal, glycolipid-containing part in the absence of denaturing agents.

Glycosylation u-PAR contains large amounts of N-linked carbohydrate which can be removed by treatment with the enzyme Peptide:N-glycosidase F (see above). When samples containing $^{125}$I-ATF cross-linked to chymotrypsin-treated u-PAR were treated with this enzyme (FIGS. 4A and 4B), the $M_r$ 32,000 conjugate was deglycosylated to yield a conjugate of approximately $M_r$ 25,000 (compare lanes A2 and B2). The conjugate formed with intact u-PAR (lane A1) was converted to the $M_r$ 50,000 product (lane B1), described above. Thus, the ligand-binding u-PAR fragment is glycosylated.

Thus, an $M_r$ 16,000 chymotryptic fragment of u-PAR was generated which, at least qualitatively, retained the binding capability towards the ligand. Quantitative binding studies were not possible with the amounts available, but the activity was demonstrated by chemical cross-linking after incubation with the radiolabelled ligand present at 1 nM; i.e. using the same conditions as previously found optimal for the demonstration of the binding activity of the intact receptor (see above).

Amino acid sequencing showed that the ligand-binding fragment had the same $NH_2$-terminus as uncleaved u-PAR, and that cleavage had occurred between Tyr 87 and Ser 88 of the intact protein. The latter amino acid residue constituted the single detectable $NH_2$-terminus in the only other degradation product observed (i.e. the larger, non-ligand-binding component), thus reflecting a strikingly specific cleavage. The molecular mass heterogeneity in this larger fragment reflected that of the parent protein (FIG. 5A), which has previously been shown to be due to glycosylation variation (see above).

The ligand-binding fragment probably covered the whole sequence 1–87, though additional cleavages close to the new COOH-terminus (which was not identified directly) cannot be excluded. The apparent molecular mass of this fragment when analyzed by SDS-PAGE (i.e. $M_r$ 16,000) was somewhat higher than that expected for an 87 amino acid residue fragment, but this discrepancy could be explained by the presence of N-linked carbohydrate. Thus, after deglycosylation, the conjugate of $^{125}$I-ATF and the ligand-binding fragment migrated as an $M_r$ 25,000 conjugate in good agreement with the expected size for an adduct formed between ATF and an 87 amino acid residue component.

All the properties observed in the present study suggest that the $NH_2$-terminal $M_r$ 16,000 fragment constitutes a distinct structural and functional domain within u-PAR. Thus, it was a well-defined ligand-binding fragment, liberated by mild protease treatment. It was not disulfide-linked to the rest of the protein, since the $M_r$ 32,000 cross-linked conjugate formed by this fragment and $^{125}$I-ATF could be observed after non-reducing sample treatment in SDS-PAGE (see FIG. 4B). Furthermore, when subjected to Triton X-114 phase separation (i.e. under non-denaturing conditions), it dissociated from the rest of the protein, and its lack of detergent binding suggests that it is water-soluble. Finally, its ability to bind the ligand was, at least qualitatively, independent on the rest of the protein, since its binding activity could be demonstrated after detergent phase separation in the same experiment.

The experimental finding that the $M_r$ 16,000 fragment behaves as a distinct, structural domain is in accordance with an analysis of internal homology in u-PAR. This analysis reveals that the amino acid sequence of the receptor, deduced from cDNA sequencing (Roldan et al., 1990), contains three repeats (repeat 1, residues 1–92; repeat 2, residues 93–191; repeat 3, residues 192–282) characterized by a unique pattern of cysteine residues (FIG. 8). In this alignment, the sequences of the second and third repeats show 22% identity; all the ten cysteines of the second repeat align with the ten cysteines of the third repeat. The first repeat appears to be more distantly related (12 and 16% identity with the third and second repeats, respectively); seven of its eight cysteines align with those of the other two repeats. These observations imply that u-PAR is organized in three structural domains; the functionally active fragment observed experimentally corresponds to the first repeat, liberated by cleavage of an inter-repeat bond (FIG. 8). This proposed domain-structure also explains the striking specificity of chymotryptic digestion of u-PAR, (i.e., by the general sensitivity of mobile peptide segments, like hinges connecting domains, to proteolysis).

The presence of the three repeats in u-PAR suggests that the receptor arose as a result of internal triplication of an ancestral domain. Indeed, a search of the protein sequence data base identified some homologous proteins possessing just a single copy of this cysteine-rich unit; the extracellular parts of T-cell-activating proteins/Ly 6 antigens (K. P. LeClair et al., *EMBO J.* 5, 1986, 3227–3234; Palfree et al., *Immunogenetics* 26, 1987, 389–391; Palfree et al., *J. Immunol.* 140, 1988, 305–310; H. Reiser et al., *Proc. Natl. Acad. Sci. USA* 85, 1988, 2255–2259) and the Ly-6-related squid protein Sgp-2 (A. F. Williams et al., *Immunogenetics* 27, 1988, 265–272) are related to the internal repeats of u-PAR (FIGS. 5A and 5B). Interestingly, like u-PAR, these proteins are attached to the cell membrane by a glycosyl-phosphatidyl-inositol anchor (A. F. Williams et al., *Immunogenetics* 27, 1988, 265–272; J. W. Hammelburger et al., *Biochem. Biophys. Res. Commun.* 148, 1987, 1304–1311). The existence of homologous glycophospholipid-anchored proteins with a solitary copy of the repeat-type found in u-PAR underlines the structural independence of these domains. Moreover, the presence of an even number of cysteines in each member of this novel domain-family is consistent with the assumption that the cysteines are involved in intradomain disulfide bonds. The fact that no disulfide bridges exist between the binding domain of u-PAR and the rest of the protein will strongly facilitate the study of the disulfide structure of the former, since only 8 out of the 28 cysteines in the u-PAR molecule are situated within residues nos. 1–87 of the deduced amino acid sequences of u-PAR.

A further chymotryptic cleavage of the $M_r$ 16,000 domain abolished the ligand-binding activity. This second cleavage occurred rather close to one of the termini of the $M_r$ 16,000 polypeptide, since an $M_r$ 13,000 product was demonstrated by SDS-PAGE under reducing conditions. It is not known whether the cleavage site involved was situated in the $NH_2$- or COOH-terminus of the $M_r$ 16,000 fragment since the amounts available were too small to allow $NH_2$-terminal amino acid sequencing of the $M_r$ 13,000 product. While the region involved in this second degradation step must be important for the binding activity of the $M_r$ 16,000 domain, it remains to be established whether it contains a linear binding determinant or whether conformational effects were responsible for the loss of activity observed.

The u-PAR amino acid sequence deduced from cDNA sequencing (Roldan et al., 1990) contains five sites potential for N-linked glycosylation; however, it has not been determined which of these are actually glycosylated in the mature protein. Since only one of these sites, i.e. Asn 52, is situated within the region of residues nos. 1–87, the deglycosylation experiment reported here identifies this asparagine as a glycosylated residue. However, the previously described carbohydrate-based difference, observed in the electrophoretic patterns of u-PAR when comparing two different strains of U937 cells after PMA stimulation (see above), was not connected to the ligand-binding domain. u-PAR preparations, purified from either of the two strains of cells, in both cases upon chymotrypsin treatment yielded an $M_r$ 16,000 ligand-binding fragment which migrated as a sharp band in SDS-PAGE. The electrophoretic difference between the parent proteins was reflected in the larger (i.e. non-ligand-binding) product (results not shown), as was the heterogeneity within each preparation, discussed above.

The functional importance which seems to be connected to u-PAR in plasmin-mediated cell surface proteolysis (V. Ellis et al., *J. Biol. Chem.* 264, 1989, 2185–2188; R. W. Stephens et al., *J. Cell Biol.* 108, 1989, 1987–1995) makes the present, separate ligand-binding domain a valuable reagent as a potential soluble u-PAR antagonist. Thus, a soluble molecule which competes with u-PAR for the binding of u-PA will be an important tool for the study of cell surface plasminogen activation in cellular invasiveness (L. Ossowski, *J. Cell Biol.* 107, 1988, 2437–2445; V. J. Hearing et al., *Cancer Res.* 48, 1988, 1270–1278) and may also have a therapeutic potential for interference with these processes.

TABLE 3

| $NH_2$-terminal amino acid sequences of chymotryptic u-PAR fragments and partial sequences of intact u-PAR. | |
|---|---|
| $M_r$ 16,000 fragment[1,2] | L R ? M Q ?(K)T N G D ? R V E E ? A ? G |
| u-PAR residue 1–20[4] | L R C M Q C K T N G D C R V E E C A L G |
| $M_r$ 35–50,000 fragment[1,3] | S R S R Y L E ?(I)S ? |
| u-PAR residue 88–98[5] | S R S R Y L E CI S C |

[1]Parentheses indicate that the identification was uncertain. Question mark indicates the lack of any identification.

[2]Determined by automatic sequencing of the electroblotted $M_r$ 16,000 u-PAR fragment (Band I of FIG. 5A). The initial yield was 24 pmol Leu at step 1. The repetitive yield, based on Gly (steps 10 and 20) was 96%. No other sequence could be detected (sequencing limit 2 pmol).

[3]Determined by automatic sequencing of the electroblotted $M_r$ 35–50,000 u-PAR fragment (Band II of FIG. 5A). The initial yield was 29 pmol Ser at step 1. The repetitive yield, based on Ser (steps 1, 3 and 10) was 90%. No other sequence could be detected (sequencing limit 2 pmol; 3 pmol for Glu and Gly).

[4]Sequence obtained from NH2-terminal amino acid sequencing of the intact protein (17), and from cDNA sequencing (18).

[5]Sequence deduced from cDNA sequencing (18). The preceding residue (i.e. No. 87) is a tyrosine.

EXAMPLE 3 u-PAR HAS A GLYCOSYL-PHOSPHATIDYLINOSITOL ANCHOR AND IS C-TERMINALLY PROCESSED

MATERIALS AND METHODS

Materials

PVDF membranes (Immobilon-P) were from Millipore. $N^w,N^{w'}$-dimethyl-Arg was from Sigma $N^w$-monomethyl-Arg from Calbiochem whereas $N^w,N^w$-dimethyl-Arg was a kind gift from Dr. T. Ogawa (University of Tokushima Japan). Ethanolamine was from Merck. $Na^{125}I$, [9,10(n)-$^3H$]-myristic acid (53 Ci/mmol), myo-[2-$^3H$]inositol (18.3 Ci/mmol) and [1-$^3H$] ethanolamine hydrochloride (19 Ci/mmol) were from Amersham.

Proteins

Acetylcholinesterases from human and bovine erythrocytes, phospholipase $A_2$ from bee venom and myelin basic protein from bovine brain were from Sigma. Phospholipase D from cabbage and phosphatidylinositol-specific phospholipase C from *Bacillus cereus* (PI-PLC) were from Boehringer Mannheim. u-PAR was purified from PMA-stimulated U937 cells as in Example 1. Active human u-PA was purchased from Serono and was DFP-inactivated as described (Nielsen et al., 1988); the amino terminal fragment (ATF) of u-PA was a kind gift from Dr. G. Cassani (LePetit, Italy). ATF, u-PAR and DFP-inhibited u-PA were radiolabelled as described (Nielsen et al., 1988) except that 0.1% (v/v) Triton X-100 was replaced by 0.1% (w/v) CHAPS in the case of u-PAR and by 0,01% (v/v) Tween 80 in the case of ATF and DFP-u-PA. Preparation of polyclonal rabbit antibodies against human u-PAR was carried out as described in Example 11.

Phospholipase Treatment of Intact U937 Cells

Adherent, PMA-stimulated U937 cells (approx. $2 \times 10^7$/dish) were initially washed with serum-free RPMI 1640 medium including 25 mM HEPES, pH 7.4 (Buffer A). The cells were subsequently acid treated for 3 min at room temperature in 50 mM glycine/HCl, 0.1M NaCl (pH 3.0) to dissociate any endogenously produced u-PA, bound to its receptor in an autocrine fashion. The supernatants were discharged immediately after neutralization with 0.2 vol of 0.5M HEPES, 0.1M NaCl (pH 7.5) and the cells were washed twice with buffer A. In some experiments exogenously added $^{125}$I-labelled DFP-uPA (1 nM) were allowed to rebind to the unoccupied u-PAR by incubation for 2 hours at 4° C. in buffer A followed by 3× wash in the same buffer without added ligand. Incubation of these adherent U937 cells with the various phospholipases were performed in buffer A at 37° C. on a shaking table.

In Vivo Labelling

Cell culture was performed as described in Example 1. Prior to metabolic labelling human U937 cells ($5 \times 10^7$ cells/dish) were PMA-stimulated (150 nM) for 5 hours in order to increase expression of u-PAR. For labelling with [$^3$H]ethanolamine and [$^3$H]myristic acid the cells were cultured in RPMI 1640 medium, while labelling with myo-[$^3$H]inositol was performed in Eagle's minimum essential medium. Both media were supplemented with: 2 mM L-glutamine, 5 mM Na-pyruvate, 200 units/ml penicillin, 25 µg/ml streptomycin, 25 mM HEPES (pH 7.4), 0.5 mg/ml defatted BSA and 4× normal concentration of non-essential amino acids. All tracers were added from stock solutions in 25 mg/ml defatted BSA, 0.1M HEPES (pH 7.4) to a final concentration of 0.1 mCi/ml in 10 ml media and metabolic labelling was allowed to proceed for 15 hours at 37° C. Subsequently, the adherent cells were acid treated, washed and lysed with 5 ml of ice-cold 1% precondensed Triton X-114, 0.1M Tris (pH 8.1), 10 µg/ml Trasylol, 1 mM PMSF and 0,2 mM $ZnCl_2$. Finally, detergent-phase separation was performed as described in Example 1.

Immunoprecipitation of Biosynthetically Labelled u-PAR

To each aliquot of 2 ml clarified detergent phase was added 12 µg of preimmune rabbit IgG and the mixture was incubated for 2 hours at 4° C. After addition of 100 µl of a 50% (v/v) suspension of Protein A Sepharose (Pharmacia) in 0.1M Tris (pH 8.1), 0.1% CHAPS and 0.1% defatted BSA, incubation at 4° C. was continued for 2 hours with concomitant mixing. The supernatant was recovered by centrifugation (5 minutes at 5,000×g) and incubation was proceeded overnight at 4° C. after addition of 12 µg of polyclonal anti-u-PAR rabbit IgG and finally for an additional 3 hours with a new aliquot of Protein A Sepharose as above. The immobilized immunocomplexes were then extensively washed in 0.1M Tris (pH 8.1)/0.1% CHAPS including either 0.1% (w/v) defatted BSA (once), 0.1% defatted BSA/1M NaCl (once) or without further additions (twice). The Protein A Sepharose thus washed was collected by centrifugation and finally suspended in 50 µl of 0.1M Tris (pH 6.8) containing 2% (w/v) SDS and boiled for 5 minutes before analysis by SDS-PAGE.

Tricine-SDS-PAGE and Amino Acid Analysis

Tricine-SDS-polyacrylamide gels were prepared according to Schägger and von Jagow, 1987 in a Bio-Rad Mini-Protean II apparatus (8 cm×7 cm×0.75 mm). The homogeneous gel (7.5% T and 3% C) was cast 1 day in advance and subjected to pre-electrophoresis at pH 8.45 with 0.5M Tris, 0.1% (w/v) SDS and 12 mM 3-mercaptopropionic acid (added as scavenger) for 4 hours at 15 mA/gel. Purified, lyophilized u-PAR was reduced by boiling for 2 minutes in 4% (w/v) SDS, 12% (w/v) glycerol, 50 mM Tris and 40 mM dithiothreitol at pH 6.8. The gel buffer used for pre-electrophoresis was replaced with the original electrophoresis buffer (Schägger and von Janow, 1987) except that 1 mM 3-mercaptopropionic acid was included in the catode buffer. Electrophoresis was performed at 60 V for 4 hours. Electrotransfer onto a 0.45 µm PVDF-membrane was performed at pH 11 in 10 mM 3-(cyclohexylamino)-1-propane sulfonic acid, 10% v/v methanol and 0.4 mM dithiotreitol by the semi-dry approach at 0.8 mA/cm$^2$ for 2 hours as previously described (Ploug et al., 1989).

The Coomassie stained u-PAR was prepared for amino acid analysis by acid hydrolysis directly on the excised PVDF-membrane at 110° C. in 100 µl of redistilled 6M HCl including 0.05% (w/v) phenol and 5 µl of 1% (w/v) DTDPA in 2M NaOH as published (Ploug et al., 1989). Amino acid analysis was performed on a Waters amino acid analyzer, equipped with o-phthaldialdehyde derivatization essentially as described (Barkholt and Jensen, 1989). However, the chromatographic system was modified slightly to increase resolution of basic amino acids. Elution was still performed by a pH-gradient resulting from mixing two non-halide buffers A and B (for composition see Barkholt and Jensen, 1989), but the gradient consisted of the following linear segments: initial eluant 100% A, 88% A and 12% B at 15 min, 60% A and 40% B at 24 min, 55% A and 45% B at 26 min, 50% A and 50% B at 36 min, 30% A and 70 B at 40 min, 25% A and 75% B at 64 min, 100% A at 65 min and 100% A from 65 to 70 min.

Miscellaneous Analyses

SDS-PAGE, chemical cross-linking with disuccinimyl suberate (DSS) and an analytical detergent phase separation was performed with Triton X-114 as described in Example 1.

Direct autoradiography (125I) and fluorography ($^3$H) were performed with an X-ray film (Kodak X-Omar) at −80° C. using intensifying screens (Cronex). In the case of fluorograms the X-ray film was pre-exposed (0,2–0,3 A) and the polyacrylamide gels were impregnated with Amplify according to the manufacturer's instructions (Amersham).

Results

Amino Acid Analysis of Purified u-PAR

Amino acid analysis of the purified u-PAR (see Example 1) revealed the presence of an unidentified compound in the acid hydrolysate that reacted with o-phthaldialdehyde and eluted just after ammonia during cation-exchange chromatography (FIG. 9A). A similar peak was observed when u-PAR was purified from non-stimulated U937 cells ($2\times10^{10}$ cells), but otherwise treated identically (data not shown). This unknown compound behaved as a covalent constituent of u-PAR, as it persisted within the purified protein despite boiling it in 2% SDS followed by Tricine-SDS-PAGE and electroblotting onto a 0.45 µm polyvinylidene difluoride (PVDF) membrane in the presence of 10% (v/v) MeOH. Furthermore, the compound was a specific constituent of the Coomassie stained u-PAR, as it was absent, when appropriate pieces of PVDF-membranes just above and below the protein stained area were excised and prepared for amino acid analysis by the same procedure (FIG. 9, insert). In addition, several stained proteins and peptides previously analyzed by this approach did not reveal the presence of this particular component (Ploug et al., 1989).

For amino acid analysis in this study, a special gradient was designed for the cation-exchange chromatography that allowed an increased resolution of common as well as various uncommon, basic amino acids without impairing reproducibility of their retention times (see Materials and Methods section). By this method the unidentified compound in u-PAR reproducibly eluted after 55.3 min, between ammonia (53.5 min) and arginine (60.8 min). As various physiological occurring arginine derivatives are expected to possess approx. similar retention times, several methylated arginine derivatives were tested, including: $N^w,N^w$-dimethylarginine (53.8 min), $N^w,N^{'w}$-dimethylarginine (54.4 min) and $N^w$-monomethylarginine (58.6 min). None of these retention times were in agreement with the one observed for the unidentified compound in u-PAR. However, when authentic ethanolamine was tested, it showed exactly the same retention time as that for the unidentified compound. Furthermore, upon hydrolysis of both human and bovine erythrocyte acetylcholinesterases, a compound with this retention time was also observed, whereas it was absent in the hydrolysate from e.g. myelin basic protein. Acetylcholinesterases isolated from erythrocytes contain ethanolamine as a covalent constituent in a glycolipid membrane anchor, while myelin basic protein possesses a partly methylated arginine residue. It is therefore concluded that u-PAR does contain ethanolamine, covalently linked to the protein by acid labile bonds (e.g. ester or amide bonds). Quantitative analysis of the data in FIG. 9A shows that each u-PAR molecule contains 2–3 ethanolamine residues (see also Table 4).

Release of u-PAR from Cell Surfaces by PI-PLC Treatment

The presence of ethanolamine in purified u-PAR suggests that this cellular receptor may be anchored to the plasma membrane by glycosyl-phosphatidylinositol (GPI). The majority of such GPI-anchored proteins are susceptible to bacterial phosphatidylinositol-specific phospholipase C (PI-PLC), which releases the proteins into the medium by removing the diacylglycerol portion of the glycolipid (Low, 1989). It was therefore investigated whether PI-PLC could release $^{125}$I-labelled DFP-treated u-PA, initially bound to the cell surface of PMA-stimulated U937 cells. As shown in FIG. 10, approx. 50% of the cell associated radioactivity was released within the first 15 min by PI-PLC. Furthermore, the rate of release was only slightly decreased when PI-PLC concentration was reduced to only 50 ng/ml (data not shown). In contrast, neither phospholipase $A_2$ (FIG. 10) nor phospholipase D (not shown) was able to induce any enhanced liberation of $^{125}$I-labelled DFP-u-PA from the cell surface as compared to the blind sample, although these phospholipases were present in rather high concentrations (>5 µg/ml, FIG. 10). Trypsin, on the other hand, efficiently released all cell surface associated radioactivity (not shown), thus demonstrating the physical accessibility of the receptor bound u-PA.

As shown in FIG. 11A, u-PA released to the medium by PI-PLC was essentially non-degraded and consisted primarily of intact two-chain u-PA (Mr 50,000) along with a smaller amount of its amino terminal fragment (ATF, Mr 17,000). The receptor-binding domain of u-PA resides in both of these components (Appella et al., 1987). Accordingly, these two molecular species did bind to the cell surface during preincubation with $^{125}$I-labelled DFP-u-PA. In contrast, the low molecular weight form of u-PA (Mr 33,000), devoid of the receptor-binding domain, was eliminated by the washing procedures. These data indicate that u-PA and ATF were released from the cell surface by PI-PLC, while they were specifically associated to u-PAR.

When cross-linking analysis was performed concomitantly with sampling in this experiment by addition of 1 mM disuccinimidyl suberate (DSS) to the withdrawn supernatants, soluble u-PA containing complexes were detected only in the media from the PI-PLC treated cells (FIG. 11B). The electrophoretic mobility of this conjugate in SDS-PAGE (Mr 110,000) was identical to that of a u-PA/u-PAR complex (Nielsen et al., 1988). The mock treated sample showed only free u-PA in the medium, reflecting a slow, spontaneous dissociation of u-PA from the u-PAR. This experiment further supports the interpretation that u-PA released by PI-PLC is in complex with u-PAR.

Finally, it was demonstrated directly that a specific release of the u-PAR protein itself by PI-PLC was the real cause for the observed release of the $^{125}$I-labelled ligands. In this experiment, PMA-stimulated U937 cells were initially acid treated to remove endogenous u-PA and then incubated with PI-PLC. Subsequently, the presence of any u-PA binding components released into the media was assayed by cross-linking to $^{125}$I-labelled DFP-u-PA. This experiment revealed that PI-PLC induced a fast conversion of the unoccupied u-PAR from a membrane-anchored form into a soluble protein (Mr 60,000) that still expressed high affinity towards $^{125}$I-labelled DFP-u-PA (FIG. 11C) as well as $^{125}$I-labelled ATF (data not shown). Furthermore, by SDS-PAGE and immunoblotting, a protein with similar Mr was detected in the serum-free medium after PI-PLC treatment of PMA-stimulated U937 cells, using a polyclonal mouse antiserum raised against purified human u-PAR (data not shown). Hence, this soluble protein resembles cell-associated u-PAR in both functional (binding specificity) and structural terms (Mr and antigenicity). Analysis of non-stimulated U937 cells in suspension revealed a similar PI-PLC dependent release of u-PAR (not shown).

A slow, endogenous release of u-PAR could, however, be detected after prolonged incubation in serum-free media without PI-PLC treatment (FIG. 11C); this finding may indicate that the cells either produce and secrete a soluble u-PAR or more likely, that they produce a GPI-specific phospholipase.

Altered Hydrophobicity of Purified u-PAR after PI-PLC Treatment

When purified u-PAR was subjected to detergent-phase separation by Triton X-114, it almost quantitatively partitioned into the detergent phase, as assessed by cross-linking to $^{125}$I-labelled ATF (FIG. 12A), thus demonstrating the very hydrophobic properties of the receptor. Incubation with PI-PLC altered the hydrophobicity of the u-PA binding protein substantially, as more than 50% of the ATF-binding activity was now recovered in the aqueous phase (FIG. 12B). It proved impossible to achieve a higher level of this conversion in the purified u-PAR preparation by increasing the concentration of PI-PLC. These data are in accordance with the fraction of cell associated u-PA which had been released in the previous experiment by PI-PLC treatment of intact PMA-stimulated U937 cells (FIG. 10). This finding may indicate that a partial resistance (approx. 50%) against bacterial PI-PLC is a genuine feature of the u-PAR population in vivo. Other phospholipases (PLD and PLA$_2$) did not induce any significant change in the hydrophobic properties of the purified u-PAR (FIG. 12C).

A similar behaviour was seen when samples of $^{125}$I-labelled u-PAR were analyzed by charge-shift electrophoresis after enzymatic treatment with various phospholipases. Only PI-PLC was able to transform a significant portion of the labelled u-PAR (again approx. 50%) into a hydrophilic form that migrated independently of the composition of detergents in the polyacrylamide gel (data not shown). This experiment shows that the PI-PLC induced change in phase-partitioning of the ATF binding activity is totally accounted for by an identical change in the hydrophobicity of the u-PAR protein itself.

In Vivo Labelling

Biosynthetic labelling of a component (Mr 50–60,000), capable of binding to DFP-u-PA, was obtained after incubation of PMA-stimulated U937 cells with either [$^3$H]-ethanolamine, myo-[$^3$H]-inositol or [$^3$H]-myristic acid (data not shown). This protein was isolated from the detergent lysates of U937 cells by immunoprecipitation with specific polyclonal antibodies against u-PAR and analysed by SDS-PAGE and fluorography (see Materials and Methods).

Post-translational Processing of the Carboxyl Terminus

Apart from demonstrating the presence of approx. 2 mol ethanolamine/mol u-PAR (FIG. 9A and Table 4), amino acid analysis revealed additional information about potential post-translational processing of this membrane receptor. When the calculated amino acid composition for the purified u-PAR was compared with that predicted for the nascent protein from cDNA sequence (Roldan et al., 1990), several reproducible and significant discrepancies arose (Table 4). In particular, the actual determinations of Ala and Leu were too low, whereas those of Tyr and Phe were too high (Table 4). Interestingly, however, it was possible to bring the calculated and the predicted amino acid compositions into perfect agreement provided that the last 29–31 COOH-terminal residues were removed during some posttranslational event (Table 4). Thus, on the basis of the determined amino acid composition and the accuracy/precision normally obtained for this equipment, it is assumed that there exists a COOH-terminal processing site in u-PAR. According to this model, processing is expected to occur at one of the residues Ser$_{282}$, Gly$_{283}$ or Ala$_{284}$—as indicated in FIG. 13.

TABLE 4

Amino acid composition of purified u-PAR compared with that deduced from its cDNA before and after the proposed COOH-terminal processing[a]

| Amino acid | Predicted from cDNA | Determined after acid hydrolysis | SD |
|---|---|---|---|
| A) Entire u-PAR sequence (Leu$_1$—Thr$_3$13) | | | |
| Asp + Asn | 29 | 32.7 | 0.5 |
| Thr[b] | 25 | 21.9 | 0.5 |
| Ser[b] | 25 | 25.8 | 0.5 |
| Glu + Gln[c] | 37 | 41.8 | 1.3 |
| Pro | 12 | 11.1 | 0.3 |
| Gly | 29 | 29.4 | 1.1 |
| Ala | 11 | 8.3 | 0.1 |
| Cys[d] | 28 | 28.8 | 1.0 |
| Val | 12 | 12.1 | 0.2 |
| Met | 7 | 6.0 | 0.6 |
| Ile | 8 | 6.7 | 0.1 |
| Leu | 31 | 26.9 | 0.7 |
| Tyr | 7 | 7.8 | 0.2 |
| Phe | 5 | 5.7 | 0.1 |
| His | 13 | 12.8 | 0.1 |
| Lys | 10 | 10.8 | 0.2 |
| Arg | 20 | 20.3 | 0.2 |
| Trp | 4 | nd | nd |
| Ethanolamine | — | 2.6 | 0.4 |
| B) Assumed u-PAR sequence after processing (Leu$_1$—Ala$_{284}$) | | | |
| Asp + Asn | 29 | 29.8 | 0.4 |
| Thr[b] | 20 | 20.0 | 0.5 |
| Ser[b] | 24 | 23.6 | 0.4 |
| Glu + Gln[c] | 36 | 38.1 | 1.2 |
| Pro | 9 | 10.2 | 0.3 |
| Gly | 26 | 26.8 | 1.0 |
| Ala | 8 | 7.6 | 0.1 |
| Cys[d] | 28 | 26.3 | 0.9 |
| Val | 12 | 11.0 | 0.2 |
| Met | 6 | 5.5 | 0.5 |
| Ile | 7 | 6.1 | 0.1 |
| Leu | 24 | 24.5 | 0.6 |
| Tyr | 7 | 7.1 | 0.1 |
| Phe | 5 | 5.2 | 0.1 |
| His | 12 | 11.6 | 0.1 |
| Lys | 10 | 9.9 | 0.2 |
| Arg | 19 | 18.6 | 0.2 |
| Trp | 2 | nd | nd |
| Ethanolamine | — | 2.4 | 0.4 |

Footnotes to Table 4
[a]Purified u-PAR was prepared for amino acid analysis as described in the legend to FIG. 9A The presented values represent the average of 3 independent determinations. The data were normalized relative to all amino acids, except tryptophan, assuming a total number of 309 residues for the nascent u-PAR and 282 for the fully processed protein (omitting 4 and 2 tryptophan residues, respectively). Amino acid numbering was based upon the cDNA sequence for u-PAR without the signal sequence (Roldan et al., 1990).
[b]The values for these hydroxyamino acids were corrected for decomposition during hydrolysis - Ser (5%) and Thr (10%).
[c]A slight overestimation is expected due to the formation of pyroglutamic acid in the amino acid standard mixture.
[d]In one sample cysteine was derivatized before hydrolysis by in situ alkylation using iodoacetamide and subsequently quantified as S-carboxymethyl-cysteine after acid hydrolysis. In general, the yield of this alkylation procedure is 95% (Ploug, 1989). Otherwise, cysteine was derivatized during hydrolysis in the presence of 3,3'-dithiodipropionic acid (DTDPA) and quantified as the mixed disulfide compound (Cys-x) formed between cysteine and DTDPA.
[e]nd = not determined.
[f]SD = standard deviation (absolute number of residues).

The results in this Example unequivocally demonstrate that u-PAR has a glycosyl-phosphatidylinositol anchor and is C-terminally processed.

EXAMPLE 4

PRODUCTION OF POLYCLONAL AND MONOCLONAL ANTIBODIES TO u-PAR

Production of Polyclonal Mouse and Rabbit Antibodies Against u-PAR

Samples of purified human u-PA receptor (Example 1) were subjected to SDS-polyacrylamide gel electrophoresis under non-reducing conditions on a 6–16% gradient gel. By the use of fluorescent molecular weight markers run in neighbouring lanes, the electrophoretic region corresponding to the antigen was excised. The gel piece was lyophilized and subsequently macerated in a Mikro-Dismembrator II apparatus (B. Braun AG, Federal Republic of Germany). The polyacrylamide powder was reconstituted in Tris-buffered saline, mixed with Freund's incomplete adjuvant and used for injection of a New Zealand white rabbit. The animal received 5 injections, each containing approximately 3 µg of the antigen, over a 10 week period, followed by a single 8 µg injection after an additional 7 weeks. Serum was drawn 1 week after the last injection, and IgG was prepared by Protein A-Sepharose chromatography. In order to remove antibodies against trace impurities in the injected antigen, the antibody was absorbed by consecutive passages through columns containing immobilized human u-PA and the protein mixture constituting the Triton X-114 detergent phase from PMA-stimulated U937 cells (see Example 1), respectively. The antibody preparation obtained did not inhibit the amidolytic or plasminogen activator activity of u-PA in solution.

A similar procedure as the one described above for intact u-PAR is useful for the production of polyclonal antibodies specific for the 16 kD u-PA binding domain of u-PAR and the Mr 35–45 kD non-u-PA binding fragment of u-PAR obtained by chymotrypsin degradation as described in Example 2. For immunization, these two fragments can be obtained separately by excision from SDS-PAGE gels as described above.

Specificity of u-PAR Polyclonal Antibodies Evaluated by Western Blotting

Electrophoresis. SDS-PAGE was carried out in slab gels with a linear 6–16% polyacrylamide concentration gradient according to Laemmli (supra). Samples were run under reducing conditions. The samples were reduced immediately before electrophoresis in Laemmli buffer except that 2-mercaptoethanol was replaced with dithiothreitol for 3 minutes at 100° C. The following molecular weight markers were used: phosphorylase b (molecular weight about 94,000), bovine serum albumin (molecular weight about 67,000), ovalbumin (molecular weight about 43,000), carbonic anhydrase (molecular weight about 30,000), soybean trypsin inhibitor (molecular weight about 20,100), and α-lactalbumin (molecular weight about 14,400).

Western Blotting—Samples of affinity purified u-PAR or detergent phase from Triton X-114 extracts of PMA-stimulated U937 cells were subjected to SDS-PAGE under reducing conditions on 6–16% gradient gels. The gels were electroblotted onto nitrocellulose sheets. The sheets were rinsed and blocked with 30% fetal calf serum in Tris-buffered saline, pH 7.4. The sheets were incubated with mouse anti-u-PAR serum or control serum (i.e. mouse antiserum against porcine mucins), diluted in fetal calf serum in Tris-buffered saline. The sheets were rinsed, incubated with secondary antibody (alkaline phosphatase-conjugated rabbit anti-mouse Ig (Dakopatts, Copenhagen)), and developed with nitro blue tetrazolium/5-bromo-4-chloro-3-indolyl phosphate/Levamisol.

Western blotting analysis of rabbit u-PAR antibody was performed in the same manner, except for the following modifications: SDS-PAGE was performed under non-reducing conditions. Newborn calf serum was used instead of fetal calf serum. Only 10% serum was included in the primary antibody incubation step. Alkaline phosphatase conjugated swine anti-rabbit Ig (Dakopatts code 306), 100-fold dilution, was used as the secondary antibody.

Assay for Inhibition of Cellular ATF Binding—U937 cells were washed and acid-treated, as described (Nielsen et al., 1988). The cells were resuspended in 100 µl of PBS, 0.1% bovine serum albumin, and 100 µl of prediluted anti-u-PAR serum was added. Control samples received 100 µl of prediluted control serum (i.e. mouse antiserum raised against porcine mucins). The samples were incubated for 1 hour at 4° C. with gentle stirring. After the incubation, 100 µl of $^{125}$I-ATF was added and incubation was continued for another hour. In the 300-µl reaction volume, the final concentration of $^{125}$I-ATF was 2.2 nM, and the final dilutions of anti-u-PAR serum/control serum ranged from 1:300 to 1:153,600. The cells were then washed 3 times with 1 ml of PBS-bovine serum albumin, and the bound radioactivity was measured in a gamma counter. Under these conditions, 12% of the radioactivity became cell-bound when no antiserum had been added. 90% of the bound radioactivity was displaced when the cells were preincubated with 700 nM non-labelled u-PA.

Results

As shown in FIG. 14, serum from immunized mice precipitated $^{125}$I-labelled purified u-PAR. The anti-u-PAR serum diluted 1:75, 1:750, 1:7500 and 1:75000 gave a 25%, 18%, 5% and 1% precipitation, respectively. The non-immune serum at the same dilutions and the other controls gave precipitations in the range of 0.5–1%.

Using a reverse solid phase radioimmunoassay, the antiserum was used to immunocapture $^{125}$I-labelled purified u-PAR (FIG. 15). A 2-fold serial dilution of the anti-u-PAR serum 1:500–1:32000 showed that the same amount of $^{125}$I-u-PAR (about 2% of total) was captured at a serum dilution up to 1:4000 and dropped to half the amount at 1:32000. The same serial dilution of non-immune serum and the other controls resulted in a capture of $^{125}$I-u-PAR of about 0.5% of total.

The reaction of immune versus non-immune serum in an ELISA is shown in FIG. 16. 1 ng of purified u-PAR coated per well was sufficient to be detected with the immune serum diluted 1:8000. Both the non-immune serum at all dilutions and other controls gave reaction values at background level.

The mouse antiserum against human u-PAR was used in a competition experiment in which U937 cells were preincubated with the antiserum followed by addition of $^{125}$I-ATF. As shown in FIG. 17A the anti-u-PAR serum was able to completely inhibit the specific binding of $^{125}$I-ATF to the cells. 50% inhibition was obtained at a 1:2400 dilution. Under the same conditions, a control serum showed only slight inhibition, i.e. about 20% at the highest concentration used (a 1:300 dilution). In Western blotting, the u-PAR contained within the detergent phase from PMA-treated U937 cells, as well as the purified u-PAR, were detected by the anti-u-PAR serum (FIG. 17B, inset, lanes 1 and 2). The control immune serum gave no reaction with the same preparations (lanes 3 and 4).

Rabbit polyclonal antibodies were prepared by immunizing a rabbit with polyacrylamide gel material containing affinity-purified u-PAR that had subsequently been subjected to preparative SDS-PAGE. The IgG fraction was isolated from the obtained antiserum and absorbed by passage through columns with immobilized human u-PA and immobilized membrane-protein mixture derived from PMA-stimulated U937 cells, respectively. The antibody recognized u-PAR in the Triton X-114 detergent phase from PMA-stimulated U937 cells (FIG. 18) (A). Thus, a protein in the 50–65 kD range was recognized (lanes 1 and 2) which could be identified as being u-PAR by the ability to form a 100–110 kD conjugate with DFP-treated u-PA after the performance of chemical cross-linking (see Example 1 for methods) (lane 3). No staining was obtained with DFP-treated u-PA alone (lanes 5 and 6), and the cross-linking procedure did not alter the electrophoretic appearance of u-PAR when no DFP-treated u-PA was added (lane 2). In none of the samples was any band stained with the pre-immune IgG from the same rabbit, prepared in the same manner FIG. 18(B).

The effect of the rabbit antibody on the ligand binding capability of u-PAR was studied in a different experiment (not shown) in which a purified sample of u-PAR (Example 1; approximately 20 ng/ml) was preincubated with the purified and absorbed IgG from the rabbit anti-u-PAR serum (final IgG concentration 90 µg/ml during preincubation). This treatment completely hindered the subsequent formation of cross-linked conjugates with $^{125}$I-ATF. The IgG from the pre-immune serum had no effect on the cross-linking assay at the same concentration.

Production of Monoclonal Mouse Antibodies to u-PAR

Immunization of Mice

Mice of the BALB/c strain were immunized with u-PAR purified from U937a cells on a diisopropylfluoride urokinase-type plasminogen activator (DFP-u-PA) ligand affinity column (see Example 1). The mice were given three intraperitoneal injections with 5 µg of u-PAR with 3 week intervals. 8–10 days after the last injection, serum was tested in both ELISA and Western blotting for reactivity against u-PAR. When positive reaction was detected, a final booster injection of 10–15 µg of u-PAR was given intraperitoneally.

Fusion and Cloning of Hybridomas

Standard protocols for fusion were followed and are briefly outlined below:

a) The spleen and peripheral lymph nodes from an immunized BALB/c mouse were mechanically disrupted, and homogeneous cell suspensions were prepared in serum-free medium.

b) Myeloma cells and X63-Ag 8.653 cells (Kearney, J. Immunol. 123: 1548–1550, 1979) in logarithmic phase of growth were isolated for fusion with BALB/c spleen lymphocytes. The myeloma cells were resuspended in serum-free medium.

c) The spleen and lymph node lymphocytes and myeloma cells were mixed in a ratio of 1:1.25 and 1:2, respectively.

d) Cells were fused by dropwise addition of 50% (wt/vol) polyethylene glycol 4000 (PEG) at 37° C. (5 ml to n×10$^8$ and 1 ml to 4.5×10$^7$ for the spleen and lymph node lymphocytes, respectively).

e) Fusion was stopped by gentle addition of serum-free medium.

f) After centrifugation, the supernatant was removed and the cells were washed once in serum containing medium. The cells were then carefully resuspended in hypoxanthine-aminopterin-thymidine (HAT)-containing medium.

g) The fused cells at an amount of approximately 7×10$^5$ cells/well (spleen fusion) and 5×10$^5$ cells/well (lymph node fusion) were distributed in 50 µl aliquots to wells of flat-bottomed microtiter plates containing 2.5×10$^4$ macrophages in 150 µl of selection medium.

h) The cells were incubated at 37° C. in 5% $CO_2$ in a humid incubator.

i) The selection medium was renewed after a week or when needed.

j) The wells were inspected for hybridoma growth. When vigorous growth and change of colour to yellow were observed, supernatants were removed for screening for antibodies reacting with u-PAR by an ELISA method (see below).

k) 10–14 days after fusion, HAT medium was replaced by HT medium and later, e.g. after 10 days, by regular medium.

l) ELISA-positive wells were transferred into cups of 24-well plates and then to small (25 cm$^2$) culture flasks.

m) ELISA-positive hybrid cells were frozen in liquid $N_2$ as early as possible.

n) Hybridomas from 4 of the ELISA positive wells were cloned by limited dilution. From each culture was prepared 36 well with an average of 0.5 cells/well, 36 well with an average of 1 cell/well and 24 with an average of 3 cells/well). Medium from wells with confluent cells were tested with ELISA and from each of the original hybridomas cultures one of the clones from wells seeded with an average of 0.5 cells/well and stably showing a strong ELISA reaction was used for further propagation.

Enzyme-linked Immunosorbent Assay (ELISA)
Used for Screening

Materials 1) 96-well plates (Flat bottom high binding capacity, Nunc).

2) u-PAR purified from U937 cells (10 µg/ml).

3) Horseradish peroxidase-conjugated rabbit anti-mouse Ig (HRP-RaM Ig).

4) PBS buffer, pH 7.4 (PBS).

5) PBS+0.1% Tween 20, pH 7.4 (PBS/Tween 20).

6) Blocking buffer: 1% skimmed milk powder (SMP) in PBS.

7) Citrate buffer: 0.1M citrate, pH 5.0.

8) Substrate solution: 1,2-Phenylenediamine dihydrochloride (OPD) tablets in citrate buffer, e.g. 3 OPD tab. in 15 ml of citrate buffer+5 µl of $H_2O_2$ (30%).

9) Stop buffer: 1M $H_2SO_4$.

Procedure

1) Coat the wells with 100 µl of purified u-PAR diluted in 0.1M Na$_2$CO$_3$, pH 9.8, to a concentration of 20 ng/ml.

2) Incubate overnight at 4° C.

3) Next day, wash the wells 4× in PBS/Tween 20.

4) Block the remaining active sites in the wells with 1% SMP/PBS, 200 µl/well, for ½ hour at RT. Gentle shaking.

5) Wash as step 3.

6) Add 100 µl/well of spent media from hybridomas secreting antibodies/immune/non-immune sera serial diluted in PBS/Tween 20+1% SMP and include relevant controls.

7) Incubate for 1 hour at 37° C. with gentle shaking.

8) Wash as step 3.

9) Add 100 µl/well of secondary antibody HRP-RaM Ig diluted 1:500 in PBS/Tween 20+1% SMP.

10) Incubate as step 7.

11) Wash as step 3.

12) Wash 1× in double distilled water.

13) Add 100 µl/well of substrate solution.

14) Stop the reaction with 150 µl/well of 1M H$_2$SO$_4$ when bright yellow colour appears, 10–30 minutes.

15) Read on an ELISA-reader with a 490 nm filter.

Purification of Monoclonal Antibodies

Materials

1. Spent media from hybridomas secreting the monoclonal antibodies.

2. MAb Trap G, complete kit for the purification of IgG (Pharmacia) containing:
   a. Protein G Sepharose 4 Fast Flow disposable column, 3 ml.
   b. Binding Buffer: 2×100 ml, 0.2M sodium phosphate (pH 7.0). 10× concentrate containing 0.05% sodium azide as a preservative.
   c. Elution Buffer: 1×100 ml, 1.0M glycine-HCl (pH 2.7). 10× concentrate. A pH of 2.7 allows excellent stability without the use of a preservative.
   d. Neutralizing Buffer: 1×100 ml, 1.0M Tris-HCl (pH 9). Contains 0.05% sodium azide as a preservative.

3. Fraction collector and UV-monitor

4. Minisorb tubes

Procedure

The Protein G Sepharose 4 FF column was opened by removing the top cap first. This will avoid air bubbles being drawn into the gel. The 20% ethanol storage solution was poured off and the Protein G Sepharose 4 FF column was equilibrated by filling it to the top with Binding Buffer (~30 ml) whereafter the column was allowed to drain. The column will stop flowing automatically as the meniscus reaches the top frit, preventing the column from drying out. The culture supernatants were centrifuged, 150×g, and filtered (0.20 µm). 50–150 ml of the prepared sample was applied and allowed to absorb into the gel. Unbound proteins were washed away by filling the columns to the top with Binding Buffer (~30 ml) and the buffer was allowed to pass through the column, eluting unbound materials. The bound IgG was eluted by filling the column with Elution Buffer (~15 ml) on the column. 1 ml fractions of eluted antibodies were collected in minisorb tubes containing 40–80 µl of neutralizing buffer, and the purity of the elution fractions were checked on a 8–25% gradient gel employing Phast gel System (Pharmacia) followed by silver staining (see Example 1).

Sub-Isotyping of Monoclonal Antibodies

Materials 1. 96-well plates (Flat bottom high binding capacity, Nunc).

2. Purified u-PAR (10 µg/ml).

3. Mouse Typer Sub-Isotyping kit (Bio-Rad).

4. Horseradish peroxidase-conjugated swine anti-rabbit Ig (HRP-SaR Ig).

5. PBS buffer, pH 7,4 (PBS).

6. PBS+0.1% Tween 20, pH 7.4 (PBS/Tween 20).

7. Blocking buffer: 1% skimmed milk powder (SMP) in PBS.

8. Citrate buffer: 0.1M citrate, pH 5,0.

9. Substrate solution: 1,2-Phenylenediamine dihydrochloride (POD) tablets in citrate buffer, e.g. 3 OPD tab. in 15 ml of citrate buffer+5 µl of H$_2$O$_2$ (30%).

10. Stop buffer: 1M H$_2$SO$_4$.

Procedure

The wells were coated with 100 µl of purified u-PAR diluted in 0.1M Na$_2$CO$_3$, pH 9.8, to a concentration of 20 ng/ml, and incubated overnight at 4° C. The wells were then washed 4× in PBS/Tween 20, and the remaining active sites in the wells were blocked with 1% SMP/PBS, 200 µl/well, for ½ hour at room temperature with gentle shaking. They were again washed as above, and 100 µl/well of spent media from the hybridomas secreting the monoclonal antibodies was added followed by incubation for 1 hour at 37° C. with gentle shaking. After washing as above, 100 µl/well of undiluted solution of Sub-Isotyping antibodies were added. After incubation for 1 hour at 37° C., the wells were washed as above. 100 µl/well of HRP-SaR Ig diluted 1:500 was added in PBS/Tween 20+1% SMP, and the wells were incubated and washed as above followed by wash with double distilled water. 100 µl/well of substrate solution was added, and the reaction was stopped with 150 µl/well of 1M H$_2$SO$_4$ after 5–10 minutes when a bright yellow colour appeared. The absorbancy was measured on an ELISA-reader with a 490 nm filter. Appropriate controls were included in each experiment.

Results 1000 wells with fused spleen cells resulted in 19, and 90 wells with fused lymph node cells resulted in 5 stably ELISA-positive hybridomas. In order to select hybridomas with different characteristics for the first cloning, conditioned medium from the stably ELISA positive hybridomas was tested for (1) its ability to stain PI-PLC solubilized u-PAR (see Example 3) in Western blotting (see Example 4), (2) inhibition of binding of the ATF part of u-PA in a radiolabelled form to U937 cells (see Example 1), and (3) staining of paraffin sections of colon adenocarcinomas, which by in situ hybridization were shown to contain cells with expression of mRNA for u-PAR (see Example 8).

On these criteria, 4 hybridomas were selected for cloning (I 4E-8, I 5A-7, I10A-4, II 1D-6). The first three were derived from the spleen cell fusion and the last from the lymph node cell fusion. The characteristics of the conditioned media from these 4 hybridomas were as follows:

|  | I 4E-8 | I 5A-7 | I 10A-4 | II 1D-6 |
|---|---|---|---|---|
| React with u-PAR in screening ELISA | + | + | + | + |
| Western blotting of solubilized u-PAR | − | + | + | + |
| Inhibit binding of $^{125}$I-ATF to U937 cells | + | − | + | − |
| Immunostaining of cells positive for u-PAR mRNA | − | + | − | + |

After cloning of the four hybridomas, approximately half of the wells seeded with an average of 0.5 cells/well showed growth and for each of the original hybridomas, one of these showing a consistently strong ELISA reaction was used for propagation and all further studies. These selected clones were designated 1R (from I 4E-8), 2R (from I 5A-7), 3R (from I 10A-4) and 4R (from II 1D-6). 1R consistently showed a weaker ELISA reaction than the three other clones. Subisotyping of the antibodies produced from these clones was performed as described above. 1R was determined as being IgG2b, Kappa while the other 3 was of the IgG1 kappa isotype. The antibodies were purified as described above and these purified preparations showing one silver stained band after electrophoresis in the Phast gel system were used for all further studies.

EXAMPLE 5

CHARACTERIZATION OF MONOCLONAL ANTIBODIES BY IMMUNOPRECIPITATION AND WESTERN BLOTTING

Specific Recognition of Purified u-PAR by Immunoprecipitation with Monoclonal Antibodies Radioimmunoprecipitation assay (RIPA). This assay was developed with the aim to specifically detect the intact u-PAR (I) or a chymotrypsin degraded form of u-PAR (D) which comprises an $M_r \cong 16,000$ u-PA binding domain and an $M_r$ 35–45,000 fragment which does not bind u-PA (described in Example 2).

Materials

1. $^{125}$I-iodinated u-PAR (I) and u-PAR (D).
2. Reaction buffer: 0.1% bovine serum albumin (BSA)+ 0.1% CHAPS+300 mM NaCl in 0.1M Tris-HCl, pH=8.1.
3. Washing buffer 0: reaction buffer. Washing buffer 1: reaction buffer without 0.1% BSA.
4. Protein A Sepharose CL 4B swollen and diluted 1:1 in reaction buffer (Prot. A Seph. solution).
5. Eppendorf plastic test tubes.

Procedure

1. Add 100 μl of radiolabelled u-PAR (I) or u-PAR (D) diluted in reaction buffer (about $3.5 \times 10^5$ cpm/ml) into Eppendorf test tubes.
2. Add 100 μl of purified monoclonal antibodies diluted to an appropriate concentration (i.e. 20 μg/ml) in reaction buffer and include relevant controls.
3. Incubate for 1 hour at 4° C. with gentle shaking.
4. Add 50 μl of Prot. A Seph. solution.
5. Incubate for 1 hour at 4° C. on an end-over-end mixer.
6. After the last incubation, spin down the samples at 10,000 rpm for 20 sec (Minifuge).
7. Resuspend the pellets in 1 ml of Washing buffer 0 and spin down the Sepharose at 10,000 rpm for 20 sec. Remove supernates.
8. Repeat step 7.
9. Resuspend the pellets in 1 ml of Washing buffer 1 and spin down the Sepharose at 10000 rpm for 20 sec. Remove supernates.
10. Repeat step 9.
11. Resuspend the pellets in 50 μl of double concentrated sample buffer for gel electrophoresis and boil the samples for 5 min.
12. Spin down the samples at 10,000 rpm for 20 sec.
13. Transfer the supernates to test tubes and count the samples in a gamma counter.
14. After counting, analyze the samples by SDS-PAGE under non-reducing conditions on a 6–16% gradient gel and autoradiography.

Results

Figure 19A:
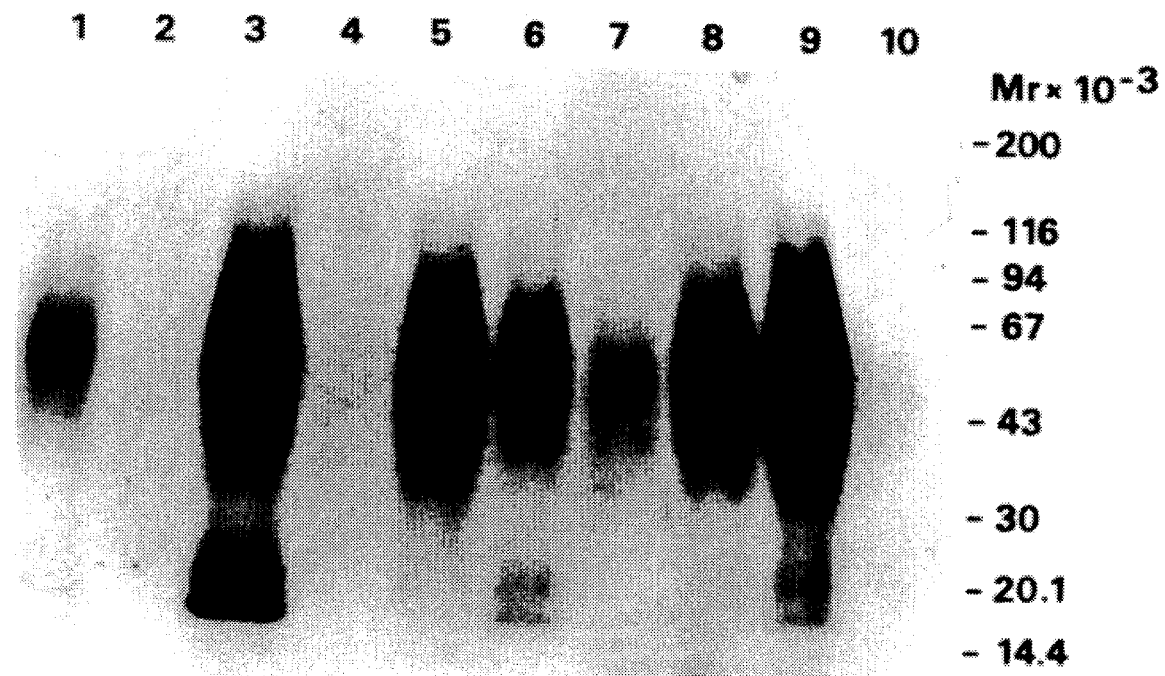
Figure 19B:
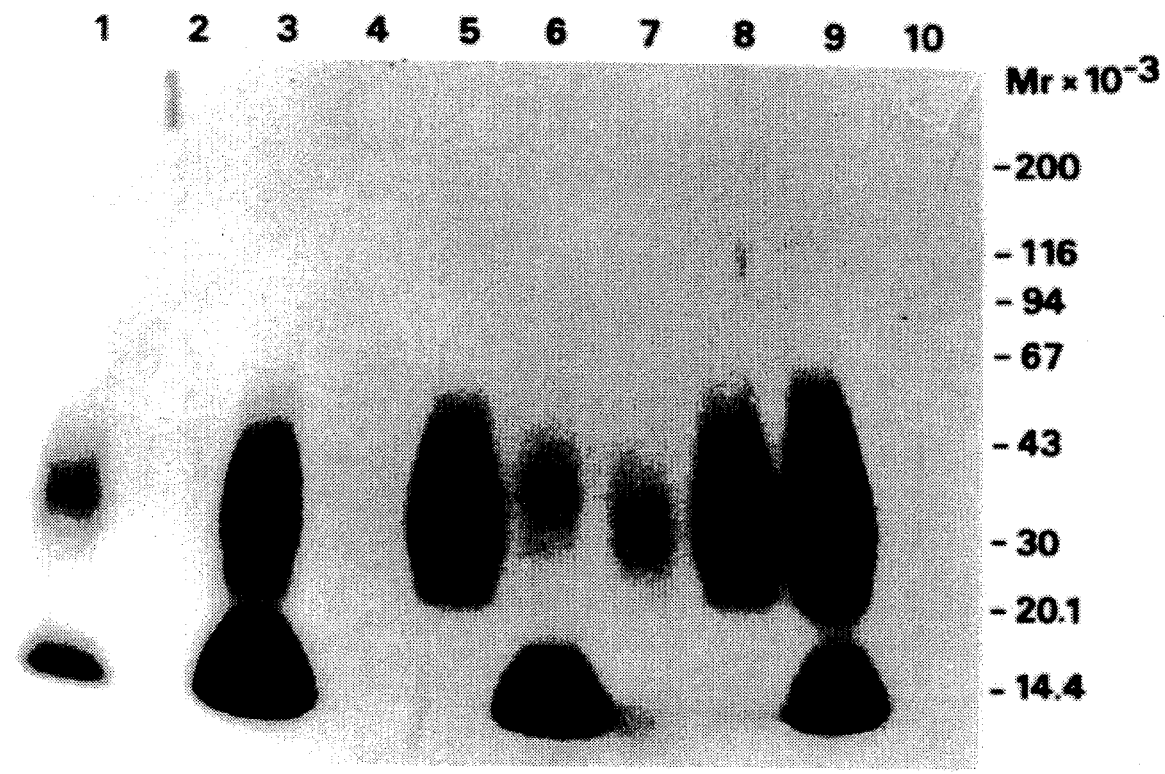

The 4 monoclonal antibodies were tested in a radioimmunoprecipitation assay for binding to purified u-PAR in an intact form and a degraded form. The chymotrypsin digestion resulted in liberation of a u-PA binding fragment of Mr 16,000 and a heterogeneous component in the Mr 30–50,000 range, which represents the rest of the molecule. The intact u-PAR is a heterogeneous component, with Mr 50–65,000. Both preparations of u-PAR, u-PAR(I) and u-PAR(D), were radiolabelled with $^{125}$I-iodine as described in Example 1 and subjected to immunoprecipitation. FIG. 19A shows that the monoclonal antibodies (1R, 2R, 3R, 4R in lanes 7, 5, 6, 8, respectively) precipitate the u-PAR(I) in the Mr 50–65,000 range with different efficiency. This difference may reflect different affinities for the purified u-PAR. 2R and 4R are equally efficient in precipitating u-PAR(I), whereas 3R is less efficient. The amount of u-PAR(I) precipitated by 1R is very small. This is in accordance with the ELISA results showing a relatively weak reaction of this antibody with purified u-PAR (see above). A pool of the 4 monoclonal antibodies reflects the combined effect of the individual antibodies. When u-PAR(D) was used as antigen the immunoprecipitation resulted in a specific recognition of the u-PA binding fragment of u-PAR with Mr 16,000 by 3R. 2R and 4R recognized the heterogeneous component in the Mr 35–50,000 range with approximately the same efficiency. 1R reacted with the same component as 2R and 4R, but with a lower affinity. The pooled monoclonal antibodies recognized both components as expected from the reaction of the individual antibodies (FIG. 19B).

Reactivity of Monoclonal Antibodies with u-PAR from PMA-treated U937 Cells as Determined by Western Blotting Procedure Electrophoresis. SDS-PAGE was carried out in slab gels with a linear 6–16% polyacrylamide concentration gradient according to Laemmli (supra). Samples were run under reducing conditions. The samples were reduced immediately before electrophoresis in Laemmli buffer except that 2-mercaptoethanol was replaced with dithiothreitol for 3 minutes at 100° C.

Western blotting. Samples of detergent phase from Triton X-114 extracts of PMA stimulated U937 cells and U937a, respectively, were subjected to SDS-PAGE under non-reducing conditions on 6–16% gradient gels. The separated proteins were electroblotted onto nitrocellulose filter sheets. The sheets were blocked with 1% skim milk powder in Tris buffered saline, pH 8.0 and cut into 5 mm strips. These were incubated with the mouse monoclonal antibodies 1R, 2R, 3R and 4R prepared as described in Example 1 against u-PAR or control sera (i.e. mouse anti-u-PAR serum and mouse non-immune serum) diluted in blocking solution. The strips were rinsed in 0.05% Tween in blocking solution (as above), incubated with secondary antibody [alkaline phosphatase-conjugated rabbit anti-mouse Ig (Dakopatts, Copenhagen)], and developed with nitroblue tetrazolium/5-bromo-4-chloro-3-indotyl phosphatase.

Results

Figure 20A:
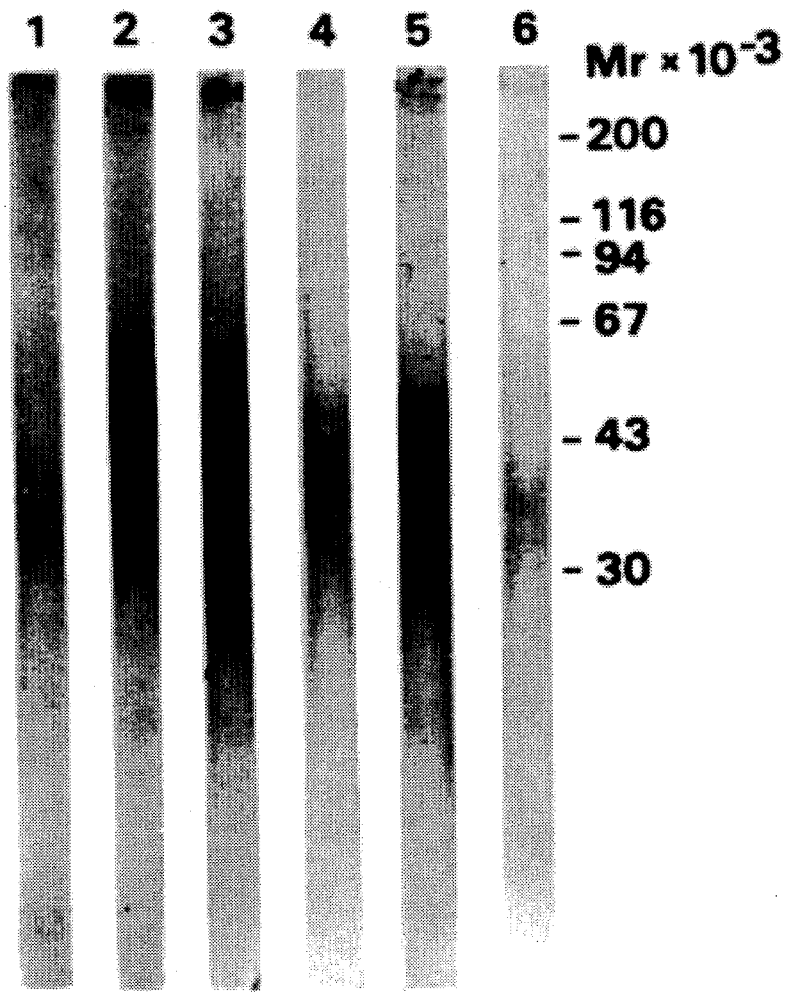
Figure 20B:
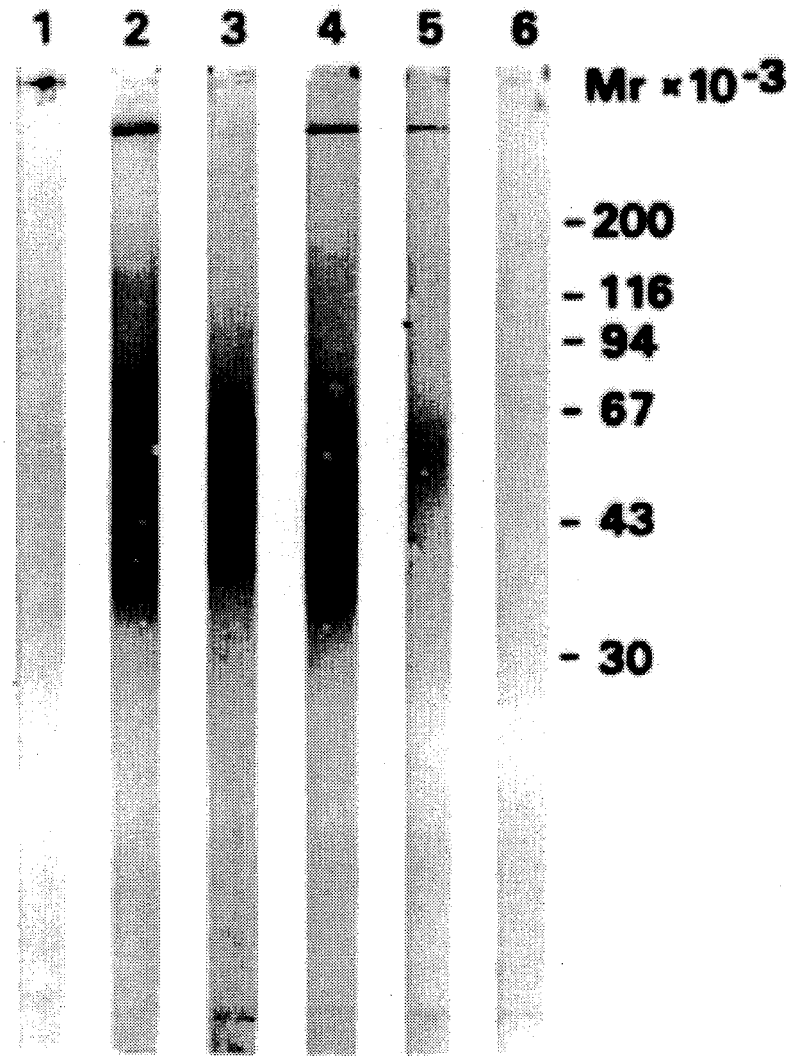

The reactivity of 4 monoclonal antibodies against u-PAR contained within the detergent phase from PMA-treated U937 and U937a cells, respectively, was analyzed by Western blotting. The U937 cells express a u-PAR protein in the 50–65 kD range and the U937a cells express in addition a u-PAR variant around 40–45 kD. As shown in FIG. 20A the monoclonal antibody 1R (lane 1) did not show any reaction in Western blotting, whereas 2R, 3R and 4R (lanes 2, 3 and 4, respectively) recognized a protein with the expected molecular weight for u-PAR. 4R gave a very weak reaction. FIG. 20B shows the pattern of reactivity with u-PAR from U937a cells. 1R (lane 1) showed no reaction with u-PAR. 2R and 3R (lanes 2 and 3, respectively) recognized both the high and low molecular weight form of u-PAR whereas 4R (lane 4) predominantly and strongly recognized the low molecular weight variant of u-PAR.

Conclusion

From the results of these experiments it is concluded that the 4 monoclonal antibodies 1R, 2R, 3R and 4R all are directed against u-PAR and that they recognize different epitopes on the u-PAR molecule.

1R: The antibody binds to the non-u-PA binding part of u-PAR. The antibody is only reactive in ELISA. When the protein is subjected to SDS-PAGE and electroblotting, the epitope recognized by this antibody is destroyed.

2R: The antibody binds to the non-u-PA binding part of u-PAR. The epitope against which it is directed is not destroyed by SDS-PAGE and electroblotting. It is different from 4R in that it reacts with both the high and low molecular weight glycosylation variants of u-PAR from PMA-stimulated U937a cells in Western blotting.

3R: The antibody binds to the u-PA binding part of u-PAR. The epitope against which it is directed is not destroyed by SDS-PAGE and electroblotting.

4R: The antibody binds to the non-u-PA binding part of u-PAR. The epitope against which it is directed is not destroyed by SDS-PAGE and electroblotting. It is different from 2R because it reacts almost exclusively with the low molecular weight glycosylation variant of u-PAR from PMA-stimulated U937a cells.

Deposits were made, under the Budapest Treaty, with the European Collection of Animal Cell Cultures, Porten Down, Salisbury, Wiltshire SP4 OJG, Great Britain, on Oct. 10, 1990, as follows:

| Hybridoma | A6 | Deposit No. |
|---|---|---|
| I4E-8 | 1R | 90101007 |
| I5A-7 | 2R | 90101008 |
| I10A-4 | 3R | 90101009 |
| I1D-6 | 4R | 90101010 |

These deposits are subject to 37 CFR § 1.801 et seq. No license to make, use or cell cultures or their antibodies is granted as a result of this deposit.

EXAMPLE 6

QUANTIFICATION OF u-PAR BY ELISA

Biological material: u-PAR affinity purified as described in Example 1. Monoclonal antibodies 1R, 2R, 3R and 4R purified as described in Example 4.

Biotinylation of monoclonal antibodies (see Guesdon J-L et al. J. Histochem. Cytochem., 27, 1979, 1131–1139)

Materials

1. Purified antibody at a concentration of 1 mg/ml.
2. Reaction buffer: 0.1M $NaHCO_3$, pH 9.5.
3. Stock solution of BXNHS (N-hydroxysuccinimide ester of biotin+spacer group) in distilled dimethyl formamide: 0.1M BXNHS.
4. PBS buffer, pH 7,4 (PBS).
5. Dialyse tubes.
6. 87% Glycerol.

Procedure 2 ml (2 mg) of purified antibody was dialysed against 500 ml of 0.1M $NaHCO_3$, pH 9.5 for 2 hr, followed by 500 ml of 0.1M $NaHCO_3$, pH 9.5 overnight at 4° C. 45.6 µl of 0.1M BXNHS was added to the dialysed antibody which was then incubated with gentle magnetic stirring for 1 hr at room temperature, protected from light. After incubation, the reaction solution was dialysed against 500 ml of PBS, pH 7.4, with 4 changes for 24 hr at 4° C. The biotinylated antibody was diluted 1:1 with 87% glycerol and stored at −20° C.

Measurement of u-PAR

Materials 1. 96-well plates (flat-bottom high binding capacity, Nunc).
2. Unlabelled purified monoclonal antibody 4R.
3. Purified monoclonal antibody 2R labelled with biotin.
4. Horseradish peroxidase-conjugated (HRP) streptavidin (DAKO, Copenhagen).
5. PBS buffer, pH 7.4 (PBS).
6. PBS+0.1% Tween 20, pH 7.4 (PBS/Tween).
7. Blocking buffer: 1% skimmed milk powder (SMP) in PBS.
8. Citrate buffer: 0.1M citrate, pH 5.0.

9. Substrate solution: 1,2-Phenylenediamine dihydrochloride (OPD) tablets in citrate buffer, e.g. 4 OPD tablets in 15 ml of citrate buffer+5 µl of $H_2O_2$ (30%).

10. Stop buffer: 1M $H_2SO_4$.

Procedure

1. Coat the wells with 100 µl of purified monoclonal antibody 4R (20 µg/ml) diluted in 0.1M $Na_2CO_3$ (pH 9.8).
2. Incubate overnight at 4° C.
3. Wash the wells 5× in PBS/Tween.
4. Block the remaining active sites in the wells with 1% SMP/PBS, 250 µl/well, for at least 1 hour at 37° C.
5. Wash as in step 3.
6. Add 100 µl of a serial dilution of an unlabelled standard antigen solution.
7. Incubate with gentle shaking for a minimum of 1.5 hours at room temperature.
8. Wash as in step 3.
9. Add 100 µl of biotin-labelled monoclonal antibody 2R (concentration 500 ng/ml).
10. Incubate as in step 7.
11. Wash as in step 3.
12. Add 100 µl of HRP-streptavidin (DAKO, Copenhagen) diluted 1:5000 in SMP/PBS/Tween.
13. Incubate as in step 7.
14. Wash as in step 3.
15. Wash 1× in double distilled water.
16. Add 100 µl/well of substrate solution.
17. Stop the reaction with 100 µl/well of 1M $H_2SO_4$, when bright yellow colour appears, 5–10 minutes.
18. Read on an ELISA reader with a 490 nm filter.

A similar experiment was carried out in which the monoclonal antibody 4R was substituted with affinity purified polyclonal antibody to u-PAR. The polyclonal antibody to u-PAR was obtained as described in Example 4 above.

Results

The quantification of purified u-PAR was analyzed by a two antibody sandwich ELISA. When the monoclonal antibody 4R was used as the catching antibody, the purified u-PAR could be measured in the 1:500 to 1:4000 dilution range under the conditions above. The irrelevant monoclonal antibody binds no u-PAR (FIG. 21). When the affinity purified polyclonal rabbit antibody to u-PAR was employed, the u-PAR could be measured in the 1:1000 to 1:4000 dilution range. The pre-immune rabbit serum showed no binding of u-PAR (FIG. 21). The sensitivity of a quantitative ELISA is dependent on the slope of the curve. In the example with 4R, the steepest slope is obtained; thus, this will give the most accurate quantification.

Based on these results and those obtained with immunoprecipitation of chymotrypsin digests of u-PAR (Example 5), it is contemplated that the following combinations of antibodies are useful for measuring u-PAR independently of whether it is complexed with u-PA or not.

A. Unlabelled catching antibody: 1R and affinity purified polyclonal anti-u-PAR rabbit antibodies. Biotin-labelled detecting antibody: 2R or 4R, affinity purified polyclonal anti-u-PAR rabbit antibodies.

B. Unlabelled catching antibody: 2R, affinity purified polyclonal anti-u-PAR rabbit antibodies. Biotin-labelled detecting antibody: 1R, 4R affinity purified polyclonal anti-u-PAR rabbit antibodies.

C. Unlabelled catching antibody: 4R and affinity purified polyclonal anti-u-PAR rabbit antibodies. Biotin-labelled detecting antibody: 1R or 2R, affinity purified polyclonal anti-u-PAR rabbit antibodies.

The following combinations of antibodies are contemplated to be useful to measure complexes of u-PAR and u-PA:

A. Unlabelled catching antibody: 4R and affinity purified polyclonal anti-u-PAR rabbit antibodies. Biotin-labelled detecting antibody: monoclonal antibody reacting with the B-chain of u-PA (e.g. clone 2 and 5, Nielsen et al, J. Immunoassay 7, 1986, 209–228).

B. Unlabelled catching antibody: monoclonal antibody reacting with the B-chain of u-PA. Biotin-labelled detecting antibody: 4R and affinity purified polyclonal anti-u-PAR rabbit antibodies.

The following combinations of reagents are contemplated to be useful to measure u-PAR which is not complexed or with u-PA:

A. Unlabelled catching antibody: monoclonal antibody 1R, 2R or 4R, affinity purified polyclonal anti-u-PAR rabbit antibodies. Detecting reagent: Biotin-labelled monoclonal antibody 3R, biotinylated DFP-u-PA.

B. Unlabelled catching reagent: 3R, DFP-u-PA. Biotin-labelled detecting antibody: monoclonal antibody 1R, 2R or 4R, affinity purified polyclonal anti-u-PAR rabbit antibodies.

In the above described different types of u-PAR ELISA, the 3R monoclonal antibody can be substituted by polyclonal antibodies developed by immunization with the 16 kD u-PA binding fragment of u-PAR. The 1R, 2R and 4R monoclonal antibodies can be substituted by polyclonal antibodies developed by immunization with the Mr 35–45 kD non-u-PA binding fragment of u-PAR as described in Example 4.

EXAMPLE 7

INHIBITION OF CELL SURFACE PLASMINOGEN ACTIVATION BY u-PAR ANTIBODIES

MATERIALS AND METHODS

Plasminogen activation by u-PAR-bound u-PA on U937 cells was determined as described in detail previously (Ellis et al., 1990). Briefly, varying concentrations of plasminogen (0.09 uM and 2.26 µM) were incubated with U937 cells (pre-incubated with active u-PA and subsequently washed) in the presence of the plasmin specific fluorogenic substrate Val-Leu-Lys-AMC (Bachem, Switzerland). Plasmin generation was determined from the rate of change of the increase in fluorescence due to substrate hydrolysis, measured at excitation and emission wavelengths of 380 nm and 480 nm, respectively. These plasmin generation rates were subsequently plotted against the plasminogen concentration in a double-reciprocal manner to determine the individual kinetic constants, $K_m$ and $V_{max}$, for the reaction. $V_{max}$, the maximum reaction velocity, was converted to $k_{cat}$, the catalytic rate constant, by division of $V_{max}$ by the concentration of u-PA bound to u-PAR.

The concentration of u-PA bound to u-PAR on U937 cells was determined using $^{125}$I-u-PA (prepared as described in Ellis et al., 1990) which was incubated with the cells in parallel incubations to the kinetic experiments and treated identically. $^{125}$I-u-PA bound to u-PAR was then quantitated using standard gamma-counting techniques.

Results

Kinetics of Plasminogen Activation by u-PA Bound to u-PAR on U937 Cells u-PA bound to u-PAR on U937 cells was found to activate its natural substrate plasminogen with different kinetic characteristics from those displayed in the absence of u-PAR. The activation of Glu-plasminogen by u-PAR-bound u-PA followed an apparently Michaelis-Menton type kinetic mechanism. This was characterized by a $K_m$ of 0.67 μM and a $k_{cat}$ of 5.6 min$^{-1}$ (FIG. 22). Both of these constants were different from those obtained with u-PA in solution, i.e. the absence of U937 cells. In this situation, the $K_m$ was much higher at 25 μM (equivalent to an approximately 40-fold lower affinity for plasminogen in the absence of cell-associated u-PAR) and the $k_{cat}$ higher at 44 min$^{-1}$ (equivalent to an approximately 8-fold higher catalytic rate in the absence of cell-associated u-PAR). Therefore, u-PA binding to u-PAR on U937 cells causes plasminogen activation to be saturated at lower plasminogen concentrations than in solution, but this is accompanied by a reduction in the catalytic rate. However, the overall effect is a 5-fold increase in the catalytic efficiency ($k_{cat}/K_m$) of u-PA when bound to u-PAR on U937 cells (Table 5). As plasminogen (and plasmin) is known to bind to U937 cells, as well as a wide variety of other cells (Ellis et al., 1989; Plow et al., 1986), these constants measure plasminogen activation taking place at the surface of cells possessing u-PAR, i.e. cell-surface plasminogen activation.

Table 5 also shows similar data for plasminogen activation by u-PA bound to u-PAR on PMA-stimulated U937 cells. The $K_m$ for plasminogen activation is now 1.43 μM, still much lower than for the reaction in solution. However, the $k_{cat}$ also falls from 5.6 min$^{-1}$ to 1.23 min$^{-1}$, resulting in an overall reduction in plasminogen activation ($k_{cat}/K_m$) of approximately 10-fold when compared to unstimulated cells.

TABLE 5

Kinetic constants for Glu-plasminogen activation in the presence of U937 associated u-PAR

|  | $K_m$ | $k_{cat}$ | $k_{cat}/K_m$ |
| --- | --- | --- | --- |
| u-PA in solution | 25 μM | 44 min$^{-1}$ | 1.76 μM$^{-1}$ min$^{-1}$ |
| u-PA - u-PAR on U937 cells | 0.67 | 5.6 | 8.36 |
| u-PA - u-PAR on PMA-U937 | 1.43 | 1.23 | 0.86 |

Inhibition of Cell-surface Plasminogen Activation by a Polyclonal Antibody to u-PAR The polyclonal rabbit antibody raised against purified u-PAR (see Example 4) was used to demonstrate that the cell-surface plasminogen activating activity of u-PA demonstrated in the previous section was indeed due to u-PA binding to u-PAR, and also to demonstrate that this antibody did block binding of u-PA to u-PAR in solution.

Firstly, the effect of this antibody on u-PA activity in solution was determined. In 4 experiments anti-u-PAR (100 μg/ml for 30 min) gave a residual u-PA activity of 90.1±9.3%, compared to 88.6±12.3% for pre-immune IgG from the same animal. Therefore the anti-u-PAR antibody gave no specific inhibition of u-PA activity.

When pre-incubated with U937 cells at a concentration of 25 μg/ml for 30 minutes, the anti-u-PAR antibody resulted in a decrease in the subsequent plasminogen activating activity of 76% (mean of three experiments, range 66%–82%). In contrast the preimmune IgG gave <1% inhibition, whilst DFP-u-PA gave 90% inhibition (range 74%–100% in three experiments). Therefore the anti-u-PAR polyclonal antibody effectively inhibits the cell-surface plasminogen activation.

Inhibition of Cell-surface Plasminogen Activation Initiated by Exogenous u-PA by a Monoclonal Antibody to u-PAR Of the 4 monoclonal antibodies 1R, 2R, 3R and 4R, 3 were found to be without effect in inhibiting cell-surface plasminogen activation at the concentrations tested (up to 50 μg/ml) by the procedure described above. These were monoclonal antibodies 1R, 2R and 4R. However, monoclonal antibody 3R strongly inhibited plasminogen activation as shown in FIG. 23. This inhibition was half-maximal at an antibody concentration of approximately 0.07 μg/ml.

The monoclonal antibody 3R also efficiently inhibited binding of $^{125}$I labelled DFP-treated u-PA to u-PAR on the U937 cells as tested by cross linking experiments performed as described in Example 1. The antibodies 1R, 2R and 4R did not inhibit the DFP-u-PA binding.

By the use of standard flow cytometry procedures with commercial FITC- (fluorescein isothiocyanate) labelled antibodies against mouse IgG, it was found that the two antibodies 3R and 4R efficiently bound to u-PAR on freshly prepared human monocytes. The binding of 3R was completely inhibited by preincubation with exogenously added u-PA while the binding of 4R was not affected by preincubation with u-PA.

The 3R antibody thus inhibits u-PA binding to its specific cellular receptor, an interaction which is essential for the generation of plasmin proteolytic activity on the cell surface.

None of the monoclonal antibodies, including 3R, had any effect on cell surface plasminogen activation with cells to which u-PA had been pre-bound, i.e. cells incubated with u-PA first followed by incubation with monoclonal antibody.

Inhibition of Cell-surface Plasminogen Activation Initiated by Exogenous pro-u-PA by a Monoclonal Antibody to u-PAR Methods The generation of plasmin from mixtures of pro-u-PA and plasminogen in the presence of U937a cells was determined by a modification of the procedure originally described (Ellis V. et al., 1989). U937a cells were washed and acid treated (Behrendt et al., 1990), to remove traces of endogenous u-PA bound to the cells, before incubation with varying concentrations of the monoclonal antibodies (0–50 μg/ml final concentration) in PBS containing 2 mg/ml fatty-acid free BSA for 30 minutes at 37° C., followed by a single wash in the same buffer. The cells were then incubated at a final concentration of 2×10$^6$ cells/ml in 0.05M Tris-HCl pH 7.4, 0.1M NaCl with pro-u-PA (1.2 nM), plasminogen 2 (0.14 μM) and 0.2 mM H-D-Val-Leu-Lys-7-amido-4-methylcoumarin (Bachem), a plasmin specific fluorogenic peptide substrate. These incubations were made in 10-mm plastic fluorimeter cuvettes which were maintained at 37° C. and gently stirred in a Perkin-Elmer LS-5 luminescence spectrometer equipped with a micromagnetic stirrer. Plasmin generation was determined from the rate of change in the fluorescence intensity (Ellis et al., 1990). In control experiments the anti-u-PAR antibodies were shown to have no effect on plasminogen activation in the absence of cells at antibody concentrations up to 50 µg/ml.

Results

Figure 24A:
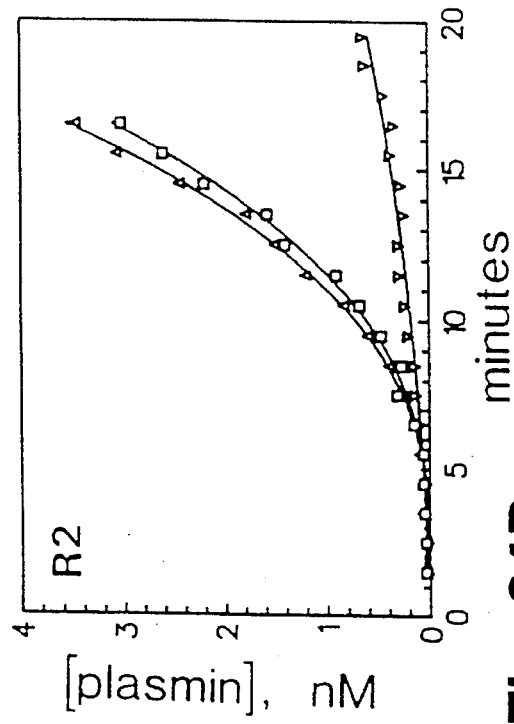
Figure 24B:
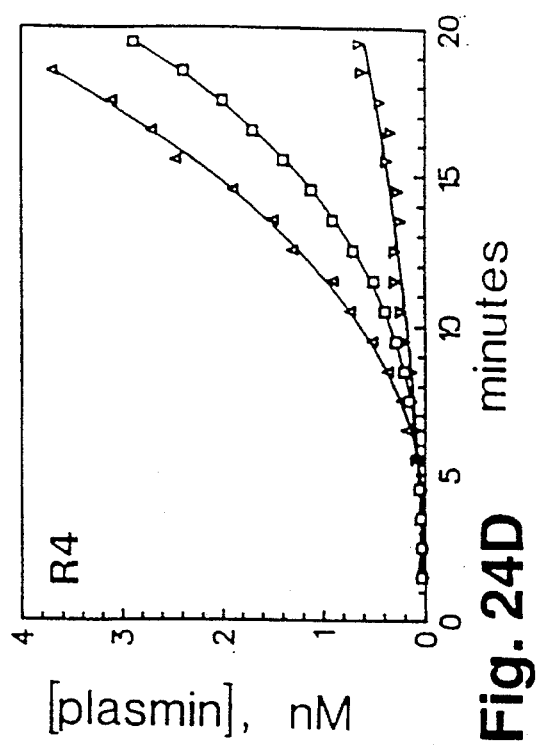
Figure 24C:
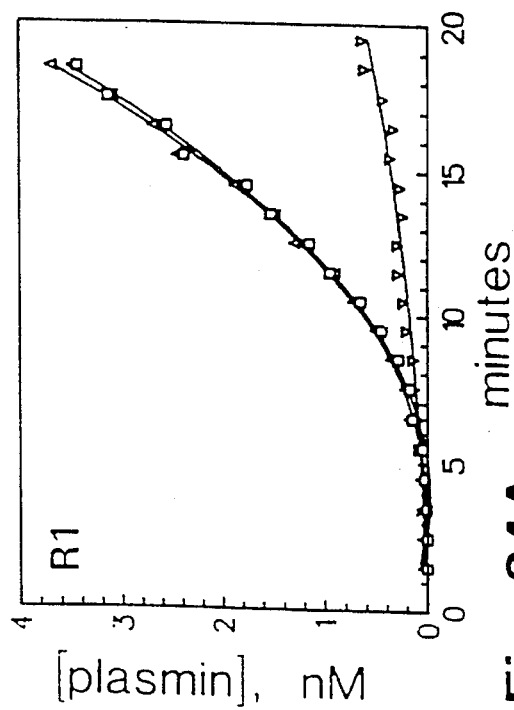
Figure 24D:
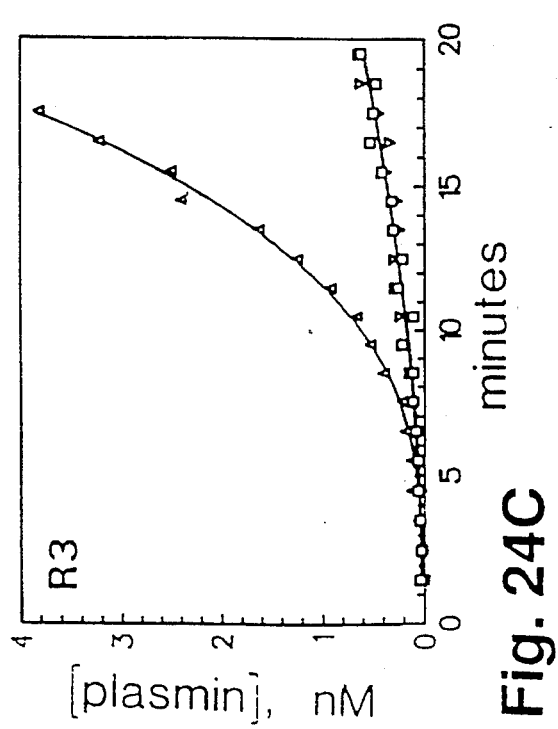

The pro-u-PA dependent plasminogen activation has been shown to be greatly enhanced in the presence of U937 cells, with this effect requiring the cellular binding of both pro-u-PA and plasminogen (Ellis et al., 1989). FIGS. 24A–24D demonstrates this effect in a system where pro-u-PA and plasminogen have been incubated with acid-washed U937a cells and plasmin generation measured directly in the presence of the cells from the time of addition of the proteins. The figure also shows the effect of pre-incubation of the cells with each of the four antibodies raised against u-PAR. It can be seen that antibody 3R at a concentration of 2 µg/ml completely abolished the increased plasmin generation observed in the presence of U937A cells (FIG. 24C). In contrast, the antibodies 1R and 2R were without any effect on the cellular enhancement of plasminogen activation at the same concentration of antibody. Concentrations of these two antibodies up to 50 µg/ml were also without significant effect on the generation of plasmin in this system. Antibody 4R gave an intermediate effect with a partial inhibition of the enhancement of plasmin generation (FIG. 24D), and this inhibitory effect was never more than approximately 50% at higher antibody concentrations (up to 50 µg/ml, data not shown). However, if cells, which had been pre-incubated with 4R as before, were further incubated with pro-u-PA for 15 minutes prior to the addition of plasminogen, the inhibitory effect of 4R on the enhancement of plasmin generation was abolished. Under the same conditions the effect of antibody 3R was unchanged.

EXAMPLE 8

IN SITU HYBRIDIZATION FOR u-PAR mRNA AND IMMUNOSTAINING OF u-PAR

In Situ Hybridization

MATERIALS AND METHODS

Materials. The following materials were obtained from the indicated sources: T7 and T3 polymerase, pBluescriptKS(+) plasmid vector (Stratagene; Calif., USA); RNasin and DNase I (Promegs, Wis., USA); $^{35}$S-UTP (1300 Ci/mmol) (NEN Dupont, Mass., USA); Dithiothreitol and restriction endonucleases (Boehringer Mannheim, Mannheim, FRG); K5 autoradiographic emulsion (Ilford, Cheshire, England); Formamide (Fluka, Buchs, Switzerland); Salmon Sperm DNA (Type III, Sigma, Mo., USA). All other materials were as described previously (Kristensen et al., 1984; Kristensen et al., 1990), or of the best commercially available grade.

Tissue preparation. Following surgery, tissue specimens from 13 patients with adenocarcinoma of the colon were dissected and placed in 4% or 10 % (wt/vol) formalin—0.9 % NaCl solution for 24–48 hours before embedding in paraffin wax.

Preparation of RNA probes. Fragments of the complete human u-PAR cDNA (see Example 3) were subcloned using standard techniques (Maniatis et al., 1982), and two subclones were prepared: pHUR04: PstI(184)–PstI(451) fragment and pHUR06: BamHI(497)–BamHI(1081) fragment in pBluescriptKS(+), base pair numbers corresponding to sequence as listed in Example 3. Pure plasmid preparations were prepared by banding in CsCl gradients and the plasmids were linearized for transcription using SmaI restriction endonuclease (pHUR04) or SpeI and EcoRI (pHUR06). 5 µg of the linearized plasmid was extracted with phenol and with chloroform/isoamylalcohol (25:1), precipitated with ethanol and redissolved in water. Each transcription reaction contained linearized DNA template (1 µg), RNasin (40 U), 40 mM Tris-Cl, pH 7.6, 6 mM $MgCl_2$, 10 mM NaCl, 2 mM Spermidine, 10 mM DTT, 1 mM GTP, 1 mM ATP, 1 mM CTP, 4 µM $[35]^S$ UTP and the relevant polymerase (T3 or T7, 40 U). The pHUR04 template was transcribed with the T3 polymerase and the pHUR06 template linearized with EcoRI was transcribed with T7 polymerase, yielding antisense transcripts. The pHUR06 template linearized by digestion with SpeI was transcribed with the T3 polymerase yielding sense transcripts.

After transcription performed for 120 min at 37° C., the template DNA was removed by addition of RNase-free DNase I (1 U), yeast t-RNA (20 µg), RNasin (20 U) and incubation at 37° C. for 15 min. After extraction with phenol and chloroform/isoamylalcohol (25:1) RNA was precipitated by ethanol by centrifugation at 15000×g, 4° C., for 10 minutes after addition of ammonium acetate (final concentration 2M), and redissolved in 10 mM DTT. The RNA was hydrolyzed in 0.1M sodium carbonate buffer, pH 10.2, containing 10 mM DTT to an average size of 100 bp. Hydrolysis time was calculated as described (Cox et al., 1984). After hydrolysis, the reaction was neutralized by addition of an equal amount of 0.2M sodium acetate buffer, pH 6.2, containing 10 mM DTT and the RNA was precipitated twice with ethanol, as above.

The RNA probe was redissolved in 10 mM DTT and radioactivity measured using scintillation counting. Probe preparations always contained more than $4 \times 10^6$ cpm/µl, and the amount of TCA precipitable material was usually above 90%. The two corresponding RNA probes transcribed from the opposite strands of the pHUR06 plasmid template were adjusted to the same radioactivity concentration by addition of 10 mM DTT, and deionized formamide was added to a final concentration of 50%. Probes were stored at −20° C. until use.

In situ hybridization. In situ hybridization was performed using a method adapted from a number of published procedures (e.g. Cox et al., 1984; Angerer et al., 1987). Slides were dipped in 0.5% gelatin, 0.5% chrome-alum, dried at room temperature, baked at 180° C. for 3 hours and stored dust-free at room temperature. Paraffin sections were cut, placed on slides, heated to 60° C. for 30 minutes, deparaffinized in xylene and rehydrated through graded alcohols to PBS (0.01M sodium phosphate buffer pH 7.4, containing 0.14M NaCl). The slides were then washed twice in PBS, acid treated in 0.2M HCl for 20 minutes and washed for 5 minutes in PBS. This was followed by incubation in 5 µg/ml Proteinase K in 50 mM Tris-Cl, pH 8.0, with 5 mM EDTA for 7.5 min, washing twice in PBS (2 min) and fixation in 4% (wt/vol) paraformaldehyde in PBS for 20 min. Fixative was removed by washing with PBS and slides were immersed in 100 mM triethanolamine in a beaker on a magnetic stirrer. As the solution was being stirred, acetic acid anhydride was added (final concentration 0.2% (vol/vol)) and the addition was repeated after 5 min. Finally, the slides were washed in PBS (5 min), dehydrated in graded ethanols and airdried at room temperature. The probe was heated to 80° C. for 3 min and allowed to cool before addition to the hybridization mix. The final hybridization solution contained RNA probe (80 pg/µl), deionized formamide (50%), dextran sulphate (10%), t-RNA (1 µg/µl), Ficoll 400 (0.02% (wt/vol), polyvinylpyrrolidone (0.02% (wt/vol)), BSA Fraction V (0.02% (wt/vol)), 10 mM DTT, 0.3M NaCl, 0.5 mM EDTA, 10 mM Tris-Cl and 10 mM NaPO$_4$ (pH 6.8). The hybridization solution was applied to the slides (approx. 20 µl per section) and sections covered by alcohol washed, autoclaved coverslips. Sections were hybridized at 47° C. overnight (16–18 hours) in a chamber humidified with 10 ml of a mixture similar to the hybridization solution, except for probe, dextran sulphate, DTT and t-RNA (washing mix). After hybridization, the position of air bubbles occasionally formed over the section was marked, and coverslips were removed by incubation in washing mix for 1 hour at 50° C. The washing mix was changed, and washing continued for 1 hour at 50° C. Sections were washed in 0.5M NaCl, 1 mM EDTA, 10 mM Tris-Cl (pH 7.2, NTE) with 10 mM DTT at 37° C. for 15 min, and treated with RNase A (20 µg/ml) in NTE at 37° C. for 30 min. This was followed by washing in NTE at 37° C. (2×30 min), and washing in 2 liters of 15 mM sodium chloride, 1.5 mM sodium citrate, pH 7.0 with 1 mM DTT for 30 min at room temperature with stirring. Sections were then dehydrated in grading solutions of ethanol, all containing 300 mM ammonium acetate until 99% ethanol, and air-dried. Finally, autoradiographic emulsion was applied following the manufacturer's recommendations, and sections were stored in black airtight boxes with desiccant at 4° C. until developed after 1–2 weeks of exposure.

Results

Tissues were analyzed with antisense transcripts from the two non-overlapping clones pHUR04 and pHUR06 and with sense transcripts from pHUR06.

Areas of normally appearing mucosa were in all cases devoid of hybridization signal (not shown).

Figure 25A:
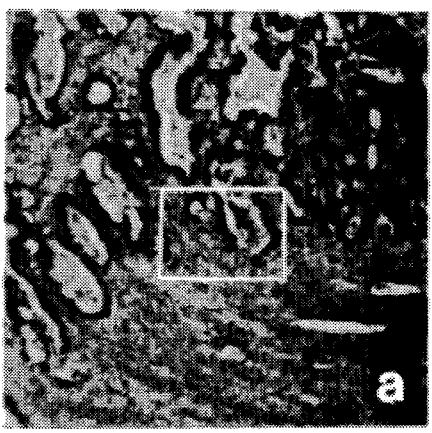
Figure 25B:
Figure 25C:
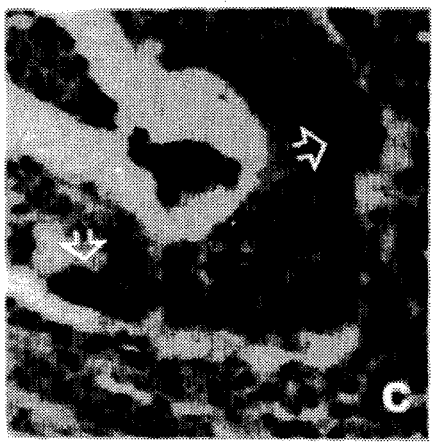
Figure 25D:
Figure 25E:
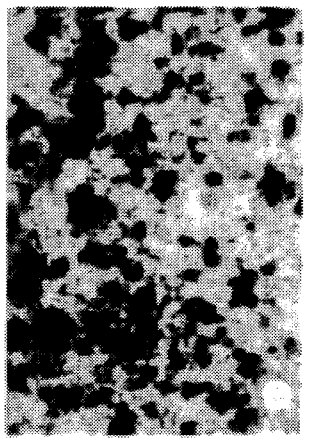

At invasive foci of carcinoma, hybridization signal was consistently seen when using pHUR06 antisense transcripts. A particularly prominent hybridization signal was found above cells at the leading edge of disrupted tumor glands in areas with clear signs of inflammation and degradation of surrounding mesenchymal tissue (FIG. 25a–b). In other areas of infiltrating carcinoma where tumor glands show a more organized structure, hybridization signal was located above cells closely associated with coherent strands of tumor cells (FIG. 25-d) or above cells integrated at the serosal surface of the neoplastic epithelium itself (FIG. 25-c). It was not possible from the sections to identify with certainty the cell type(s) in question, nor could the identity of some cells in areas of neovascularization that showed hybridization signal be firmly established (FIG. 25-e). After intensive photographing at high magnification (400–1000×) of selected areas of the tumor, silver bromide crystals were removed by immersion in periodic acid for 5 min and the slides were reexamined. By this technique, cells showing hybridization signal can be studied in greater detail and this technique is at present being pursued for a final assessment of cell type(s).

The hybridization signals obtained with pHUR06 antisense transcripts were confirmed on adjacent sections using antisense transcripts from pHUR04 (not shown). Unspecific binding of radioactive probe was demonstrated using sense transcripts from pHUR06 and in all tumors analyzed gave rise to a signal uniformly distributed above tissue sections and with an intensity comparable to that obtained with pHUR06 antisense transcripts in areas of no hybridization (e.g. normally appearing mucosa) (not shown).

Immunohistochemical Detection of u-PAR in Paraffin-embedded, Formalin-fixed Human Neoplasms Antibodies: Monoclonal antibodies against u-PAR, clones 2R and 4R, purified IgG.

Tissue-sections: Routinely processed, formalin-fixed and paraffin-embedded tissue blocks from 3 cases of colon adenocarcinomas and 1 case of lung squamous cell carcinoma were used. Thin sections (3–5 microns) were cut on a microtome.

Method: Sections were deparaffinized in xylene for 2×5 min, rehydrated through graded ethanol baths to TBS-Triton and treated with a 0.01% trypsin solution in 50 mM Tris/HCl with 0.1% CaCl$_2$ for 10 min at room temperature (by immersion). Sections were then washed for 5 min in running deionized water, then blocked in 5% rabbit serum-TBS-BSA for 15 min at room temperature. After a brief (5–10 sec) wash in TBS-Triton, primary antibody was applied to the sections in a concentration of 1–10 µg/ml diluted in TBS-BSA. The primary antibodies were m-anti-u-PAR clones 2R and 4R and, as a negative control, a m-anti-TNP antibody. Incubation was overnight at 4° C. or at 37° C. for 1 hour in a humidified chamber to prevent drying out of sections. After washing sections for 5×5 min in TBS-Triton, a secondary rabbit-anti-mouse antibody was applied (DAKOPATTS Z259, diluted 1:50 in 5% rabbit serum-TBS-BSA) for 30 min at room temperature, followed by 5×5 min washing in TBS-Triton. Alkaline phosphatase-conjugated mouse-anti-alkaline phosphatase was then applied to sections (DAKOPATTS D651, diluted 1:20 in 5% rabbit serum-TBS-BSA) for 30 min at room temperature. A final wash was performed in TBS-Triton for 5×5 min, then 2×5 min in AP-buffer. Development with the chromogenic substrate NBT/BCIP was for 30 min in the dark at room temperature as described (Kristensen et al., 1990, Histochemistry, 93, 559–562). Sections were contrast-stained with Kernechtrot, 0.025% before being coverslipped with Eukitt.

Buffers: TBS: 50 mM Tris/HCl, 150 mM NaCl pH 7.4

TBS-Triton: TBS with 1% Triton X-100

TBS-BSA: TBS with 0.25 % bovine serum albumin

5% rabbit serum-TBS-BSA: TBS-BSA with 5% normal rabbit serum

AP-buffer: 100 mM Tris/HCl, pH 9.5 with 5 mM MgCl$_2$, 100 mM NaCl

Results

The antibodies 2R and 4R reacted with the same tissue components in all 4 specimens, although the antibody 2R showed a considerable higher staining intensity than 4R when compared at the same immunoglobulin concentration. Immunoreactive material was consistently found in neutrophils, in a subset of histiocytes and in cells at the tumoralstromal interface at invasive foci. No staining was seen on sections incubated with the m-anti-TNP antibody used as control. Tissue sections from the same specimens were previously tested by in situ hybridization for the localization of specific u-PAR mRNA (see above). The immunohistochemical localization of u-PAR as seen with antibodies 2R and 4R in these tumors was virtually identical to the distribution of u-PAR mRNA (detected by in situ hybridization) as regards positive cells at invasive foci, histiocytic cells and neutrophils that are found in the interstitial tissue or are present in granulation tissue. As far as neutrophils contained in vessels are concerned, a heavy u-PAR immunoreactivity could be seen, but no u-PAR mRNA could be found in these cells.

EXAMPLE 9

Substance Screening Scheme

The following substance screening scheme comprising various successive steps has been established to identify substances which can be used to inhibit the interaction between u-PA and u-PAR and thereby be used as drugs to inhibit the invasive and metastatic process. The initial screening of the substances is performed using the below described substance screening ELISA and if the substances show inhibitory effect, the further screening of substances is performed using the next steps in the scheme.

1. Substance screening ELISA for use in the screening of substances capable of inhibiting u-PA/u-PAR interaction A two antibody sandwich ELISA assay has been developed for screening substances for their capability to inhibit the interaction between u-PA and u-PAR in solution. The effect of the compound or antibody to be screened to inhibit the interaction can be tested at various concentration. In the present case, the compound Suramin tested and the effect of Suramin on the interaction is examined.

Materials 1) 96-well plates (flat-bottom high binding capacity, NUNC).

2) Unlabelled purified 4R

3) Purified anti-u-PA clone 5 (Nielsen et al., 1986) labeled with biotin.

4) Horseradish peroxidase-conjugated (HRP) avidin.

5) Affinity purified u-PAR.

6) DFP-u-PA

7) Suramin (Germanine®, Bayer)

8) PBS buffer, pH 7.4 (PBS)

9) PBS+0.1% Tween 20, pH 7.4 (PBS/Tween)

10) Blocking buffer: 1% skimmed milk powder (SMP) in PBS

11) Citrate buffer: 0.1M citrate, pH 5.0.

12) Substrate solution: 1,2-Phenylenediamine dihydrochloride (OPD) tablets in citrate buffer, e.g. 3 OPD tablets in 15 ml of citrate.

13) Stop buffer: 1M $H_2SO_4$.

Procedure

1) Coat the wells with 100 µl of 4R (20 µg/ml) diluted in 0.1M $Na_2CO_3$.

2) Incubate overnight at 4° C.

3) Wash the wells 5× in PBS/Tween.

4) Block the remaining active sites in the wells with 1% SMP/PBS, 200 µl/well, for at least 1 hour at RT. Gentle shaking.

5) Wash as in step 3).

6) Add 100 µl of u-PAR (20 ng/ml).

7) Incubate with gentle shaking for 1 hour at RT.

8) Wash as in step 3).

9) Add a mixture of 100 µl of DFP-u-PA (10 ng/ml) and 100 µl of blocking buffer or a mixture of 100 µl of DFP-u-PA (10 ng/ml) and 100 µl of serial dilution of Suramin.

10) Incubate as in step 7).

11) Wash as in step 3).

12) Add 199 µl of biotinylated anti-u-PA clone 5 (2 µg/ml).

13) Incubate as in step 7).

14) Wash as in step 3).

15) Add 100 µl of HRP-avidin diluted 1:5000 in SMP/PBS/Tween.

16) Incubate as in step 7).

17) Wash as in step 3).

18) Wash 1× in distilled water.

19) Add 100 µl/well of substrate solution.

20) Stop the reaction with 100 µl/well of 1M $H_2SO_4$, when bright yellow colour appears.

21) Read on an ELISA-reader with 490 nm filter with 540 nm filter as a background reference.

Results

The drug screening assay constructed as a two antibody sandwich ELISA was used to examine the effect of Suramin on the interaction between u-PA and u-PAR (FIG. 27) shows that the Suramin blocks the binding reaction in a dose-dependent manner and that Suramin added in serial dilution with a fixed concentration of DFP-u-PA to purified u-PAR has an increasing inhibitory effect in the screening ELISA with increasing concentration of Suramin.

2. Further test of substances by cross-linking to examine their capability of inhibiting u-PA/u-PAR interaction Further testing of substances found to inhibit the interaction between u-PA and u-PAR in the above described screening ELISA is performed in order to establish that the inhibition indicated in the above described ELISA is indeed caused by the inhibition of the binding between u-PA and u-PAR. In the present example, the nature of the above shown inhibition of the binding of u-PA to u-PAR by the compound suramin as a genuine inhibition of the binding between u-PA and u-PAR is verified.

Materials

HEp-2 larynx epidermoid carcinoma cell line containing u-PAR (Behrendt et al., 1990) was purchased from ATCC. A clarified lysate of HEp-2 cells was produced as described above for U937 cells except that 1% CHAPS was used instead of 1% Triton X-114. Suramin was used in various concentrations.

Method

The HEp-2 cell lysate was diluted 40-fold and incubated in the presence of $^{125}I$-labeled ATF and varying concentration of suramin followed by chemical cross-linking and analysis by SDS-PAGE and autoradiography. The cross-linking and analysis procedure was performed as described in Example 1.

Results

Suramin was found to inhibit the binding reaction between u-PAR and $^{125}$I-labeled ATF in a dose-dependent manner as appears from FIG. 28. No binding activity was detected in the presence of a concentration of 1 mg/ml suramin and more than 50% inhibition of the binding activity was obtained in the presence of a concentration of 0.1 mg/ml suramin. The binding activity was defined as the formation of radio-labeled covalent conjugate.

It can therefore be concluded that the above described substances screening ELISA can be used to identifying a substance capable of inhibiting the binding between u-PA and u-PAR.

3. Screening of substances for their capability to inhibit the binding of u-PA to u-PAR on the cell surface of cultured cells The capability of a compound or antibody to inhibit the binding of u-PA to u-PAR is suitably examined as a step of the scheme using the method described in Example 4. In this example, the effect of the inhibition of the binding by the polyclonal antibodies is examined. From FIG. 17A it can be seen that polyclonal antibodies inhibit the binding of u-PA to u-PAR. By replacing the polyclonal antibodies with the compound or antibody under test in various concentrations or with monoclonal antibodies, the capability of the compound or the antibodies to inhibit the binding of u-PA to u-PAR on the cell surface can be evaluated.

4. Screening of substances for their capability to inhibit the plasminogen activation in different types of cultured cancer cells The effect of compounds or antibodies in the inhibition of the plasminogen activation is examined for different types of cancer cells as various types of cancer cells are known to differ with respect to the expression of u-PAR and u-PA. The effect is examined for cancer cell types expressing u-PAR but not u-PA and therefore not possessing endogenous pro-u-PA and for cancer cell types expressing both u-PAR and u-PA and therefore possessing endogenous pro-u-PA. Depending on the aim of the screening, cancer cell types from different sources are used in the assay.

4a. Screening of substances for their capability to inhibit activation in a cancer cell culture expressing u-PAR but not expressing u-PA This screening assay is performed with the cancer cell type MDA-MB-435 (Price J. et al., 1987) expressing u-PAR but not expressing u-PA essentially as described in Example 7.

From FIG. 23 it appears that the monoclonal antibody 3R but not 1R, 2R and 4R is capable of inhibiting the activation. By replacing the monoclonal antibodies with a substance under test in various concentrations or with other monoclonal antibodies, the capability of the compound or the antibodies with respect to inhibiting the activation can be examined.

4b. Screening of substances for their capability to inhibit activation in cancer cell culture expressing both u-PAR as well as pro-u-PA This screening assay should be performed on cancer cells expressing both u-PAR and u-PA and thereby containing both u-PAR and pro-u-PA and below is described an example in which the effect of the monoclonal antibody 3R to inhibit the activation is shown.

MDA-MD-231 cells obtained from ATCC, Md., USA, were seeded into 24 well culture plates at a density of $0.25 \times 10^6$ cells/ml in DMEM (Flow Laboratories, Scotland) supplemented with 5% foetal calf serum, and in the presence or absence of 100 µg/ml of the monoclonal antibody 3R. The cells were cultured for 5 days i.e. to confluence, without change of medium. Counting of the cells after this period demonstrated that the growth of the cells was unaffected by the presence of the antibody.

For each determination of u-PAR-mediated plasmin generation 12 wells were washed 3 times in DMEM buffered with 25 mM Hepes pH 7.4, and once in PBS containing 0.2% BSA. Subsequently, the wells were incubated with 200 µl per well of 15 µg/ml Glu-plasminogen and 0.2 mM of the plasmin specific fluorogenic substrate H-D-Val-Leu-Lys-AMC in PBS containing $Ca^{++}$ and $Mg^{++}$. At 3 minute intervals 150 µl of 0.05M Tris-HCl pH 7.4, 0.1M NaCl were placed in a micro fluorimeter cuvette. The fluorescence due to cleavage of the substrate by the generated plasmin activity was measured in a Perkin-Elmer LS5 spectrofluorometer using excitation and emission wavelengths of 380 and 480 nm, respectively. The generated plasmin was quantified by determining the rate of change in fluorescence over each 3 minute time interval, and comparing this to calibration curves made using active-site titrated plasmin (Ellis et al., 1989).

In FIGS. 24A–24D is shown the effect of culturing MDA-MB-231 cells in the presence of monoclonal antibody 3R on the plasmin generation. Antibody 3R reduces the rate of plasmin generation to 20% of that of the control cells cultured in the absence of the antibody. It is thus demonstrated that 3R is effective in blocking the binding of endogenously secreted pro-u-PA to PAR and thereby the activation of plasminogen.

By replacing the monoclonal antibodies in the below example with the compound or antibody to be screened in various concentration or with other monoclonal or polyclonal antibodies, the effect of the compound or antibodies to inhibit the activation can be evaluated.

5. Screening of substances for their capability to inhibit the invasive and metastatic process of human cancer cells in nude mice The last step in the screening of substances which have been shown in the above described previous steps of the substance screening scheme to inhibit the interaction between u-PA and u-PAR and which thereby are potential substances to be used as drugs to inhibit the invasive and metastatic process is to evaluate the effect of the substance to inhibit the invasive and metastatic process in vivo. A mouse model in which the invasive and metastatic process of human cancer cells can be measured has been developed to evaluate this effect.

Method

Nude female mice 6–8 weeks-old nu/nu-META/Bom (Bomholtgaard, Denmark) are inoculated with the below transduced human cancer cells. The following types of human cancer cells can be used: MDA-MB-231, MDA-MB-435, HT1080 (Andreasen et al, 1986), U937 and MIII (Clark R et al, 1989).

Retroviral Transduction

To visualize the metastatic tumors, the human cancer cell type to be used in the assay is labeled by transducing the cells with a LacZ gene whereby the cells can be visualized by X-gal staining. This transduction has previously been performed by Lin et al. (1990) using ras-transduced mouse 3T3 cells transfected with the LacZ gene whereas in the present example, a human cancer cell line is used. The lacZ gene codes for β-D-galactosidase, the activity of which can be detected by staining with the chromogenic substrate 5-bromo-4-chloro-3-indolyl-β-D-galactopyranoside (X-gal), which gives a dark blue reaction. Thereby also microscopic metastatic tumors can be detected.

The transduction of the human cancer cells chosen can be performed as described below.

Pharmacokinetics of the Substance

The pharmacokinetic characteristics of the compound or antibody to be screened should be clarified in order to administer and retain the compound or antibody in an effective concentration in the mouse.

The administration of the compound or antibody to be screened depends on the chemical nature of the compound or antibody and may be performed by interperitoneal injection or subcutaneous injection, by oral administration or local application. Below is described an example in which the pharmacokinetic characteristics of a monoclonal antibody has been examined.

Pretreatment of Mouse and Transduced Cancer Cells

It may be an advantage to pretreat the mouse with the compound or antibody to be screened before injecting the transduced cancer cells in order to obtain satisfactory concentrations of the compound or antibody. Furthermore, the transduced cancer cells to be injected into the mouse may be preincubated in a solution containing the compound or antibody in order to ensure a contact between the cells and the compound or antibody. Normally several experiments in which this pretreatment is varied or excluded should be performed in order to clarify and ascertain the overall effect of the compound or the antibody.

Cancer Cell Inoculation

The transduced cancer cells can be inoculated either subcutaneously or interperitoneally.

Measurement of Tumor Growth

The growth of the tumors should be measured in order to elucidate whether the compound or antibody under test affects the growth of the tumor in addition to the possible effect on the invasive and metastatic process. The growth is measured as described below.

Duration of the Screening Assay

The duration of the assay depends on the nature of the compound or antibody and on the effect of the compound or antibody on the invasive and metastatic process.

Evaluation of the Invasive and Metastatic Process

The effect of the compound or antibody on the invasive and metastatic process and on the growth of the tumor can be evaluated locally and/or in the lungs, the lymph nodes and in the interperitoneal cavity utilizing the very distinct differentiation between human cells and mouse cells rendered possible by the staining. An example of such an evaluation is given below under section 6).

This result of the inhibition of the invasive and metastatic process by the substance tested shows that the substance is a good candidate to be an anti-invasive and anti-metastatic drug in types of human cancer in which u-PA/u-PAR interaction is believed to play a crucial role for these processes such as colon adenocarcinoma, ductal mammary carcinoma and squamous skin cancer. After appropriate toxicological studies they therefore should be tested in phase I and II clinical trials.

6) Inhibition of the invasive and metastatic process in mice using monoclonal antibodies directed against u-PA The significance of the enzymatic activity of u-PA in the invasive and metastatic process of cancer cells was examined as described below and the results of this experiment substantiates together with the results obtained in the previous steps of the screening scheme that this mode will be valuable for testing the anti-invasive and anti-metastatic effect of substances inhibiting u-PA/u-PAR interaction.

Materials and Methods

Cell Lines

The human breast cancer cell lines MDA-MB-231 and MDA-MB-435 were routinely propagated in DMEM with 10% Fetal Calf Serum (D10). Cells for nude mouse experiments were harvested using a cell scraper instead of using enzymes. The cell lines were tested and found free from Mycoplasma contamination.

Mice

Nude female mice 6–8 weeks-old nu/nu-META/Bom (Bomholtgaard, Denmark) were used. The mice were kept in laminar flow clean benches and all equipment used was autoclaved.

Retroviral Transduction

Viral stocks of the BAG vector (containing LTR - LAC-Z - SV 40 PROMOTOR - NEO® - LTR) (Price J et al, 1987) packed in PA317 cells (Miller A. D. et al, 1986) containing the LacZ gene were used to transduce the cells. The neomycin resistance gene was used for selection of the transduced cells. The human cancer cells were plated one day before infection at a 1:10 split ratio. To infect the cells, the culture medium was replaced with 5 ml of viral supernatant containing 4 µg/ml of polyprene and incubated for 2 hours at 37° C. in a 5% $CO_2$ incubator. An additional 5 ml of D10 were then added and the so transduced human cancer cells were returned to the incubator. The medium was replaced with fresh D10 the next day. The resulting transduced cell lines were named MDA-MB-231 BAG and MDA-MB-435 BAG.

Selection Procedure

To enrich for cells containing the BAG vector, the infected cell populations were grown in medium containing 500 µg/ml G418. The selected cells, however, did not all express β-galactosidase as determined by X-gal staining as described above. Therefore, cells were subjected to fluorescein-di-β-D-galactopyranoside (FDG)-FACS selection as described by Nolan et al. (1988). In this procedure, the release of fluorescein from non-fluorescent substrate by cells expressing the lacZ gene product, β-galactosidase, allows cell separation in a flow cytometer. A confluent 100 mm dish was trypsinized and the single cell suspension was adjusted to $1-5 \times 10^7$ cells/ml in D10. 100 µl of the cell suspension were incubated at 37° C. in a Falcon 2058 tube. Uptake of the substrate FDG by the cells was accomplished by hypotonic shock with the addition of 100 µl of 2 mM FDG in dH₂O. Following a 1 minute incubation at 37° C., the substrate was trapped within the cells by the addition of 1.8 ml of ice cold D10. The cells were incubated on ice for 1 hour and sorted on a Becton Dickinson dual laser FACStar Plus flow cytometer set to 488 nm wavelength.

Cell Inoculation

A total number of $2 \times 10^6$ tumor cells were inoculated subcutaneously into each of the flanks. The tumor cells were always placed inferior to the thoracic wall. One day before inoculation with the cells 500 µg of antibodies were injected into the mice and 21 days later another 500 µg was injected. The mice were sacrificed 6 weeks after inoculation.

Antibodies

An-u-PA-antibodies clone 5 (Nielsen et al., 1986) was used to inhibit the enzymatic activity and as irrelevant control antibodies was used an IgG1 mouse monoclonal antibody against a barley protein.

Examination of the Transduced Human Breast Cancer Cell Line

The transduced cell line was examined for the presence of mRNA coding for both u-PA and u-PAR by Northern blotting.

Total RNA was extracted from MDA-MB-231 BAG xenografts as previously described (Chirgwin et al., 1979). 25 µg of RNA was size fractionated by electrophoresis in a 1.2% agarose gel containing 2.2M formaldehyde. The RNA was blotted onto a nitrocellulose filter and hybridized with $^{32}$P-labeled cDNA probes at 58° C. for 18 hours in standard hybridization buffer (Chomczynski et al., 1987). The cDNA for u-PA comprises pHUK8 (Lund et al., 1987) and the cDNA for the u-PAR comprises p-u-PAR-1 (Roldan et al., 1990). Following hybridization, filters were washed with three changes of 0.1×SSC for a total of 1 hour at 65° C. Autoradiography was performed at 80° C. using two Chronex Quanta III intensifying screens.

X-gal Staining of Cells in Culture

Cells in culture were plated on glass slides and allowed to grow for two days before they were fixed with 0.5% (vol/vol) glutaraldehyde in PBS for 5 minutes followed by 3 times wash with PBS and overnight incubation at 37° C. in X-gal staining solution (1 mg of X-gal/ml; 35 mM potassium ferricyanide; 2 mM MgCl₂ in PBS). The sections were counterstained with Kernechtrot.

Tumor Growth

The tumor growth was measured in two dimensions three times weekly and tumor area calculated. Using the transformed Gompertz function (Rygaard K and Spang-Thomsen M, 1989), the growth rate (slope of the transformed Gompertz growth curve) of the individual tumors was calculated.

Evaluation of Local Invasion

Six weeks after cell inoculation, all animals were sacrificed by cervical dislocation. Primary subcutaneous tumors located at the site of cell inoculation were excised from the direction of the intraperitoneal cavity towards the skin, thus leaving the peritoneal muscle wall at one site and the skin on the other site of each tumor. Each tumor was divided into two by an incision perpendicular to the longest diameter of the tumor. Another incision was made close to the border of the tumor. Histological sections were made from the site of incision. Local invasion is defined as tumor cells placed between the peritoneal muscle fibers. No attempt was made to relate the treatment to invasion into the skin. In cases where the tumor cells were located close to the muscle fibers but without splitting the muscle, additional sections were made to exclude invasion.

Evaluation of Metastases

At autopsy liver, diaphragm, spleen, pancreas, intestine and lungs were excised from each animal. The organs were rinsed in 1×PBS and then fixed for 3 hours in 4% paraformaldehyde and 0.5% glutaraldehyde. The organs were then rinsed three times in 1×PBS and stained overnight with X-gal solution (1 mg of X-gal/ml; 35 mM potassium ferricyanide; 2 mM MgCl₂ in PBS) at 4° C. The day after, the organs were rinsed in 1×PBS and kept in sodium-azide until evaluated and photographed using an inverted stereomicroscope equipped with a Laitz MPS 52 camera. To confirm the presence of human tumor cell metastases, blue areas from various organs were fixed in 4% formalin and processed for routine histology. If an organ presented one or more blue areas, it was registered as positive for metastatic lesions.

Frozen Sections

Organs were fixed at 4° C. for 2 hours in 2% paraformaldehyde in 0.1M PBS pH=7.4, followed by rinsing with 0.1M PBS and dehydration in 0.1M PBS with 7% sucrose for 2 hours and 15% sucrose for additional 2 hours before being processed for cryo-sections. The cryo-sections were then stained with X-gal following the procedure used for the cell lines.

Cross-linking Assay

To establish that the transduced cells continued to express u-PAR, the presence of u-PAR was examined by a cross-linking assay as described above in section 2) using as the ligand binding to u-PAR $^{125}$I ATF.

Inhibition of Cell-surface Plasminogen Activation by anti-u-PA Antibodies

The capacity of MDA-MB-435 BAG cells to activate plasminogen was determined by a modification of the method previously described for use with suspension-growing cells (Ellis et al., 1990). Briefly, the MDA-MB-231 cells were grown to confluence in 24 well Costar trays maintained in serum-free DMEM (Flow Laboratories, Scotland) in the presence of the plasmin inhibitor aprotinin (10 µg/ml) (Bayer, Germany). Prior to assay the cells were washed 3 times in Hepes-buffered DMEM, followed by incubation for 15 minutes at room temperature in the presence or absence of 10 µg/ml of a monoclonal antibody to u-PA (clone 5). After 2 subsequent washes the cells were incubated with plasminogen (20 µg/ml) and the specific fluorogenic plasmin specific substrate H-D-Val-Leu-Lys-AMC (0.2 mM) in PBS containing 0.2% BSA (200 µl in each of 12 wells per incubation) at 37° C. At timed intervals 150 µl of the cell supernatant was removed, diluted with 150 µl of 0.05M Tris pH 7.4, 0.1 NaCl and the fluorescence intensity measured using micro-cuvettes in a Perkin Elmer LS-5 luminescence spectrometer with excitation end emission wavelengths of 380 and 480 nm, respectively. Plasmin concentrations were then determined by calculation of substrate hydrolysis (dF/ dt) over each time interval, and comparison with calibration curves constructed using active site-titrated plasmin (Ellis et al., 1990).

Pharmacokinetics of anti-u-PA-antibodies

Seven groups each of 5 nude mice were injected intraperitoneally with a single dose of 500 μg of anti-u-PA-antibodies clone 5. At 0, 1, 2, 4, 8, 16 and 32 days after this injection a group of 5 mice was bled and serum was pooled. Furthermore, in the experiment with tumor-bearing animals, serum was obtained from all anti-u-PA-antibody-treated animals day 14 after antibody injection. Nunc Immunoplates (Flat bottom Maxisorb, Nunc A/S, Denmark) were coated overnight at 4° C. with 1 μg/ml of u-PA (UKIDAN Leo) in 0.1M $Na_2CO_3$, pH 9.8. Excess u-PA was washed away and additional protein binding sites were blocked by a one hour incubation with 1% skimmed milk powder in PBS. After washing the plates were incubated for 1 hour at 37° C. with standard dilutions of anti-u-PA antibody clone 5 in mouse serum or sample to be tested. The plates were washed again and then incubated for another hour with biotinylated rabbit anti-mouse IgG (Dako). After an additional wash the plates were incubated with peroxidase-coupled avidin (Dako) for one hour and the peroxidase reaction was developed using OPD-tablets and $H_2O_2$ in 0.1M citrate-phosphate buffer, pH 5.0. The reaction was stopped by adding 100 μl of 1M $H_2SO_4$ and the absorbance was read at 490 nm. All the samples were run in duplicates.

Results

LacZ Transduction and Selection of Cells

MDA-MB-231 and MDA-MB-435 cells do not stain with X-gal unless they have been infected with the BAG vector and have received the LacZ gene as the cells shown in FIG. 30. Because of low viral titer ($-5 \times 10^4$ cfu/ml), only about 1% of either cell line was initially found to stain positive with X-gal. Following G418 selection, approximately 60–70% of the G418-resistant cells expressed the lacZ gene as based upon X-gal staining. In order to enrich for lacZ-expressing cells, both breast cancer cell lines were subjected to FDG-FACS selection. This enriched both cell populations to more than 95% X-gal positivity. In order to determine the stability of the lacZ transduction, cells in passage 20 following transduction were stained with X-gal. As seen in FIG. 30B, MDA-MB-435 BAG cells showed only a slight loss in the relative number of lacZ expressing cells. Similar results were obtained with MDB-MB-231 BAG cells (not shown).

Result of the Examination of the Transduced Human Breast Cancer Cell Line

MDA-MB-231 BAG tumors expressed abundant mRNA for both u-PA and u-PAR and the cross-linking experiment using $^{125}I$ ATF clearly demonstrated the presence of u-PAR protein in the detergent phase of the cell lysate.

Comparative Studies Between Non-transduced and Transduced Tumor Cells

The purpose of transducing the human tumor cells with the LacZ gene was to be able to localize the cells after their dissemination in the nude mouse. Primary subcutaneous tumors of either of the transduced cell lines demonstrated highly specific X-gal staining, whereas tumors from non-transduced cells did not stain blue. This is shown for MDA-MB-231 and MDA-MB-231 BAG tumors in FIG. 30 (C and D respectively). Identical results were seen following staining of MDA-MB-435 and MDA-MB-435 BAG.

Detection of Human Tumor Cells In Vivo

Both BAG lines were serially passaged in nude mice, and they retained lacZ expression following at least three passages. In cryo-sections of the primary tumors the X-gal staining was also confined to the BAG transduced human cancer cells (FIGS. 31A–31H).

Both untransduced and transduced tumors were locally invasive with penetration of the peritoneal wall of the animals (not shown). X-gal staining of mouse liver, spleen, pancreas, intestine and lungs from mice with transduced subcutaneous tumors of either tumor line demonstrated blue staining of secondary tumor formation within organs located in the peritoneal cavity (FIG. 31 (B and D)). The secondary tumors were locally invasive in various intraperitoneal organs (FIG. 31 (E and F)).

Histological examination of the blue stained areas in lungs confirmed the presence of micrometastases (FIG. 31 (G)). No positive X-gal staining in mice inoculated with uninfected tumor cells or in organs without tumor metastases was found.

Inhibition of the Invasive and Metastatic Process in Mice Using anti-u-PA Antibodies MDA-MB-231 BAG tumors in mice not injected with anti-u-PA antibodies grew invasively into the peritoneal muscle layer of the mice. The cancer cells expand into the muscle fibers, and often tumor cells can be located at the peritoneal side of the muscles. The irrelevant antibody had no effect on local tumor invasion as appears from Table 6. In contrast, the anti-u-PA antibodies inhibited the local spread of the tumor cells. As seen from Table 6, 5 out of 8 mice had metastatic spread of the cancer cells to intraperitoneal organs. Most commonly, tumor cells were found in the portal tract of the liver and in pancreas. The irrelevant antibody had no effect on the metastatic formation to the interperitoneal cavity. Injection with anti-u-PA antibodies significantly inhibited the extension of the tumor cells into intraperitoneal organs as appears from Table 6 below. There was also a significant reduction in the number of animals with blue dots on the lungs following injection with anti-u-PA antibodies. In order to confirm the presence of cancer cells in the blue spots, some of the spots were excised and processed for routine histology.

TABLE 6

|  | Local invasion | Intraperitoneal diss. | Lung metastases |
| --- | --- | --- | --- |
| Control | 12/16 | 5/8 | 8/8 |
| Barley antib. | 17/20 | 5/10 | 9/10 |
| anti-u-PA antib. | 6/16 | 0/8 | 1/8 |

Effect of anti-u-PA Antibodies on the Growth of the Tumor

Examination of the effect of the anti-u-PA antibodies on the growth of the tumor showed that neither anti-u-PA antibodies nor irrelevant antibodies did cause significant changes in tumor growth (not shown).

Pharmacokinetics

A single interperitoneal injection of 100 µg of anti-u-PA antibody resulted in a serum concentration of the antibody of approximately 25 ng/ml. The serum concentration only declines slowly with an estimated $T_{1/2}$ of about 21 days.

REFERENCES

Andreasen P A, Nielsen L S, Kristensen P, Grøndahl-Hansen J, Skriver L, Danø K (1986) Plasminogen activator inhibitor from human fibrosarcoma cells binds urokinase-type plasminogen activator, but not its proenzyme. J Biol Chem 261: 7644–7651

Andreasen P A et al, Endocrinology, 1990, 126: 2567–2576

Angerer L M, Stoler M H, Angerer R C (1987) In Situ Hybridization with RNA probes: An annotated Recipe. In In situ hybridization. Applications to Neurobiology. Oxford University Press, Oxford, pp. 71–96.

Appella E, Robinson E A, Ullrich S J, Stoppelli M P, Corti A, Cassani G, Blasi F (1987) The receptor-binding sequence of urokinase. A biological function for the growth-factor module of proteases. J Biol Chem 262: 4437–4440

Appella E, Weber I T, Blasi F (1988) Structure and function of epidermal growth factor-like regions in proteins. FEBS L. 231: 1–4

Bajpai A, Baker J B (1985) Cryptic urokinase binding sites on human foreskin fibroblasts. Biochem Biophys Res Commun 133: 475–482

Bajpai, A, Baker J B (1985a) Biochem Biophys Res Commun 133: 994–1000

Baker J B, Low D A, Simmer R L, Cunningham D D (1980) Cell 21: 37–45

Barkholt V, Jensen A L (1989) Amino acid analysis: Determination of cysteine plus half-cysteine in proteins after hydrochloric acid hydrolysis with a disulfide compound as additive. Anal Biochem 177: 318–322

Barnathan E S, Cines D B, Barone K, Kuo A, Larsen G R (1988) Differential binding of recombinant wild type and variant t-PA to human endothelial cells. Fibrinolysis 2, Suppl 1: 28

Beebe D P (1987) Binding of tissue plasminogen activator to human umbilical vein endothelial cells. Thromb Res. 46: 241–254

Behrendt N et al, 1990, J. Biol. Chem 265: 6453–6460

Bell G I, Fong N M, Stempien M M, Wormsted M A, Caput D, Ku L, Urdea M S, Rail S B, Sanchez-Pescador L (1986) Human epidermal growth factor precursor: cDNA sequence, expression in vitro and gene organization. Nucl. Ac. Res. 14: 8427–8446

Blasi F (1988) Surface receptors for urokinase plasminogen activator. Fibrinolysis 2: 73–84

Blasi F, Stoppelli M P, Cubellis M V (1986) The receptor for urokinase-plasminogen activator. J Cell Biochem 32: 179–186

Blasi F, Vassalli J-D, Danø K (1987) Urokinase-type plasminogen activator: proenzyme, receptor, and inhibitors. J Cell Biol 104: 801–804

Bordier C (1981) Phase Separation of integral membrane proteins in Triton X-114 solution. J Biol Chem 256: 1604–1607

Boyd D, Florent G, Kim P, Brattain M (1988a) Determination of the levels of urokinase and its receptor in human colon carcinoma cell lines. Cancer Res 48: 3112–3116

Boyd D, Florent G, Murano G, Brattain M (1988b) Modulation of the urokinase receptor in human colon cell lines by N,N-dimethylformamide. Biochim Biophys Acta 947: 96–100 de Bruin PAF, Crama-Bohbouth G, Werspaget H W, Verheijen J H, Dooijewaard G, Weterman I T, LLamers CBH W (1988) Thrombosis and Haemostasis 60: 2; 262–266

Burridge K (1986) Substrate adhesions in normal and transformed fibroblasts: Organization and regulation of cytoskeletal, membrane and extracellular matrix components at focal contacts. Cancer Rev 4: 18–78

Burtin P, Fondaneche M-C (1988) Receptor for plasmin on human carcinoma cells. J Natl Cancer Inst 80: 762–765

Carpenter G, Cohen S (1976) J Cell Biol 71: 159–171

Chirgwin J M, et al. (1979) Bioch. 24: 5294–5299.

Chomczynski P, Sacchi, N (1987) Single-step method of RNA isolation by acid guanidinium thiocyanate-phenol-chloroform extraction. Anal Biochem 162: 156–159.

Clark R, et al. (1989) PNAS 86: 3649–3653.

Collen D, Zamarron C, Lijnen H R, Hoylaerts M (1986) Activation of plasminogen by pro-urokinase. II. Kinetics. J Biol Chem 261: 1259–1266

Corsaro C M, Pearson M L (1981) Enhancing the efficiency of DNA-mediated gene transfer in mammalian cells. Somat. Cell Gen. 7: 603–616

Cox, K H, DeLeon D V, Angerer L M, Angerer R C (1984) Detection of mRNAs in Sea Urchin Embryos by in Situ Hybridization Using Asymmetric RNA Probes. Develop Biol 101: 485–502

Cubellis M V, Nolli M L, Cassani G, Blasi F (1986) Binding of single-chain pro-urokinase to the urokinase receptor of human U937 cells. J Biol Chem 261: 15819–15822

Cubellis M V, Andreasen P A, Ragno P, Mayer M, Danø K, Blasi F (1989) Proc Natl Acad Sci USA 86: 4828–4830

Danø K, Andreasen P A, Grøndahl-Hansen J, Kristensen P, Nielsen L S, Skriver L (1985) Plasminogen activators, tissue degradation and cancer. Adv Cancer Res 44: 139–266

Danø K, Nielsen L S, Pyke C and Kellermann, G M (1988) Plasminogen activators and neoplasia. In: Tissue-Type Plasminogen Activator (t-PA): Physiological and Clinical Aspects. C. Kluft, ed., CRC Press, Boca Raton. 1988, pp. 19–46

Danø K et al, 1990, Molecular Biology of the Cardiovascular System, Vol. 132, pp. 173–186 de Duve C, du Barsy T, Poole B, Trouet A, Tulkens P, Van Hoof F (1974) Biochem Pharmacol 23: 2495–2531

Eaton D L, Scott R W, Baker J B (1984) Purification of human fibroblast urokinase proenzyme and analysis of its regulation by proteases and protease nexin. J Biol Chem 259: 6241–6247

Ellis V, Scully M F, Kakkar W (1987) Plasminogen activation by single-chain urokinase in functional isolation. J Biol Chem 262: 14998–15003

Ellis V, Scully M F, Kakkar V V (1988) Role of human U937 monocytes in controlling single-chain urokinase-initiated plasminogen activation. Fibrinolysis 2: supp. 1, 112

Ellis V, Scully M F, Kakkar V V (1989) Plasminogen activation initiated by single-chain urokinase-type plasminogen activator. J Biol Chem 264, 2185–88

Ellis V, Tze-Chein Wun, Behrendt N, Renne E, Danø K (1990) Inhibition of Receptor-bound Urokinase by Plasminogen-activator Inhibitors. J Biol Chem 265, 9904–9908

Estreicher A, Wohlwend A, Belin D, Schleuning W-D, Vassalli J-D (1989) Characterization of the cellular binding site for the urokinase-type plasminogen activator. J Biol Chem 264: 1180–1189

Ferguson and Williams (1988) Cell surface anchoring of proteins via glycosyl-phosphatidyl inositol structures. Ann Rev Blochem 57: 285–320

Genton C, Kruithof E K O, Schleuning W-D (1987) J Cell Biol 104: 705–712

Grøndahl-Hansen J, Agerlin N, Munkholm-Larsen P, Bach F, Nielsen L S, Dombernowsky P, Danø K (1988) Sensitive and specific enzyme-linked immunosorbent assay for urokinase-type plasminogen activator and its application to plasma from patients with breast cancer. J Lab Clin Med 111: 42–51

Grøndahl-Hansen J, Lund L R, Ralfkiær E, Ottevanger V, Danø K (1988) Urokinase- and tissue-type plasminogen activators in keratinocytes during wound reepithelialization in vivo. The Journal of Investigative Dermatology 90: 790–795

Gurewich V, Pannell R, Louie S, Kelley P, Suddith R L, Greenlee R (1984) Effective and fibrin-specific clot lysis by a zymogen precursor form of urokinase (pro-urokinase). A study In Vitro and in two animal species. J Clin Invest 73: 1731–1739

Haigler H T, Maxfield F R, Willingham M C, Pastan I (1980) J Biol Chem 255: 1239–1241

Hajjar K A, Harpel P C, Jaffe E A, Nachman R L (1986) Binding of plasminogen to cultured human endothelial cells. J Biol Chem 261: 11656–11662

Hajjar K A, Nachmann R L (1988) Assembly of the fibrinolytic system on cultured endothelial cells. Fibrinolysis 2, Suppl 1: 118

Hashimoto F, Horigome T, Kanbayashi M, Yoshida K, Sugano H (1983) An improved method for separation of low-molecular-weight polypeptides by electrophoresis in sodium dodecyl sulfate-polyacrylamide gel. Anal Biochem 129: 192–199

Hearing V J, Law L W, Corti A, Appella E, Blasi F (1988) Modulation of metastatic potential by cell surface urokinase of murine melanoma cells. Cancer Res 48: 1270–1278

Hébert C A, Baker J B (1988) Linkage of extracellular plasminogen activator to the fibroblast cytoskeleton: Colocalization of cell surface urokinase with vinculin. J Cell Biol 106: 1241–1247

Heukeshoven J, Dernick R (1988) Improved silver staining procedure for fast staining in Phast System Development Unit. Electrophoresis 9: 28–32

Hopp T P, Woods K R (1981) Prediction of protein antigenic determinants from amino acid sequences. Proc. Natl. Acad. Sci. USA 78: 3824–3828

Hoylaerts M, Rijken D C, Lijnen H R, Collen D (1982) Kinetics of the activation of plasminogen by human tissue plasminogen activator. Role of fibrin. J Biol Chem 257: 2912–2919

Jänicke F, Schmitt M, Hafter A, Hollrieder A, Babic R, Ulm K, Gössner W, Graeff H (1990) Urokinase-type plasminogen activator (u-PA) antigen is a predictor of early relapse in breast cancer. Fibrinolysis 1–10

Jänicke F, Schmitt M, Ulm K, Gössner W, Graeff H (1989) Urokinase-type plasminogen activator antigen and early relapse in breast cancer. The Lancet, 1049

Kasai S, Arimura H, Nishida M, Suyama T (1985) Proteolytic cleavage of single-chain pro-urokinase induces conformational change which follows activation of the zymogen and reduction of its high affinity for fibrin. J Biol Chem 260: 12377–12381

Kielberg V, Andreasen P A, Grøndahl-Hansen J, Nielsen L S, Skriver L, Danø K (1985) Proenzyme to urokinase-type plasminogen activator in the mouse in vivo. FEBS Lett 182: 441–445

Kristensen P, Larsson L-I, Nielsen L S, Grøndahl-Hansen J, Andreasen P A, Danø K (1984) Human endothelial cells contain one type of plasminogen activator. FEBS Lett 168: 33–37

Kristensen P, Pyke C, Lund L R, Andreasen P A, Danø K (1990) Plasminogen activator inhibitor type 1 in Lewis lung carcinoma. Histochemistry 93: 559–566

Kozak M (1987) An analysis of 5'-noncoding sequences from 699 vertebrate messenger RNAs. Nucl. Ac. Res. 15: 8125–8132

Kuiper J, Otter M, Rijken D C, van Berkel T J C (1988) In vivo interaction of tissue-type plasminogen activator with rat liver cells. Fibrinolysis 2, Suppl 1: 28

Kyte J, Doolittle R F (1982) A simple method for displaying the hydropathic character of a protein. J. Mol. Biol 157: 105–132

Laemmli U K (1970) Cleavage of the structural proteins during the assembly of the head of bacteriophage T4. Nature 227: 680–685

Lijnen H R, Zamarron C, Blaber M, Winkler M E, Collen D (1986) Activation of plasminogen by pro-urokinase. I. Mechanism. J Biol Chem 261: 1253–1258

Lin W-C, Pretlow II T P, Culp L A (1990) Bacterial Lac Z gene as a highly sensitive marker to detect micrometastasis formation during tumor progression: Cancer Res. 50: 2808–2817

Liotta L A (1986) Tumor invasion and metastases—role of the extracellular matrix: Rhodes Memorial Award Lecture. Cancer Res. 46: 1–7

Low M G (1989) The glycosyl-phosphatidylinositol anchor of membrane proteins. Biochim Biophys Acta 988: 427–454

Lund L R, Riccio A, Andreasen P A, Nielsen L S, Kristensen P, Laiho M, Saksela O, Blasi F, Danø K (1987) Transforming growth factor-β is a strong and fast acting positive regulator of the level of type-1 plasminogen activator inhibitor mRNA in WI-38 human lung fibroblasts. EMBO J 6: 1281–1286

Lund L R, Georg B, Nielsen L S, Mayer M, Danø K, Andreasen P (1988) Mol Cell Endocrinol 60: 43–53

Maniatis et al. (1982) Molecular Cloning: A Laboratory Manual. Cold Spring Harbor Laboratory Mann K G, Jenny R J, Krishnaswamy S (1988) Cofactor proteins in the assembly and expression of blood clotting enzyme complexes. Ann Rev Biochem 57: 915–956

Matsudaira P (1987) Sequence from picomole quantities of proteins electroblotted onto polyvinylidene difluoride membranes. J Biol Chem 262: 10035–10038

Matsuo O, Tanaka S, Kikuchi H (1988) Effect of urinary trypsin inhibitor on osteoarthritis. Trombosis Research 52: 237–245

Mayer M, Lund L R, Riccio A, Skouv J, Nielsen L S, Stacey S N, Danø K,

Andreasen P A (1988) Plasminogen activator inhibitor type-1 protein, mRNA and gene transcription are increased by phorbol esters in human rhabdomyosarcoma cells. J Biol Chem 263: 15688–15693

Mignatti P, Robbins E, Rifkin D B (1986) Tumor invasion through the human amniotic membrane: Requirement for a proteinase cascade. Cell 47: 487–498

Miles L A, Dahlberg C M, Plow E F (1988) The cell-binding domains of plasminogen and their function in plasma. J Biol Chem 263: 11928–11934

Miles L A, Ginsberg M H, White J G, Plow E F (1986) Plasminogen interacts with human platelets through two distinct mechanisms. J Clin Invest 77: 2001–2009

Miles L A, Plow E F (1985) Binding and activation of plasminogen on the platelet surface. J Biol Chem 260: 4303–4311

Miles L A, Plow E F (1986) Topography of the high-affinity lysine binding site of plasminogen as defined with a specific antibody probe. Biochemistry 25: 6926–6933

Miles L A, Plow E F (1987) Receptor mediated binding of the fibrinolytic components, plasminogen and urokinase, to peripheral blood cells. Thromb Haemostas 58: 936–942

Miller A D, Buttimore C (1986) Redesign of retrovirus packaging cell lines to avoid recombination leading to helper virus production. Mol. Cell. Biol. 6: 2895–2902

Morrissey J H, Falhrai H, Edgington T S (1987) Molecular cloning of the cDNA for tissue factor, the cellular receptor for the initiation of the coagulation protease cascade. Cell 50: 129–135

Müller-Eberhard H J (1988) Molecular organization and function of the complement system. Ann Rev Biochem 57: 321–347

Needham G K, Sherbet G V, Farndon J R, Harris A L (1987) Binding of urokinase to specific receptor sites on human breast cancer membranes. Eur J Cancer 55: 13–16

Nelles L, Lijnen H R, Collen D, Holmes W E (1987) Characterization of recombinant human single chain urokinase-type plasminogen activator mutants produced by site-specific mutagenesis of lysine 158. J Biol Chem 262: 5682–5689

Nielsen L S, Hansen J G, Skriver L, Wilson E L, Kaltoft K, Zeuthen J, Danø K (1982) Purification of zymogen to plasminogen activator from human glioblastoma cells by affinity chromatography with monoclonal antibody. Biochemistry 24: 6410–6415

Nielsen L S, Kellerman G M, Behrendt N, Picone R, Danø K, Blasi F (1988) A 55,000–60,000 $M_r$ receptor protein for urokinase-type plasminogen activator. J Biol Chem 263: 2358–2363

Nielsen L S, Andreasen P A, Grøndahl-Hansen J, Huang J-Y, Kristensen P, Danø K (1986) Thromb. Haemost. 55: 206–212

Nolan G P, Fiering S, Nicolas J-F, Herzenberg L A (1988) Fluorescence-activated cell analysis and sorting of viable mammalian cells based on B-D-galactosidase activity after transduction of *Escherichia coli* LacZ. Proc. Natl. Acad. Sci. USA, 85: 2603–2607.

Nolli M L, Sarubbi E, Corti A, Robbiati F, Soffientini A, Blasi F, Parenti F, Cassani G (1989) Production and characterization of human recombinant single chain urokinase-type plasminogen activator from mouse cells. Fibrinolysis 3: 101–106

Okayama H, Berg P (1983) A cDNA cloning vector that permits expression of cDNA inserts in mammalian cells. Mol Cell Biol 3: 280–289

Ossowski L (1988) Plasminogen activator dependent pathways in the dissemination of human tumor cells in the chick embryo. Cell 52: 321–328

Ossowski L, Reich E (1983) Antibodies to plasminogen activator inhibit human tumor metastasis. Cell 35: 611–619

Pannell R, Gurewich V (1987) Activation of plasminogen by single-chain urokinase or by two-chain urokinase—a demonstration that single-chain urokinase has a low catalytic activity (pro-urokinase). Blood 69: 22–26

Petersen L C, Lund L R, Nielsen L S, Danø K, Skriver L (1988) One-chain urokinase-type plasminogen activator from human sarcoma cells is a proenzyme with little or no intrinsic activity. J Biol Chem 263: 11189–11195

Picone R, Kajtaniak E L, Nielsen L S, Behrendt N, Mastronicola M R, Cubellis M V, Stoppelli M P, Pedersen S, Danø K, Blasi F (1989) Regulation of urokinase receptors in monocyte-like U937 cells by phorbol ester PMA. J Cell Biol 108: 693–702

Ploug M, Jensen A L, Barkholt V (1989) Determination of amino acid compositions and $NH_2$-terminal sequences of peptides electroblotted onto PVDF membranes from tricine-sodium dodecyl sulfate-polyacrylamide gel electrophoresis: Application to peptide mapping of human complement component C3. Anal Biochem 181: 33–39

Plow E F, Freaney D E, Plescia J, Miles L A (1986) The plasminogen system and cell surfaces: evidence for plasminogen and urokinase receptors on the same cell type. J Cell Biol 103: 2411–2420

Pöllänen J, Hedman K, Nielsen L S, Danø K, Vaheri A (1988) Ultrastructural localization of plasma membrane-associated urokinase-type plasminogen activator at focal contacts. J Cell Biol 106: 87–95

Pöllänen J, Saksela O, Salonen E-M, Andreasen P, Nielsen L S, Danø K, Vaheri A (1987) Distinct localizations of urokinase-type plasminogen activator and its type-1 inhibitor under cultured human fibroblasts and sarcoma cells. J Cell Biol 104: 1085–1096

Ponte P, Gunning P, Blau H, Kedes L (1983) Human actin genes are single copy for α-cardiac actin, but multicopy for β- and α-cytoskeletal genes: 3'-untranslated regions are isotype specific but are conserved in evolution. Mol Cell Biol 3: 1783–1791

Pozzatti R, Muscel R, Williams S J, Padmanabhan R, Howard B, Liotta L, Khoury G (1986) Primary rat embryo cells transformed by one or two oncogenes show different metastatic potential. Science 232: 223–227

Price J, Turner D, Cepko, C (1987) Lineage analysis in the vertebrate system by retrovirus-mediated gene transfer. Proc. Natl. Acad. Sci. USA, 84; 156–160

Reich R, Thompson E, Iwamoto Y, Martin G R, Deason J R, Fuller G C, Miskin R (1988) Inhibition of plasminogen activator, serine proteinases and collagenase IV prevents the invasion of basement membranes by metastatic cells. In press Roldan A L, Cubellis M V, Masucci M T, Behrendt N, Lund L R, Danø K, Appella E, Blasi F (1990) Cloning and expression of the receptor for human urokinase plasminogen activator, a central molecule in cell surface, plasmin dependent proteolysis. The EMBO Journal 9, 467–474

Russell D W, Schneider W J, Yamamoto T, Luskey K L, Brown M S, Goldstein J L (1984) Domain map of the LDL receptor: sequence homology with the epidermal growth factor precursor. Cell 37: 577–585

Saksela O (1985) Plasminogen activation and regulation of pericellular proteolysis. Biochim Biophys Acta 823: 35–65

Salonen E-M, Saksela O, Vartio T, Vaheri A, Nielsen L S, Zeuthen J (1985) Plasminogen and tissue-type plasminogen activator bind to immobilized fibronectin. J Biol Chem 260: 12302–12307

Salonen E-M, Zitting A, Vaheri A (1984) Laminin interacts with plasminogen and its tissue-type activator. FEBS Lett 172: 29–32

Schägger H, von Jagow G (1987) Tricine-sodium dodecyl sulfate-polyacrylamide gel electrophoresis for the separation of proteins in the range from 1–100 kDa. Anal Biochem 166: 368–379

Selvaraj P, Rosse W, Silber R, Springer T A (1988) The major Fc receptor in blood has a phosphatidylinositol anchor and is deficient in paroxysmal nocturnal haemoglobinuria. Nature 333: 565–567

Silverstein R L, Leung L L K, Harpel P C, Nachman P (1984) Complex formation of platelet thrombospondin with plasminogen. Modulation of activation by tissue activator. J Clin Invest 74: 1625–1633

Skriver L, Larsson L-I, Kielberg V, Nielsen L S, Andresen P B, Kristensen P, Danø K (1984) Immunocytochemical localization of urokinase-type plasminogen activator in Lewis lung carcinoma. J Cell Biol 99: 753–758

Skriver L, Nielsen L S, Stephens R, Danø K (1982) Plasminogen activator released as inactive proenzyme from murine cells transformed by sarcoma virus. Eur J Biochem 124: 409–414

Stephens R W, Alitalo R, Tapiovaara H, Vaheri A (1988) Production of an active urokinase by leukemia cell lines: a novel distinction from cell lines of solid tumors. Leukemia Res 12: 419–422

Stephens R W, Fordham C J, Doe W F (1987) Proenzyme to urokinase-type plasminogen activator in human colon cancer: in vitro inhibition by monocyte minactivin after proteolytic activation. Eur J Cancer Clin Oncol 23: 213–222

Stephens R W, Leung K-C, Pöllänen J, Salonen E-M, Vaheri A (1987) Microplate immunocapture assay for plasminogen activators and their specific inhibitors. J Immunol Meth 105: 245–251

Stephens et al, 1989, J. Cell Biol. 108: 1987–1995

Stoppelli M P, Corti A, Soffientini A, Cassani G, Blasi F, Assoian R K (1985) Differentiation-enhanced binding of the amino-terminal fragment of human urokinase plasminogen activator to a specific receptor on U937 monocytes. Proc Natl Acad Sci USA 82: 4939–4943

Stoppelli M P, Tacchetti C, Cubellis M V, Corti A, Hearing V J, Cassani G, Appella E, Blasi F (1986) Autocrine saturation of pro-urokinase receptors on human A431 cells. Cell 45: 675–684

Stump D C, Lijnen H R, Collen D (1986a) Purification and characterization of single-chain urokinase-type plasminogen activator from human cell cultures. J Biol Chem 261: 1274–1278

Stump D C, Thienpont M, Collen D (1986b) Urokinase-related proteins in human urine. J Biol Chem 261: 1267–1273

Tarentino A L, Gomez C L, Plummer T H (1985) Deglycosylation of asparagine-linked glycans by Peptide-N-Glycosidase F. Biochemistry 24: 4665–4671

Thorsen S, Glas-Greenwalt P, Astrup T (1972) Differences in the binding to fibrin of urokinase and tissue plasminogen activator. Thrombos Diathes Haemorrh 28: 65–74

Tryggvason K, Höyhtyä M, Salo T (1987) Proteolytic degradation of extracellular matrix in tumor invasion. Biochim Biophys Acta 907: 191–217

Urano T, de Serrano V S, Gaffney P J, Castellino F J (1988) The activation of human (Glu$^1$)plasminogen by human single-chain urokinase. Arch Biochem Biophys 264: 222–230

Vassalli J-D, Hamilton J, Reich E (1977) Macrophage plasminogen activator: induction by concanavalin A and phorbol myristate acetate. Cell 11: 695–705

Vassalli J-D, Baccino D, Belin D (1985) A cellular binding site for the $M_r$ 55,000 form of the human plasminogen activator, urokinase. J Cell Biol 100: 86–92

Vassalli J-D, Dayer J-M, Wohlwend A, Belin D (1984) Concomitant secretion of prourokinase and of a plasminogen activator-specific inhibitor by cultured human monocytes-macrophages. J Exp Med 159: 1652–1668

Wun T-C, Ossowski L, Reich E (1982) A proenzyme form of human urokinase. J Biol Chem 157: 7262–7268

Wun T-C, Reich E (1987) An inhibitor of plasminogen activation from human placenta. J Biol Chem 262: 3646–3653

Yarden Y, Ullrich A (1988) Molecular analysis of signal transduction by growth factors. Biochemistry 27: 3113–3119

---

We claim:

1. A monoclonal or polyclonal antibody which specifically binds u-PAR, which:

1) when used as the immobilized antibody in a sandwich ELISA specifically binds u-PAR or 2) when used as a biotin-labelled detecting antibody in a sandwich ELISA detects u-PAR, 3) when used in an ELISA, specifically binds immobilized u-PAR, or 4) when used as the immobilized antibody in a sandwich ELISA specifically binds u-PAR in such a way that u-PAR retains its u-PA binding capacity, or 5) in a radioimmunoprecipitation assay precipitates purified u-PAR in an intact form, or 6) in a radioimmunoprecipitation assay precipitates a u-PA binding $M_r$ 16,000 fragment of u-PAR obtained by chymotrypsin digestion, or 7) in a radioimmunoprecipitation assay precipitates a $M_r$ 30,000–50,000 fragment of u-PAR which is obtained by chymotrypsin digestion and which does not bind u-PA, or 8) specifically binds u-PAR in Western blotting where detergent phase of a u-PAR-containing extract has been subjected to separation on SDS-PAGE under non-reducing conditions on 6–16% gradient gels, or 9) in Western blotting does not specifically bind a u-PAR glycosylation variant in the 50–65 kD range produced by U937 cells, and does not specifically bind a u-PAR glycosylation variant around 40–45 kD produced by U937a cells, or 10) in Western blotting, specifically binds a u-PAR glycosylation variant in the 50–65 kD range produced by U937 cells, and specifically binds a u-PAR glycosylation variant around 40–45 kD produced by U937a cells, 11) in Western blotting, weakly specifically binds a u-PAR glycosylation variant in the 50–65 kD range produced by U937 cells, and strongly specifically binds a u-PAR glycosylation variant around 40–45 kD produced by U937a cells, or 12) in sections of formalin-fixed and paraffin-embedded colon cancer tissue blocks immunostains cancer cells at the invasive front, the localization of the immunostained cells being virtually identical to the distribution of u-PAR mRNA as detected by in situ hybridization, or 13) inhibits the binding of pro-u-PA and active u-PA, and cell surface plasminogen activation, or 14) specifically binds the u-PA binding domain of u-PAR and thereby inhibits the binding of pro-u-PA and active u-PA, and cell surface plasminogen activation, or 15) is capable of binding to u-PAR in tissue sections including paraffin-embedded tissue sections, when used as the immobilized antibody in tissue sections which specifically binds u-PAR and thereby being useful for immunohistochemical detection of u-PAR, or 16) is capable of selectively binding to a particular glycosylation variant of u-PAR, when used as the immobilized antibody in binding to glycosylation variants of u-PAR, or 17) specifically binds the non-u-PA binding part of the u-PAR molecule comprising its C-terminal part and starting with amino acid residue 88 in the intact u-PAR molecule, or 18) when using flow cytometry with fluorescein isothiocyanate-labelled antibodies against mouse IgG binds to human monocytes, the binding not being affected by pre-incubation with exogenously added u-PA, or 19) when using flow cytometry with fluorescein isothiocyanate-labelled antibodies against mouse IgG binds to human monocytes, the binding being completely inhibited by pre-incubation with exogenously added u-PA.

2. Antibodies according to claim 1 which specifically bind the u-PA binding domain of u-PAR, but not complexes between u-PA and u-PAR.

3. Antibodies according to claim 1 which specifically bind u-PAR, but not its u-PA binding domain.

4. Antibodies according to claim 1, which specifically bind free u-PAR, but not complexes between u-PA and u-PAR.

5. Antibodies according to claim 1, which specifically bind both free u-PAR and complexes between u-PA and u-PAR.

6. A monoclonal antibody according to claim 2 which specifically binds the u-PA binding domain of u-PAR.

7. A monoclonal antibody according to claim 4, which specifically binds free u-PAR, but not complexes between u-PA and u-PAR.

8. A monoclonal antibody according to claim 3 specifically binds u-PAR, but not its u-PA binding domain.

9. A monoclonal antibody according to claim 5, which specifically binds both free u-PAR and complexes between u-PA and u-PAR.

10. The monoclonal antibody of claim 1 wherein the antibody is the antibody secreted by the hybridoma I 4E-8, ECACC 90101007, or an antibody which binds the same epitope as ECACC 90101007.

11. The monoclonal antibody of claim 1 wherein the antibody is the antibody secreted by the hybridoma I 5A-7, ECACC 90101008, or an antibody which binds the same epitope as ECACC 90101008.

12. The monoclonal antibody of claim 1 wherein the antibody is the antibody secreted by the hybridoma I 10A-4, ECACC 90101009, or an antibody which binds the same epitope as ECACC 90101009.

13. The monoclonal antibody of claim 1 wherein the antibody is the antibody secreted by the hybridoma II 1D-6, ECACC 90101010, or an antibody which binds the same epitope as ECACC 90101010.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Leu  Xaa  Xaa  Met  Gln  Xaa  Lys  Thr  Asn  Gly  Asp  Xaa  Arg  Val  Glu  Glu
1                  5                       10                      15
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Leu  Xaa  Cys  Met  Gln  Cys  Lys  Thr  Asn  Gly  Asp  Cys  Arg  Val  Glu  Glu
1              5                        10                        15

His  Ala  Leu  Gly  Gln  Xaa  Leu  Xaa  Arg  Thr  Thr  Ile  Val  Xaa
               20             25                        30
```

( 2 ) INFORMATION FOR SEQ ID NO:3:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Leu  Arg  Cys  Met  Gln  Cys  Lys  Thr  Asn  Gly  Asp  Cys  Arg  Val  Glu  Glu
1              5                        10                        15

Cys  Ala  Leu  Gly  Gln  Asp  Leu  Cys  Arg  Thr  Thr  Ile  Val  Arg  Leu  Trp
               20                       25                       30

Glu  Glu  Gly  Glu  Glu  Leu  Glu  Leu  Val  Glu  Lys  Ser  Cys  Thr  His  Ser
               35                       40                  45

Glu  Lys  Thr  Asn  Arg  Thr  Leu  Ser  Tyr  Arg  Thr  Gly  Leu  Lys  Ile  Thr
     50                       55                       60

Ser  Leu  Thr  Glu  Val  Val  Cys  Gly  Leu  Asp  Leu  Cys  Asn  Gln  Gly  Asn
65                       70                  75                            80

Ser  Gly  Arg  Ala  Val  Thr  Tyr  Ser  Arg  Ser  Arg  Tyr
               85                       90
```

( 2 ) INFORMATION FOR SEQ ID NO:4:

( i ) SEQUENCE CHARACTERISTICS:
        ( A ) LENGTH: 99 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Leu  Glu  Cys  Ile  Ser  Cys  Gly  Ser  Ser  Asp  Met  Ser  Cys  Glu  Arg  Gly
1              5                        10                       15

Arg  His  Gln  Ser  Leu  Gln  Cys  Arg  Ser  Pro  Glu  Glu  Gln  Cys  Leu  Asp
               20                       25                       30

Val  Val  Thr  His  Trp  Ile  Gln  Glu  Gly  Glu  Glu  Gly  Arg  Pro  Lys  Asp
               35                       40                       45

Asp  Arg  His  Leu  Arg  Gly  Cys  Gly  Tyr  Leu  Pro  Gly  Cys  Pro  Gly  Ser
     50                       55                       60

Asn  Gly  Phe  His  Asn  Asn  Asp  Thr  Phe  His  Phe  Leu  Lys  Cys  Cys  Asn
65                       70                       75                       80

Thr  Thr  Lys  Cys  Asn  Glu  Gly  Pro  Ile  Leu  Glu  Leu  Glu  Asn  Leu  Pro
               85                       90                       95

Gln  Asn  Gly
```

( 2 ) INFORMATION FOR SEQ ID NO:5:

( i ) SEQUENCE CHARACTERISTICS:
        ( A ) LENGTH: 90 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Arg Gln Cys Tyr Ser Cys Lys Gly Asn Ser Thr His Gly Cys Ser Ser
1               5                   10                  15

Glu Glu Thr Phe Leu Ile Asp Cys Arg Gly Pro Met Asn Gln Cys Leu
                20                  25                  30

Val Ala Thr Gly Thr His Glu Pro Lys Asn Gln Ser Tyr Met Val Arg
            35                  40                  45

Gly Cys Ala Thr Ala Ser Met Cys Gln His Ala His Leu Gly Asp Ala
    50                  55                  60

Phe Ser Met Asn His Ile Asp Val Ser Cys Cys Thr Lys Ser Gly Cys
65                  70                  75                  80

Asn His Pro Asp Leu Asp Val Gln Tyr Arg
                85                  90

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Glu Pro Gly Ala Ala Thr Leu Lys Ser Val Ala Leu Pro Phe Ala Ile
1               5                   10                  15

Ala Ala Ala Ala Leu Val Ala Ala Phe
                20                  25

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Cys Lys Asp Ser Ser Ile Val Leu Thr Lys Lys Phe Ala Leu Thr Val
1               5                   10                  15

Val Ser Ala Ala Phe Val Ala Leu Leu Phe
                20                  25

( 2 ) INFORMATION FOR SEQ ID NO:8:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Thr Thr Asp Ala Ala His Pro Gly Arg Ser Val Val Pro Ala Leu Leu
1               5                   10                  15

Pro Leu Leu Ala Gly Thr Leu Leu Leu Leu Glu Thr Ala Thr Ala Pro
                20                  25                  30

( 2 ) INFORMATION FOR SEQ ID NO:9:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

| Val | Ser | Ala | Ser | Gly | Thr | Ser | Pro | Gly | Leu | Ser | Ala | Gly | Ala | Thr | Val |
|---|---|---|---|---|---|---|---|---|---|---|---|---|---|---|---|
| 1 | | | | 5 | | | | | 10 | | | | | 15 | |

| Gly | Ile | Met | Ile | Gly | Val | Leu | Val | Gly | Val | Ala | Leu | Ile |
|---|---|---|---|---|---|---|---|---|---|---|---|---|
| | | | 20 | | | | | 25 | | | | |

( 2 ) INFORMATION FOR SEQ ID NO:10:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

| Val | Lys | Cys | Gly | Gly | Ile | Ser | Leu | Leu | Val | Gln | Asn | Thr | Ser | Trp | Leu |
|---|---|---|---|---|---|---|---|---|---|---|---|---|---|---|---|
| 1 | | | | 5 | | | | | 10 | | | | | 15 | |

| Leu | Leu | Leu | Leu | Leu | Ser | Leu | Ser | Phe | Leu | Gln | Ala | Thr | Asp | Lys | Ile |
|---|---|---|---|---|---|---|---|---|---|---|---|---|---|---|---|
| | | | 20 | | | | | 25 | | | | | 30 | | |

Ser Leu ( 2 ) INFORMATION FOR SEQ ID NO:11:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

| Tyr | Arg | Ser | Gly | Ala | Ala | Pro | Gln | Pro | Gly | Pro | Ala | His | Leu | Ser | Leu |
|---|---|---|---|---|---|---|---|---|---|---|---|---|---|---|---|
| 1 | | | | 5 | | | | | 10 | | | | | 15 | |

| Thr | Ile | Thr | Leu | Leu | Met | Thr | Ala | Arg | Leu | Trp | Gly | Gly | Thr | Leu | Leu |
|---|---|---|---|---|---|---|---|---|---|---|---|---|---|---|---|
| | | | 20 | | | | | 25 | | | | | 30 | | |

Trp Thr ( 2 ) INFORMATION FOR SEQ ID NO:12:

( i ) SEQUENCE CHARACTERISTICS:
        ( A ) LENGTH: 1400 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 47..1054

( x i ) SEQUENCE DESCRIPTION: SEQ ID NO:12:

AGAGAAGACG TGCAGGGACC CCGCGCACAG GAGCTGCCCT CGCGAC ATG GGT CAC    55
                                                                                 Met Gly His
                                                                                  1

| | | | | | | | | | | | | | | | | |
|---|---|---|---|---|---|---|---|---|---|---|---|---|---|---|---|---|
| CCG | CCG | CTG | CTG | CCG | CTG | CTG | CTG | CTG | CTC | CAC | ACC | TGC | GTC | CCA | GCC | 103 |
| Pro | Pro | Leu | Leu | Pro | Leu | Leu | Leu | Leu | Leu | His | Thr | Cys | Val | Pro | Ala | |
| | 5 | | | | 10 | | | | | | 15 | | | | | |
| TCT | TGG | GGC | CTG | CGG | TGC | ATG | CAG | TGT | AAG | ACC | AAC | GGG | GAT | TGC | CGT | 151 |
| Ser | Trp | Gly | Leu | Arg | Cys | Met | Gln | Cys | Lys | Thr | Asn | Gly | Asp | Cys | Arg | |
| 20 | | | | | 25 | | | | | 30 | | | | | 35 | |
| GTG | GAA | GAG | TGC | GCC | CTG | GGA | CAG | GAC | CTC | TGC | AGG | ACC | ACG | ATC | GTG | 199 |
| Val | Glu | Glu | Cys | Ala | Leu | Gly | Gln | Asp | Leu | Cys | Arg | Thr | Thr | Ile | Val | |
| | | | | 40 | | | | | 45 | | | | | 50 | | |
| CGC | TTG | TGG | GAA | GAA | GGA | GAA | GAG | CTG | GAG | CTG | GTG | GAG | AAA | AGC | TGT | 247 |
| Arg | Leu | Trp | Glu | Glu | Gly | Glu | Glu | Leu | Glu | Leu | Val | Glu | Lys | Ser | Cys | |
| | | 55 | | | | | 60 | | | | | 65 | | | | |
| ACC | CAC | TCA | GAG | AAG | ACC | AAC | AGG | ACC | CTG | AGC | TAT | CGG | ACT | GGC | TTG | 295 |
| Thr | His | Ser | Glu | Lys | Thr | Asn | Arg | Thr | Leu | Ser | Tyr | Arg | Thr | Gly | Leu | |
| | | 70 | | | | | 75 | | | | | 80 | | | | |
| AAG | ATC | ACC | AGC | CTT | ACC | GAG | GTT | GTG | TGT | GGG | TTA | GAC | TTG | TGC | AAC | 343 |
| Lys | Ile | Thr | Ser | Leu | Thr | Glu | Val | Val | Cys | Gly | Leu | Asp | Leu | Cys | Asn | |
| | 85 | | | | | 90 | | | | | 95 | | | | | |
| CAG | GGC | AAC | TCT | GGC | CGG | GCT | GTC | ACC | TAT | TCC | CGA | AGC | CGT | TAC | CTC | 391 |
| Gln | Gly | Asn | Ser | Gly | Arg | Ala | Val | Thr | Tyr | Ser | Arg | Ser | Arg | Tyr | Leu | |
| 100 | | | | | 105 | | | | | 110 | | | | | 115 | |
| GAA | TGC | ATT | TCC | TGT | GGC | TCA | TCA | GAC | ATG | AGC | TGT | GAG | AGG | GGC | CGG | 439 |
| Glu | Cys | Ile | Ser | Cys | Gly | Ser | Ser | Asp | Met | Ser | Cys | Glu | Arg | Gly | Arg | |
| | | | | 120 | | | | | 125 | | | | | 130 | | |
| CAC | CAG | AGC | CTG | CAG | TGC | CGC | AGC | CCT | GAA | GAA | CAG | TGC | CTG | GAT | GTG | 487 |
| His | Gln | Ser | Leu | Gln | Cys | Arg | Ser | Pro | Glu | Glu | Gln | Cys | Leu | Asp | Val | |
| | | | 135 | | | | | 140 | | | | | 145 | | | |
| GTG | ACC | CAC | TGG | ATC | CAG | GAA | GGT | GAA | GAA | GGG | CGT | CCA | AAG | GAT | GAC | 535 |
| Val | Thr | His | Trp | Ile | Gln | Glu | Gly | Glu | Glu | Gly | Arg | Pro | Lys | Asp | Asp | |
| | | 150 | | | | | 155 | | | | | 160 | | | | |
| CGC | CAC | CTC | CGT | GGC | TGT | GGC | TAC | CTT | CCC | GGC | TGC | CCG | GGC | TCC | AAT | 583 |
| Arg | His | Leu | Arg | Gly | Cys | Gly | Tyr | Leu | Pro | Gly | Cys | Pro | Gly | Ser | Asn | |
| | 165 | | | | | 170 | | | | | 175 | | | | | |
| GGT | TTC | CAC | AAC | AAC | GAC | ACC | TTC | CAC | TTC | CTG | AAA | TGC | TGC | AAC | ACC | 631 |
| Gly | Phe | His | Asn | Asn | Asp | Thr | Phe | His | Phe | Leu | Lys | Cys | Cys | Asn | Thr | |
| 180 | | | | | 185 | | | | | 190 | | | | | 195 | |
| ACC | AAA | TGC | AAC | GAG | GGC | CCA | ATC | CTG | GAG | CTT | GAA | AAT | CTG | CCG | CAG | 679 |
| Thr | Lys | Cys | Asn | Glu | Gly | Pro | Ile | Leu | Glu | Leu | Glu | Asn | Leu | Pro | Gln | |
| | | | | 200 | | | | | 205 | | | | | 210 | | |
| AAT | GGC | CGC | CAG | TGT | TAC | AGC | TGC | AAG | GGG | AAC | AGC | ACC | CAT | GGA | TGC | 727 |
| Asn | Gly | Arg | Gln | Cys | Tyr | Ser | Cys | Lys | Gly | Asn | Ser | Thr | His | Gly | Cys | |
| | | | 215 | | | | | 220 | | | | | 225 | | | |
| TCC | TCT | GAA | GAG | ACT | TTC | CTC | ATT | GAC | TGC | CGA | GGC | CCC | ATG | AAT | CAA | 775 |
| Ser | Ser | Glu | Glu | Thr | Phe | Leu | Ile | Asp | Cys | Arg | Gly | Pro | Met | Asn | Gln | |
| | | 230 | | | | | 235 | | | | | 240 | | | | |
| TGT | CTG | GTA | GCC | ACC | GGC | ACT | CAC | GAA | CCG | AAA | AAC | CAA | AGC | TAT | ATG | 823 |
| Cys | Leu | Val | Ala | Thr | Gly | Thr | His | Glu | Pro | Lys | Asn | Gln | Ser | Tyr | Met | |
| | 245 | | | | | 250 | | | | | 255 | | | | | |
| GTA | AGA | GGC | TGT | GCA | ACC | GCC | TCA | ATG | TGC | CAA | CAT | GCC | CAC | CTG | GGT | 871 |
| Val | Arg | Gly | Cys | Ala | Thr | Ala | Ser | Met | Cys | Gln | His | Ala | His | Leu | Gly | |
| 260 | | | | | 265 | | | | | 270 | | | | | 275 | |
| GAC | GCC | TTC | AGC | ATG | AAC | CAC | ATT | GAT | GTC | TCC | TGC | TGT | ACT | AAA | AGT | 919 |
| Asp | Ala | Phe | Ser | Met | Asn | His | Ile | Asp | Val | Ser | Cys | Cys | Thr | Lys | Ser | |
| | | | | 280 | | | | | 285 | | | | | 290 | | |
| GGC | TGT | AAC | CAC | CCA | GAC | CTG | GAT | GTC | CAG | TAC | CGC | AGT | GGG | GCT | GCT | 967 |
| Gly | Cys | Asn | His | Pro | Asp | Leu | Asp | Val | Gln | Tyr | Arg | Ser | Gly | Ala | Ala | |
| | | | 295 | | | | | 300 | | | | | 305 | | | |
| CCT | CAG | CCT | GGC | CCT | GCC | CAT | CTC | AGC | CTC | ACC | ATC | ACC | CTG | CTA | ATG | 1015 |
| Pro | Gln | Pro | Gly | Pro | Ala | His | Leu | Ser | Leu | Thr | Ile | Thr | Leu | Leu | Met | |
| | | 310 | | | | | 315 | | | | | 320 | | | | |

| | | | | | | | | | | | | | |
|---|---|---|---|---|---|---|---|---|---|---|---|---|---|
| ACT | GCC | AGA | CTG | TGG | GGA | GGC | ACT | CTC | CTC | TGG | ACC | TAAACCTGAA | 1061 |
| Thr | Ala | Arg | Leu | Trp | Gly | Gly | Thr | Leu | Leu | Trp | Thr | | |
| | 325 | | | | 330 | | | | | | 335 | | |

```
ATCCCCTCT  CTGCCCTGGC  TGGATCCGGG  GGACCCCTTT  GCCCTTCCCT  CGGCTCCCAG   1121

CCCTACAGAC  TTGCTGTGTG  ACCTCAGGCC  AGTGTGCCGA  CCTCTCTGGG  CCTCAGTTTT   1181

CCCAGCTATG  AAAACAGCTA  TCTCACAAAG  TTGTGTGAAG  CAGAAGAGAA  AAGCTGGAGG   1241

AAGGCCGTGG  GCAATGGGAG  AGCTCTTGTT  ATTATTAATA  TTGTTGCCGC  TGTTGTGTTG   1301

TTGTTATTAA  TTAATATTCA  TATTATTTAT  TTTATACTTA  CATAAAGATT  TTGTACCAGT   1361

GGAAAAAAAA  AAAAAAAAAA  AAAAAAAAAA  AAAAAAAA                             1400
```

( 2 ) INFORMATION FOR SEQ ID NO:13:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met  Gly  His  Pro  Pro  Leu  Leu  Pro  Leu  Leu  Leu  Leu  Leu  His  Thr  Cys
 1              5                        10                       15

Val  Pro  Ala  Ser  Trp  Gly  Leu  Arg  Cys  Met  Gln  Cys  Lys  Thr  Asn  Gly
              20                        25                       30

Asp  Cys  Arg  Val  Glu  Glu  Cys  Ala  Leu  Gly  Gln  Asp  Leu  Cys  Arg  Thr
          35                        40                       45

Thr  Ile  Val  Arg  Leu  Trp  Glu  Glu  Gly  Glu  Glu  Leu  Glu  Leu  Val  Glu
     50                        55                       60

Lys  Ser  Cys  Thr  His  Ser  Glu  Lys  Thr  Asn  Arg  Thr  Leu  Ser  Tyr  Arg
 65                       70                       75                       80

Thr  Gly  Leu  Lys  Ile  Thr  Ser  Leu  Thr  Glu  Val  Val  Cys  Gly  Leu  Asp
                    85                       90                       95

Leu  Cys  Asn  Gln  Gly  Asn  Ser  Gly  Arg  Ala  Val  Thr  Tyr  Ser  Arg  Ser
               100                      105                      110

Arg  Tyr  Leu  Glu  Cys  Ile  Ser  Cys  Gly  Ser  Ser  Asp  Met  Ser  Cys  Glu
          115                      120                      125

Arg  Gly  Arg  His  Gln  Ser  Leu  Gln  Cys  Arg  Ser  Pro  Glu  Glu  Gln  Cys
     130                      135                      140

Leu  Asp  Val  Val  Thr  His  Trp  Ile  Gln  Glu  Gly  Glu  Glu  Gly  Arg  Pro
145                      150                      155                      160

Lys  Asp  Asp  Arg  His  Leu  Arg  Gly  Cys  Gly  Tyr  Leu  Pro  Gly  Cys  Pro
                    165                      170                      175

Gly  Ser  Asn  Gly  Phe  His  Asn  Asn  Asp  Thr  Phe  His  Phe  Leu  Lys  Cys
               180                      185                      190

Cys  Asn  Thr  Thr  Lys  Cys  Asn  Glu  Gly  Pro  Ile  Leu  Glu  Leu  Glu  Asn
          195                      200                      205

Leu  Pro  Gln  Asn  Gly  Arg  Gln  Cys  Tyr  Ser  Cys  Lys  Gly  Asn  Ser  Thr
     210                      215                      220

His  Gly  Cys  Ser  Ser  Glu  Glu  Thr  Phe  Leu  Ile  Asp  Cys  Arg  Gly  Pro
225                      230                      235                      240

Met  Asn  Gln  Cys  Leu  Val  Ala  Thr  Gly  Thr  His  Glu  Pro  Lys  Asn  Gln
                    245                      250                      255

Ser  Tyr  Met  Val  Arg  Gly  Cys  Ala  Thr  Ala  Ser  Met  Cys  Gln  His  Ala
               260                      265                      270
```

| | | | | | | | | | | | | | | |
|---|---|---|---|---|---|---|---|---|---|---|---|---|---|---|
| His | Leu | Gly | Asp | Ala | Phe | Ser | Met | Asn | His | Ile | Asp | Val | Ser | Cys Cys |
| | | 275 | | | | | 280 | | | | | 285 | | |
| Thr | Lys | Ser | Gly | Cys | Asn | His | Pro | Asp | Leu | Asp | Val | Gln | Tyr | Arg Ser |
| | 290 | | | | | 295 | | | | | 300 | | | |
| Gly | Ala | Ala | Pro | Gln | Pro | Gly | Pro | Ala | His | Leu | Ser | Leu | Thr | Ile Thr |
| 305 | | | | | 310 | | | | | 315 | | | | 320 |
| Leu | Leu | Met | Thr | Ala | Arg | Leu | Trp | Gly | Gly | Thr | Leu | Leu | Trp | Thr |
| | | | | 325 | | | | | 330 | | | | | 335 |